United States Patent
Dousis et al.

(10) Patent No.: US 12,180,518 B2
(45) Date of Patent: Dec. 31, 2024

(54) RNA POLYMERASE VARIANTS FOR CO-TRANSCRIPTIONAL CAPPING

(71) Applicant: ModernaTX, Inc., Cambridge, MA (US)

(72) Inventors: Athanasios Dousis, Somerville, MA (US); Kanchana Ravichandran, Cambridge, MA (US); Amy E. Rabideau, Waltham, MA (US); Margaret Franklin, Cambridge, MA (US); Kevin Smith, Cambridge, MA (US); Michelle Lynn Hall, Roxbury, MA (US)

(73) Assignee: ModernaTX, Inc., Cambridge, MA (US)

( * ) Notice: Subject to any disclaimer, the term of this patent is extended or adjusted under 35 U.S.C. 154(b) by 198 days.

(21) Appl. No.: 17/816,696

(22) Filed: Aug. 1, 2022

(65) Prior Publication Data

US 2023/0104080 A1 Apr. 6, 2023

Related U.S. Application Data

(63) Continuation of application No. 17/325,883, filed on May 20, 2021, now Pat. No. 11,485,960, which is a continuation of application No. PCT/US2020/018779, filed on Feb. 19, 2020.

(60) Provisional application No. 62/885,928, filed on Aug. 13, 2019, provisional application No. 62/832,314, filed on Apr. 11, 2019, provisional application No. 62/808,182, filed on Feb. 20, 2019.

(51) Int. Cl.
*C12N 9/12* (2006.01)
*C12P 19/34* (2006.01)

(52) U.S. Cl.
CPC ............ *C12N 9/1247* (2013.01); *C12P 19/34* (2013.01); *C12Y 207/07006* (2013.01)

(58) Field of Classification Search
CPC ...... C12N 9/1247; C12N 15/10; C12N 15/52; C12Q 1/6844; C12P 19/34; C12Y 207/07006
USPC ........... 435/6.1, 69.1, 91.1, 91.31, 455, 458; 514/44 R; 536/23.1
See application file for complete search history.

(56) References Cited

U.S. PATENT DOCUMENTS

| | | |
|---|---|---|
| 7,335,471 B2 | 2/2008 | Guillerez et al. |
| 8,710,200 B2 | 4/2014 | Schrum et al. |
| 8,754,062 B2 | 6/2014 | De Fougerolles et al. |
| 8,822,663 B2 | 9/2014 | Schrum et al. |
| 8,846,348 B2 | 9/2014 | Jendrisak et al. |
| 8,916,352 B2 | 12/2014 | Cheng |
| 8,980,864 B2 | 3/2015 | Hoge et al. |
| 8,999,380 B2 | 4/2015 | Bancel et al. |
| 9,005,930 B2 | 4/2015 | Jendrisak et al. |
| 9,045,740 B2 | 6/2015 | Martin et al. |
| 9,115,380 B2 | 8/2015 | Jendrisak et al. |
| 9,163,246 B2 | 10/2015 | Barnes |
| 9,193,959 B2 | 11/2015 | Sobek et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 9,950,068 B2 | 4/2018 | de Fougerolles et al. |
| 10,023,626 B2 | 7/2018 | Bolen et al. |
| 10,034,951 B1 | 7/2018 | Roy et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,144,942 B2 | 12/2018 | Strack-Logue et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 10/2019 | Chen et al. |
| 10,493,143 B2 | 11/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,898,574 B2 | 1/2021 | de Fougerolles et al. |
| 10,925,958 B2 | 2/2021 | Ciaramella |
| 11,027,025 B2 | 6/2021 | Hoge et al. |

(Continued)

FOREIGN PATENT DOCUMENTS

| | | |
|---|---|---|
| CN | 102076847 A | 5/2011 |
| CN | 102177236 A | 9/2011 |

(Continued)

OTHER PUBLICATIONS

International Search Report and Written Opinion for International Application No. PCT/US2020/018779 mailed May 4, 2020.

(Continued)

*Primary Examiner* — Jane J Zara

(74) *Attorney, Agent, or Firm* — Wolf, Greenfield & Sacks, P.C.

(57) ABSTRACT

The present disclosure provides RNA polymerase variants for high efficiency transcription.

20 Claims, 34 Drawing Sheets

Specification includes a Sequence Listing.

(56) References Cited

U.S. PATENT DOCUMENTS

| | | |
|---|---|---|
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 2011/0081374 A1 | 4/2011 | Bublot et al. |
| 2013/0102034 A1 | 4/2013 | Schrum et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0368625 A1 | 12/2015 | Segall-Shapiro et al. |
| 2015/0376581 A1 | 12/2015 | Brakmann et al. |
| 2016/0024140 A1 | 1/2016 | Issa et al. |
| 2016/0024141 A1 | 1/2016 | Issa et al. |
| 2016/0032261 A1 | 2/2016 | Sobek et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0073028 A1 | 3/2018 | Mirsky et al. |
| 2018/0105551 A1 | 4/2018 | Chivukula et al. |
| 2018/0237817 A1 | 8/2018 | Roos et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0085916 A1 | 3/2020 | Martini et al. |
| 2020/0109420 A1 | 4/2020 | Brito et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0368162 A1 | 11/2020 | Martini |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |

FOREIGN PATENT DOCUMENTS

| | | |
|---|---|---|
| CN | 102573901 A | 7/2012 |
| CN | 106244608 A | 12/2016 |
| CN | 108366604 A | 8/2018 |
| CN | 111032863 A | 4/2020 |
| EP | 2042606 A1 | 4/2009 |
| EP | 2377938 A1 | 10/2011 |
| JP | 2011-223982 A | 11/2011 |
| WO | WO 2011/128444 A2 | 10/2011 |
| WO | WO 2013/050609 A1 | 4/2013 |
| WO | WO 2013/102203 A1 | 7/2013 |
| WO | WO 2014/152027 A1 | 9/2014 |
| WO | WO 2014/159813 A1 | 10/2014 |
| WO | WO 2016/164762 A1 | 10/2016 |
| WO | WO 2016/201377 A1 | 12/2016 |
| WO | WO 2017/011773 A2 | 1/2017 |
| WO | WO 2017/015457 A1 | 1/2017 |
| WO | WO 2017/020026 A1 | 2/2017 |
| WO | WO 2017/053297 A1 | 3/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070624 A1 | 4/2017 |
| WO | WO 2017/123748 A1 | 7/2017 |
| WO | WO 2017/127750 A1 | 7/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |
| WO | WO 2018/053209 A1 | 3/2018 |
| WO | WO 2018/075980 A1 | 4/2018 |
| WO | WO 2018/081459 A1 | 5/2018 |
| WO | WO 2018/081788 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |

(56) References Cited

FOREIGN PATENT DOCUMENTS

| WO | WO 2018/232357 | A1 | 12/2018 |
|----|----|----|----|
| WO | WO 2019/005539 | A1 | 1/2019 |
| WO | WO 2019/005540 | A1 | 1/2019 |
| WO | WO 2019/036670 | A1 | 2/2019 |
| WO | WO 2019/036682 | A1 | 2/2019 |
| WO | WO 2019/036683 | A1 | 2/2019 |
| WO | WO 2019/036685 | A1 | 2/2019 |
| WO | WO 2019/103993 | A1 | 5/2019 |
| WO | WO 2019/148101 | A1 | 8/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |
| WO | WO 2020/061367 | A1 | 3/2020 |
| WO | WO 2020/097291 | A1 | 5/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/155243 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/067010 | A1 | 3/2022 |
| WO | WO 2022/150717 | A1 | 7/2022 |
| WO | WO 2022/155524 | A1 | 7/2022 |
| WO | WO 2022/155530 | A1 | 7/2022 |
| WO | WO 2022/187698 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A2 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/232585 | A1 | 11/2022 |

OTHER PUBLICATIONS

Bandwar et al. The Transition to an Elongation Complex by T7 RNA Polymerase Is a Multistep Process. J. Biol. Chem. Jun. 4, 2007; 282: 22879-22886.

Bandwar et al., Sequential release of promoter contacts during transcription initiation to elongation transition. J Mol Biol. Jul. 7, 2006;360(2):466-83. Epub May 26, 2006.

Brieba et al., Scanning mutagenesis reveals roles for helix n of the bacteriophage T7 RNA polymerase thumb subdomain in transcription complex stability, pausing, and termination. J Biol Chem. Mar. 30, 2001;276(13):10306-13. Epub Dec. 21, 2000.

Bull et al., Experimental evolution yields hundreds of mutations in a functional viral genome. J Mol Evol. Sep. 2003;57(3):241-8. doi: 10.1007/s00239-003-2470-1.

Gaal et al., DNA-binding determinants of the alpha subunit of RNA polymerase: novel DNA-binding domain architecture. Genes Dev. Jan. 1, 1996;10(1):16-26.

Gardner et al. Initiation, elongation, and processivity of carboxyl-terminal mutants of T7 RNA polymerase. Biochemistry. Mar. 11, 1997;36(10):2908-18.

Grosjean, H., Modification and editing of RNA: historical overview and important facts to remember. Fine-tuning of RNA functions by modification and editing. Topics Curr Gen. Jan. 2005;12: 1-22.

Huang et al., Complete genome sequence of IME15, the first T7-like bacteriophage lytic to pan-antibiotic-resistant Stenotrophomonas maltophilia. J Virol. Dec. 2012;86(24):13839-40. doi: 10.1128/JVI.02661-12.

Ma et al. Probing conformational changes in T7 RNA polymerase during initiation and termination by using engineered disulfide linkages. Proc Natl Acad Sci U S A. Dec. 6, 2005;102(49):17612-7. Epub Nov. 21, 2005.

Pickard et al., A conserved acetyl esterase domain targets diverse bacteriophages to the Vi capsular receptor of *Salmonella enterica* serovar Typhi. J Bacteriol. Nov. 2010;192(21):5746-54. doi: 10.1128/JB.00659-10. Epub Sep. 3, 2010.

Tang et al. Relaxed rotational and scrunching changes in P266L mutant of T7 RNA polymerase reduce short abortive RNAs while delaying transition into elongation. PLoS One. Mar. 20, 2014;9(3):e91859. doi: 10.1371/journal.pone.0091859. eCollection 2014.

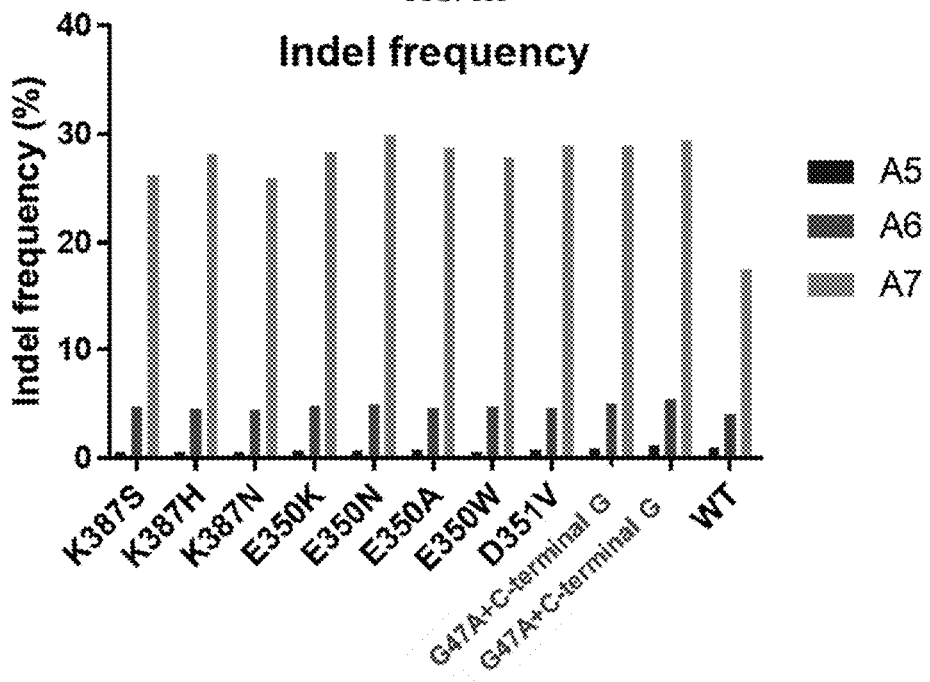
FIG. 1H
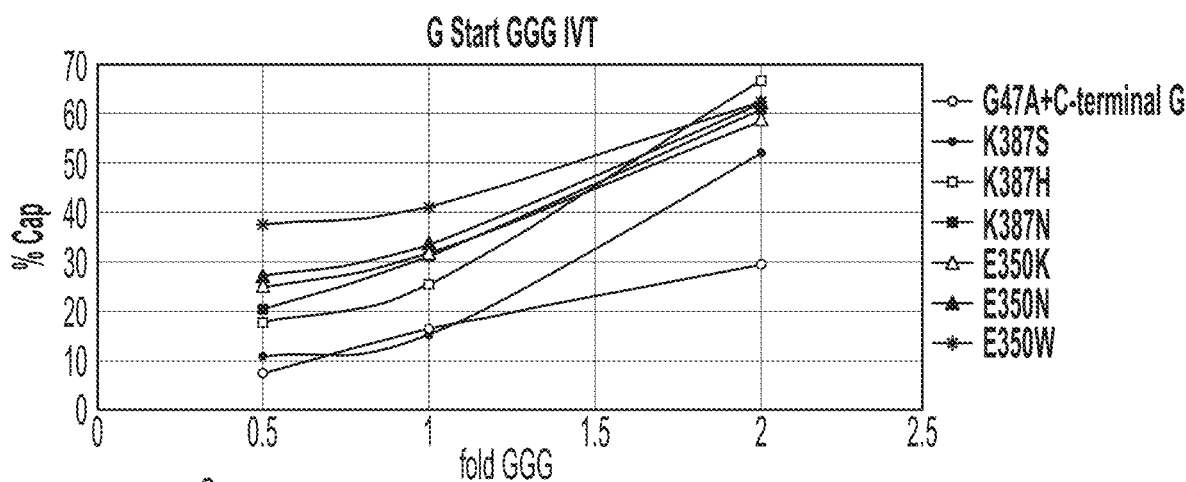
FIG. 2A
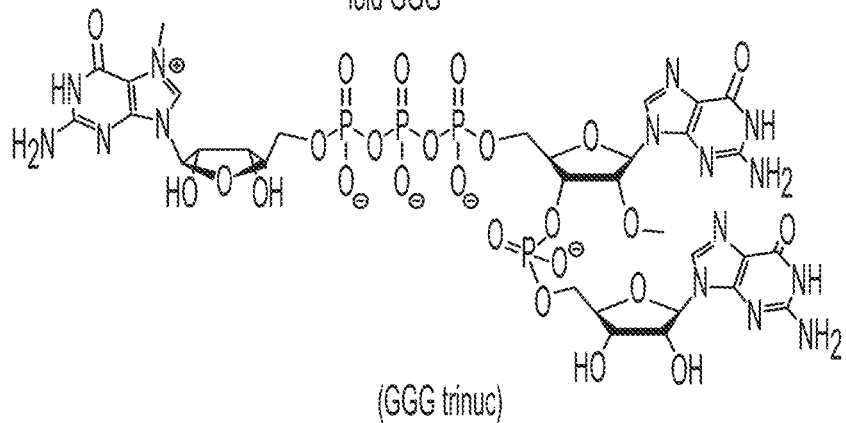
(GGG trinuc)

(m6A trinuc)

(e6A trinuc)

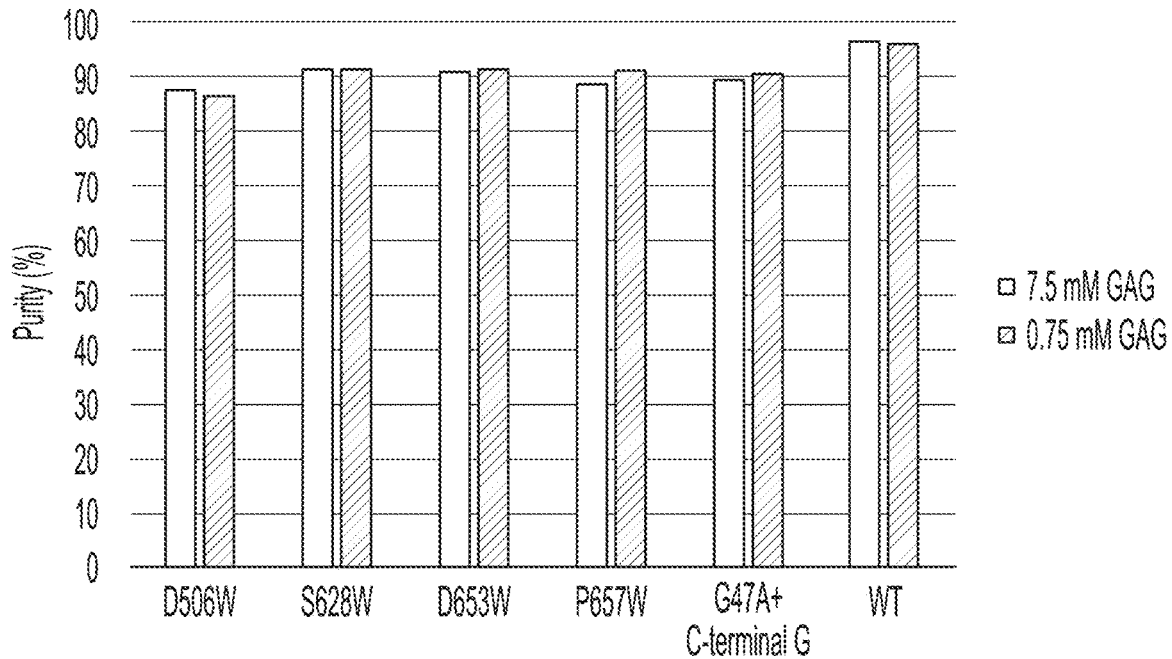
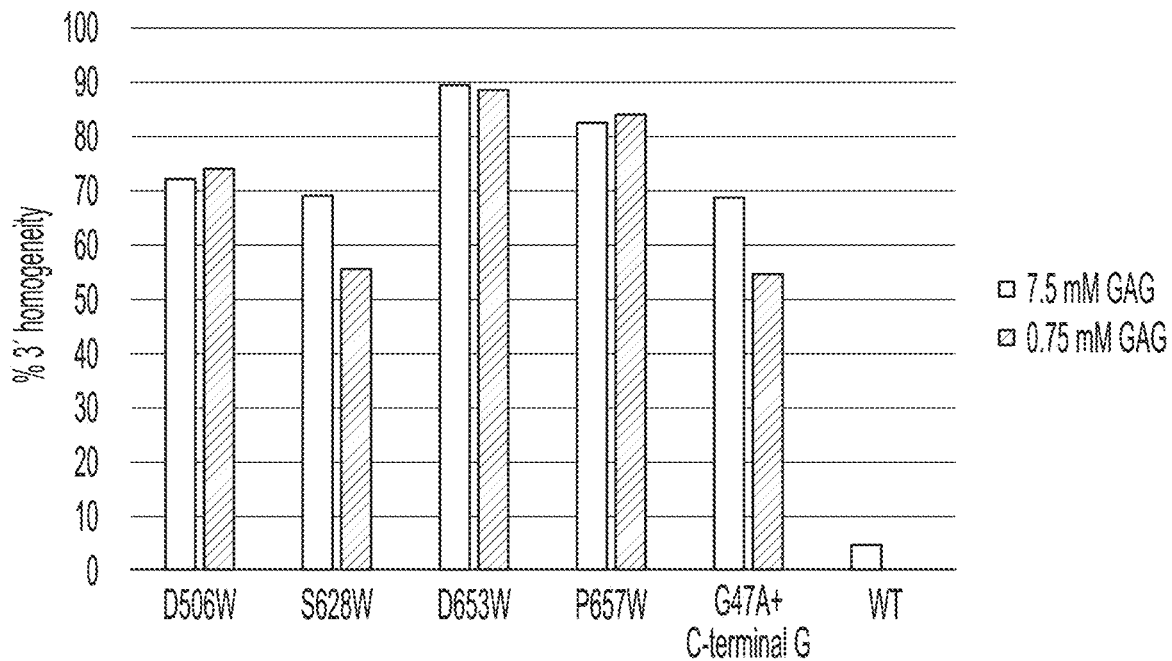

(GGAG tetranuc)

RNA POLYMERASE VARIANTS FOR CO-TRANSCRIPTIONAL CAPPING

RELATED APPLICATIONS

This application is a continuation of U.S. application Ser. No. 17/325,883, filed May 20, 2021, which is a continuation of international application number PCT/US2020/018779, filed Feb. 19, 2020, which claims the benefit under 35 U.S.C. § 119 (e) of U.S. provisional application No. 62/808,182, filed Feb. 20, 2019, U.S. provisional application No. 62/832,314, filed Apr. 11, 2019, and U.S. provisional application No. 62/885,928, filed Aug. 13, 2019, each of which is incorporated by reference herein in its entirety.

REFERENCE TO SEQUENCE LISTING SUBMITTED AS A TEXT FILE VIA EFS-WEB

The instant application contains a sequence listing which has been submitted in ASCII format via EFS-Web and is hereby incorporated by reference in its entirety. Said ASCII copy, created on Aug. 1, 2022, is named M137870117US04-SEQ-MSB.xml and is 542,211 bytes in size.

BACKGROUND

In vitro transcription (IVT) uses bacteriophage DNA-dependent ribonucleic acid (RNA) polymerases (e.g., SP6, T3 and T7) to synthesize template-directed mRNA transcripts. Problems in the IVT reaction can result in complete failure (e.g., no transcript generated) or in transcripts that are the incorrect size (e.g., shorter or longer than expected). Specific problems associated with IVT reactions include, for example, abortive (truncated) transcripts, run-on transcripts, polyA tail variants/3' heterogeneity, mutated transcripts, and/or double-stranded contaminants produced during the reactions.

RNA polymerases exhibit three phases of transcription—initiation, elongation and termination. During the initiation phase, the RNA polymerase binds to a specific promoter DNA sequence, opens the DNA duplex and feeds the template strand into the active site. T7 RNA polymerase, for example, forms a structure referred to as initiation complex, which includes a six-helix bundle sub-domain (the promoter binding domain) that interacts with the promoter to initiate DNA duplex melting. While bound to the promoter, the polymerase produces many short (truncated) transcripts from 2-12 nucleotides (nt) in length, a process often referred to as abortive synthesis/initiation. The truncated RNA transcripts cannot be converted to full-length transcripts by RNA polymerase and become by-products that accumulate during transcription. After the transition to the elongation phase and release of the promoter, the polymerase proceeds down the DNA template producing a full-length RNA transcript.

During the elongation phase, RNA polymerase often continues to transcribe DNA beyond the point at which termination should be initiated, generating longer than expected RNA transcripts ("run-on transcripts"). T7 RNA polymerase, for example, adds nucleotides to the end of a transcript before 'falling off' the template. Studies suggest that more than 70% of transcripts generated by T7 RNA polymerase in vitro may be run-on transcripts. In some cases, these aberrant RNA products are twice the length of the encoded sequence. Because run-on transcription is stochastic, there is often great 3' heterogeneity among products in a given IVT reaction. This 3' heterogeneity is problematic for downstream applications, such as ligation reactions, which are dependent on RNA transcripts of a defined length and/or nucleotide composition.

SUMMARY

Provided herein, in some aspects, are RNA polymerase variants and in vitro transcription methods using these variants. The RNA polymerase variants of the present disclosure have been shown, in some embodiments, that when used in an in vitro transcription reaction, for example, the polymerase variants, increase transcription efficiency, increase co-transcriptional capping efficiency, increase yield of RNA and improve 3' homogeneity of RNA at half the concentration of a cap analog, improve fidelity of transcription, and/or lower the amount of dsRNA contamination.

Some aspects of the present disclosure provide a ribonucleic acid (RNA) polymerase variant comprising a RNA polymerase that comprises at least one amino acid substitution.

In some embodiments, the RNA polymerase variant comprises a RNA polymerase that comprises at least one amino acid substitution at a position selected from the group consisting of E350, D351, K387, N437, K441, D506, R632, D653, S628, P657, F880, and G884 relative to a RNA polymerase comprising the amino acid sequence of SEQ ID NO: 44.

In some embodiments, the RNA polymerase variant comprises a RNA polymerase that comprises amino acid substitutions at two of the positions selected from the group consisting of E350, D351, K387, and D653, relative to a wild-type RNA polymerase comprising the amino acid sequence of SEQ ID NO: 1. In some embodiments, the two amino acid substitutions are E350 and D351. In some embodiments, the two amino acid substitutions are E350 and K387. In some embodiments, the two amino acid substitutions are K387 and D653.

In some embodiments, the RNA polymerase comprises an amino acid substitution at E350. In some embodiments, the RNA polymerase comprises an amino acid substitution at D351. In some embodiments, the RNA polymerase comprises an amino acid substitution at K387. In some embodiments, the RNA polymerase comprises an amino acid substitution at N437. In some embodiments, the RNA polymerase comprises an amino acid substitution at K441. In some embodiments, the RNA polymerase comprises an amino acid substitution at D506. In some embodiments, the RNA polymerase comprises an amino acid substitution at R632. In some embodiments, the RNA polymerase comprises an amino acid substitution at D653. In some embodiments, the RNA polymerase comprises an amino acid substitution at S628. In some embodiments, the RNA polymerase comprises an amino acid substitution at P657. In some embodiments, the RNA polymerase comprises an amino acid substitution at F880. In some embodiments, the RNA polymerase comprises an amino acid substitution at G884.

In some embodiments, the RNA polymerase comprises at least two, at least three, at least four, or at least five amino acid substitutions at positions selected from the group consisting of E350, D351, K387, N437, K441, D506, R632, D653, S628, P657, F880, and G884.

In some embodiments, the RNA polymerase comprises amino acid substitutions at positions selected from the group consisting of: E350 and D351; E350 and K387; E350 and N437; E350 and K441; E350 and D506; E350 and R632; E350 and D653; E350 and S628; E350 and P657; E350 and F880; E350 and G884; D351 and K387, D351 and N437; D351 and K441; D351 and D506; D351 and R632; D351 and D653; D351 and S628; D351 and P657; D351 and F880; D351 and G884; K387 and N437; K387 and K441; K387 and D506; K387 and R632; K387 and D653; K387 and S628; K387 and P657; K387 and F880; and K387 and G884; N437 and K441; N437 and D506; N437 and R632; N437 and D653; N437 and S628; N437 and P657; N437 and F880; N437 and G884; K441 and D506; K441 and R632; K441 and D653; K441 and S628; K441 and P657; K441 and F880; K441 and G884; D506 and R632; D506 and D653; D506 and S628; D506 and P657; D506 and F880; D506 and G884; R632 and D653; R632 and S628; R632 and P657; R632 and F880; R632 and G884; D653 and S628; D653 and P657; D653 and F880; D653 and G884; S628 and P657; S628 and F880; S628 and G884; P657 and F880; P657 and G884; and F880 and G884.

In some embodiments, the RNA polymerase comprises acid substitutions at positions selected from the group consisting of: K387, D653, and G884; E350, D351, and K387; and D653, P657, and R632.

In some embodiments, the amino acid substitution at E350 is selected from the group consisting of E350A, E350K, E350N, and E350W, optionally wherein the amino acid substitution at E350 is E350N.

In some embodiments, the amino acid substitution at D351 is D351V.

In some embodiments, the amino acid substitution at K387 is selected from the group consisting of K387H, K387N, and K387S, optionally wherein the amino acid substitution at K387 is K387N.

In some embodiments, the amino acid substitution at N437 is selected from the group consisting of N437F, N437I, N437T, and N437Y, optionally wherein the amino acid substitution at N437 is N437F.

In some embodiments, the amino acid substitution at K441 is K441R.

In some embodiments, the amino acid substitution at D506 is selected from the group consisting of D506F, D506L, D506R, D506W, and D506Y.

In some embodiments, the amino acid substitution at R632 is R632K or R632T.

In some embodiments, the amino acid substitution at D653 is selected from the group consisting of D653A, D653F, D653G, D653H, D653I, D653K, D653L, D653M, D653N, D653P, D653Q, D653R, D653S, D653T, D653V, D653W, and D653Y, optionally wherein the amino acid substitution at D653 is D653W.

In some embodiments, the amino acid substitution at S628 is S628W.

In some embodiments, the amino acid substitution at P657 is selected from the group consisting of P657A, P657R, and P657W.

In some embodiments, the amino acid substitution at F880 is F880Y.

In some embodiments, the amino acid substitution at G884 is selected from the group consisting of G884A, G884S, G884T, and G884P.

In some embodiments, the RNA polymerase comprises any one amino acid sequence as described herein.

Other aspects of the present disclosure provide a method comprising producing a mRNA in an in vitro transcription reaction that comprises a DNA template, nucleoside triphosphates, any one of the RNA polymerase variants as described herein, and optionally a cap analog. In some embodiments, the reaction comprises the cap analog. In some embodiments, the reaction comprises a concentration of the cap analog that is at least 5-fold lower than a concentration of the cap analog required to produce an equivalent amount of mRNA using a T7 RNA polymerase that comprises the amino acid sequence of SEQ ID NO: 44.

In some embodiments, greater than 80% of the mRNA produced includes a functional cap, greater the 50% of the mRNA produced is homogeneous at the 3' end, and/or the reaction comprises less than 5 ng dsRNA per 25 µg of mRNA produced.

In some embodiments, the cap analog and nucleoside triphosphates are present in the reaction at equimolar concentrations, or a molar ratio of cap analog to nucleoside triphosphates in the reaction is greater than 1:1. In some embodiments, the cap analog is a dinucleotide cap, a trinucleotide cap, or a tetranucleotide cap. In some embodiments, the cap analog is a trinucleotide cap analog comprising a GAG sequence In some embodiments, the GAG cap analog comprises a compound selected from:

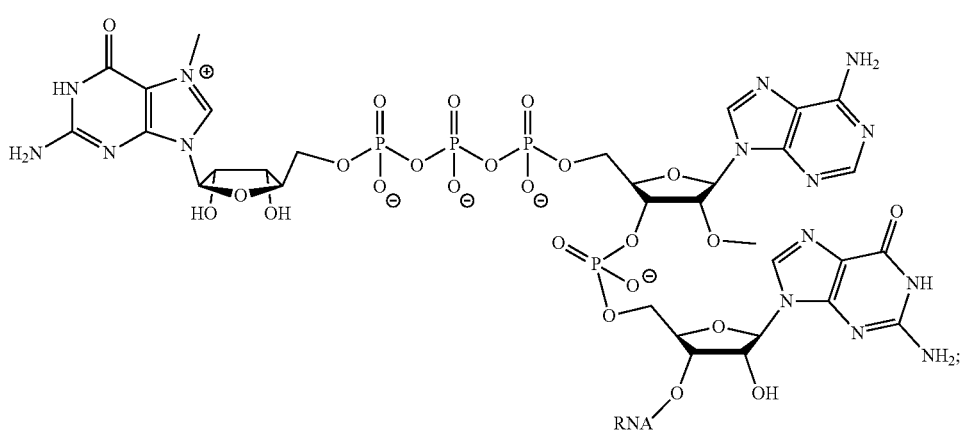

(i)

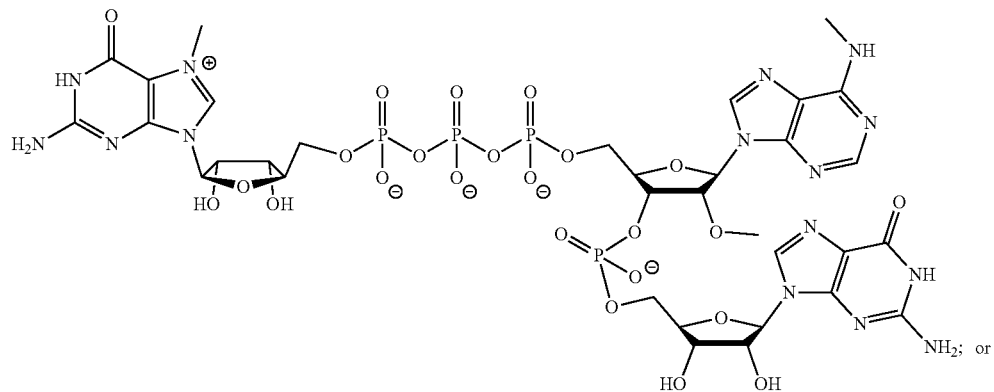
(ii)
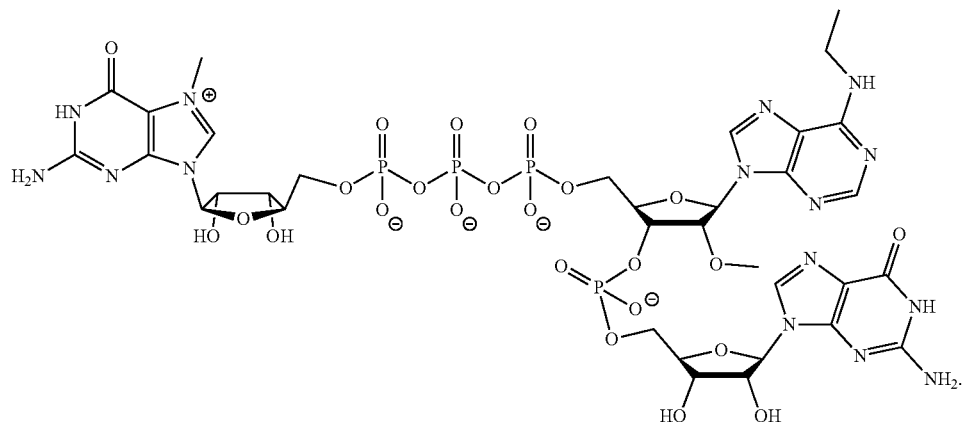
(iii)
In some embodiments, the cap analog is a tetranucleotide cap analog comprising a GGAG sequence.
In some embodiments, the tetranucleotide cap analog comprises a compound selected from:
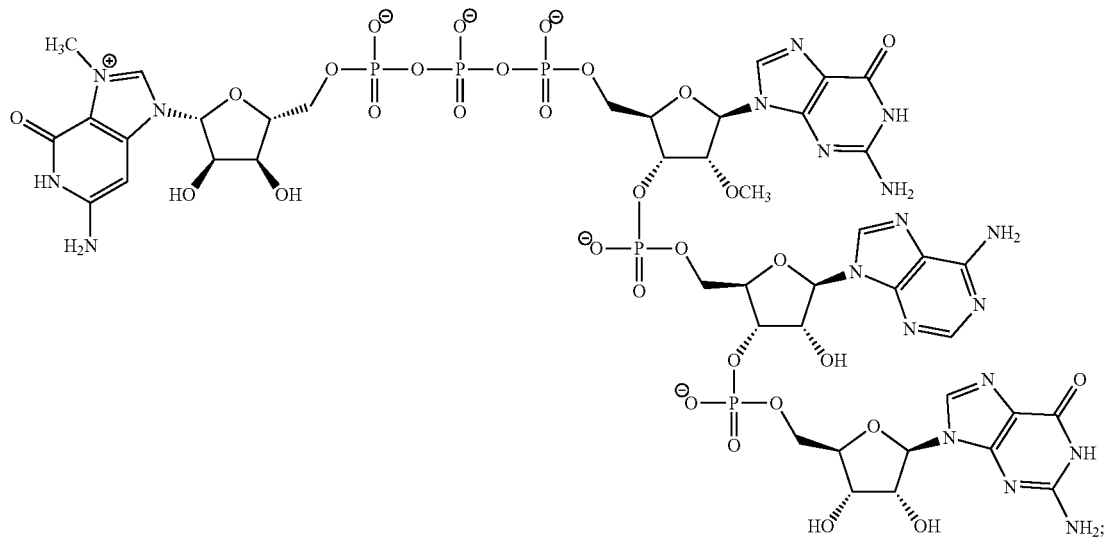
(iv)

-continued

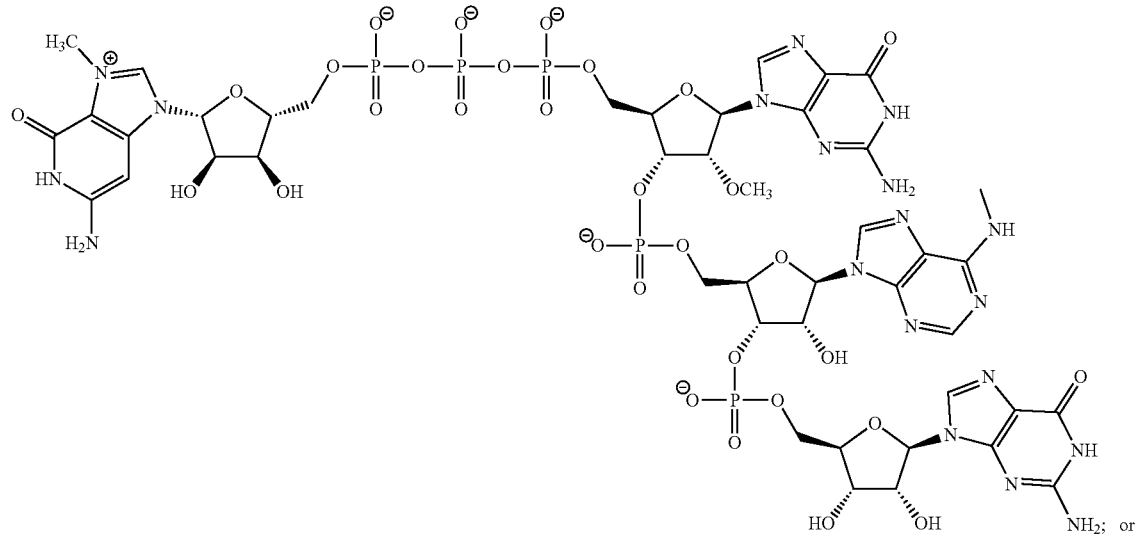

(v)

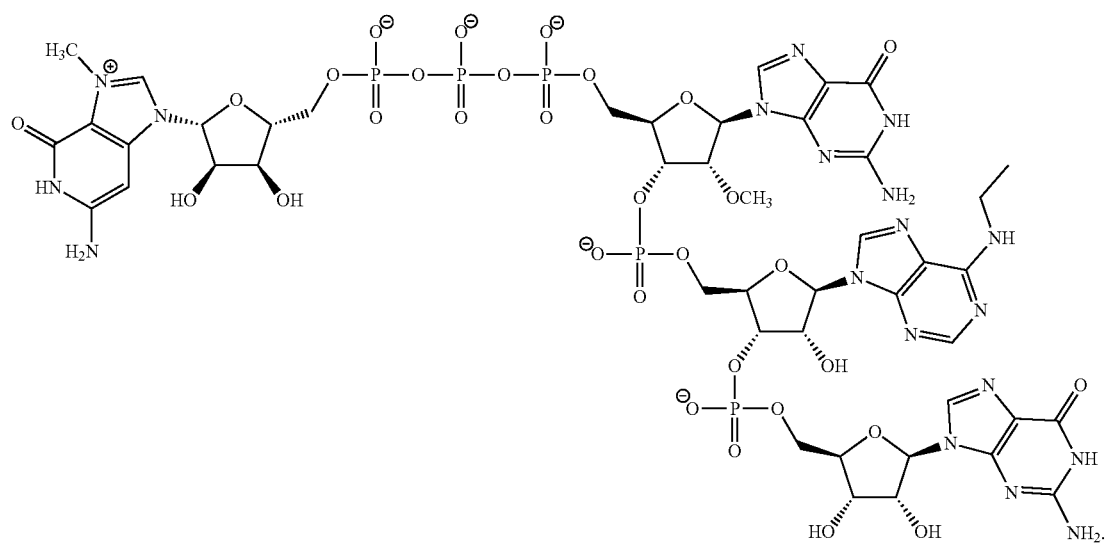

(vi)

In some embodiments, the polynucleotide template includes a 2'-deoxythymidine residue or a 2'-deoxycytidine residue at template position +1.

Other aspects of the present disclosure provide a composition or kit comprising any one of the RNA polymerase variants as described herein and an IVT reaction component, optionally selected from the group consisting of a polynucleotide template, nucleoside triphosphates, and a cap analog.

Other aspects of the present disclosure provide a nucleic acid encoding any one of the RNA polymerase variants as described herein.

BRIEF DESCRIPTION OF THE DRAWINGS

FIGS. 1A-1H show graphs depicting the functional characteristics of transcribed RNA products resulting from in vitro transcription (IVT) reactions involving mutant variants of a control T7 RNA polymerase variant (G47A+C-terminal G) in the presence of varying levels of GAG cap analog. Following an oligo dT purification, transcribed RNA products were analyzed for yield (FIG. 1A), 3' homogeneity (FIG. 1B), amount of dsRNA (FIG. 1C), percent capped RNA (FIG. 1D and FIG. 1E), purity according to a DBAA (dibutylammonium acetate) HPLC method (FIG. 1F), percent tailed (i.e., percent of RNA comprising a polyA tail) according to a Tris RP (reverse-phase) method (FIG. 1G), and indel frequency (FIG. 1H).

FIGS. 2A-2C show graphs depicting the percent capped RNA resulting from in vitro transcription (IVT) reactions involving mutant variants of a control T7 RNA polymerase variant (G47A+C-terminal G) in the presence of varying levels of GGG cap (FIG. 2A), m6A cap (FIG. 2B), and e6A cap (FIG. 2C).

FIGS. 3A-3E show graphs depicting the functional characteristics of transcribed RNA products resulting from in vitro transcription (IVT) reactions involving mutant variants of a control T7 RNA polymerase variant (G47A+C-terminal G) in the presence of varying levels of GAG cap analog. Following an oligo dT purification, transcribed RNA products were analyzed for concentration (FIG. 3A), percent tailed (i.e., percent of RNA comprising a polyA tail) according to a Tris RP (reverse-phase) method (FIG. 3B), purity according to a DBAA (dibutylammonium acetate) HPLC method (FIG. 3C), 3' homogeneity (FIG. 3D), and amount of dsRNA (FIG. 3E).

FIGS. 8E-8I are normalized to an IVT reaction involving WT T7 RNA polymerase.

DETAILED DESCRIPTION

Figure 1A:
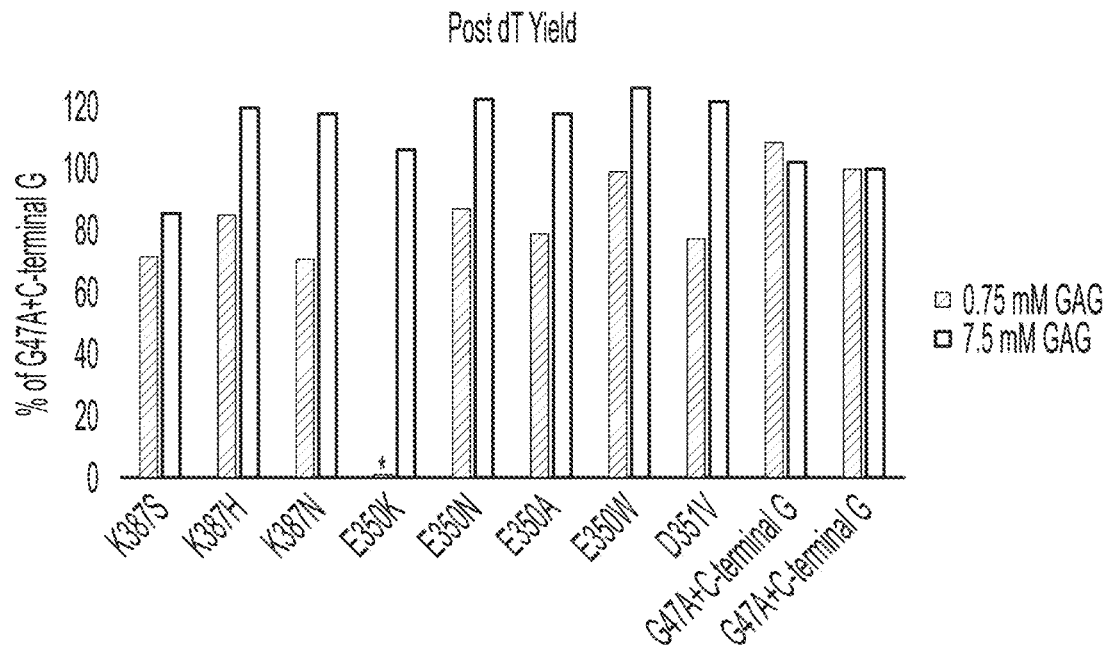

RNA polymerase (DNA-dependent RNA polymerase) is an enzyme that catalyzes the sequential addition of a ribonucleotide to the 3' end of a growing RNA chain (transcription of RNA in the 5'→3' direction), with nucleoside triphosphates (NTPs) acting as substrates for the enzyme and with the sequence of nucleotides specified by a DNA template. Transcription relies on the complementary pairing of bases. The two strands of a double helix separate locally, and one of the separated strands serves as a template (DNA template). RNA polymerase then catalyzes the alignment of free nucleotides on the DNA template by their complementary bases in the template. Thus, a RNA polymerase is considered to have RNA polymerase activity if the polymerase catalyzes the sequential addition of a ribonucleotide to the 3' end of a growing RNA chain.

DNA-directed RNA polymerases are capable of initiating synthesis of RNA without primers; the first catalytic stage of initiation is referred to as de novo RNA synthesis. De novo synthesis is a unique phase in the transcription cycle where the RNA polymerase binds two nucleotides rather than a nascent RNA polymer and a single nucleotide. For bacteriophage T7 RNA polymerase, transcription begins with a marked preference for GTP at the +1 and +2 positions. Initiating nucleotides bind RNA polymerase in locations distinct from those described for elongation complexes (Kennedy W P et al. *J Mol Biol.* 2007; 370 (2): 256-68). Selection bias in favor of GTP as an initiating nucleotide is achieved by shape complementarity, extensive protein side-chain, and strong base-stacking interactions for the guanine moiety in the enzyme active site. Thus, an initiating GTP provides the largest stabilization force for the open promoter conformation (Kennedy et al. 2007). The RNA polymerase variants of the present disclosure, in some embodiments, comprise one or more amino acid substitution(s) at one or more binding site residue(s) for de novo RNA synthesis, which, without being bound by theory, alters RNA polymerase affinity to the cap analog of an in vitro transcription reaction, for example, such that there is an improvement in capping efficiency at low cap analog concentrations.

Thus, the present disclosure, in some aspects, provides RNA polymerase variants that comprises a RNA polymerase that includes an amino acid substitution at a binding site residue for de novo RNA synthesis. A RNA polymerase variant is an enzyme having RNA polymerase activity and at least one substitution and/or modification relative to the counterpart wild-type RNA polymerase. In some embodiments, the amino acid substitution at a binding site residue is a substitution at a position selected from positions 350, 351, 387, 394, 425, 427, 437, 441, 506, 628, 632, 653, 657, 811, and 880, relative to the wild-type RNA polymerase, wherein the wild-type RNA polymerase comprises the amino acid sequence of SEQ ID NO: 1. In some embodiments, the amino acid substitution at a binding site residue is a substitution at a position selected from positions 350, 351, 387, 394, 437, 441, 506, 628, 632, 653, and 657, relative to the wild-type RNA polymerase, wherein the wild-type RNA polymerase comprises the amino acid sequence of SEQ ID NO: 1.

Structural studies of T7 RNA polymerase have shown that the conformation of the N-terminal domain changes substantially between the initiation phase and elongation phase of transcription. The N-terminal domain comprises a C-helix subdomain and the promoter binding domain, which includes two segments separated by subdomain H. The promoter binding domain and the bound promoter rotate by approximately 45 degrees upon synthesis of an 8-nt RNA transcript, allowing the promoter contacts to be maintained while the active site is expanded to accommodate a growing heteroduplex. The C-helix subdomain moves modestly toward its elongation conformation, whereas subdomain H remains in its initiation-rather than its elongation-phase location, more than 70 angstroms away. Comparison of the structures of the T7 RNA polymerase initiation and elongation complexes reveal extensive conformational changes within the N-terminal 267 residues (N-terminal domain) and little change in the rest of the RNA polymerase. A rigid body rotation of the promoter binding domain as well as the refolding of the N-terminal C-helix (residues 28-71) and H (residues 151-190) subdomains are responsible for abolishing the promoter binding site, enlarging the active site and creating an exit tunnel for the RNA transcript. In particular, residues F42-G47 of T7 RNA polymerase, which exist as a β-loop structure in the initiation complex, adopt an α-helical structure in the elongation complex. The structural changes within the N-terminal domain account for the increased stability and the processivity of the elongation complex (see, e.g., Durniak, K. J. et al., *Science* 322 (5901): 553-557, 2008, incorporated herein by reference).

Provided herein, in some aspects, are RNA polymerase variants (e.g., T7 RNA polymerase variants) that facilitate the conformational change from the RNA polymerase initiation complex to the RNA polymerase elongation complex. In some embodiments, a RNA polymerase variant comprises at least one amino acid modification, relative to wild-type RNA polymerase, that causes at least one three-dimensional loop structure of the RNA polymerase variant to undergo a conformational change to a helix structure as the RNA polymerase variant transitions from an initiation complex to an elongation complex. Thus, in some embodiments, at least one amino acid modification has a high-helix propensity, relative to wild-type amino acid. In some embodiments, a RNA polymerase variant comprises an amino acid substitution at one or more of positions 42, 43, 44, 45, 46, and 47, relative to the wild-type RNA polymerase, wherein the wild-type RNA polymerase comprises the amino acid sequence of SEQ ID NO: 1. In some embodiments, the amino acid substitution at position 47 is G47A.

Examples of loop structures include but are not limited to amino acid (aa) 42-47 in the C-helix structure (e.g., aa 28-71 of SEQ ID NO:1) of the T7 RNA polymerase initiation complex (IC) conformation and aa 257-262 in the C-linker structure (e.g., aa 258-266 of SEQ ID NO:1) of the IC.

Thus, some aspects of the present disclosure provide RNA polymerase variants that comprise multiple amino acid substitutions and/or modifications, relative to wild-type RNA polymerase. In some embodiments, a RNA polymerase variant comprise a RNA polymerase that includes (a) an amino acid substitution at a binding site residue for de novo RNA synthesis, and (b) an amino acid substitution that facilitates the conformational change from the RNA polymerase initiation complex to the RNA polymerase elongation complex.

Further, the RNA polymerase variants provided herein, in some embodiments, includes an amino acid modification comprising at least one additional amino acid at the C terminus of the polymerase. The at least one additional amino acid, in some embodiments, is selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In some embodiments, the at least one additional amino acid is a polar amino acid. In some embodiments, the at least one additional amino acid is a non-polar amino acid. In some embodiments, the at least one additional amino acid is glycine. In some embodiments, the at least one additional amino acid is alanine. In some embodiments, the at least one additional amino acid is serine.

Use of the RNA polymerase variants of the present disclosure, for example, in an in vitro transcription reaction, in some embodiments, increases transcription efficiency, relative to a control RNA polymerase. For example, use of a RNA polymerase variant may increase the transcription efficiency (e.g., RNA yield and/or rate of transcription) by at least 20%. In some embodiments, use of a RNA polymerase variant increases the transcription efficiency (e.g., RNA yield and/or rate of transcription) by at least 30%, at least 40%, at least 50%, at least 60%, at least 70%, at least 80%, at least 90%, or at least 10%. In some embodiments, use of a RNA polymerase variant increases the transcription efficiency by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. In some embodiments, use of a RNA polymerase variant increases the total RNA yield by at least 30%, at least 40%, at least 50%, at least 60%, at least 70%, at least 80%, at least 90%, or at least 10%. In some embodiments, use of a RNA polymerase variant increases the total RNA yield by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. In some embodiments, use of a RNA polymerase variant increases the rate of transcription by at least 30%, at least 40%, at least 50%, at least 60%, at least 70%, at least 80%, at least 90%, or at least 10%. In some embodiments, use of a RNA polymerase variant increases the rate of transcription by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. In some embodiments, the control RNA polymerase is a wild-type RNA polymerase comprising the amino acid sequence of SEQ ID NO: 1 ("wild-type T7 RNA polymerase"). In other embodiments, the control RNA polymerase is a RNA polymerase variant comprising an amino acid sequence of SEQ ID NO: 1 modified to include G47A substitution and an additional glycine at its C-terminus ("control T7 RNA polymerase variant" or "G47A+C-terminal G T7 RNA polymerase variant" or "control RNA polymerase variant" or "G47A+C-terminal G RNA polymerase variant").

Surprisingly, the data provided herein show that use of the RNA polymerase variants of the present disclosure in an in vitro transcription reaction enable the use of a much lower concentration (amount) of cap analog to produce an amount of capped RNA equivalent to that produced using the wild-type T7 RNA polymerase or the control RNA polymerase variant. In some embodiments, use of the RNA polymerase variants of the present disclosure, for example, in an in vitro transcription reaction increases the yield of capped RNA when half the concentration of a cap analog use in the in vitro transcription reaction. In some embodiments, use of the RNA polymerase variants of the present disclosure, for example, in an in vitro transcription reaction increases the yield of capped RNA when only 25%, 50%, or 75% of the concentration of a cap analog is use in the in vitro transcription reaction. For example, use of a RNA polymerase variant may increase the yield of capped RNA by at least 20%, when only 25%, 50%, or 75% of the concentration of a cap analog is use in the in vitro transcription reaction. In some embodiments, use of a RNA polymerase variant increases the yield of capped RNA by at least 30%, at least 40%, at least 50%, at least 60%, at least 70%, at least 80%, at least 90%, or at least 100%, when only 25%, 50%, or 75% of the concentration of a cap analog is use in the in vitro transcription reaction. In some embodiments, use of a RNA polymerase variant increases the yield of capped RNA by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%, when only 25%, 50%, or 75% of the concentration of a cap analog is use in the in vitro transcription reaction. In some embodiments, the control RNA polymerase is a wild-type T7 RNA polymerase. In other embodiments, the control RNA polymerase is a control RNA polymerase variant.

In some embodiments, use of a RNA polymerase variant increases the total yield of capped RNA by at least 30%, at least 40%, at least 50%, at least 60%, at least 70%, at least 80%, at least 90%, or at least 10%. In some embodiments, use of a RNA polymerase variant increases the total yield of capped RNA by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%.

In some embodiments, use of the RNA polymerase variants of the present disclosure, for example, in an in vitro transcription reaction increases the co-transcriptional capping efficiency. For example, use of a RNA polymerase variant may increase the co-transcriptional capping efficiency (e.g., percentage of transcript comprising cap analog) by at least 20%. In some embodiments, use of a RNA polymerase variant increases the co-transcriptional capping efficiency (e.g., percentage of transcript comprising cap analog) by at least 30%, at least 40%, at least 50%, at least 60%, at least 70%, at least 80%, at least 90%, or at least 100%. In some embodiments, use of a RNA polymerase variant increases the co-transcriptional capping efficiency by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. In some embodiments, the control RNA polymerase is a wild-type T7 RNA polymerase. In other embodiments, the control RNA polymerase is a control RNA polymerase variant.

In some embodiments, at least 50% of the mRNA comprises a functional cap analog. For example, at least 50%, at least 55%, at least 60%, at least 65%, at least 70%, at least 75%, at least 80%, at least 85%, at least 95%, or 100% of the mRNA may comprise a cap analog. In some embodiments, 50%-100%, 50%-90%, 50%-80%, or 50%-70% of the mRNA comprises a cap analog.

In some embodiments, use of the RNA polymerase variants of the present disclosure, for example, in an in vitro transcription reaction improves 3' homogeneity of RNA at half the concentration of a cap analog use in the in vitro transcription reaction. For example, use of a RNA polymerase variant may improve 3' homogeneity of RNA by at least 20%, when only 25%, 50%, or 75% of the concentration of a cap analog is use in the in vitro transcription reaction. In some embodiments, use of a RNA polymerase variant improves 3' homogeneity by at least 30%, at least 40%, at least 50%, at least 60%, at least 70%, at least 80%, at least 90%, or at least 100%, when only 25%, 50%, or 75% of the concentration of a cap analog is use in the in vitro transcription reaction. In some embodiments, use of a RNA polymerase variant improves 3' homogeneity by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%, when only 25%, 50%, or 75% of the concentration of a cap analog is use in the in vitro transcription reaction. In some embodiments, the control RNA polymerase is a wild-type T7 RNA polymerase. In other embodiments, the control RNA polymerase is a control RNA polymerase variant.

In some embodiments, at least 50% of the mRNA produced in an in vitro transcription reaction that comprises a RNA polymerase variant of the present disclosure exhibits 3' homogeneity. For example, at least 55%, at least 60%, at least 65%, at least 70%, at least 75%, at least 80%, at least 85%, at least 95%, or 100% of the mRNA exhibits 3' homogeneity. In some embodiments, 50%-100%, 50%-90%, 50%-80%, or 50%-70% of the mRNA exhibits 3' homogeneity.

In some embodiments, the mRNA produced in an in vitro transcription reaction that comprises a RNA polymerase variant of the present disclosure has greater than a threshold 3' homogeneity. In some embodiments, the threshold is 50% or at least 50%. For example, the threshold may be 55%, 60%, 65%, 70%, 75%, 80%, 85%, or 90%.

In some embodiments, use of the RNA polymerase variants of the present disclosure, for example, in an in vitro transcription reaction improves fidelity (e.g., mutation rate) of transcription. For example, use of a RNA polymerase variant may improve fidelity of transcription by at least 20%. In some embodiments, use of a RNA polymerase variant improves fidelity of transcription by at least 30%, at least 40%, at least 50%, at least 60%, at least 70%, at least 80%, at least 90%, or at least 100%. In some embodiments, use of a RNA polymerase variant improves fidelity of transcription by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. A RNA polymerase variant of the present disclosure that improves fidelity of transcription will produce RNA transcript (e.g., mRNA transcript) with a lower rate or total number of mutations than a control RNA polymerase. In some embodiments, the control RNA polymerase is a wild-type T7 RNA polymerase. In other embodiments, the control RNA polymerase is a control RNA polymerase variant.

In some embodiments, the mRNA produced using a RNA polymerase variant of the present disclosure has less than 1 mutation per 100 nucleotides relative to the DNA template. For example, the mRNA produced may have less than 1 mutation per 200, 300, 400, 500, 600, 700, 800, 900 or 1000 nucleotides relative to the DNA template.

In some embodiments, use of the RNA polymerase variants of the present disclosure, for example, in an in vitro transcription reaction lowers the amount of double-stranded RNA (dsRNA) contamination in the in vitro transcription reaction. For example, use of a RNA polymerase variant may lower the amount of dsRNA contamination in the in vitro transcription reaction by at least 20%. In some embodiments, use of a RNA polymerase variant lowers the amount of dsRNA contamination in the in vitro transcription reaction by at least 30%, at least 40%, at least 50%, at least 60%, at least 70%, at least 80%, at least 90%, or at least 100%. In some embodiments, use of a RNA polymerase variant lowers the amount of dsRNA contamination in the in vitro transcription reaction by 20-100%, 20-90%, 20-80%, 20-70%, 20-60%, 20-50%, 30-100%, 30-90%, 30-80%, 30-70%, 30-60%, 30-50%, 40-100%, 40-90%, 40-80%, 40-70%, 40-60%, 40-50%, 50-100%, 50-90%, 50-80%, 50-70%, or 50-60%. In some embodiments, the control RNA polymerase is a wild-type T7 RNA polymerase. In other embodiments, the control RNA polymerase is a control RNA polymerase variant.

In some embodiments, the concentration of dsRNA contamination is less than 10 ng per 25 µg of mRNA product. In some embodiments, the concentration of dsRNA contamination is less than 5 ng per 25 µg of mRNA product. For example, the concentration of dsRNA contamination may be less than 4 ng per 25 µg of mRNA product, less than 3 ng per 25 µg of mRNA product, less than 2 ng per 25 µg of mRNA product, or less than less than 1 ng per 25 µg of mRNA product. In some embodiments, the concentration of dsRNA contamination is 0.5-1, 0.5-2, 0.5-3, 0-0.4, or 0.5-5 ng per 25 µg of mRNA product.

In some embodiments, the mRNA produced in an in vitro transcription reaction that comprises a RNA polymerase variant of the present disclosure has lower than a threshold quantity of dsRNA. In some embodiments, the threshold is 10 ng. In some embodiments, the threshold is 5 ng. In some embodiments, the threshold is 4 ng, 3 nm, 2 ng, or 1 ng.

Amino Acid Substitutions and Modifications

RNA polymerase variants of the present disclosure include at least one amino acid substitution, relative to the wild type (WT) RNA polymerase. For example, with reference to WT T7 RNA polymerase having an amino acid sequence of SEQ ID NO: 1, the glycine at position 47 is considered a "wild-type amino acid," whereas a substitution of the glycine for alanine at position 47 is considered an "amino acid substitution" that has a high-helix propensity. In some embodiments, the RNA polymerase variant is a T7 RNA polymerase variant comprising at least one (one or more) amino acid substitution relative to WT RNA polymerase (e.g., WT T7 RNA polymerase having an amino acid sequence of SEQ ID NO:1).

In some embodiments, a RNA polymerase variant comprises a RNA polymerase that includes an (at least one) amino acid modification causes a loop structure of the RNA polymerase variant to undergo a conformational change to a helix structure as the RNA polymerase variant transitions from an initiation complex to an elongation complex. In some embodiments, the amino acid modification is an amino acid substitution at one or more of positions 42, 43, 44, 45, 46, and 47, relative to the wild-type RNA polymerase, wherein the wild-type RNA polymerase comprises the amino acid sequence of SEQ ID NO: 1. The amino acid substitution, in some embodiments, is a high propensity amino acid substitution. Examples of high-helix propensity amino acids include alanine, isoleucine, leucine, arginine, methionine, lysine, glutamine, and/or glutamate. In some embodiments, the amino acid substitution at position 47 is G47A.

In some embodiments, a RNA polymerase variant comprise a RNA polymerase that includes an additional C-terminal amino acid, relative to the wild-type RNA polymerase. The additional C-terminal amino acid, in some embodiments, is selected from glycine, alanine, threonine, proline, glutamine, and serine. In some embodiments, the additional C-terminal amino acid (e.g., at position 884 relative to wild-type RNA polymerase comprising the amino acid sequence of SEQ ID NO: 1) is glycine.

In some embodiments, a RNA polymerase variant comprises a RNA polymerase that includes an (at least one) amino acid modification at a position that is not a conserved amino acid residue. Conserved amino acid residues are amino acids or amino acid types (e.g., individual amino acids such as Gly or Ser, or groups of amino acids that share similar properties such as amino acids with acidic functional groups) that are generally shared across multiple homologous sequences of the same protein. Conserved amino acid residues can be identified using sequence alignments of homologous amino acid sequences. A sequence alignment of approximately 1000 RNA polymerase sequences obtained using a Basic Local Alignment search allowed for a determination of the 240 positions of SEQ ID NO: 1 that are most likely to be conserved across RNA polymerase sequences. These 240 positions of SEQ ID NO: 1 that are most likely to be conserved across RNA polymerase sequences are at positions 5-6, 39, 269-277, 279, 281-282, 323-333, 411-448, 454-470, 472-474, 497-516, 532-560, 562-573, 626-646, 691, 693-702, 724-738, 775-794, 805-820, 828-833, 865-867, and 877-879. Accordingly, in some embodiments, a RNA polymerase variant of the present disclosure comprises a RNA polymerase that includes an (at least one) amino acid modification at a position that is not one of positions 5-6, 39, 269-277, 279, 281-282, 323-333, 411-448, 454-470, 472-474, 497-516, 532-560, 562-573, 626-646, 691, 693-702, 724-738, 775-794, 805-820, 828-833, 865-867, and 877-879 of SEQ ID NO: 1. In some embodiments, a RNA polymerase variant as described herein may further comprise any number of amino acid modifications at any number of positions that are not one of positions 5-6, 39, 269-277, 279, 281-282, 323-333, 411-448, 454-470, 472-474, 497-516, 532-560, 562-573, 626-646, 691, 693-702, 724-738, 775-794, 805-820, 828-833, 865-867, and 877-879 of SEQ ID NO: 1. In some embodiments, a RNA polymerase variant comprising a RNA polymerase of any one of SEQ ID NO: 2-247 may further comprise an (at least one) additional amino acid modification at a position that is not one of positions 5-6, 39, 269-277, 279, 281-282, 323-333, 411-448, 454-470, 472-474, 497-516, 532-560, 562-573, 626-646, 691, 693-702, 724-738, 775-794, 805-820, 828-833, 865-867, and 877-879. Conversely, the amino acid positions that are not conserved are most likely to be modified or mutated. Accordingly, in some embodiments, a RNA polymerase variant of the present disclosure comprises a RNA polymerase that includes an (at least one) amino acid modification at positions 1-4, 7-38, 40-268, 278, 280, 283-322, 334-410, 449-453, 471, 475-496, 517-531, 561, 574-625, 647-690, 692, 703-723, 739-774, 795-804, 821-827, 834-864, 868-876, and 880-883. In some embodiments, a RNA polymerase variant comprising a RNA polymerase of any one of SEQ ID NO: 2-247 may further comprise an (at least one) additional amino acid modification at positions 1-4, 7-38, 40-268, 278, 280, 283-322, 334-410, 449-453, 471, 475-496, 517-531, 561, 574-625, 647-690, 692, 703-723, 739-774, 795-804, 821-827, 834-864, 868-876, and 880-883.

In some embodiments, a RNA polymerase variant comprising a RNA polymerase of any one of SEQ ID NO: 2-247 may further comprise an (at least one) amino acid modification at any amino acid position that does not disrupt the secondary or tertiary structure of the RNA polymerase protein. In some embodiments, a RNA polymerase variant comprising a RNA polymerase of any one of SEQ ID NO: 2-247 may further comprise an (at least one) amino acid modification at any amino acid position that does not disrupt the ability of the RNA polymerase protein to fold. In some embodiments, a RNA polymerase variant comprising a RNA polymerase of any one of SEQ ID NO: 2-247 may further comprise an (at least one) amino acid modification at any amino acid position that does not disrupt the ability of the RNA polymerase protein to bind to nucleic acids (e.g., DNA).

In some embodiments, a RNA polymerase variant comprises a RNA polymerase that includes (a) an amino acid substitution at a position selected from positions 350, 351, 387, 394, 425, 427, 437, 441, 506, 628, 632, 653, 657, 811, and 880, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, a RNA polymerase variant comprises a RNA polymerase that includes (a) an amino acid substitution at a position selected from positions 350, 351, 387, 394, 437, 441, 506, 628, 632, 653, and 657, and (b) an additional amino acid substitution and/or an amino acid modification at the C-terminal end, relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 350, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a lysine (K) at position 350 (E350K), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an asparagine (N) at position 350 (E350N), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an alanine (A) at position 350 (E350A), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan at position 350 (E350W), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 351, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a valine (V) at position 351 (D351V), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 387, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a serine at position 387 (K387S), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a histidine (H) at position 387 (K387H), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an asparagine at position 387 (K387N), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 394, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 425, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 427, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 437, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a threonine at position 437 (N437T), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an isoleucine at position 437 (N437I), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tyrosine at position 437 (N437Y), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a phenylalanine at position 437 (N437F), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 441, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an arginine at position 441 (K441R), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 506, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan (W) at position 506 (D506W), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, the amino acid substitution at position 506 is D506A, D506R, D506N, D506C, D506E, D506Q, D506G, D506H, D506I, D506L, D506K, D506M, D506F, D506P, D506S, D506T, D506W, D506Y, or D506V.

In some embodiments, a RNA polymerase variant comprises a RNA polymerase that includes an amino acid substitution at position 47 (e.g., G47A), an amino acid substitution at position 628, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan (W) at position 628 (S628W), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, the amino acid substitution at position 628 is S628A, S628R, S628N, S628D, S628C, S628E, S628Q, S628G, S628H, S628I, S628L, S628K, S628M, S628F, S628P, S628T, S628W, S628Y, or S628V.

In some embodiments, a RNA polymerase variant comprises a RNA polymerase that includes an amino acid substitution at position 47 (e.g., G47A), an amino acid substitution at position 632, and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), an amino acid substitution at position 653, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan (W) at position 653 (D563W), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, the amino acid substitution at position 653 is D653A, D653R, D653N, D653C, D653E, D653Q, D653G, D653H, D653I, D653L, D653K, D653M, D653F, D653P, D653S, D653T, D653W, D653Y, or D653V.

In some embodiments, a RNA polymerase variant comprises a RNA polymerase that includes an amino acid substitution at position 47 (e.g., G47A), an amino acid substitution at position 657, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tryptophan (W) at position 657 (P657W), and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), an amino acid substitution at position 811, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, the amino acid substitution at position 657 is P657A, P657R, P657N, P657D, P657C, P657E, P657Q, P657G, P657H, P657I, P657L, P657K, P657M, P657F, P657S, P657T, P657W, P657Y, or P657V.

In some embodiments, a RNA polymerase variant comprises a RNA polymerase that includes an amino acid substitution at position 47 (e.g., G47A), an amino acid substitution at position 880, and/or an additional amino acid (e.g., G) at the C-terminal end (at position 884), relative to wild-type RNA polymerase, wherein the wild-type RNA polymerase comprises the amino acid sequence of SEQ ID NO: 1. In some embodiments, a RNA polymerase variant comprises a RNA polymerase that includes an amino acid substitution at position 47 (e.g., G47A), a tyrosine at position 880 (F880Y), and/or an additional amino acid (e.g., G) at the C-terminal end (at position 884), relative to wild-type RNA polymerase, wherein the wild-type RNA polymerase comprises the amino acid sequence of SEQ ID NO: 1.

In some embodiments, a RNA polymerase variant comprises a RNA polymerase that includes an amino acid substitution at position 47 (e.g., G47A), and an additional amino acid at the C-terminal end (at position 884), relative to wild-type RNA polymerase, wherein the wild-type RNA polymerase comprises the amino acid sequence of SEQ ID NO: 1. In some embodiments, the additional amino acid at the C-terminal end is threonine (T). In some embodiments, the additional amino acid at the C-terminal end is serine(S). In some embodiments, the additional amino acid at the C-terminal end is alanine (A). In some embodiments, the additional amino acid at the C-terminal end is proline (P).

In some embodiments, a RNA polymerase variant comprises a RNA polymerase that comprises an amino acid substitution at position 350, relative to wild-type RNA polymerase, wherein the wild-type RNA polymerase comprises the amino acid sequence of SEQ ID NO: 1. In some embodiments, the amino acid substitution at position 350 is selected from the group consisting of E350R, E350K, E350H, E350D, E350Q, E350N, E350T, E350S, E350C, E350G, E350A, E350V, E350I, E350M, E350P, E350Y, E350W, and E350F. In some embodiments, the amino acid substitution at position 350 is E350R. In some embodiments, the amino acid substitution at position 350 is E350K. In some embodiments, the amino acid substitution at position 350 is E350H. In some embodiments, the amino acid substitution at position 350 is E350D. In some embodiments, the amino acid substitution at position 350 is E350Q. In some embodiments, the amino acid substitution at position 350 is E350N. In some embodiments, the amino acid substitution at position 350 is E350T. In some embodiments, the amino acid substitution at position 350 is E350S. In some embodiments, the amino acid substitution at position 350 is E350C. In some embodiments, the amino acid substitution at position 350 is E350G. In some embodiments, the amino acid substitution at position 350 is E350A. In some embodiments, the amino acid substitution at position 350 is E350V. In some embodiments, the amino acid substitution at position 350 is E350I. In some embodiments, the amino acid substitution at position 350 is E350M. In some embodiments, the amino acid substitution at position 350 is E350P. In some embodiments, the amino acid substitution at position 350 is E350Y. In some embodiments, the amino acid substitution at position 350 is E350W. In some embodiments, the amino acid substitution at position 350 is E350F.

In some embodiments, a RNA polymerase variant comprises a RNA polymerase that comprises an amino acid substitution at position 351, relative to wild-type RNA polymerase, wherein the wild-type RNA polymerase comprises the amino acid sequence of SEQ ID NO: 1. In some embodiments, the amino acid substitution at position 351 is selected from the group consisting of D351R, D351K, D351H, D351E, D351Q, D351N, D351T, D351S, D351C, D351G, D351A, D351V, D351I, D351M, D351P, D351Y, D351W, and D351F. In some embodiments, the amino acid substitution at position 351 is D351R. In some embodiments, the amino acid substitution at position 351 is D351K. In some embodiments, the amino acid substitution at position 351 is D351H. In some embodiments, the amino acid substitution at position 351 is D351E. In some embodiments, the amino acid substitution at position 351 is D351Q. In some embodiments, the amino acid substitution at position 351 is D351N. In some embodiments, the amino acid substitution at position 351 is D351T. In some embodiments, the amino acid substitution at position 351 is D351S. In some embodiments, the amino acid substitution at position 351 is D351C. In some embodiments, the amino acid substitution at position 351 is D351G. In some embodiments, the amino acid substitution at position 351 is D351A. In some embodiments, the amino acid substitution at position 351 is D351V. In some embodiments, the amino acid substitution at position 351 is D351I. In some embodiments, the amino acid substitution at position 351 is D351M. In some embodiments, the amino acid substitution at position 351 is D351P. In some embodiments, the amino acid substitution at position 351 is D351Y. In some embodiments, the amino acid substitution at position 351 is D351W. In some embodiments, the amino acid substitution at position 351 is D351F.

In some embodiments, a RNA polymerase variant comprises a RNA polymerase that comprises an amino acid substitution at position 387, relative to wild-type RNA polymerase, wherein the wild-type RNA polymerase comprises the amino acid sequence of SEQ ID NO: 1. In some embodiments, the amino acid substitution at position 387 is selected from the group consisting of K387R, K387H, K387E, K387D, K387Q, K387N, K387T, K387S, K387C, K387G, K387A, K387V, K387I, K387M, K387P, K387Y, K387W, and K387F. In some embodiments, the amino acid substitution at position 387 is K387R. In some embodiments, the amino acid substitution at position 387 is K387H. In some embodiments, the amino acid substitution at position 387 is K387E. In some embodiments, the amino acid substitution at position 387 is K387D. In some embodiments, the amino acid substitution at position 387 is K387Q. In some embodiments, the amino acid substitution at position 387 is K387N. In some embodiments, the amino acid substitution at position 387 is K387T. In some embodiments, the amino acid substitution at position 387 is K387S. In some embodiments, the amino acid substitution at position 387 is K387C. In some embodiments, the amino acid substitution at position 387 is K387G. In some embodiments, the amino acid substitution at position 387 is K387A. In some embodiments, the amino acid substitution at position 387 is K387V. In some embodiments, the amino acid substitution at position 387 is K387I. In some embodiments, the amino acid substitution at position 387 is K387M. In some embodiments, the amino acid substitution at position 387 is K387P. In some embodiments, the amino acid substitution at position 387 is K387Y. In some embodiments, the amino acid substitution at position 387 is K387W. In some embodiments, the amino acid substitution at position 387 is K387F.

In some embodiments, a RNA polymerase variant comprises a RNA polymerase that comprises an amino acid substitution at position 394, relative to wild-type RNA polymerase, wherein the wild-type RNA polymerase comprises the amino acid sequence of SEQ ID NO: 1. In some embodiments, the amino acid substitution at position 394 is selected from the group consisting of R394K, R394H, R394E, R394D, R394Q, R394N, R394T, R394S, R394C, R394G, R394A, R394V, R394I, R394M, R394P, R394Y, R394W, and R394F. In some embodiments, the amino acid substitution at position 394 is R394K. In some embodiments, the amino acid substitution at position 394 is R394H. In some embodiments, the amino acid substitution at position 394 is R394E. In some embodiments, the amino acid substitution at position 394 is R394D. In some embodiments, the amino acid substitution at position 394 is R394Q. In some embodiments, the amino acid substitution at position 394 is R394N. In some embodiments, the amino acid substitution at position 394 is R394T. In some embodiments, the amino acid substitution at position 394 is R394S. In some embodiments, the amino acid substitution at position 394 is R394C. In some embodiments, the amino acid substitution at position 394 is R394G. In some embodiments, the amino acid substitution at position 394 is R394A. In some embodiments, the amino acid substitution at position 394 is R394V. In some embodiments, the amino acid substitution at position 394 is R394I. In some embodiments, the amino acid substitution at position 394 is R394M. In some embodiments, the amino acid substitution at position 394 is R394P. In some embodiments, the amino acid substitution at position 394 is R394Y. In some embodiments, the amino acid substitution at position 394 is R394W. In some embodiments, the amino acid substitution at position 394 is R394F.

In some embodiments, a RNA polymerase variant comprises a RNA polymerase that comprises an amino acid substitution at position 425, relative to wild-type RNA polymerase, wherein the wild-type RNA polymerase comprises the amino acid sequence of SEQ ID NO: 1. In some embodiments, the amino acid substitution at position 425 is selected from the group consisting of R425K, R425H, R425E, R425D, R425Q, R425N, R425T, R425S, R425C, R425G, R425A, R425V, R425I, R425M, R425P, R425Y, R425W, and R425F. In some embodiments, the amino acid substitution at position 425 is R425K. In some embodiments, the amino acid substitution at position 425 is R425H. In some embodiments, the amino acid substitution at position 425 is R425E. In some embodiments, the amino acid substitution at position 425 is R425D. In some embodiments, the amino acid substitution at position 425 is R425Q. In some embodiments, the amino acid substitution at position 425 is R425N. In some embodiments, the amino acid substitution at position 425 is R425T. In some embodiments, the amino acid substitution at position 425 is R425S. In some embodiments, the amino acid substitution at position 425 is R425C. In some embodiments, the amino acid substitution at position 425 is R425G. In some embodiments, the amino acid substitution at position 425 is R425A. In some embodiments, the amino acid substitution at position 425 is R425V. In some embodiments, the amino acid substitution at position 425 is R425I. In some embodiments, the amino acid substitution at position 425 is R425M. In some embodiments, the amino acid substitution at position 425 is R425P. In some embodiments, the amino acid substitution at position 425 is R425Y. In some embodiments, the amino acid substitution at position 425 is R425W. In some embodiments, the amino acid substitution at position 425 is R425F.

In some embodiments, a RNA polymerase variant comprises a RNA polymerase that comprises an amino acid substitution at position 427, relative to wild-type RNA polymerase, wherein the wild-type RNA polymerase comprises the amino acid sequence of SEQ ID NO: 1. In some embodiments, the amino acid substitution at position 427 is selected from the group consisting of Y427R, Y427K, Y427H, Y427E, Y427D, Y427Q, Y427N, Y427T, Y427S, Y427C, Y427G, Y427A, Y427V, Y4271, Y427M, Y427P, Y427W, and Y427F. In some embodiments, the amino acid substitution at position 427 is Y427R. In some embodiments, the amino acid substitution at position 427 is Y427K. In some embodiments, the amino acid substitution at position 427 is Y427H. In some embodiments, the amino acid substitution at position 427 is Y427E. In some embodiments, the amino acid substitution at position 427 is Y427D. In some embodiments, the amino acid substitution at position 427 is Y427Q. In some embodiments, the amino acid substitution at position 427 is Y427N. In some embodiments, the amino acid substitution at position 427 is Y427T. In some embodiments, the amino acid substitution at position 427 is Y427S. In some embodiments, the amino acid substitution at position 427 is Y427C. In some embodiments, the amino acid substitution at position 427 is Y427G. In some embodiments, the amino acid substitution at position 427 is Y427A. In some embodiments, the amino acid substitution at position 427 is Y427V. In some embodiments, the amino acid substitution at position 427 is Y4271. In some embodiments, the amino acid substitution at position 427 is Y427M. In some embodiments, the amino acid substitution at position 427 is Y427P. In some embodiments, the amino acid substitution at position 427 is Y427W. In some embodiments, the amino acid substitution at position 427 is Y427F.

In some embodiments, a RNA polymerase variant comprises a RNA polymerase that comprises an amino acid substitution at position 437, relative to wild-type RNA polymerase, wherein the wild-type RNA polymerase comprises the amino acid sequence of SEQ ID NO: 1. In some embodiments, the amino acid substitution at position 437 is selected from the group consisting of N437R, N437K, N437H, N437E, N437D, N437Q, N437T, N437S, N437C, N437G, N437A, N437V, N437I, N437M, N437P, N437Y, N437W, and N437F. In some embodiments, the amino acid substitution at position 437 is N437R. In some embodiments, the amino acid substitution at position 437 is N437K. In some embodiments, the amino acid substitution at position 437 is N437H. In some embodiments, the amino acid substitution at position 437 is N437E. In some embodiments, the amino acid substitution at position 437 is N437D. In some embodiments, the amino acid substitution at position 437 is N437Q. In some embodiments, the amino acid substitution at position 437 is N437T. In some embodiments, the amino acid substitution at position 437 is N437S. In some embodiments, the amino acid substitution at position 437 is N437C. In some embodiments, the amino acid substitution at position 437 is N437G. In some embodiments, the amino acid substitution at position 437 is N437A. In some embodiments, the amino acid substitution at position 437 is N437V. In some embodiments, the amino acid substitution at position 437 is N4371. In some embodiments, the amino acid substitution at position 437 is N437M. In some embodiments, the amino acid substitution at position 437 is N437P. In some embodiments, the amino acid substitution at position 437 is N437Y. In some embodiments, the amino acid substitution at position 437 is N437W. In some embodiments, the amino acid substitution at position 437 is N437F.

In some embodiments, a RNA polymerase variant comprises a RNA polymerase that comprises an amino acid substitution at position 441, relative to wild-type RNA polymerase, wherein the wild-type RNA polymerase comprises the amino acid sequence of SEQ ID NO: 1. In some embodiments, the amino acid substitution at position 441 is selected from the group consisting of K441R, K441H, K441E, K441D, K441Q, K441N, K441T, K441S, K441C, K441G, K441A, K441V, K441I, K441M, K441P, K441Y, K441W, and K441F. In some embodiments, the amino acid substitution at position 441 is K441R. In some embodiments, the amino acid substitution at position 441 is K441H. In some embodiments, the amino acid substitution at position 441 is K441E. In some embodiments, the amino acid substitution at position 441 is K441D. In some embodiments, the amino acid substitution at position 441 is K441Q. In some embodiments, the amino acid substitution at position 441 is K441N. In some embodiments, the amino acid substitution at position 441 is K441T. In some embodiments, the amino acid substitution at position 441 is K441S. In some embodiments, the amino acid substitution at position 441 is K441C. In some embodiments, the amino acid substitution at position 441 is K441G. In some embodiments, the amino acid substitution at position 441 is K441A. In some embodiments, the amino acid substitution at position 441 is K441V. In some embodiments, the amino acid substitution at position 441 is K441I. In some embodiments, the amino acid substitution at position 441 is K441M. In some embodiments, the amino acid substitution at position 441 is K441P. In some embodiments, the amino acid substitution at position 441 is K441Y. In some embodiments, the amino acid substitution at position 441 is K441W. In some embodiments, the amino acid substitution at position 441 is K441F.

In some embodiments, a RNA polymerase variant comprises a RNA polymerase that comprises an amino acid substitution at position 632, relative to wild-type RNA polymerase, wherein the wild-type RNA polymerase comprises the amino acid sequence of SEQ ID NO: 1. In some embodiments, the amino acid substitution at position 632 is selected from the group consisting of R632K, R632H, R632E, R632D, R632Q, R632N, R632T, R632S, R632C, R632G, R632A, R632V, R632I, R632M, R632P, R632Y, R632W, and R632F. In some embodiments, the amino acid substitution at position 632 is R632K. In some embodiments, the amino acid substitution at position 632 is R632H. In some embodiments, the amino acid substitution at position 632 is R632E. In some embodiments, the amino acid substitution at position 632 is R632D. In some embodiments, the amino acid substitution at position 632 is R632Q. In some embodiments, the amino acid substitution at position 632 is R632N. In some embodiments, the amino acid substitution at position 632 is R632T. In some embodiments, the amino acid substitution at position 632 is R632S. In some embodiments, the amino acid substitution at position 632 is R632C. In some embodiments, the amino acid substitution at position 632 is R632G. In some embodiments, the amino acid substitution at position 632 is R632A. In some embodiments, the amino acid substitution at position 632 is R632V. In some embodiments, the amino acid substitution at position 632 is R632I. In some embodiments, the amino acid substitution at position 632 is R632M. In some embodiments, the amino acid substitution at position 632 is R632P. In some embodiments, the amino acid substitution at position 632 is R632Y. In some embodiments, the amino acid substitution at position 632 is R632W. In some embodiments, the amino acid substitution at position 632 is R632F.

In some embodiments, a RNA polymerase variant comprises a RNA polymerase that comprises an amino acid substitution at position 811, relative to wild-type RNA polymerase, wherein the wild-type RNA polymerase comprises the amino acid sequence of SEQ ID NO: 1. In some embodiments, the amino acid substitution at position 811 is selected from the group consisting of H811R, H811K, H811E, H811D, H811Q, H811N, H811T, H811S, H811C, H811G, H811A, H811V, H811I, H811M, H811P, H811Y, H811W, and H811F. In some embodiments, the amino acid substitution at position 811 is H811R. In some embodiments, the amino acid substitution at position 811 is H811K. In some embodiments, the amino acid substitution at position 811 is H811E. In some embodiments, the amino acid substitution at position 811 is H811D. In some embodiments, the amino acid substitution at position 811 is H811Q. In some embodiments, the amino acid substitution at position 811 is H811N. In some embodiments, the amino acid substitution at position 811 is H811T. In some embodiments, the amino acid substitution at position 811 is H811S. In some embodiments, the amino acid substitution at position 811 is H811C. In some embodiments, the amino acid substitution at position 811 is H811G. In some embodiments, the amino acid substitution at position 811 is H811A. In some embodiments, the amino acid substitution at position 811 is H811V. In some embodiments, the amino acid substitution at position 811 is H811I. In some embodiments, the amino acid substitution at position 811 is H811M. In some embodiments, the amino acid substitution at position 811 is H811P. In some embodiments, the amino acid substitution at position 811 is H811Y. In some embodiments, the amino acid substitution at position 811 is H811W. In some embodiments, the amino acid substitution at position 811 is H811F.

In some embodiments, a RNA polymerase variant comprises a RNA polymerase that comprises an amino acid substitution at position 880, relative to wild-type RNA polymerase, wherein the wild-type RNA polymerase comprises the amino acid sequence of SEQ ID NO: 1. In some embodiments, the amino acid substitution at position 880 is selected from the group consisting of F880R, F880K, F880H, F880E, F880D, F880Q, F880N, F880T, F880S, F880C, F880G, F880A, F880V, F880I, F880M, F880P, F880Y, and F880W. In some embodiments, the amino acid substitution at position 880 is F880R. In some embodiments, the amino acid substitution at position 880 is F880K. In some embodiments, the amino acid substitution at position 880 is F880H. In some embodiments, the amino acid substitution at position 880 is F880E. In some embodiments, the amino acid substitution at position 880 is F880D. In some embodiments, the amino acid substitution at position 880 is F880Q. In some embodiments, the amino acid substitution at position 880 is F880N. In some embodiments, the amino acid substitution at position 880 is F880T. In some embodiments, the amino acid substitution at position 880 is F880S. In some embodiments, the amino acid substitution at position 880 is F880C. In some embodiments, the amino acid substitution at position 880 is F880G. In some embodiments, the amino acid substitution at position 880 is F880A. In some embodiments, the amino acid substitution at position 880 is F880V. In some embodiments, the amino acid substitution at position 880 is F880I. In some embodiments, the amino acid substitution at position 880 is F880M. In some embodiments, the amino acid substitution at position 880 is F880P. In some embodiments, the amino acid substitution at position 880 is F880Y. In some embodiments, the amino acid substitution at position 880 is F880W.

In should be understood that the RNA polymerase variants of the present disclosure may include more than one (e.g., 2, 3, 4, 5, or more) amino acid substitution and/or modification. It should also be understood that any of the RNA polymerase variants may include a G47A substitution and/or an additional C-terminal amino acid, such as glycine, relative to a wild-type RNA polymerase comprising the amino acid sequence of SEQ ID NO: 1.

In some embodiments, a RNA polymerase variant comprises a RNA polymerase that includes (a) an amino acid substitution at positions 350, 351, and 387, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 350 is E350A. In some embodiments, the additional amino acid substitution at position 350 is E350K. In some embodiments, the additional amino acid substitution at position 350 is E350N. In some embodiments, the additional amino acid substitution at position 350 is E350W. In some embodiments, the additional amino acid substitution at position 351 is D351V. In some embodiments, the additional amino acid substitution at position 387 is K387S. In some embodiments, the additional amino acid substitution at position 387 is K387H. In some embodiments, the additional amino acid substitution at position 387 is K387N. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 437 and 441, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 437 is N437T. In some embodiments, the additional amino acid substitution at position 437 is N437Y. In some embodiments, the additional amino acid substitution at position 437 is N437I. In some embodiments, the additional amino acid substitution at position 437 is N437F. In some embodiments, the additional amino acid substitution at position 441 is K441R. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 880, and (b) an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 880 is F880Y. In some embodiments, the amino acid modification at the C-terminal end is an additional alanine (A). In some embodiments, the amino acid modification at the C-terminal end is an additional serine(S). In some embodiments, the amino acid modification at the C-terminal end is an additional threonine (T). In some embodiments, the amino acid modification at the C-terminal end is an additional proline (P). In some embodiments, the RNA polymerase variant comprises a G47A substitution.

In some embodiments, a RNA polymerase variant comprises a RNA polymerase that includes (a) an amino acid substitution at positions 632, 653, and 657, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 632 is R632K. In some embodiments, the additional amino acid substitution at position 632 is R632T. In some embodiments, the additional amino acid substitution at position 653 is D653T. In some embodiments, the additional amino acid substitution at position 653 is D653K. In some embodiments, the additional amino acid substitution at position 657 is P657W. In some embodiments, the additional amino acid substitution at position 657 is P657R. In some embodiments, the additional amino acid substitution at position 657 is P657A. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 628, 632, 653, and 657, and (b) an additional amino acid substitution and/or an amino acid modification at the C-terminal end, relative to wild-type RNA polymerase, wherein the wild-type RNA polymerase comprises the amino acid sequence of SEQ ID NO: 1. In some embodiments, the additional amino acid substitution at position 628 is S628W. In some embodiments, the additional amino acid substitution at position 632 is R632K. In some embodiments, the additional amino acid substitution at position 632 is R632T. In some embodiments, the additional amino acid substitution at position 653 is D653T. In some embodiments, the additional amino acid substitution at position 653 is D653K. In some embodiments, the additional amino acid substitution at position 657 is P657W. In some embodiments, the additional amino acid substitution at position 657 is P657R. In some embodiments, the additional amino acid substitution at position 657 is P657A. In some embodiments, the RNA polymerase variant comprises a G47A substitution. In some embodiments, the RNA polymerase variant comprises an additional glycine at the C-terminus.

In some embodiments, a RNA polymerase variant comprises a RNA polymerase that includes (a) an amino acid substitution at positions 387, 657, and 884, and (b) an additional amino acid substitution and/or an amino acid modification at the C-terminal end, relative to wild-type RNA polymerase, wherein the wild-type RNA polymerase comprises the amino acid sequence of SEQ ID NO: 1.

It should also be understood that the present disclosure encompasses RNA polymerases that have at least 90%, at least 91%, at least 92%, at least 93%, at least 94%, at least 95%, at least 96%, at least 97%, at least 98%, or at least 99% identity to the RNA polymerase variants of described herein. It should also be understood that any of the RNA polymerase variants described herein may share at least 90%, at least 91%, at least 92%, at least 93%, at least 94%, at least 95% identity with a RNA polymerase comprising the amino acid sequence of SEQ ID NO: 1.

The term "identity" refers to a relationship between the sequences of two or more polypeptides (e.g. enzymes) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related proteins or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

Nucleotide Cap Analogs

Also provided herein are co-transcriptional capping methods for ribonucleic acid (RNA) synthesis, using any of the RNA polymerase variants described herein. That is, RNA is produced in a "one-pot" reaction, without the need for a separate capping reaction. Thus, the methods, in some embodiments, comprise reacting a polynucleotide template with a RNA polymerase variant, nucleoside triphosphates, and a cap analog under in vitro transcription reaction conditions to produce RNA transcript.

A cap analog may be, for example, a dinucleotide cap, a trinucleotide cap, or a tetranucleotide cap. In some embodiments, a cap analog is a dinucleotide cap. In some embodiments, a cap analog is a trinucleotide cap. In some embodiments, a cap analog is a tetranucleotide cap.

A nucleotide cap (e.g., a trinucleotide cap or tetranucleotide cap), in some embodiments, comprises a compound of formula (I)

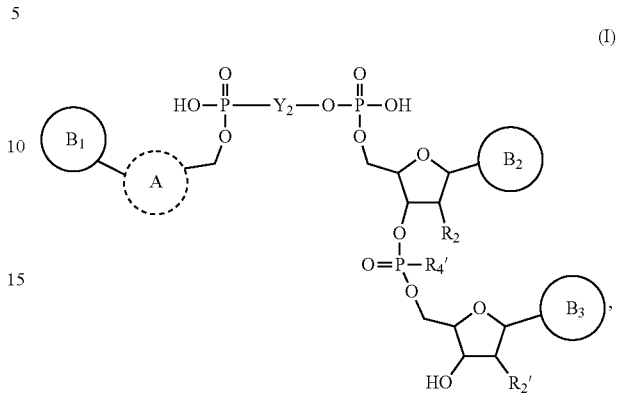

(I), or a stereoisomer, tautomer or salt thereof, wherein

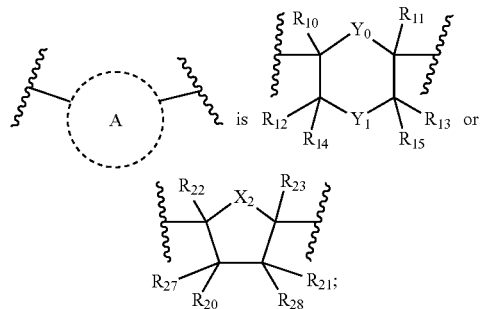

ring $B_1$ is a modified or unmodified Guanine;
ring $B_2$ and ring $B_3$ each independently is a nucleobase or a modified nucleobase;
$X_2$ is O, $S(O)_p$, $NR_{24}$ or $CR_{25}R_{26}$ in which p is 0, 1, or 2;
$Y_0$ is O or $CR_6R_7$;
$Y_1$ is O, $S(O)_n$, $CR_6R_7$, or $NR_8$, in which n is 0, 1, or 2;
each - - - is a single bond or absent, wherein when each - - - is a single bond, $Y_i$ is O, $S(O)_n$, $CR_6R_7$, or $NR_8$; and when each - - - is absent, $Y_1$ is void;
$Y_2$ is $(OP(O)R_4)$ m in which m is 0, 1, or 2, or —O—$(CR_{40}R_{41})$ u-$Q_0$-$(CR_{42}R_{43})$ v-, in which $Q_0$ is a bond, O, $S(O)_r$, $NR_{44}$, or $CR_{45}R_{46}$, r is 0, 1, or 2, and each of u and v independently is 1, 2, 3 or 4;
each $R_2$ and $R_2'$ independently is halo, LNA, or $OR_3$;
each $R_3$ independently is H, $C_1$-$C_6$ alkyl, $C_2$-$C_6$ alkenyl, or $C_2$-$C_6$ alkynyl and $R_3$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;
each $R_4$ and $R_4'$ independently is H, halo, $C_1$-$C_6$ alkyl, OH, SH, SeH, or $BH_3^-$;
each of $R_6$, $R_7$, and $R_8$, independently, is -$Q_1$-$T_1$, in which Q is a bond or $C_1$-$C_3$ alkyl linker optionally substituted with one or more of halo, cyano, OH and $C_1$-$C_6$ alkoxy, and $T_1$ is H, halo, OH, COOH, cyano, or $R_{s1}$, in which $R_{s1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, $NR_{31}R_{32}$, $(NR_{31}R_{32}R_{33})^+$, 4 to 12-membered heterocycloalkyl, or 5- or 6-membered heteroaryl, and $R_{s1}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl;

each of $R_{10}$, $R_{11}$, $R_{12}$, $R_{13}$ $R_{14}$, and $R_{15}$, independently, is -$Q_2$-$T_2$, in which $Q_2$ is a bond or $C_1$-$C_3$ alkyl linker optionally substituted with one or more of halo, cyano, OH and $C_1$-$C_6$ alkoxy, and $T_2$ is H, halo, OH, $NH_2$, cyano, $NO_2$, $N_3$, $R_{s2}$, or $OR_{s2}$, in which $R_{s2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—$C_1$-$C_6$ alkyl, $NR_{31}R_{32}$, $(NR_{31}R_{32}R_{33})^+$, 4 to 12-membered heterocycloalkyl, or 5- or 6-membered heteroaryl, and $R_{s2}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl; or alternatively $R_{12}$ together with $R_{14}$ is oxo, or $R_{13}$ together with $R_{15}$ is oxo, each of $R_{20}$, $R_{21}$, $R_{22}$, and $R_{23}$ independently is-$Q_3$-$T_3$, in which $Q_3$ is a bond or $C_1$-$C_3$ alkyl linker optionally substituted with one or more of halo, cyano, OH and $C_1$-$C_6$ alkoxy, and $T_3$ is H, halo, OH, $NH_2$, cyano, $NO_2$, $N_3$, $R_{S3}$, or $OR_{S3}$, in which $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—$C_1$-$C_6$ alkyl, mono-$C_1$-$C_6$ alkylamino, di-$C_1$-$C_6$ alkylamino, 4 to 12-membered heterocycloalkyl, or 5- or 6-membered heteroaryl, and $Rs_3$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_{24}$, $R_{25}$, and $R_{26}$ independently is H or $C_1$-$C_6$ alkyl;

each of $R_{27}$ and $R_{28}$ independently is H or $OR_{29}$; or $R_{27}$ and $R_{28}$ together form O—$R_{30}$—O; each $R_{29}$ independently is H, $C_1$-$C_6$ alkyl, $C_2$-$C_6$ alkenyl, or $C_2$-$C_6$ alkynyl and $R_{29}$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

$R_{30}$ is $C_1$-$C_6$ alkylene optionally substituted with one or more of halo, OH and $C_1$-$C_6$ alkoxyl;

each of $R_{31}$, $R_{32}$, and $R_{33}$, independently, is H, $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl;

each of $R_{40}$, $R_{41}$, $R_{42}$, and $R_{43}$ independently is H, halo, OH, cyano, $N_3$, $OP(O)R_{47}R_{48}$, or $C_1$-$C_6$ alkyl optionally substituted with one or more $OP(O)R_{47}R_{48}$, or one $R_{41}$ and one $R_{43}$, together with the carbon atoms to which they are attached and $Q_0$, form $C_4$-$C_{10}$ cycloalkyl, 4- to 14-membered heterocycloalkyl, $C_6$-$C_{10}$ aryl, or 5- to 14-membered heteroaryl, and each of the cycloalkyl, heterocycloalkyl, phenyl, or 5- to 6-membered heteroaryl is optionally substituted with one or more of OH, halo, cyano, $N_3$, oxo, $OP(O)R_{47}R_{48}$, $C_1$-$C_6$ alkyl, $C_1$-$C_6$ haloalkyl, COOH, C(O)O—$C_1$-$C_6$ alkyl, $C_1$-$C_6$ alkoxyl, $C_1$-$C_6$ haloalkoxyl, amino, mono-$C_1$-$C_6$ alkylamino, and di-$C_1$-$C_6$ alkylamino;

$R_{44}$ is H, $C_1$-$C_6$ alkyl, or an amine protecting group;

each of $R_{45}$ and $R_{46}$ independently is H, $OP(O)R_{47}R_{48}$, or $C_1$-$C_6$ alkyl optionally substituted with one or more $OP(O)R_{47}R_{48}$, and each of $R_{47}$ and $R_{48}$, independently is H, halo, $C_1$-$C_6$ alkyl, OH, SH, SeH, or $BH_3^-$.

It should be understood that a cap analog, as provided herein, may include any of the cap analogs described in international publication WO 2017/066797, published on 20 Apr. 2017, incorporated by reference herein in its entirety.

In some embodiments, the $B_2$ middle position can be a non-ribose molecule, such as arabinose.

In some embodiments $R_2$ is ethyl-based.

Thus, in some embodiments, a trinucleotide cap comprises the following structure:

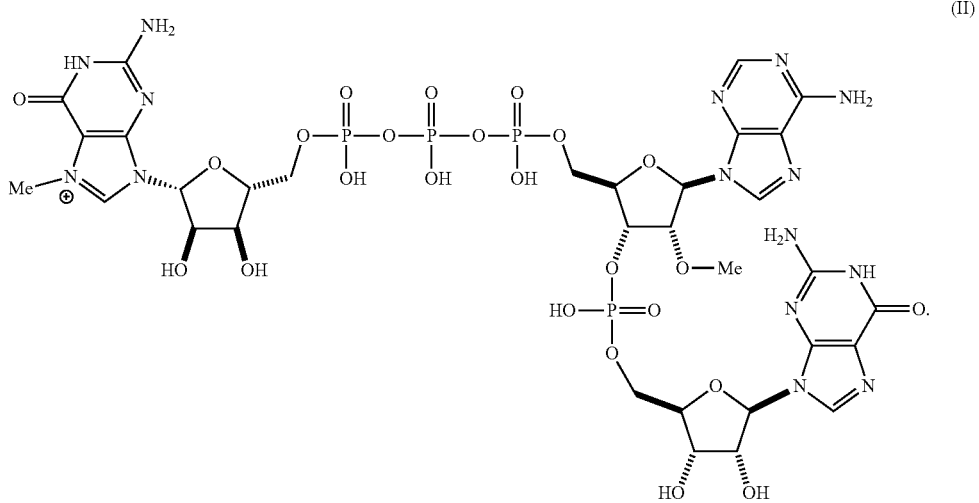

(II)

In other embodiments, a trinucleotide cap comprises the following structure:
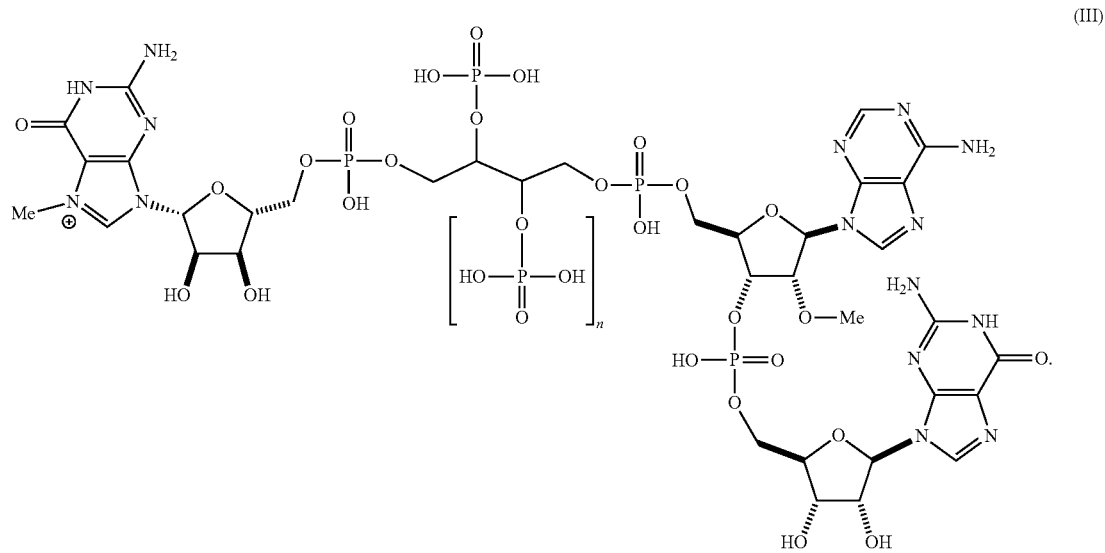
(III)
In yet other embodiments, a trinucleotide cap comprises the following structure:
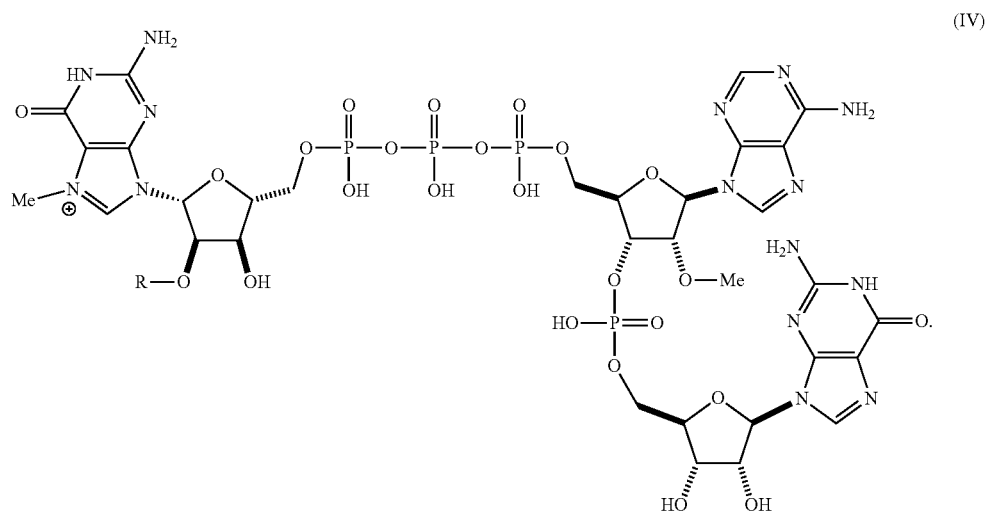
(IV)

In still other embodiments, a trinucleotide cap comprises the following structure:
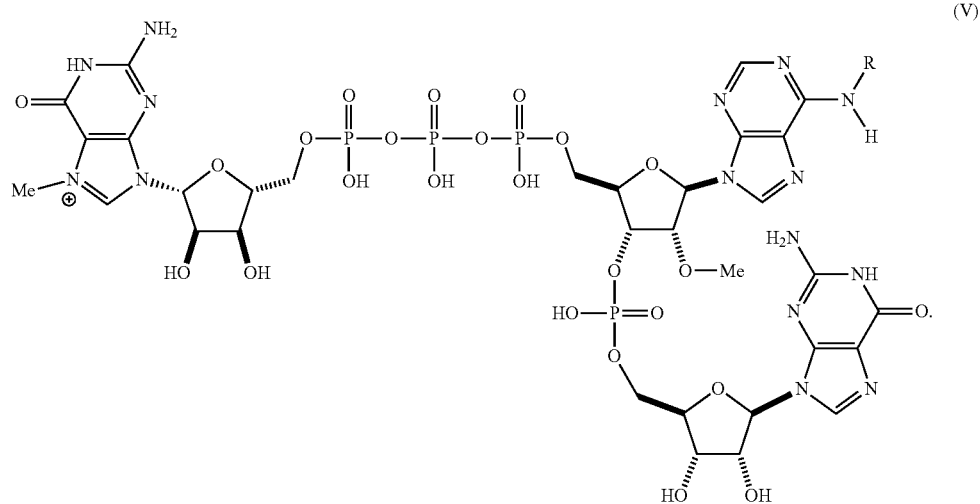
(V)
Thus, in some embodiments, a tetranucleotide cap comprises the following structure:
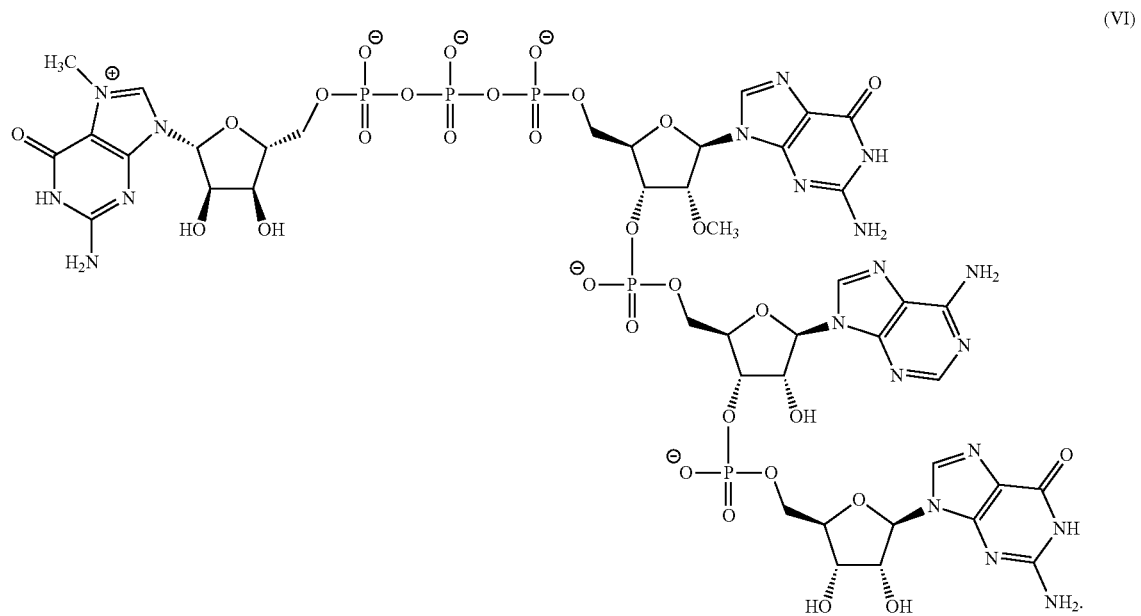 [SMILES: CO[C@@H]1[C@H](OP(=O)([O-])OC[C@H]2O[C@@H](n3cnc4c(N)ncnc43)[C@H](O)[C@@H]2OP(=O)([O-])OC[C@H]2O[C@@H](n3cnc4c(=O)[nH]c(N)nc43)[C@H](O)[C@@H]2O)[C@@H](COP(=O)([O-])OP(=O)([O-])OP(=O)([O-])OC[C@H]2O[C@@H](n3c[n+](C)c4c(=O)[nH]c(N)nc43)[C@H](O)[C@@H]2O)O[C@H]1n1cnc2c(=O)[nH]c(N)nc21]
(VI)

In other embodiments, a tetranucleotide cap comprises the following structure:
(VII)
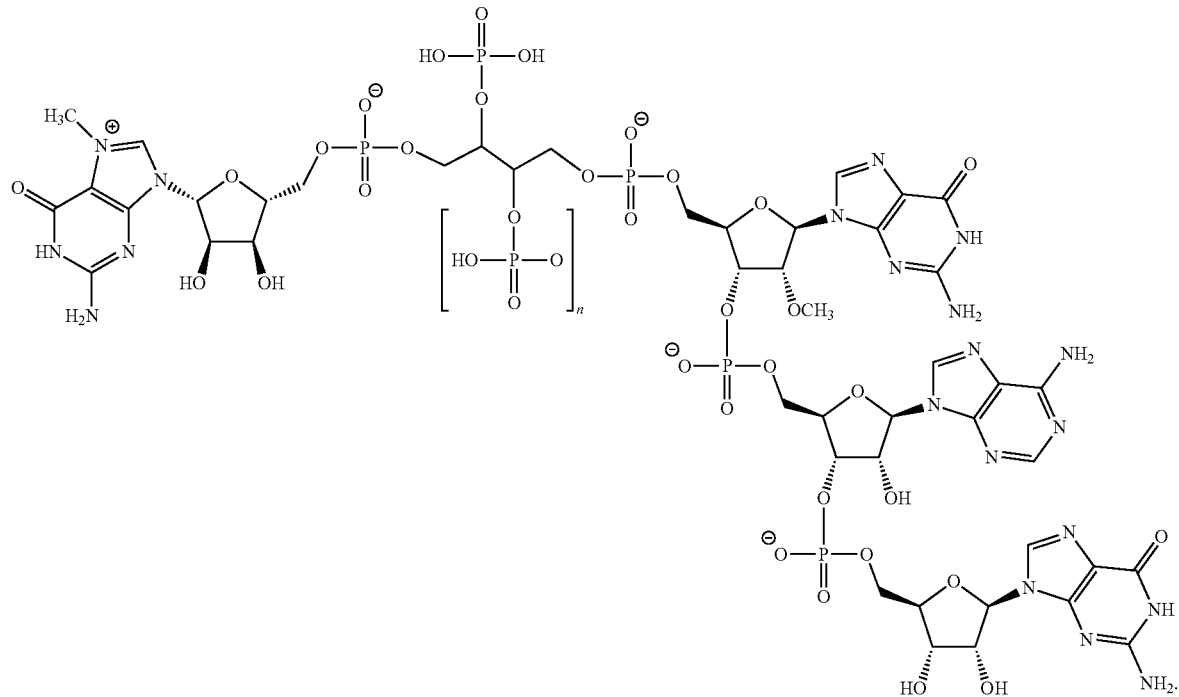
In yet other embodiments, a tetranucleotide cap comprises the following structure:
(VIII)
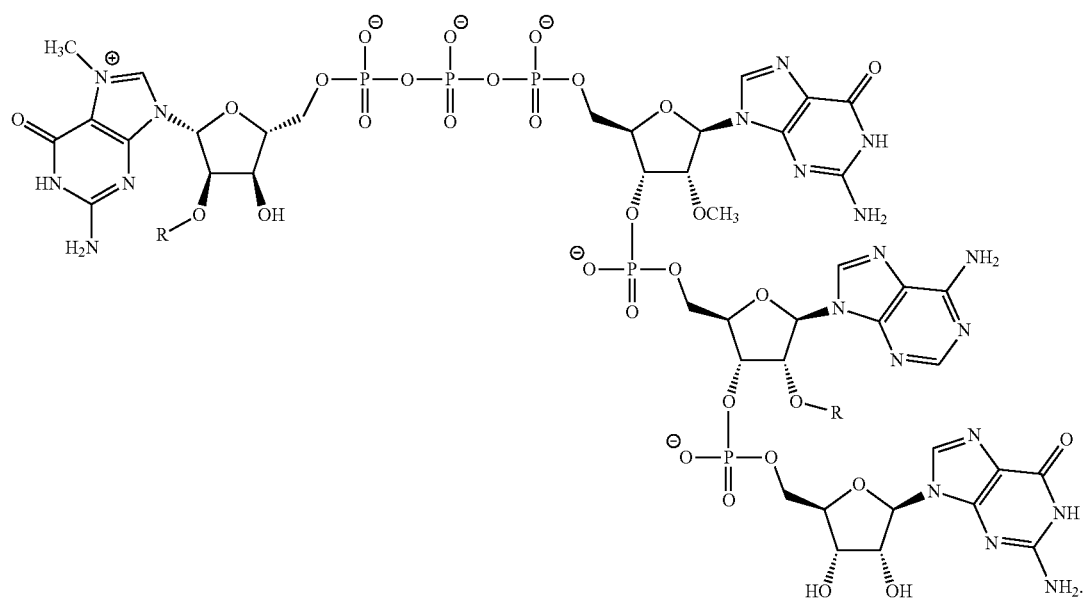

In yet other embodiments, a tetranucleotide cap comprises the following structure:

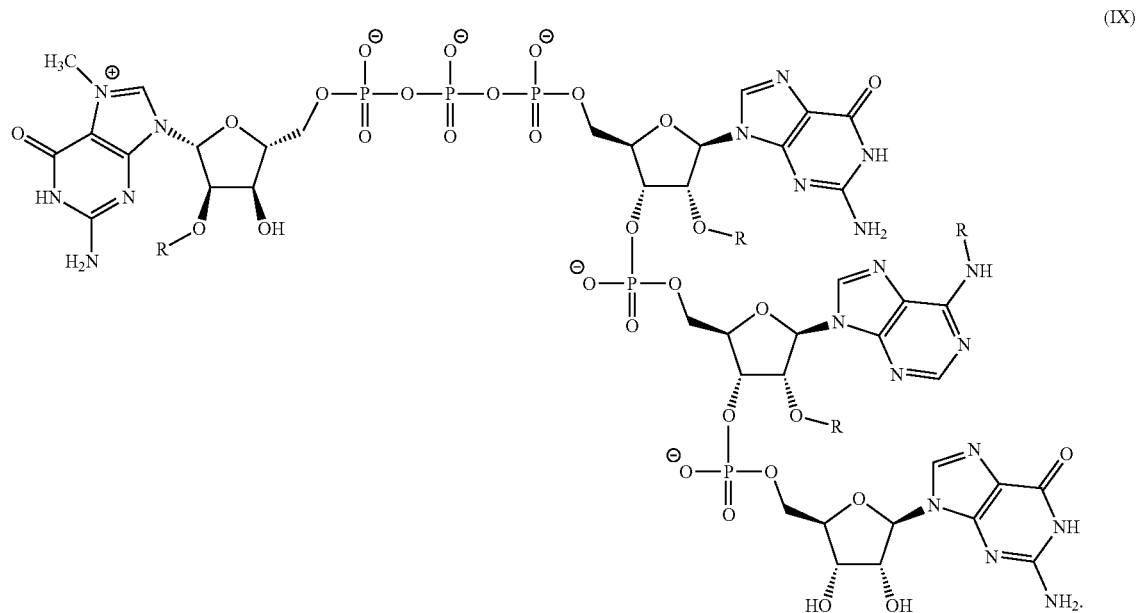

(IX)

In some embodiments, R is an alkyl (e.g., $C_1$-$C_6$ alkyl). In some embodiments, R is a methyl group (e.g., $C_1$ alkyl). In some embodiments, R is an ethyl group (e.g., $C_2$ alkyl). In some embodiments, R is a hydrogen.

A trinucleotide cap, in some embodiments, comprises a sequence selected from the following sequences: GAA, GAC, GAG, GAU, GCA, GCC, GCG, GCU, GGA, GGC, GGG, GGU, GUA, GUC, GUG, and GUU. In some embodiments, a trinucleotide cap comprises GAA. In some embodiments, a trinucleotide cap comprises GAC. In some embodiments, a trinucleotide cap comprises GAG. In some embodiments, a trinucleotide cap comprises GAU. In some embodiments, a trinucleotide cap comprises GCA. In some embodiments, a trinucleotide cap comprises GCC. In some embodiments, a trinucleotide cap comprises GCG. In some embodiments, a trinucleotide cap comprises GCU. In some embodiments, a trinucleotide cap comprises GGA. In some embodiments, a trinucleotide cap comprises GGC. In some embodiments, a trinucleotide cap comprises GGG. In some embodiments, a trinucleotide cap comprises GGU. In some embodiments, a trinucleotide cap comprises GUA. In some embodiments, a trinucleotide cap comprises GUC. In some embodiments, a trinucleotide cap comprises GUG. In some embodiments, a trinucleotide cap comprises GUU.

In some embodiments, a trinucleotide cap comprises a sequence selected from the following sequences: $m^7$GpppApA, $m^7$GpppApC, $m^7$GpppApG, $m^7$GpppApU, $m^7$GpppCpA, $m^7$GpppCpC, $m^7$GpppCpG, $m^7$GpppCpU, $m^7$GpppGpA, $m^7$GpppGpC, $m^7$GpppGpG, $m^7$GpppGpU, $m^7$GpppUpA, $m^7$GpppUpC, $m^7$GpppUpG, and $m^7$GpppUpU.

In some embodiments, a trinucleotide cap comprises $m^7$GpppApA. In some embodiments, a trinucleotide cap comprises $m^7$GpppApC. In some embodiments, a trinucleotide cap comprises $m^7$GpppApG. In some embodiments, a trinucleotide cap comprises $m^7$GpppApU. In some embodiments, a trinucleotide cap comprises $m^7$GpppCpA. In some embodiments, a trinucleotide cap comprises $m^7$GpppCpC. In some embodiments, a trinucleotide cap comprises $m^7$GpppCpG. In some embodiments, a trinucleotide cap comprises $m^7$GpppCpU. In some embodiments, a trinucleotide cap comprises $m^7$GpppGpA. In some embodiments, a trinucleotide cap comprises m'GpppGpC. In some embodiments, a trinucleotide cap comprises $m^7$GpppGpG. In some embodiments, a trinucleotide cap comprises $m^7$GpppGpU. In some embodiments, a trinucleotide cap comprises $m^7$GpppUpA. In some embodiments, a trinucleotide cap comprises $m^7$GpppUpC. In some embodiments, a trinucleotide cap comprises $m^7$GpppUpG. In some embodiments, a trinucleotide cap comprises $m^7$GpppUpU.

A trinucleotide cap, in some embodiments, comprises a sequence selected from the following sequences: $m^7G_{3'OMe}$pppApA, $m^7G_{3'OMe}$pppApC, $m^7G_{3'OMe}$pppApG, $m^7G_{3'OMe}$pppApU, $m^7G_{3'OMe}$pppCpA, $m^7G_{3'OMe}$pppCpC, $m^7G_{3'OMe}$pppCpG, $m^7G_{3'OMe}$pppCPU, $m^7G_{3'OMe}$pppGpA, $m^7G_{3'OMe}$pppGpC, $m^7G_{3'OMe}$pppGpG, $m^1G_{3'OMe}$pppGpU, $m^7G_{3'OMe}$pppUpA, $m^7G_{3'OMe}$pppUpC, $m^7G_{3'OMe}$pppUpG, and $m^7G_{3'OMe}$pppUpU.

In some embodiments, a trinucleotide cap comprises $m^7G_{3'OMe}$pppApA. In some embodiments, a trinucleotide cap comprises $m^7G_{3'OMe}$pppApC. In some embodiments, a trinucleotide cap comprises $m^7G_{3'OMe}$pppApG. In some embodiments, a trinucleotide cap comprises $m^7G_{3'OMe}$pppApU. In some embodiments, a trinucleotide cap comprises $m^7G_{3'OMe}$pppCpA. In some embodiments, a trinucleotide cap comprises $m^7G_{3'OMe}$pppCpC. In some embodiments, a trinucleotide cap comprises $m^7G_{3'OMe}$pppCpG. In some embodiments, a trinucleotide cap comprises m⁷G$_{3'OMe}$pppCpU. In some embodiments, a trinucleotide cap comprises m⁷G$_{3'OMe}$pppGpA. In some embodiments, a trinucleotide cap comprises m⁷G$_{3'OMe}$pppGpC. In some embodiments, a trinucleotide cap comprises m⁷G$_{3'OMe}$pppGpG. In some embodiments, a trinucleotide cap comprises m⁷G$_{3'OMe}$pppGpU. In some embodiments, a trinucleotide cap comprises m⁷G$_{3'OMe}$pppUpA. In some embodiments, a trinucleotide cap comprises m⁷G$_{3'OMe}$pppUpC. In some embodiments, a trinucleotide cap comprises m⁷G$_{3'OMe}$pppUpG. In some embodiments, a trinucleotide cap comprises m⁷G$_{3'OMe}$pppUpU.

A trinucleotide cap, in other embodiments, comprises a sequence selected from the following sequences: m⁷G$_{3'OMe}$pppA$_{2'OMe}$pA, m⁷G$_{3'OMe}$pppA$_{2'OMe}$pC, m⁷G$_{3'OMe}$pppA$_{2'OMe}$pG, m⁷G$_{3'OMe}$pppA$_{2'OMe}$pU, m⁷G$_{3'OMe}$pppC$_{2'OMe}$pA, m⁷G$_{3'OMe}$pppC$_{2'OMe}$pC, m⁷G$_{3'OMe}$pppC$_{2'OMe}$pG, m⁷G$_{3'OMe}$pppC$_{2'OMe}$pU, m⁷G$_{3'OMe}$pppG$_{2'OMe}$pA, m⁷G$_{3'OMe}$pppG$_{2'OMe}$pC, m⁷G$_{3'OMe}$pppG$_{2'OMe}$pG, m⁷G$_{3'OMe}$pppG$_{2'OMe}$pU, m⁷G$_{3'OMe}$pppU$_{2'OMe}$pA, m⁷G$_{3'OMe}$pppU$_{2'OMe}$pC, m⁷G$_{3'OMe}$pppU$_{2'OMe}$pG, and m⁷G$_{3'OMe}$pppU$_{2'OMe}$pU.

In some embodiments, a trinucleotide cap comprises m⁷G$_{3'OMe}$pppA$_{2'OMe}$pA. In some embodiments, a trinucleotide cap comprises m⁷G$_{3'OMe}$pppA$_{2'OMe}$pC. In some embodiments, a trinucleotide cap comprises m⁷G$_{3'OMe}$pppA$_{2'OMe}$pG. In some embodiments, a trinucleotide cap comprises m⁷G$_{3'OMe}$pppA$_{2'OMe}$pU. In some embodiments, a trinucleotide cap comprises m⁷G$_{3'OMe}$pppC$_{2'OMe}$PA. In some embodiments, a trinucleotide cap comprises m⁷G$_{3'OMe}$pppC$_{2'OMe}$pC. In some embodiments, a trinucleotide cap comprises m⁷G$_{3'OMe}$pppC$_{2'OMe}$pG. In some embodiments, a trinucleotide cap comprises m⁷G$_{3'OMe}$pppC$_{2'OMe}$pU. In some embodiments, a trinucleotide cap comprises m⁷G$_{3'OMe}$pppG$_{2'OMe}$pA. In some embodiments, a trinucleotide cap comprises m⁷G$_{3'OMe}$pppG$_{2'OMe}$PC. In some embodiments, a trinucleotide cap comprises m⁷G$_{3'OMe}$pppG$_{2'OMe}$PG. In some embodiments, a trinucleotide cap comprises m⁷G$_{3'OMe}$pppG$_{2'OMe}$pU. In some embodiments, a trinucleotide cap comprises m⁷G$_{3'OMe}$pppU$_{2'OMe}$pA. In some embodiments, a trinucleotide cap comprises m⁷G$_{3'OMe}$pppU$_{2'OMe}$PC. In some embodiments, a trinucleotide cap comprises m⁷G$_{3'OMe}$pppU$_{2'OMe}$pG. In some embodiments, a trinucleotide cap comprises m⁷G$_{3'OMe}$pppU$_{2'OMe}$pU.

A trinucleotide cap, in still other embodiments, comprises a sequence selected from the following sequences: m⁷GpppA$_{2'OMe}$pA, m⁷GpppA$_{2'OMe}$PC, m⁷GpppA$_{2'OMe}$pG, m⁷GpppA$_{2'OMe}$PU, m⁷GpppC$_{2'OMe}$pA, m⁷GpppC$_{2'OMe}$PC, m⁷GpppC$_{2'OMe}$pG, m⁷GpppC$_{2'OMe}$PU, m⁷GpppG$_{2'OMe}$pA, m⁷GpppG$_{2'OMe}$PC, m⁷GpppG$_{2'OMe}$pG, m⁷GpppG$_{2'OMe}$PU, m⁷GpppU$_{2'OMe}$pA, m⁷GpppU$_{2'OMe}$PC, m⁷GpppU$_{2'OMe}$pG, and m⁷GpppU$_{2'OMe}$pU.

In some embodiments, a trinucleotide cap comprises m⁷GpppA$_{2'OMe}$pA. In some embodiments, a trinucleotide cap comprises m⁷GpppA$_{2'OMe}$pC. In some embodiments, a trinucleotide cap comprises m⁷GpppA$_{2'OMe}$pG. In some embodiments, a trinucleotide cap comprises m⁷GpppA$_{2'OMe}$pU. In some embodiments, a trinucleotide cap comprises m⁷GpppC$_{2'OMe}$pA. In some embodiments, a trinucleotide cap comprises m⁷GpppC$_{2'OMe}$pC. In some embodiments, a trinucleotide cap comprises m⁷GpppC$_{2'OMe}$pG. In some embodiments, a trinucleotide cap comprises m⁷GpppC$_{2'OMe}$pU. In some embodiments, a trinucleotide cap comprises m⁷GpppG$_{2'OMe}$PA. In some embodiments, a trinucleotide cap comprises m⁷GpppG$_{2'OMe}$PC. In some embodiments, a trinucleotide cap comprises m⁷GpppG$_{2'OMe}$pG. In some embodiments, a trinucleotide cap comprises m⁷GpppG$_{2'OMe}$pU. In some embodiments, a trinucleotide cap comprises m²GpppU$_{2'OMe}$pA. In some embodiments, a trinucleotide cap comprises m⁷GpppU$_{2'OMe}$PC. In some embodiments, a trinucleotide cap comprises m⁷GpppU$_{2'OMe}$pG. In some embodiments, a trinucleotide cap comprises m⁷GpppU$_{2'OMe}$pU.

In some embodiments, a trinucleotide cap comprises m⁷Gpppm⁶A$_{2'Ome}$pG. In some embodiments, a trinucleotide cap comprises m⁷Gpppe⁶A$_{2'Ome}$pG.

In some embodiments, a trinucleotide cap comprises GAG. In some embodiments, a trinucleotide cap comprises GCG. In some embodiments, a trinucleotide cap comprises GUG. In some embodiments, a trinucleotide cap comprises GGG.

In some embodiments, a trinucleotide cap comprises any one of the following structures:

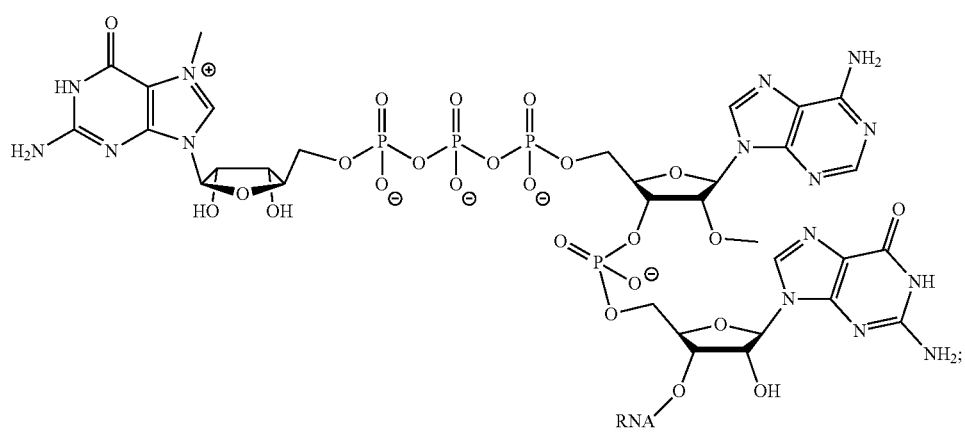

(i)

-continued
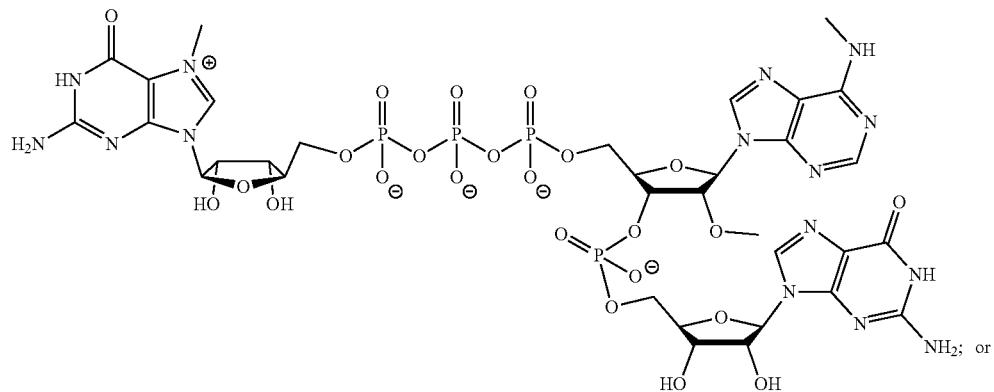
(ii)
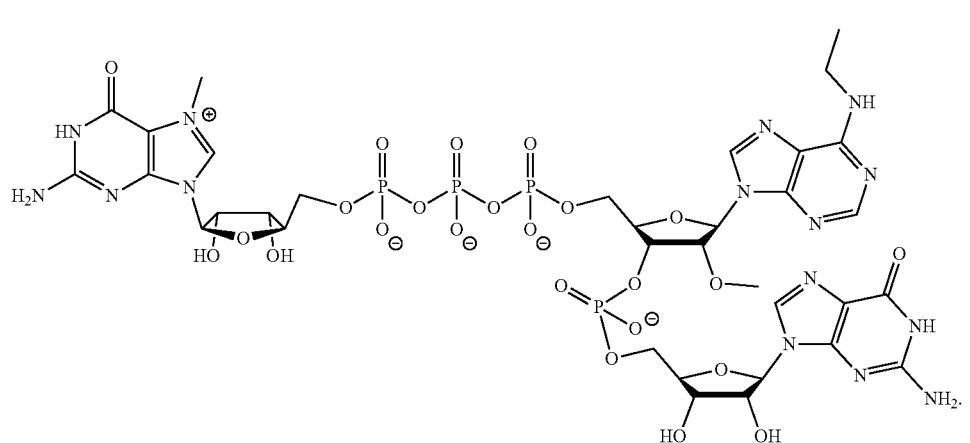
(iii)
In some embodiments, a tetranucleotide cap comprises GGAG.
In some embodiments, a tetranucleotide cap comprises any one of the following structures:
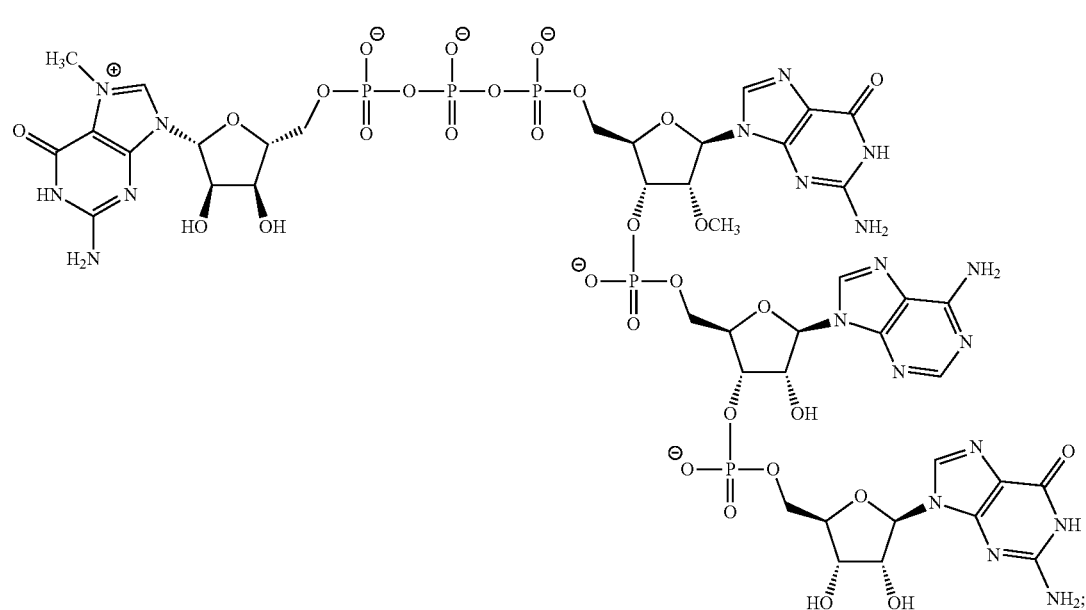
(iv)

(v)

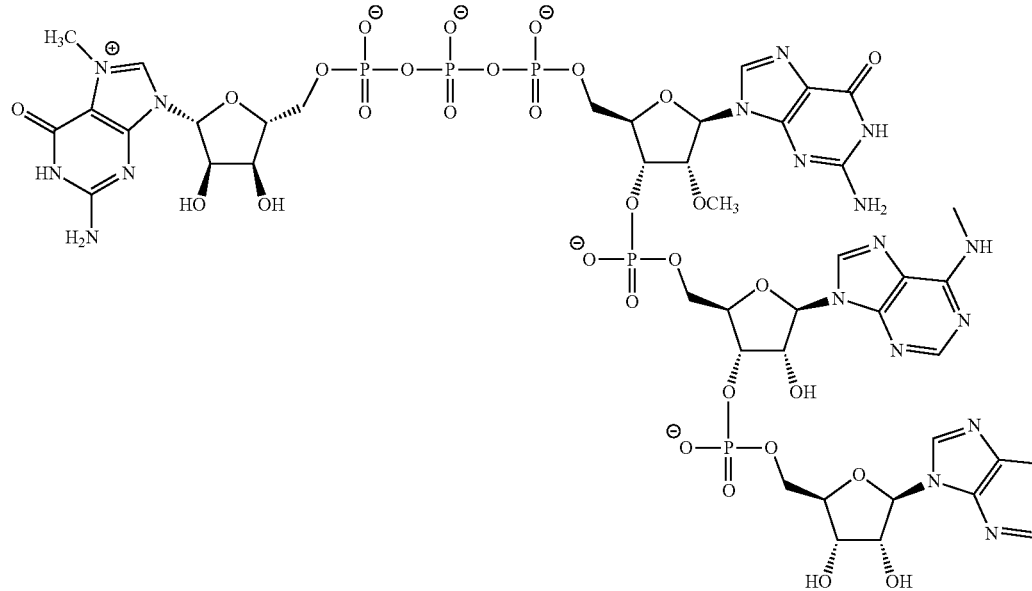

(vi)

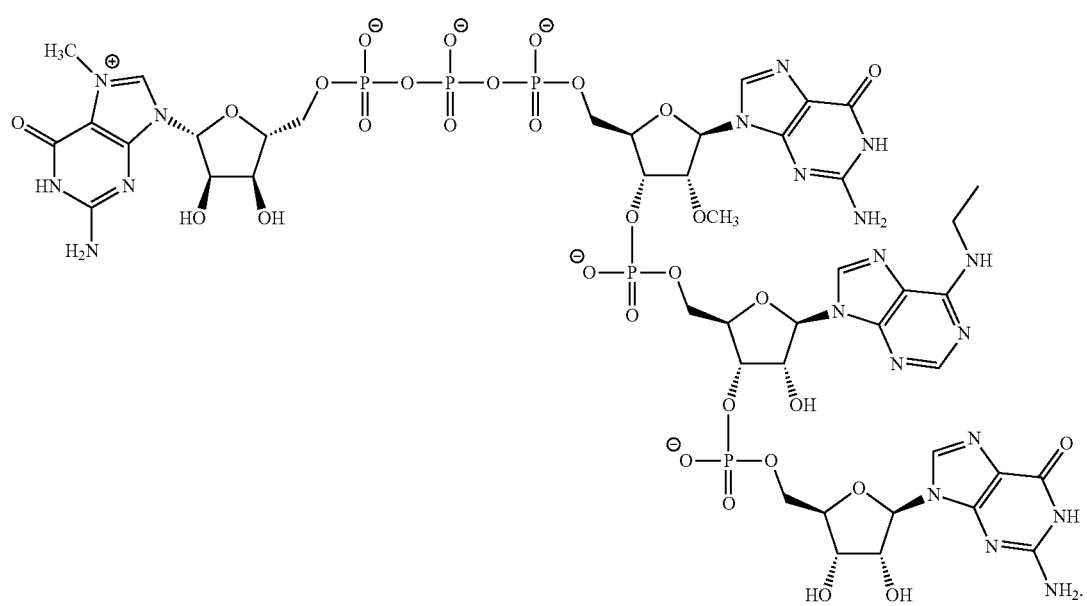

In Vitro Transcription Methods

Some aspects of the present disclosure provide methods of producing (synthesizing) a RNA transcript (e.g., mRNA transcript) comprising contacting a DNA template with a RNA polymerase (e.g., a T7 RNA polymerase such as a T7 RNA polymerase variant) under conditions that result in the production of RNA transcript.

In some embodiments, the methods comprise contacting a DNA template with a T7 RNA polymerase variant that comprises an (at least one) additional C terminal amino acid (e.g., Gly, Ala, GlyGly, AlaAla, GlyAla, or AlaGly).

In some aspects, the present disclosure provides methods of performing an IVT reaction, comprising contacting a DNA template with the RNA polymerase (e.g., a T7 RNA polymerase, such as a T7 RNA polymerase variant) in the presence of nucleoside triphosphates and buffer under conditions that result in the production of RNA transcripts.

Other aspects of the present disclosure provide co-transcriptional capping methods that comprise reacting a polynucleotide template with a T7 RNA polymerase variant, nucleoside triphosphates, and a cap analog under in vitro transcription reaction conditions to produce RNA transcript.

In some embodiments, a co-transcriptional capping method for RNA synthesis comprises reacting a polynucleotide template with (a) a T7 RNA polymerase variant comprising at least one amino acid substitution, relative to wild-type RNA polymerase, that causes at least one loop structure of the RNA polymerase variant to undergo a conformational change to a helix structure as the RNA polymerase variant transitions from an initiation complex to an elongation complex (e.g., at least one amino acid substitution positions 42, 43, 44, 45, 46, and/or 47), (b) nucleoside triphosphates, and (c) a trinucleotide cap comprising sequence GpppA$_{2'Ome}$pG, under in vitro transcription reaction conditions to produce RNA transcript, wherein the polynucleotide template includes a 2'-deoxythymidine residue at template position +1.

IVT conditions typically require a purified linear DNA template containing a promoter, nucleoside triphosphates, a buffer system that includes dithiothreitol (DTT) and magnesium ions, and a RNA polymerase. The exact conditions used in the transcription reaction depend on the amount of RNA needed for a specific application. Typical IVT reactions are performed by incubating a DNA template with a RNA polymerase and nucleoside triphosphates, including GTP, ATP, CTP, and UTP (or nucleotide analogs) in a transcription buffer. A RNA transcript having a 5' terminal guanosine triphosphate is produced from this reaction.

A deoxyribonucleic acid (DNA) is simply a nucleic acid template for RNA polymerase. A DNA template may include a polynucleotide encoding a polypeptide of interest (e.g., an antigenic polypeptide). A DNA template, in some embodiments, includes a RNA polymerase promoter (e.g., a T7 RNA polymerase promoter) located 5' from and operably linked to polynucleotide encoding a polypeptide of interest. A DNA template may also include a nucleotide sequence encoding a polyadenylation (polyA) tail located at the 3' end of the gene of interest.

Polypeptides of interest include, but are not limited to, biologics, antibodies, antigens (vaccines), and therapeutic proteins. The term "protein" encompasses peptides.

A RNA transcript, in some embodiments, is the product of an IVT reaction. A RNA transcript, in some embodiments, is a messenger RNA (mRNA) that includes a nucleotide sequence encoding a polypeptide of interest linked to a polyA tail. In some embodiments, the mRNA is modified mRNA (mmRNA), which includes at least one modified nucleotide.

A nucleotide includes a nitrogenous base, a five-carbon sugar (ribose or deoxyribose), and at least one phosphate group. Nucleotides include nucleoside monophosphates, nucleoside diphosphates, and nucleoside triphosphates. A nucleoside monophosphate (NMP) includes a nucleobase linked to a ribose and a single phosphate; a nucleoside diphosphate (NDP) includes a nucleobase linked to a ribose and two phosphates; and a nucleoside triphosphate (NTP) includes a nucleobase linked to a ribose and three phosphates. Nucleotide analogs are compounds that have the general structure of a nucleotide or are structurally similar to a nucleotide. Nucleotide analogs, for example, include an analog of the nucleobase, an analog of the sugar and/or an analog of the phosphate group(s) of a nucleotide.

A nucleoside includes a nitrogenous base and a 5-carbon sugar. Thus, a nucleoside plus a phosphate group yields a nucleotide. Nucleoside analogs are compounds that have the general structure of a nucleoside or are structurally similar to a nucleoside. Nucleoside analogs, for example, include an analog of the nucleobase and/or an analog of the sugar of a nucleoside.

It should be understood that the term "nucleotide" includes naturally-occurring nucleotides, synthetic nucleotides and modified nucleotides, unless indicated otherwise. Examples of naturally-occurring nucleotides used for the production of RNA, e.g., in an IVT reaction, as provided herein include adenosine triphosphate (ATP), guanosine triphosphate (GTP), cytidine triphosphate (CTP), uridine triphosphate (UTP), and 5-methyluridine triphosphate ($m^5$UTP). In some embodiments, adenosine diphosphate (ADP), guanosine diphosphate (GDP), cytidine diphosphate (CDP), and/or uridine diphosphate (UDP) are used.

Examples of nucleotide analogs include, but are not limited to, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia or ligase), a nucleotide labeled with a functional group to facilitate ligation/conjugation of cap or 5' moiety (IRES), a nucleotide labeled with a 5' $PO_4$ to facilitate ligation of cap or 5' moiety, or a nucleotide labeled with a functional group/protecting group that can be chemically or enzymatically cleaved. Examples of antiviral nucleotide/nucleoside analogs include, but are not limited to, Ganciclovir, Entecavir, Telbivudine, Vidarabine and Cidofovir.

Modified nucleotides may include modified nucleobases. For example, a RNA transcript (e.g., mRNA transcript) of the present disclosure may include a modified nucleobase selected from pseudouridine (ψ), 1-methylpseudouridine (m1ψ), 1-ethylpseudouridine, 2-thiouridine, 4'-thiouridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine (mo5U) and 2'-O-methyl uridine. In some embodiments, a RNA transcript (e.g., mRNA transcript) includes a combination of at least two (e.g., 2, 3, 4 or more) of the foregoing modified nucleobases.

The nucleoside triphosphates (NTPs) as provided herein may comprise unmodified or modified ATP, modified or unmodified UTP, modified or unmodified GTP, and/or modified or unmodified CTP. In some embodiments, NTPs of an IVT reaction comprise unmodified ATP. In some embodiments, NTPs of an IVT reaction comprise modified ATP. In some embodiments, NTPs of an IVT reaction comprise unmodified UTP. In some embodiments, NTPs of an IVT reaction comprise modified UTP. In some embodiments, NTPs of an IVT reaction comprise unmodified GTP. In some embodiments, NTPs of an IVT reaction comprise modified GTP. In some embodiments, NTPs of an IVT reaction comprise unmodified CTP. In some embodiments, NTPs of an IVT reaction comprise modified CTP.

The concentration of nucleoside triphosphates and cap analog present in an IVT reaction may vary. In some embodiments, NTPs and cap analog are present in the reaction at equimolar concentrations. In some embodiments, the molar ratio of cap analog (e.g., trinucleotide cap) to nucleoside triphosphates in the reaction is greater than 1:1. For example, the molar ratio of cap analog to nucleoside triphosphates in the reaction may be 2:1, 3:1, 4:1, 5:1, 6:1, 7:1, 8:1, 9:1, 10:1, 15:1, 20:1, 25:1, 50:1, or 100:1. In some embodiments, the molar ratio of cap analog (e.g., trinucleotide cap) to nucleoside triphosphates in the reaction is less than 1:1. For example, the molar ratio of cap analog (e.g., trinucleotide cap) to nucleoside triphosphates in the reaction may be 1:2, 1:3, 1:4, 1:5, 1:6, 1:7, 1:8, 1:9, 1:10, 1:15, 1:20, 1:25, 1:50, or 1:100.

The composition of NTPs in an IVT reaction may also vary. For example, ATP may be used in excess of GTP, CTP and UTP. As a non-limiting example, an IVT reaction may include 7.5 millimolar GTP, 7.5 millimolar CTP, 7.5 millimolar UTP, and 3.75 millimolar ATP. The same IVT reaction may include 3.75 millimolar cap analog (e.g., trinucleotide cap). In some embodiments, the molar ratio of G:C:U:A:cap is 1:1:1:0.5:0.5. In some embodiments, the molar ratio of G:C:U:A:cap is 1:1:0.5:1:0.5. In some embodiments, the molar ratio of G:C:U:A:cap is 1:0.5:1:1:0.5. In some embodiments, the molar ratio of G:C:U:A:cap is 0.5:1:1:1:0.5.

In some embodiments, a RNA transcript (e.g., mRNA transcript) includes a modified nucleobase selected from pseudouridine (ψ), 1-methylpseudouridine (m¹ψ), 5-methoxyuridine (mo⁵U), 5-methylcytidine (m⁵C), α-thio-guanosine and α-thio-adenosine. In some embodiments, a RNA transcript (e.g., mRNA transcript) includes a combination of at least two (e.g., 2, 3, 4 or more) of the foregoing modified nucleobases.

In some embodiments, a RNA transcript (e.g., mRNA transcript) includes pseudouridine (ψ). In some embodiments, a RNA transcript (e.g., mRNA transcript) includes 1-methylpseudouridine (m¹ψ). In some embodiments, a RNA transcript (e.g., mRNA transcript) includes 5-methoxyuridine (mo⁵U). In some embodiments, a RNA transcript (e.g., mRNA transcript) includes 5-methylcytidine (m⁵C). In some embodiments, a RNA transcript (e.g., mRNA transcript) includes α-thio-guanosine. In some embodiments, a RNA transcript (e.g., mRNA transcript) includes α-thio-adenosine.

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 1-methylpseudouridine (m¹ψ), meaning that all uridine residues in the mRNA sequence are replaced with 1-methylpseudouridine (m¹ψ). Similarly, a polynucleotide can be uniformly modified for any type of nucleoside residue present in the sequence by replacement with a modified residue such as any of those set forth above. Alternatively, the polynucleotide (e.g., RNA polynucleotide, such as mRNA polynucleotide) may not be uniformly modified (e.g., partially modified, part of the sequence is modified). Each possibility represents a separate embodiment of the present invention.

In some embodiments, the buffer system contains tris. The concentration of tris used in an IVT reaction, for example, may be at least 10 mM, at least 20 mM, at least 30 mM, at least 40 mM, at least 50 mM, at least 60 mM, at least 70 mM, at least 80 mM, at least 90 mM, at least 100 mM or at least 110 mM phosphate. In some embodiments, the concentration of phosphate is 20-60 mM or 10-100 mM.

In some embodiments, the buffer system contains dithiothreitol (DTT). The concentration of DTT used in an IVT reaction, for example, may be at least 1 mM, at least 5 mM, or at least 50 mM. In some embodiments, the concentration of DTT used in an IVT reaction is 1-50 mM or 5-50 mM. In some embodiments, the concentration of DTT used in an IVT reaction is 5 mM.

In some embodiments, the buffer system contains magnesium. In some embodiments, the molar ratio of NTP to magnesium ions ($Mg^{2+}$; e.g., $MgCl_2$) present in an IVT reaction is 1:1 to 1:5. For example, the molar ratio of NTP to magnesium ions may be 1:1, 1:2, 1:3, 1:4 or 1:5.

In some embodiments, the molar ratio of NTP plus cap analog (e.g., trinucleotide cap, such as GAG) to magnesium ions ($Mg^{2+}$; e.g., $MgCl_2$) present in an IVT reaction is 1:1 to 1:5. For example, the molar ratio of NTP+trinucleotide cap (e.g., GAG) to magnesium ions may be 1:1, 1:2, 1:3, 1:4 or 1:5.

In some embodiments, the buffer system contains Tris-HCl, spermidine (e.g., at a concentration of 1-30 mM), TRITON® X-100 (polyethylene glycol p-(1,1,3,3-tetramethylbutyl)-phenyl ether) and/or polyethylene glycol (PEG).

The addition of nucleoside triphosphates (NTPs) to the 3' end of a growing RNA strand is catalyzed by a polymerase, such as T7 RNA polymerase, for example, any one or more of the T7 RNA polymerase variants (e.g., G47A) of the present disclosure. In some embodiments, the RNA polymerase (e.g., T7 RNA polymerase variant) is present in a reaction (e.g., an IVT reaction) at a concentration of 0.01 mg/ml to 1 mg/ml. For example, the RNA polymerase may be present in a reaction at a concentration of 0.01 mg/mL, 0.05 mg/ml, 0.1 mg/ml, 0.5 mg/ml or 1.0 mg/ml.

Surprisingly, use of the combination of a T7 RNA polymerase variant (e.g., G47A) as provided herein with a cap analog (e.g., $GpppA_{2'Ome}pG$), in an in vitro transcription reaction, for example, results in the production of RNA transcript, wherein greater than 80% of the RNA transcript produced includes a functional cap. In some embodiments, greater than 85% of the RNA transcript produced includes a functional cap. In some embodiments, greater than 90% of the RNA transcript produced includes a functional cap. In some embodiments, greater than 95% of the RNA transcript produced includes a functional cap. In some embodiments, greater than 96% of the RNA transcript produced includes a functional cap. In some embodiments, greater than 97% of the RNA transcript produced includes a functional cap. In some embodiments, greater than 98% of the RNA transcript produced includes a functional cap. In some embodiments, greater than 99% of the RNA transcript produced includes a functional cap.

Also surprising was the finding that use of a polynucleotide template that includes a 2'-deoxythymidine residue or 2'-deoxycytidine residue at template position +1 results in the production of RNA transcript, wherein greater than 80% (e.g., greater than 85%, greater than 90%, or greater than 95%) of the RNA transcript produced includes a functional cap. Thus, in some embodiments, a polynucleotide (e.g., DNA) template used, for example, in an IVT reaction, includes a 2'-deoxythymidine residue at template position +1. In other embodiments, a polynucleotide (e.g., DNA) template used, for example, in an IVT reaction, includes a 2'-deoxycytidine residue at template position +1.

Multi-Substitution RNA T7 Polymerases Variants

Various aspects of the present disclosure provide RNA T7 polymerase variants that comprise at least two amino acid substitutions. In some embodiments, an RNA T7 polymerase variant comprises at least three amino acid substitutions. In some embodiments, an RNA T7 polymerase variant comprises at least four amino acid substitutions. In some embodiments, an RNA T7 polymerase variant comprises at least five amino acid substitutions. A RNA T7 polymerase variant that includes a G47A substitution, relative to a wild-type T7 RNA polymerase (e.g., comprising the amino acid sequence of SEQ ID NO: 1) may be referred to herein as a "G47A T7 Pol variant."

Table 1 below provides examples of multi-substitution RNA T7 polymerase variants of the present disclosure. It should be understood that each of the T7 polymerase variants included in Table 1 comprises a G47A substitution, relative to a wild-type T7 RNA polymerase that comprises the amino acid sequence of SEQ ID NO: 1. It should also be understood that each of the T7 polymerase variants included in Table 1 comprises an additional C-terminal amino acid at position 884, relative to a wild-type T7 RNA polymerase that comprises the amino acid sequence of SEQ ID NO: 1. This additional C-terminal amino acid is glycine (G884) unless otherwise indicated: G884T denotes a T7 RNA polymerase variant that includes a threonine at position 884 (instead of the glycine); G884S denotes a T7 RNA polymerase variant that includes a serine at position 884 (instead of the glycine); G884P denotes a T7 RNA polymerase variant that includes a proline at position 884 (instead of the glycine); and G884A denotes a T7 RNA polymerase variant that includes an alanine at position 884 (instead of the glycine). All substitutions in Table 1 are relative to a wild-type T7 RNA polymerase variant that comprises the amino acid sequence of SEQ ID NO: 1.

TABLE 1

Multi-Substitution RNA T7 Polymerase Variants

| Substitutions and/or C-terminal Modification | SEQ ID NO: |
|---|---|
| G47A, K387N, G884 | 61 |
| G47A, G884T | 62 |
| G47A, G884T, K387N | 63 |
| G47A, G884S | 64 |
| G47A, G884S, K387N | 65 |
| G47A, G884P | 66 |
| G47A, G884P, K387N | 67 |
| G47A, D653W, G884 | 68 |
| G47A, D653W, K387N, G884 | 69 |
| G47A, D653W, G884T | 70 |
| G47A, D653W, G884T, K387N | 71 |
| G47A, D653W, G884S | 72 |
| G47A, D653W, G884S, K387N | 73 |
| G47A, D653W, G884P | 74 |
| G47A, D653W, G884P, K387N | 75 |
| G47A, D653T, G884 | 76 |
| G47A, D653T, K387N, G884 | 77 |
| G47A, D653T, G884T | 78 |
| G47A, D653T, G884T, K387N | 79 |
| G47A, D653T, G884S | 80 |
| G47A, D653T, G884S, K387N | 81 |
| G47A, D653T, G884P | 82 |
| G47A, D653T, G884P, K387N | 83 |
| G47A, D653K, G884 | 84 |
| G47A, D653K, K387N, G884 | 85 |
| G47A, D653K, G884T | 86 |
| G47A, D653K, G884T, K387N | 87 |
| G47A, D653K, G884S | 88 |
| G47A, D653K, G884S, K387N | 89 |
| G47A, D653K, G884P | 90 |
| G47A, D653K, G884P, K387N | 91 |
| G47A, K387S, G884 | 92 |
| G47A, K387H, G884 | 93 |
| G47A, E350A, G884 | 94 |
| G47A, E350A, K387S, G884 | 95 |
| G47A, E350A, K387H, G884 | 96 |
| G47A, E350A, K387N, G884 | 97 |
| G47A, E350K, G884 | 98 |
| G47A, E350K, K387S, G884 | 99 |
| G47A, E350K, K387H, G884 | 100 |
| G47A, E350K, K387N, G884 | 101 |
| G47A, E350N, G884 | 102 |
| G47A, E350N, K387S, G884 | 103 |
| G47A, E350N, K387H, G884 | 104 |
| G47A, E350N, K387N, G884 | 105 |
| G47A, E350W, G884 | 106 |
| G47A, E350W, K387S, G884 | 107 |
| G47A, E350W, K387H, G884 | 108 |
| G47A, E350W, K387N, G884 | 109 |
| G47A, D351V, G884 | 110 |
| G47A, D351V, K387S, G884 | 111 |
| G47A, D351V, K387H, G884 | 112 |
| G47A, D351V, K387N, G884 | 113 |
| G47A, D351V, E350A, G884 | 114 |
| G47A, D351V, E350A, K387S, G884 | 115 |
| G47A, D351V, E350A, K387H, G884 | 116 |
| G47A, D351V, E350A, K387N, G884 | 117 |
| G47A, D351V, E350K, G884 | 118 |
| G47A, D351V, E350K, K387S, G884 | 119 |
| G47A, D351V, E350K, K387H, G884 | 120 |
| G47A, D351V, E350K, K387N, G884 | 121 |
| G47A, D351V, E350N, G884 | 122 |
| G47A, D351V, E350N, K387S, G884 | 123 |
| G47A, D351V, E350N, K387H, G884 | 124 |
| G47A, D351V, E350N, K387N, G884 | 125 |

TABLE 1-continued

Multi-Substitution RNA T7 Polymerase Variants

| Substitutions and/or C-terminal Modification | SEQ ID NO: |
|---|---|
| G47A, D351V, E350W, G884 | 126 |
| G47A, D351V, E350W, K387S, G884 | 127 |
| G47A, D351V, E350W, K387H, G884 | 128 |
| G47A, D351V, E350W, K387N, G884 | 129 |
| G47A, D653A, G884 | 130 |
| G47A, D653F, G884 | 131 |
| G47A, D653G, G884 | 132 |
| G47A, D653H, G884 | 133 |
| G47A, D653I, G884 | 134 |
| G47A, D653L, G884 | 135 |
| G47A, D653M, G884 | 136 |
| G47A, D653N, G884 | 137 |
| G47A, D653P, G884 | 138 |
| G47A, D653Q, G884 | 139 |
| G47A, D653R, G884 | 140 |
| G47A, D653S, G884 | 141 |
| G47A, D653V, G884 | 142 |
| G47A, D653Y, G884 | 143 |
| G47A, P657W, G884 | 144 |
| G47A, P657R, G884 | 145 |
| G47A, P657A, G884 | 146 |
| G47A, D653W, P657W, G884 | 147 |
| G47A, D653W, P657R, G884 | 148 |
| G47A, D653W, P657A, G884 | 149 |
| G47A, D653T, P657W, G884 | 150 |
| G47A, D653T, P657R, G884 | 151 |
| G47A, D653T, P657A, G884 | 152 |
| G47A, D653K, P657W, G884 | 153 |
| G47A, D653K, P657R, G884 | 154 |
| G47A, D653K, P657A, G884 | 155 |
| G47A, N437T, G884 | 156 |
| G47A, N437Y, G884 | 157 |
| G47A, N437I, G884 | 158 |
| G47A, N437F, G884 | 159 |
| G47A, K441R, G884 | 160 |
| G47A, K441R, N437T, G884 | 161 |
| G47A, K441R, N437Y, G884 | 162 |
| G47A, K441R, N437I, G884 | 163 |
| G47A, K441R, N437F, G884 | 164 |
| G47A, S628W, G884 | 165 |
| G47A, D506W, G884 | 166 |
| G47A, D506W, S628W, G884 | 167 |
| G47A, D506F, G884 | 168 |
| G47A, D506F, S628W, G884 | 169 |
| G47A, D506Y, G884 | 170 |
| G47A, D506Y, S628W, G884 | 171 |
| G47A, D506R, G884 | 172 |
| G47A, D506R, S628W, G884 | 173 |
| G47A, D506L, G884 | 174 |
| G47A, D506L, S628W, G884 | 175 |
| G47A, D653C, G884 | 176 |
| G47A, D653E, G884 | 177 |
| G47A, R632K, G884 | 178 |
| G47A, R632T, G884 | 179 |
| G47A, P657W, R632K, G884 | 180 |
| G47A, P657W, R632T, G884 | 181 |
| G47A, P657R, R632K, G884 | 182 |
| G47A, P657R, R632T, G884 | 183 |
| G47A, P657A, R632K, G884 | 184 |
| G47A, P657A, R632T, G884 | 185 |
| G47A, D653W, R632K, G884 | 186 |
| G47A, D653W, R632T, G884 | 187 |
| G47A, D653W, P657W, R632K, G884 | 188 |
| G47A, D653W, P657W, R632T, G884 | 189 |
| G47A, D653W, P657R, R632K, G884 | 190 |
| G47A, D653W, P657R, R632T, G884 | 191 |
| G47A, D653W, P657A, R632K, G884 | 192 |
| G47A, D653W, P657A, R632T, G884 | 193 |
| G47A, D653F, R632K, G884 | 194 |
| G47A, D653F, R632T, G884 | 195 |
| G47A, D653F, P657W, G884 | 196 |
| G47A, D653F, P657W, R632K, G884 | 197 |
| G47A, D653F, P657W, R632T, G884 | 198 |
| G47A, D653F, P657R, G884 | 199 |
| G47A, D653F, P657R, R632K, G884 | 200 |
| G47A, D653F, P657R, R632T, G884 | 201 |

TABLE 1-continued

Multi-Substitution RNA T7 Polymerase Variants

| Substitutions and/or C-terminal Modification | SEQ ID NO: |
| --- | --- |
| G47A, D653F, P657A, G884 | 202 |
| G47A, D653F, P657A, R632K, G884 | 203 |
| G47A, D653F, P657A, R632T, G884 | 204 |
| G47A, D653Y, R632K, G884 | 205 |
| G47A, D653Y, R632T, G884 | 206 |
| G47A, D653Y, P657W, G884 | 207 |
| G47A, D653Y, P657W, R632K, G884 | 208 |
| G47A, D653Y, P657W, R632T, G884 | 209 |
| G47A, D653Y, P657R, G884 | 210 |
| G47A, D653Y, P657R, R632K, G884 | 211 |
| G47A, D653Y, P657R, R632T, G884 | 212 |
| G47A, D653Y, P657A, G884 | 213 |
| G47A, D653Y, P657A, R632K, G884 | 214 |
| G47A, D653Y, P657A, R632T, G884 | 215 |
| G47A, D653T, R632K, G884 | 216 |
| G47A, D653T, R632T, G884 | 217 |
| G47A, D653T, P657W, R632K, G884 | 218 |
| G47A, D653T, P657W, R632T, G884 | 219 |
| G47A, D653T, P657R, R632K, G884 | 220 |
| G47A, D653T, P657R, R632T, G884 | 221 |
| G47A, D653T, P657A, R632K, G884 | 222 |
| G47A, D653T, P657A, R632T, G884 | 223 |
| G47A, D653K, R632K, G884 | 224 |
| G47A, D653K, R632T, G884 | 225 |
| G47A, D653K, P657W, R632K, G884 | 226 |
| G47A, D653K, P657W, R632T, G884 | 227 |
| G47A, D653K, P657R, R632K, G884 | 228 |
| G47A, D653K, P657R, R632T, G884 | 229 |
| G47A, D653K, P657A, R632K, G884 | 230 |
| G47A, D653K, P657A, R632T, G884 | 231 |
| G47A, F880Y, G884 | 232 |
| G47A, F880Y, G884S | 233 |
| G47A, F880Y, G884T | 234 |
| G47A, F880Y, G884P | 235 |
| E350W, D351V | 236 |
| E350W, K387N | 237 |
| E350W, D653T | 238 |
| D351V, K387N | 239 |
| D351V, D653T | 240 |
| K387N, D653T | 241 |

Applications

The RNA transcripts produced according to the present disclosure include mRNA (including modified mRNA and/or unmodified RNA), lncRNA, self-replicating RNA, circular RNA, CRISPR guide RNA, and the like. In embodiments, the RNA is RNA (e.g., mRNA or self-replicating RNA) that encodes a polypeptide (e.g., a therapeutic polypeptide). Thus, the RNA transcripts produced using RNA polymerase variants of the present disclosure may be used in a myriad of applications.

For example, the RNA transcripts may be used to produce polypeptides of interest, e.g., therapeutic proteins, vaccine antigen, and the like. In some embodiments, the RNA transcripts are therapeutic RNAs. A therapeutic mRNA is an mRNA that encodes a therapeutic protein (the term 'protein' encompasses peptides). Therapeutic proteins mediate a variety of effects in a host cell or in a subject to treat a disease or ameliorate the signs and symptoms of a disease. For example, a therapeutic protein can replace a protein that is deficient or abnormal, augment the function of an endogenous protein, provide a novel function to a cell (e.g., inhibit or activate an endogenous cellular activity, or act as a delivery agent for another therapeutic compound (e.g., an antibody-drug conjugate). Therapeutic mRNA may be useful for the treatment of the following diseases and conditions: bacterial infections, viral infections, parasitic infections, cell proliferation disorders, genetic disorders, and autoimmune disorders. Other diseases and conditions are encompassed herein.

A protein of interest encoded by an mRNA as provided herein can be essentially any protein. In some embodiments, the therapeutic protein is a cytokine, a growth factor, an antibody or a fusion protein. Non-limiting examples of therapeutic proteins include blood factors (such as Factor VIII and Factor VII), complement factors, Low Density Lipoprotein Receptor (LDLR) and MUT1. Non-limiting examples of cytokines include interleukins, interferons, chemokines, lymphokines and the like. Non-limiting examples of growth factors include erythropoietin, EGFs, PDGFs, FGFs, TGFs, IGFs, TNFs, CSFs, MCSFs, GMCSFs and the like. Non-limiting examples of antibodies include adalimumab, infliximab, rituximab, ipilimumab, tocilizumab, canakinumab, itolizumab, tralokinumab. Non-limiting examples of fusion proteins include, for example, etanercept, abatacept and belatacept.

In some embodiments, the protein of interest is human erythropoietin, LDLR (for use in inhibiting cholesterol), or MUT1 (for use in the treatment of methylmalonic acidemia (MMA)). In other embodiments, the protein of interest encoded by the mRNA is a therapeutic antibody, including but not limited to the antibodies listed above.

A RNA transcript produced using a RNA polymerase variant as disclosed herein may encode one or more biologics. A biologic is a polypeptide-based molecule that may be used to treat, cure, mitigate, prevent, or diagnose a serious or life-threatening disease or medical condition. Biologics include, but are not limited to, allergenic extracts (e.g. for allergy shots and tests), blood components, gene therapy products, human tissue or cellular products used in transplantation, vaccines, monoclonal antibodies, cytokines, growth factors, enzymes, thrombolytics, and immunomodulators, among others.

One or more biologics currently being marketed or in development may be encoded by the RNA of the present invention. While not wishing to be bound by theory, it is believed that incorporation of the encoding polynucleotides of a known biologic into the RNA of the present disclosure will result in improved therapeutic efficacy due at least in part to the specificity, purity and/or selectivity of the construct designs.

A RNA transcript produced using a RNA polymerase variant as disclosed herein may encode one or more antibodies. The term "antibody" includes monoclonal antibodies (including full length antibodies which have an immunoglobulin Fc region), antibody compositions with poly-epitopic specificity, multispecific antibodies (e.g., bispecific antibodies, diabodies, and single-chain molecules), as well as antibody fragments. The term "immunoglobulin" (Ig) is used interchangeably with "antibody" herein. A monoclonal antibody is an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

Monoclonal antibodies specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity. Chimeric antibodies include, but are not limited to, "primatized" antibodies comprising variable domain antigen-binding sequences derived from a non-human primate (e.g., Old World Monkey, Ape etc.) and human constant region sequences.

Antibodies encoded in the RNA of the present disclosure may be utilized to treat conditions or diseases in many therapeutic areas such as, but not limited to, blood, cardiovascular, CNS, poisoning (including antivenoms), dermatology, endocrinology, gastrointestinal, medical imaging, musculoskeletal, oncology, immunology, respiratory, sensory and anti-infective.

A RNA transcript produced using a RNA polymerase variant as disclosed herein may encode one or more vaccine antigens. A vaccine antigen is a biological preparation that improves immunity to a particular disease or infectious agent. One or more vaccine antigens currently being marketed or in development may be encoded by the RNA of the present disclosure. Vaccine antigens encoded in the RNA may be utilized to treat conditions or diseases in many therapeutic areas such as, but not limited to, cancer, allergy and infectious disease. In some embodiments, a cancer vaccine may be a personalized cancer vaccine in the form of a concatemer or individual RNAs encoding peptide epitopes or a combination thereof.

A RNA transcript produced using a RNA polymerase variant as disclosed herein may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals. The anti-microbial polypeptides may block cell fusion and/or viral entry by one or more enveloped viruses (e.g., HIV, HCV). For example, the anti-microbial polypeptide can comprise or consist of a synthetic peptide corresponding to a region, e.g., a consecutive sequence of at least about 5, 10, 15, 20, 25, 30, 35, 40, 45, 50, 55, or 60 amino acids of the transmembrane subunit of a viral envelope protein, e.g., HIV-1 gp120 or gp41. The amino acid and nucleotide sequences of HIV-1 gp120 or gp41 are described in, e.g., Kuiken et al., (2008). "HIV Sequence Compendium," Los Alamos National Laboratory.

In some embodiments, RNA transcripts are used as radio-labeled RNA probes. In some embodiments, RNA transcripts are used for non-isotopic RNA labeling. In some embodiments, RNA transcripts are used as guide RNA (gRNA) for gene targeting. In some embodiments, RNA transcripts (e.g., mRNA) are used for in vitro translation and micro injection. In some embodiments, RNA transcripts are used for RNA structure, processing and catalysis studies. In some embodiments, RNA transcripts are used for RNA amplification. In some embodiments, RNA transcripts are used as anti-sense RNA for gene expression experiment. Other applications are encompassed by the present disclosure.

Additional Embodiments

Additional embodiments of the present disclosure are encompassed by the following numbered paragraphs:

1. A ribonucleic acid (RNA) polymerase variant comprising a RNA polymerase that comprises:
   (a) an amino acid substitution at a binding site residue for de novo RNA synthesis; and
   (b) an amino acid modification that causes increased transcription efficiency, relative to wild-type RNA polymerase.

2. The RNA polymerase variant of paragraph 1, wherein the amino acid modification causes a loop structure of the RNA polymerase variant to undergo a conformational change to a helix structure as the RNA polymerase variant transitions from an initiation complex to an elongation complex.

3. The RNA polymerase variant of paragraph 2, wherein the amino acid modification is an amino acid substitution at position 47, relative to the wild-type RNA polymerase, wherein the wild-type RNA polymerase comprises the amino acid sequence of SEQ ID NO: 1.

4. The RNA polymerase variant of paragraph 3, wherein the amino acid substitution at position 47 is G47A.

5. The RNA polymerase variant of any one of paragraphs 1-4, wherein the amino acid modification comprises an additional C-terminal amino acid, relative to the wild-type RNA polymerase.

6. The RNA polymerase variant of paragraph 5, wherein the additional C-terminal amino acid is glycine.

7. The RNA polymerase variant of any one of paragraphs 1-6, wherein the amino acid substitution at a binding site residue causes at least one of the following benefits, relative to the wild-type RNA polymerase:
   (i) increased transcription efficiency,
   (ii) increased co-transcriptional capping efficiency;
   (iii) increased yield of RNA at ½ concentration of a cap analog;
   (iv) improved 3' homogeneity of RNA at ½ concentration of a cap analog;
   (v) improved fidelity of transcription; and/or
   (vi) lower amount of dsRNA contamination.

8. The polymerase variant of any one of paragraphs 1-6, wherein the amino acid substitution at a binding site residue causes at least one of the following benefits, relative to the amino acid modification of (b):
   (i) increased transcription efficiency,
   (ii) increased co-transcriptional capping efficiency;
   (iii) increased yield of RNA at ½ concentration of a cap analog;
   (iv) improved 3' homogeneity of RNA at ½ concentration of a cap analog;
   (v) improved fidelity of transcription; and/or
   (vi) lower amount of dsRNA contamination.

9. The RNA polymerase variant of any one of paragraphs 1-8, wherein the amino acid substitution at the binding site residue is a substitution at a position selected from positions 350, 351, 387, 394, 425, 427, 437, 441, 506, 628, 632, 653, 657, 811, and 880, relative to the wild-type RNA polymerase, wherein the wild-type RNA polymerase comprises the amino acid sequence of SEQ ID NO: 1.

10. A RNA polymerase variant comprising a RNA polymerase that comprises:
    (a) an amino acid substitution at a position selected from positions 350, 351, 387, 394, 425, 427, 437, 441, 506, 628, 632, 653, 657, 811, and 880; and
    (b) an additional amino acid substitution and/or an amino acid modification at the C-terminal end, relative to wild-type RNA polymerase, wherein the wild-type RNA polymerase comprises the amino acid sequence of SEQ ID NO: 1.

11. The RNA polymerase variant of paragraph 10 comprising the additional amino acid substitution of (b).

12. The RNA polymerase variant of paragraph 11, wherein the additional amino acid substitution of (b) is at position 47.

13. The RNA polymerase variant of paragraph 12, wherein the additional amino acid substitution at position 47 is G47A.

14. The RNA polymerase variant of any one of paragraphs 10-13 comprising the amino acid modification at the C-terminal end.

15 The RNA polymerase variant of paragraph 14, wherein the amino acid modification at the C-terminal end comprises an additional C-terminal amino acid.

16. The RNA polymerase variant of paragraph 15, wherein the additional C-terminal amino acid is selected from glycine, serine, alanine, proline, and threonine.

17. The RNA polymerase variant of paragraph 16, wherein the additional C-terminal amino acid is glycine.

18. The RNA polymerase variant of paragraph 16, wherein the additional C-terminal amino acid is alanine.

19. The RNA polymerase variant of paragraph 17 or 18 comprising a RNA polymerase that comprises
   (a) an amino acid substitution at a position selected from positions 350, 351, 387, 394, 425, 427, 437, 441, 506, 628, 632, 653, 657, 811, and 880;
   (b) an additional amino acid substitution; and
   (c) an amino acid modification at the C-terminal end, relative to a wild-type RNA polymerase, wherein the wild-type RNA polymerase comprises the amino acid sequence of SEQ ID NO: 1.

20. The RNA polymerase variant of paragraph 19, wherein the additional amino acid substitution is at position 47.

21. The RNA polymerase variant of paragraph 20, wherein the additional amino acid substitution at position 47 is G47A.

22. The RNA polymerase variant of any one of paragraphs 19-21, wherein the amino acid modification at the C-terminal end comprises an additional C-terminal amino acid.

23. The RNA polymerase variant of paragraph 22, wherein the additional C-terminal amino acid is selected from glycine, serine, alanine, proline, glutamine, and threonine.

24. The RNA polymerase variant of paragraph 23, wherein the additional C-terminal amino acid is glycine.

25. The RNA polymerase variant of any one of paragraphs 1-24, wherein the additional amino acid substitution of (a) is at a position selected from position 387, 350, 351, 506, 628, 653, and 657, relative to the wild-type RNA polymerase, wherein the wild-type RNA polymerase comprises the amino acid sequence of SEQ ID NO: 1.

26. The RNA polymerase variant of paragraph 25, wherein the additional amino acid substitution is selected from K387S, K387H, and K387N.

27. The RNA polymerase variant of paragraph 25, wherein the additional amino acid substitution is selected from E350K, E350N, E350A, and E350W.

28. The RNA polymerase variant of paragraph 25, wherein the additional amino acid substitution is D351V.

29. The RNA polymerase variant of paragraph 25, wherein the additional amino acid substitution is D506W.

30. The RNA polymerase variant of paragraph 25, wherein the additional amino acid substitution is S628W.

31. The RNA polymerase variant of paragraph 25, wherein the additional amino acid substitution is D653W.

32. The RNA polymerase variant of paragraph 25, wherein the additional amino acid substitution is P657W.

33. The RNA polymerase variant of any one of paragraphs 1-24, wherein the additional amino acid substitution of (a) is at a position selected from position 350, 351, 387, and 437, relative to the wild-type RNA polymerase, wherein the wild-type RNA polymerase comprises the amino acid sequence of SEQ ID NO: 1.

34. The RNA polymerase variant of paragraph 33, wherein the additional amino acid substitution of (a) is at position 350, and the additional amino acid substitution at position 350 is selected from E350R, E350K, E350D, E350Q, E350N, E350T, E350S, E350C, E350G, E350A, E350V, E350L, E350I, E350P, E350Y, E350W, and E350F.

35. The RNA polymerase variant of paragraph 33, wherein the additional amino acid substitution of (a) is at position 351, and the additional amino acid substitution at position 350 is selected from D351R, D351K, D351Q, D351T, D351S, D351C, D351V, D351L, D351I, D351M, D351P, D351Y, and D351W.

36. The RNA polymerase variant of paragraph 33, wherein the additional amino acid substitution of (a) is at position 387, and the additional amino acid substitution at position 387 is selected from K387R, K387H, K387T, K387S, K387V, K387L, K387I, and K387M.

37. The RNA polymerase variant of paragraph 33, wherein the additional amino acid substitution of (a) is at position 437, and the additional amino acid substitution at position 437 is selected from N437Q, N437T, N437S, N437G, and N437F.

38. The RNA polymerase variant of paragraph 22, wherein the additional C-terminal amino acid is serine or alanine.

39. The RNA polymerase variant of paragraph 33, wherein the additional amino acid substitution of (a) is at position 350, and the additional amino acid substitution at position 350 is selected from E350N, E350C, E350G, E350Y, E350W, and E350F.

40. The RNA polymerase variant of paragraph 33, wherein the additional amino acid substitution of (a) is at position 351, and the additional amino acid substitution at position 351 is selected from D351R, D351S, D351L, D351M, and D351Y.

41. The RNA polymerase variant of paragraph 33, wherein the additional amino acid substitution of (a) is at position 387, and the additional amino acid substitution at position 387 is selected from K387R, K387T, K387L, and K387M.

42. The RNA polymerase variant of paragraph 33, wherein the additional amino acid substitution of (a) is at position 437, and the additional amino acid substitution at position 437 is selected from N437R, N437K, N437H, N437T, N437V, N437I, and N437W.

43. The RNA polymerase variant of paragraph 22, wherein the additional C-terminal amino acid is glutamine, threonine, or proline.

44. The RNA polymerase variant of any one of paragraphs 1-24, wherein the additional amino acid substitution of (a) is at a position selected from position 350, 351, 387, 437, 441, 632, and 880, relative to the wild-type RNA polymerase, wherein the wild-type RNA polymerase comprises the amino acid sequence of SEQ ID NO: 1.

45. The RNA polymerase variant of paragraph 44, wherein the additional amino acid substitution of (a) is at position 350, and the additional amino acid substitution at position 350 is selected from E350R, E350K, E350D, E350Q, E350N, E350T, E350S, E350C, E350G, E350A, E350V, E350L, E350I, E350Y, E350W, and E350F.

46. The RNA polymerase variant of paragraph 44, wherein the additional amino acid substitution of (a) is at position 351, and the additional amino acid substitution at position 351 is selected from D351R, D351K, D351Q, D351T, D351C, D351V, D351L, D351M, and D351W.

47. The RNA polymerase variant of paragraph 44, wherein the additional amino acid substitution of (a) is at position 387, and the additional amino acid substitution at position 387 is selected from K387H, K387E, K387N, K387T, K387S, K387G, K387A, K387Y, K387W, and K387F.

48. The RNA polymerase variant of paragraph 44, wherein the additional amino acid substitution of (a) is at position 437, and the additional amino acid substitution at position 437 is selected from N437T, N437I, N437Y, N437W, and N437F.

49. The RNA polymerase variant of paragraph 44, wherein the additional amino acid substitution of (a) is at position 444, and the additional amino acid substitution at position 444 is K444R.

50. The RNA polymerase variant of paragraph 44, wherein the additional amino acid substitution of (a) is at position 632, and the additional amino acid substitution at position 632 is selected from R632K and R632T.

51. The RNA polymerase variant of paragraph 44, wherein the additional amino acid substitution of (a) is at position 880, and the additional amino acid substitution at position 880 is F880Y.

52. The RNA polymerase variant of paragraph 22, wherein the additional C-terminal amino acid is glutamine, threonine, and proline.

53. The RNA polymerase variant of paragraph 44, wherein the additional amino acid substitution of (a) is at position 350, and the additional amino acid substitution at position 350 is selected from E350K, E350N, E350A, and E350W.

54. The RNA polymerase variant of paragraph 44, wherein the additional amino acid substitution of (a) is at position 351, and the additional amino acid substitution at position 351 is D351V.

55. The RNA polymerase variant of paragraph 44, wherein the additional amino acid substitution of (a) is at position 387, and the additional amino acid substitution at position 387 is selected from K387H, K387N, and K387S.

56. The RNA polymerase variant of paragraph 44, wherein the additional amino acid substitution of (a) is at position 437, and the additional amino acid substitution at position 437 is selected from N437T, N437I, N437Y, and N437F.

57. The RNA polymerase variant of paragraph 44, wherein the additional amino acid substitution of (a) is at position 444, and the additional amino acid substitution at position 444 is selected from K444R.

58. The RNA polymerase variant of paragraph 44, wherein the additional amino acid substitution of (a) is at position 880, and the additional amino acid substitution at position 880 is F880Y.

59. The RNA polymerase variant of paragraph 22, wherein the additional C-terminal amino acid is threonine, serine, alanine, and proline.

60. A RNA polymerase variant comprising a RNA polymerase that comprises:
(a) an amino acid substitution at positions 350, 351, and 387; and
(b) an additional amino acid substitution and/or an amino acid modification at the C-terminal end, relative to wild-type RNA polymerase, wherein the wild-type RNA polymerase comprises the amino acid sequence of SEQ ID NO: 1.

61. The RNA polymerase variant of paragraph 60, wherein:
the additional amino acid substitution at position 350 is selected from E350A, E350K, E350N, and E350W;
the additional amino acid substitution at position 351 is D351V; and/or
the additional amino acid substitution at position 387 is selected from K387S, K387H, and K387N.

62. A RNA polymerase variant comprising a RNA polymerase that comprises:
(a) an amino acid substitution at positions 437 and 441; and
(b) an additional amino acid substitution and/or an amino acid modification at the C-terminal end, relative to wild-type RNA polymerase, wherein the wild-type RNA polymerase comprises the amino acid sequence of SEQ ID NO: 1.

63. The RNA polymerase variant of paragraph 62, wherein:
the additional amino acid substitution at position 437 is selected from N437T, N437Y, N437I, and N437F; and/or
the additional amino acid substitution at position 441 is K441R.

64. A RNA polymerase variant comprising a RNA polymerase that comprises:
(a) an amino acid substitution at positions 880; and
(b) an amino acid modification at the C-terminal end, relative to wild-type RNA polymerase, wherein the wild-type RNA polymerase comprises the amino acid sequence of SEQ ID NO: 1.

65. The RNA polymerase variant of paragraph 64, wherein:
the additional amino acid substitution at position 880 is F880Y; and/or
the amino acid modification at the C-terminal end is an additional amino acid selected from alanine, serine, threonine, and proline.

66. A RNA polymerase variant comprising a RNA polymerase that comprises:
(a) an amino acid substitution at positions 632, 653, and 657; and
(b) an additional amino acid substitution and/or an amino acid modification at the C-terminal end, relative to wild-type RNA polymerase, wherein the wild-type RNA polymerase comprises the amino acid sequence of SEQ ID NO: 1.

67. The RNA polymerase variant of paragraph 66, wherein:
the additional amino acid substitution at position 632 is selected from R632K and R632T;
the additional amino acid substitution at position 653 is selected from D653T and D653K; and/or.
the additional amino acid substitution at position 657 is selected from P657W, P657R, or P657A.

68. The RNA polymerase variant of any one of paragraphs 60-67 comprising the additional amino acid substitution of (b).

69. The RNA polymerase variant of paragraph 68, wherein the additional amino acid substitution of (b) is at position 47.

70. The RNA polymerase variant of paragraph 69, wherein the additional amino acid substitution of (b) at position 47 is G47A.

71. The RNA polymerase variant of any one of paragraphs 60-70 comprising the amino acid modification at the C-terminal end.

72. The RNA polymerase variant of paragraph 71, wherein the amino acid modification at the C-terminal end comprises an additional C-terminal amino acid.

73. The RNA polymerase variant of paragraph 72, wherein the additional C-terminal amino acid is glycine.

74. The RNA polymerase variant of any one of paragraphs 1-73 comprising an amino acid sequence having at least 90% identity to the wild-type RNA polymerase, wherein the wild-type RNA polymerase comprises the amino acid sequence of SEQ ID NO: 1.

75. A method comprising producing a ribonucleic acid (RNA) transcript in an in vitro transcription reaction that comprises a polynucleotide template, nucleoside triphosphates, a cap analog, and a RNA polymerase comprising at least one mutation relative to a wild-type RNA polymerase, wherein the reaction comprises a concentration of the cap analog that is at least 5-fold lower than a concentration of the cap analog required to produce an equivalent amount of RNA transcript using wild-type RNA polymerase, optionally wherein the wild-type RNA polymerase is wild-type T7 RNA polymerase.

76. The method of paragraph 75, wherein greater than 80% of the RNA transcript produced includes a functional cap.

77. The method of paragraph 75 or 76, wherein the RNA transcript produced has greater than a threshold 3' homogeneity, wherein the threshold 3' homogeneity is at least 50% 3' homogeneity.

78. The method of any one of paragraph 75-77, wherein the RNA transcript produced has lower than a threshold quantity of dsRNA, wherein the threshold quantity of dsRNA is 5 ng dsRNA per 25 μg of mRNA.

79. A method comprising producing a RNA transcript in an in vitro transcription reaction that comprises a polynucleotide template, nucleoside triphosphates, and the RNA polymerase variant of any one of paragraphs 1-74.

80. A method comprising producing a RNA transcript in an in vitro transcription reaction that comprises a polynucleotide template, nucleoside triphosphates, a cap analog, and the RNA polymerase variant of any one of paragraphs 1-72.

81. The method of paragraph 79 or 80, wherein the nucleoside triphosphates comprise unmodified or modified ATP, modified or unmodified UTP, modified or unmodified GTP, and/or modified or unmodified CTP.

82. The method of paragraph 80 or 81, wherein the reaction comprises a concentration of the cap analog that is at least 2-fold lower, at least 5-fold lower, or at least 10-fold lower than a concentration of the cap analog required to produce an equivalent amount of RNA transcript using the wild-type RNA polymerase.

83. The method of any one of paragraphs 80-82, wherein greater than 80%, greater than 85%, greater than 90%, or greater than 95% of the RNA transcript produced includes a functional cap.

84. The method of any one of paragraphs 80-83, wherein the nucleoside triphosphates and cap analog are present in the reaction at equimolar concentrations.

85. The method of any one of paragraphs 80-84, wherein a molar ratio of cap analog to nucleoside triphosphates in the reaction is greater than 1:1 or equal to 1:1.

86. The method of any one of paragraphs 80-85, wherein the cap analog is a dinucleotide cap, a trinucleotide cap, or a tetranucleotide cap.

87. The method of any one of paragraphs 80-86, wherein the cap analog is a natural cap analog or a synthetic cap analog.

88. The method of paragraph 86 or 87, wherein the cap analog is a trinucleotide cap comprising a sequence selected from the following sequences: GAA, GAC, GAG, GAU, GCA, GCC, GCG, GCU, GGA, GGC, GGG, GGU, GUA, GUC, GUG, and GUU.

89. The method of paragraph 88, wherein the trinucleotide cap comprises a sequence selected from the following sequences: GAG, GCG, GUG, and GGG.

90. The method of paragraph 89, wherein the trinucleotide cap comprises sequence GAG.

91. The method of paragraph 90, wherein the trinucleotide cap comprises a sequence selected from the following sequences:

(a) $m^7$GpppApA, $m^7$GpppApC, $m^7$GpppApG, $m^7$GpppApU, $m^7$GpppCpA, $m^7$GpppCpC, $m^7$GpppCpG, $m^7$GpppCpU, $m^2$GpppGpA, $m^7$GpppGpC, $m^7$GpppGpG, $m^7$GpppGpU, $m^7$GpppUpA, $m^7$GpppUpC, $m^7$GpppUpG, and $m^7$GpppUpU;

(b) $m^7G_{3'OMe}$pppApA, $m^7G_{3'OMe}$pppApC, $m^7G_{3'OMe}$pppApG, $m^7G_{3'OMe}$pppApU, $m^7G_{3'OMe}$pppCpA, $m^7G_{3'OMe}$pppCpC, $m^7G_{3'OMe}$pppCpG, $m^7G_{3'OMe}$pppCPU, $m^7G_{3'OMe}$pppGpA, $m^7G_{3'OMe}$pppGpC, $m^7G_{3'OMe}$pppGpG, $m^7G_{3'OMe}$pppGpU, $m^7G_{3'OMe}$pppUpA, $m^7G_{3'OMe}$pppUpC, $m^7G_{3'OMe}$pppUpG, and $m^7G_{3'OMe}$pppUpU;

(c) $m^7G_{3'OMe}$pppA$_{2'OMe}$pA, $m^1G_{3'OMe}$pppA$_{2'OMe}$pC, $m^1G_{3'OMe}$pppA$_{2'OMe}$pG, $m^7G_{3'OMe}$pppA$_{2'OMe}$pU, $m^7G_{3'OMe}$pppC$_{2'OMe}$pA, $m^7G_{3'OMe}$pppC$_{2'OMe}$PC, $m^7G_{3'OMe}$pppC$_{2'OMe}$pG, $m^7G_{3'OMe}$pppC$_{2'OMe}$pU, $m^7G_{3'OMe}$pppG$_{2'OMe}$pA, $m^7G_{3'OMe}$pppG$_{2'OMe}$PC, $m^7G_{3'OMe}$pppG$_{2'OMe}$pG, $m^7G_{3'OMe}$pppG$_{2'OMe}$PU, $m^7G_{3'OMe}$pppU$_{2'OMe}$pA, $m^7G_{3'OMe}$pppU$_{2'OMe}$PC, $m^7G_{3'OMe}$pppU$_{2'OMe}$pG, and $m^7G_{3'OMe}$pppU$_{2'OMe}$pU; or (d) $m^7$GpppA$_{2'OMe}$pA, $m^7$GpppA$_{2'OMe}$pC, $m^7$GpppA$_{2'OMe}$pG, $m^7$GpppA$_{2'OMe}$pU, $m^7$GpppC$_{2'OMe}$pA, $m^7$GpppC$_{2'OMe}$PC, $m^7$GpppC$_{2'OMe}$pG, $m^7$GpppC$_{2'OMe}$PU, $m^7$GpppG$_{2'OMe}$pA, $m^7$GpppG$_{2'OMe}$PC, $m^7$GpppG$_{2'OMe}$pG, $m^7$GpppG$_{2'OMe}$pU, $m^7$GpppU$_{2'OMe}$pA, $m^7$GpppU$_{2'OMe}$PC, $m^7$GpppU$_{2'OMe}$pG, and $m^7$GpppU$_{2'OMe}$pU.

92. The method of paragraph 91, wherein the trinucleotide cap comprises GpppA$_{2'Ome}$pG.

93. The method of any one of paragraphs 75-92, wherein the polynucleotide template includes a 2'-deoxythymidine residue or a 2'-deoxycytidine residue at template position +1.

94. The method of any one of paragraphs 75-93, wherein the RNA transcript produced, when delivered to cells, optionally in unpurified form, stimulates a cytokine response that is at least 50% lower relative to RNA produced using wild-type RNA polymerase.

95. The method of any one of paragraphs 75-94, wherein the concentration of double-stranded RNA (dsRNA) transcript produced is at least 50% lower relative to dsRNA transcript produced using wild-type RNA polymerase.

96. The method of any one of paragraphs 75-95, wherein less than 50%, less than 25%, or less than 10% of the RNA transcript produced is dsRNA.

97. The method of any one of paragraphs 75-96, wherein less than 30% or less than 20% of the RNA transcripts produced exhibit 3' heterogeneity.

98. The method of any one of paragraphs 75-97, wherein less than 50%, less than 25%, or less than 10% of the RNA transcript produced is run-on RNA transcript.

99. The method of any one of paragraphs 75-98, wherein the amount of full-length RNA transcript produced is at least 15 times greater than the amount of the polynucleotide template.

100. The method of any one of paragraphs 75-99, wherein the ratio of dsRNA:full-length RNA transcript produced is less than 1:1.

101. The method of any one of paragraphs 75-100, wherein the RNA transcript produced has less than 1 mutation per 100 nucleotides relative to the polynucleotide template.

102. A nucleic acid encoding the RNA polymerase variant of any one of paragraphs 1-74.

103. A composition comprising the RNA polymerase variant of any one of paragraphs 1-74 and optionally nucleoside triphosphates.

104. A kit comprising the RNA polymerase variant of any one of paragraphs 1-74 and an in vitro transcription (IVT) reagent.

105. A ribonucleic acid (RNA), optionally a messenger RNA (mRNA), produced by the method of any one of paragraphs 75-104.

106. A lipid nanoparticle comprising the RNA of paragraph 103, optionally wherein the lipid nanoparticle comprises a molar ratio of 20-60% ionizable amino lipid, 5-25% non-cationic lipid, 25-55% sterol, and 0.5-15% PEG-modified lipid.

107. A RNA polymerase variant derived from a starting RNA polymerase that has an amino acid modification at position G47 and an additional C-terminal amino acid relative to a wild type amino acid sequence of T7 RNA polymerase comprising the sequence of SEQ ID NO: 1, wherein the variant comprises at least one substitution that affects first nucleotide binding to the D-site within the RNA polymerase variant as it is in the conformational state for de novo initiation of RNA synthesis, and wherein the amino acid substitution causes at least one of the following benefits relative to the starting RNA polymerase:
  (i) increased transcription efficiency;
  (ii) increased co-transcriptional capping efficiency;
  (iii) increased yield of RNA;
  (iv) improved 3' homogeneity of RNA transcripts;
  (v) improved fidelity of transcription; and
  (vi) lower amounts of dsRNA in the reaction mixture.

108. A RNA polymerase variant comprising the amino acid sequence of any one of SEQ ID NOS: 3-14, 45-48, or 242-247, wherein X is any amino acid selected from R, K, H, E, D, Q, N, T, S, C, G, A, V, L, I, M, P, Y, W, and F.

109. The RNA polymerase of paragraph 108 comprising the amino acid sequence of SEQ ID NO: 47.

110. The RNA polymerase of paragraph 109, wherein X is W.

111. The RNA polymerase variant of any one of paragraphs 108-110 further comprising a G47A substitution.

112. The RNA polymerase variant of any one of paragraphs 108-111 further comprising an additional C-terminal amino acid.

113. The RNA polymerase variant of paragraph 112, wherein the additional C-terminal amino acid is glycine.

114. A RNA polymerase variant comprising the amino acid sequence of any one of SEQ ID NOS: 61-241.

115. A nucleic acid encoding the RNA polymerase variant of paragraph 114.

116. A method comprising producing a RNA transcript in an in vitro transcription reaction that comprises a polynucleotide template, nucleoside triphosphates, and the RNA polymerase variant of paragraph 114.

117. A method comprising producing a RNA transcript in an in vitro transcription reaction that comprises a polynucleotide template, nucleoside triphosphates, a cap analog, and the RNA polymerase variant of paragraph 114.

118. A RNA polymerase variant comprising a RNA polymerase that comprises:
  (a) an amino acid substitution at position E350, K387, N437, F880, or D653;
  (b) an amino acid substitution at position G47; and/or
  (c) an amino acid modification at the C-terminal end, relative to a wild-type RNA polymerase comprising the amino acid sequence of SEQ ID NO: 1.

119. The RNA polymerase of paragraph 118, wherein the amino acid substitution of (a) is selected from the group consisting of E350N, K387N, N437F, F880Y, and D653W.

120. The RNA polymerase variant of paragraph 119, wherein the amino acid substitution of (a) is D653W.

121. The RNA polymerase variant of any one of paragraphs 118-120, wherein the amino acid substitution at position G47 is G47A.

122. The RNA polymerase variant of any one of paragraphs 118-121, wherein the amino acid modification at the C-terminal end is an additional glycine, an additional alanine, an additional threonine, or an additional proline.

123. A RNA polymerase variant comprising a RNA polymerase that comprises amino acid substitution at two of the positions selected from the group consisting of E350, D351, K387, N437, K441, D506, R632, D653, S628, P657, and F880, relative to a wild-type RNA polymerase comprising the amino acid sequence of SEQ ID NO: 1.

124. The RNA polymerase variant of paragraph 123 comprising amino acid substitutions at E350 and D351.

125. The RNA polymerase variant of paragraph 123 comprising amino acid substitutions at E350 and K387.

126. The RNA polymerase variant of paragraph 123 comprising amino acid substitutions at K387 and D653.

127. The RNA polymerase variant of any one of paragraphs 123-125, wherein the amino acid substitution at position E350 is E350W, E350A, E350K, or E350N.

128. The RNA polymerase variant of paragraph 123 or 124, wherein the amino acid substitution at position D351 is D351V.

129. The RNA polymerase variant of any one of paragraphs 123, 125, or 126, wherein the amino acid substitution at position K387 is K387N, K387S, or K387H.

130. The RNA polymerase variant of paragraph 123 or 126, wherein the amino acid substitution at position D653 is D653T or D653K.

131. A method comprising producing a RNA transcript in an in vitro transcription reaction that comprises a polynucleotide template, nucleoside triphosphates, a cap analog, and the RNA polymerase variant of any one of the preceding paragraphs, wherein the cap analog is a trinucleotide cap analog or a tetranucleotide cap analog.

132. The method of any one of the preceding paragraphs, wherein the cap analog is a trinucleotide cap analog that comprises GAG.

133. The method of paragraph 132, wherein the GAG cap analog is selected from:
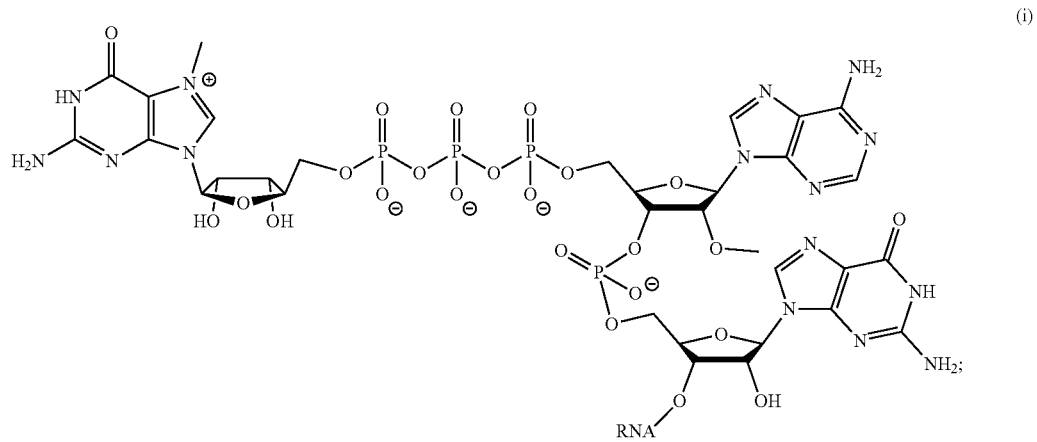
(i)
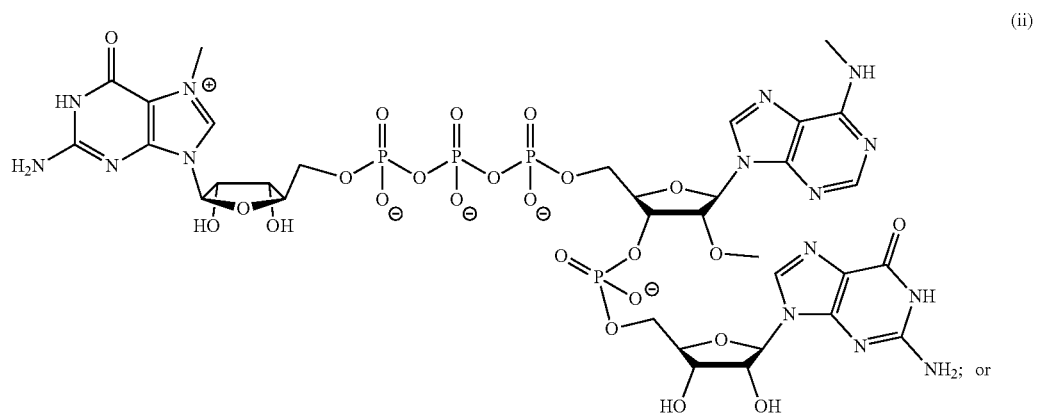
(ii)
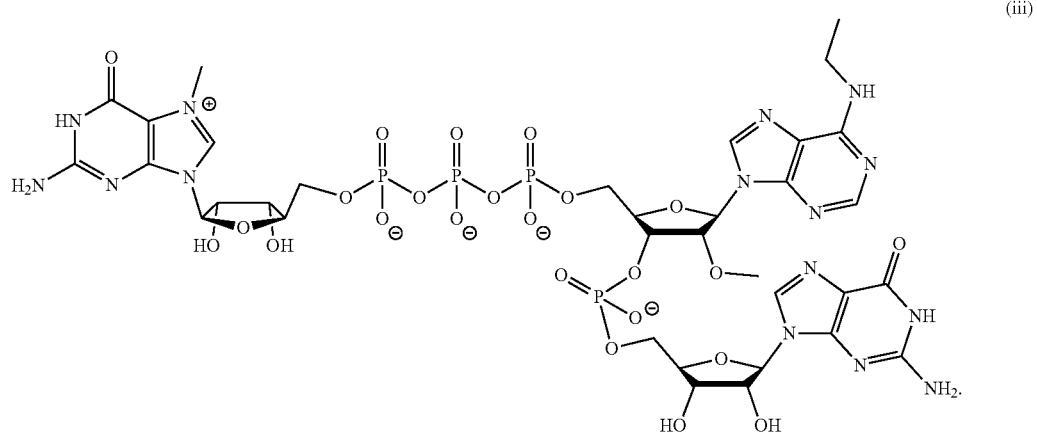
(iii)

134. The method of any one of the preceding paragraphs, wherein the cap analog is a tetranucleotide cap analog that comprises GGAG.
135. The method of paragraph 134, wherein the tetranucleotide cap analog is selected from:
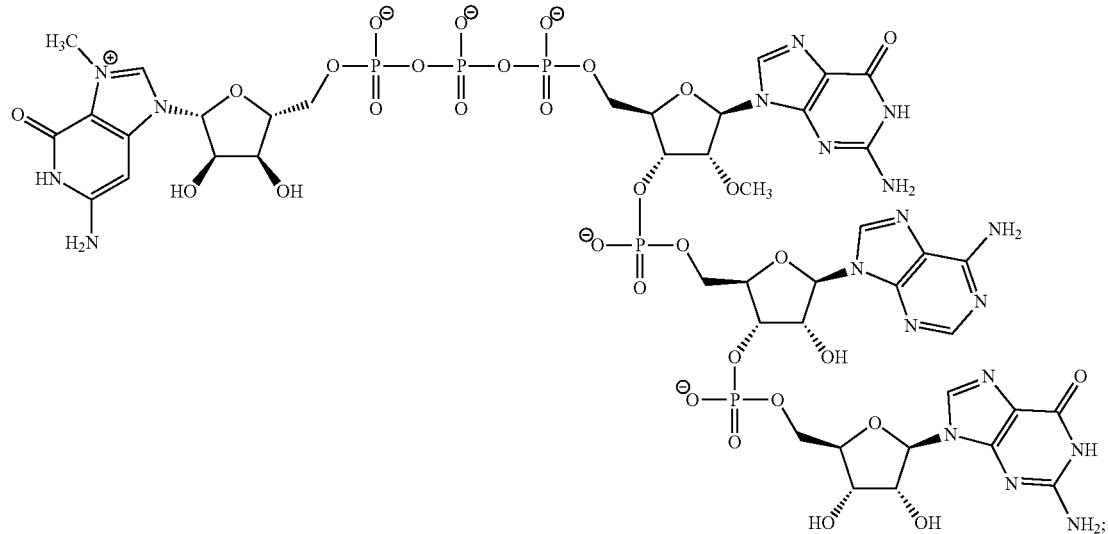
(iv)
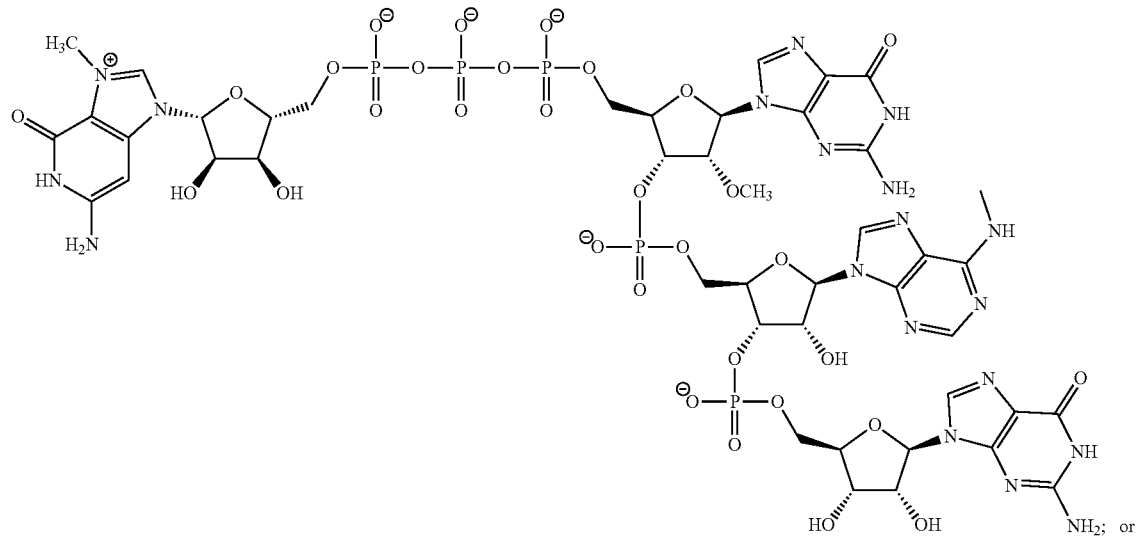
(v)
or

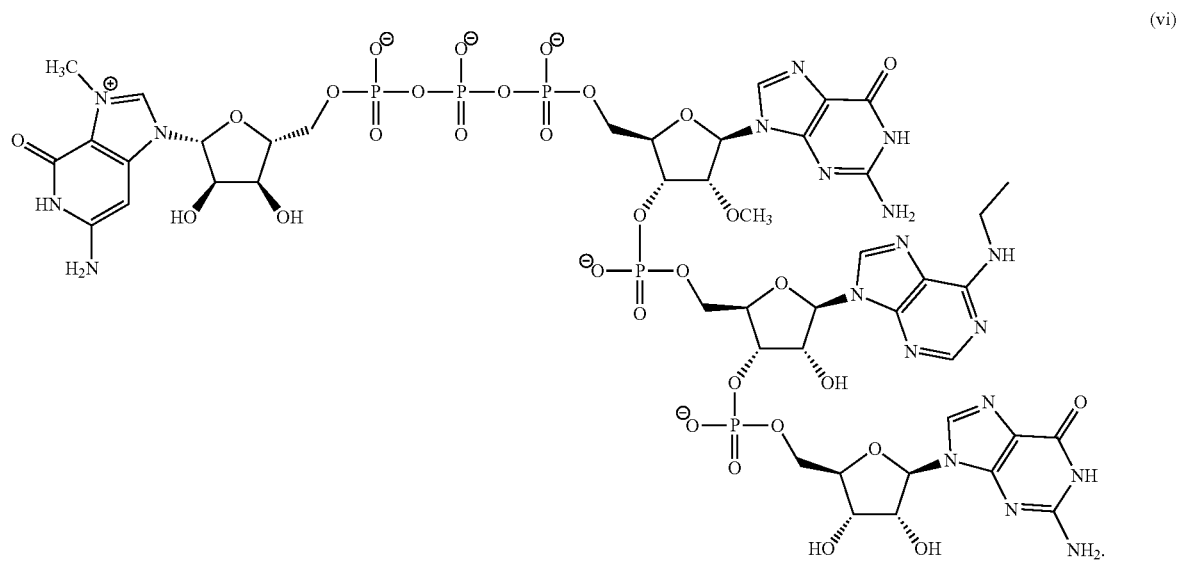

(vi)

136. The method of any one of the preceding paragraphs, wherein greater than 80%, greater than 85%, greater than 90%, or greater than 95% of the RNA transcript produced includes a cap analog.

137. The method of any one of the preceding paragraphs, wherein the method produces at least 50%, at least 60%, or at least 75% more RNA transcript comprising a cap analog than a control in vitro transcription reaction comprising a wild-type RNA polymerase of SEQ ID NO: 1.

138. The method of any one of the preceding paragraphs, wherein a molar ratio of cap analog to nucleoside triphosphates in the reaction is between 1:10 and 1:1.

139. The method of any one of the preceding paragraphs, wherein less than 1%, less than 0.5%, or less than 0.1% of the RNA transcript produced is double-stranded RNA (dsRNA).

140. The method of any one of the preceding paragraphs, wherein the reaction produces at least 5 mg/mL, at least 6 mg/mL, at least 7 mg/mL, at least 8 mg/mL, at least 9 mg/mL, or at least 10 mg/mL of RNA transcript.

141. The method of any one of the preceding paragraphs, wherein at least 85%, at least 90%, or at least 95% of RNA transcript produced is a full-length RNA transcript.

142. The method of any one of the preceding paragraphs, wherein the method produces at least 10%, at least 25%, or at least 50% more RNA transcript comprising a cap analog than a control in vitro transcription reaction involving a control RNA polymerase variant, wherein the control RNA polymerase variant is derived from SEQ ID NO:1 and comprises a G47A mutation and an additional glycine at the C-terminal end.

143. A method comprising producing a RNA transcript in an in vitro transcription reaction that comprises a polynucleotide template, nucleoside triphosphates, a cap analog, and a wild-type RNA polymerase, wherein the cap analog is a trinucleotide cap analog or a tetranucleotide cap analog.

144. The method of paragraph 143, wherein the wild-type RNA polymerase comprises an amino acid sequence of SEQ ID NO: 1.

145. The method of paragraph 143 or 144, wherein the cap analog is a tetranucleotide cap analog that comprises GGAG.

146. The method of any one of paragraphs 143-145, wherein the tetranucleotide cap analog is selected from:
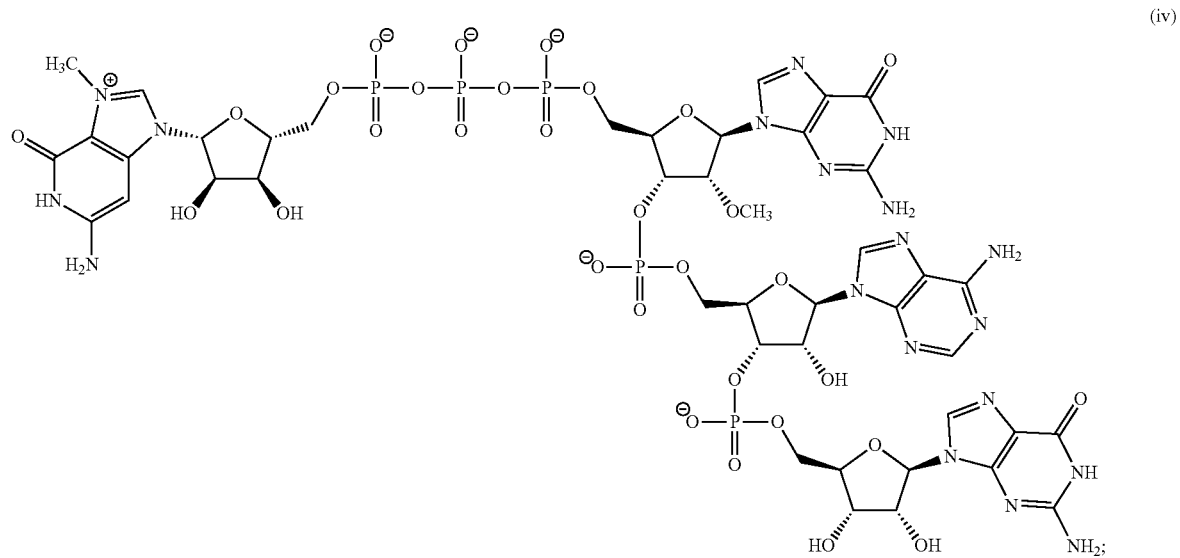
(iv)
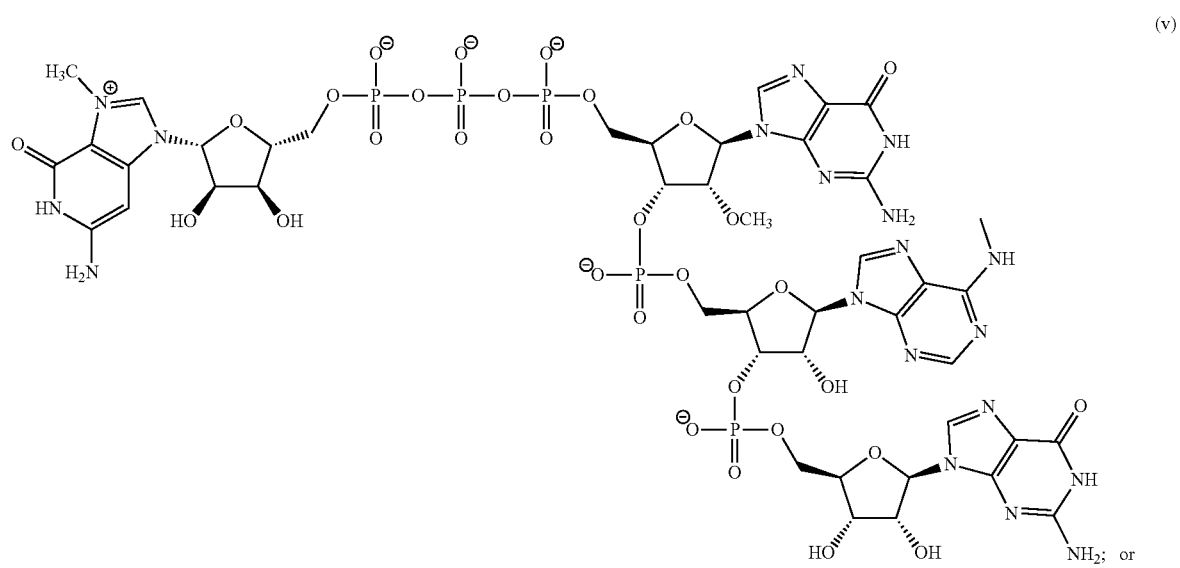
(v)
or

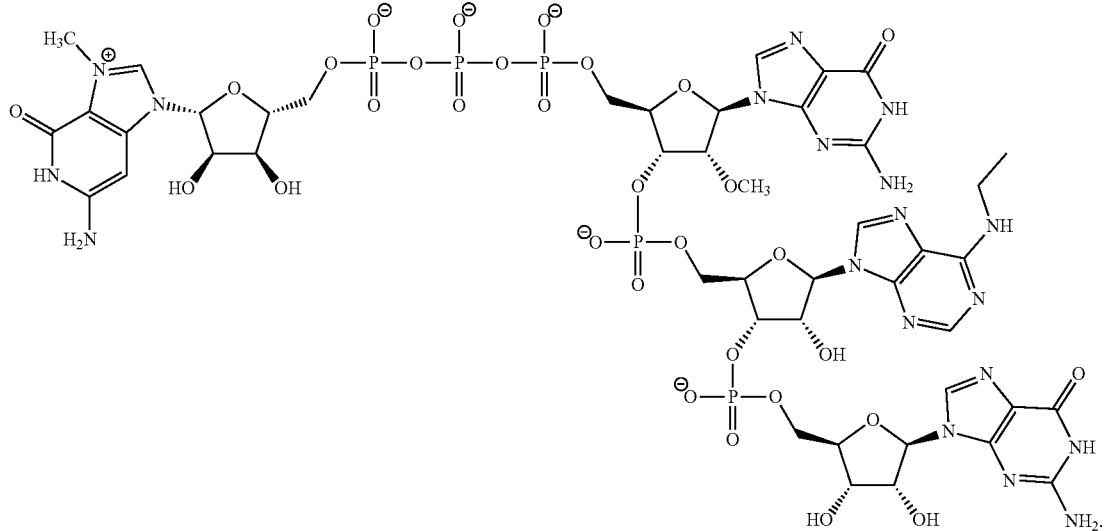

(vi)

```
Wild-type T7 RNA Polymerase
                                                           (SEQ ID NO: 1)
MNTINIAKNDFSDIELAAIPFNTLADHYGERLAREQLALEHESYEMGEARFRKMFERQLKAGEVADNAAAKPLITTL

LPKMIARINDWFEEVKAKRGKRPTAFQFLQEIKPEAVAYITIKTTLACLTSADNTTVQAVASAIGRAIEDEARFGRI

RDLEAKHFKKNVEEQLNKRVGHVYKKAFMQVVEADMLSKGLLGGEAWSSWHKEDSIHVGVRCIEMLIESTGMVSLHR

QNAGVVGQDSETIELAPEYAEAIATRAGALAGISPMFQPCVVPPKPWTGITGGGYWANGRRPLALVRTHSKKALMRY

EDVYMPEVYKAINIAQNTAWKINKKVLAVANVITKWKHCPVEDIPAIEREELPMKPEDIDMNPEALTAWKRAAAAVY

RKDKARKSRRISLEFMLEQANKFANHKAIWFPYNMDWRGRVYAVSMFNPQGNDMTKGLLTLAKGKPIGKEGYYWLKI

HGANCAGVDKVPFPERIKFIEENHENIMACAKSPLENTWWAEQDSPFCFLAFCFEYAGVQHHGLSYNCSLPLAFDGS

CSGIQHFSAMLRDEVGGRAVNLLPSETVQDIYGIVAKKVNEILQADAINGTDNEVVTVTDENTGEISEKVKLGTKAL

AGQWLAYGVTRSVTKRSVMTLAYGSKEFGFRQQVLEDTIQPAIDSGKGLMFTQPNQAAGYMAKLIWESVSVTVVAAV

EAMNWLKSAAKLLAAEVKDKKTGEILRKRCAVHWVTPDGFPVWQEYKKPIQTRLNLMFLGQFRLQPTINTNKDSEID

AHKQESGIAPNFVHSQDGSHLRKTVVWAHEKYGIESFALIHDSFGTIPADAANLFKAVRETMVDTYESCDVLADFYD

QFADQLHESQLDKMPALPAKGNLNLRDILESDFAFA

Control T7 RNA Polymerase Variant (G47A + C-terminal G)
                                                           (SEQ ID NO: 44)
MNTINIAKNDFSDIELAAIPFNTLADHYGERLAREQLALEHESYEMAEARFRKMFERQLKAGEVADNAAAKPLITTL

LPKMIARINDWFEEVKAKRGKRPTAFQFLQEIKPEAVAYITIKTTLACLTSADNTTVQAVASAIGRAIEDEARFGRI

RDLEAKHFKKNVEEQLNKRVGHVYKKAFMQVVEADMLSKGLLGGEAWSSWHKEDSIHVGVRCIEMLIESTGMVSLHR

QNAGVVGQDSETIELAPEYAEAIATRAGALAGISPMFQPCVVPPKPWTGITGGGYWANGRRPLALVRTHSKKALMRY

EDVYMPEVYKAINIAQNTAWKINKKVLAVANVITKWKHCPVEDIPAIEREELPMKPEDIDMNPEALTAWKRAAAAVY

RKDKARKSRRISLEFMLEQANKFANHKAIWFPYNMDWRGRVYAVSMFNPQGNDMTKGLLTLAKGKPIGKEGYYWLKI

HGANCAGVDKVPFPERIKFIEENHENIMACAKSPLENTWWAEQDSPFCFLAFCFEYAGVQHHGLSYNCSLPLAFDGS

CSGIQHFSAMLRDEVGGRAVNLLPSETVQDIYGIVAKKVNEILQADAINGTDNEVVTVTDENTGEISEKVKLGTKAL

AGQWLAYGVTRSVTKRSVMTLAYGSKEFGFRQQVLEDTIQPAIDSGKGLMFTQPNQAAGYMAKLIWESVSVTVVAAV
```

EAMNWLKSAAKLLAAEVKDKKTGEILRKRCAVHWVTPDGFPVWQEYKKPIQTRLNLMFLGQFRLQPTINTNKDSEID

AHKQESGIAPNFVHSQDGSHLRKTVVWAHEKYGIESFALIHDSFGTIPADAANLFKAVRETMVDTYESCDVLADFYD

QFADQLHESQLDKMPALPAKGNLNLRDILESDFAFAG

EXAMPLES

Example 1. Production of RNA Polymerases Variants

RNA polymerase variants were generated with the substitutions shown in Tables 2-6.

TABLE 2

RNA Polymerase Variants

| RNA Polymerase Variants | Amino Acid Sequence | SEQ ID NO |
|---|---|---|
| | For the amino acid sequences of SEQ ID NO: 2-14, 45-48, and 242-247, X may be any amino acid selected from R, K, H, E, D, Q, N, T, S, C, G, A, V, L, I, M, P, Y, W, and F. | |
| G47X | MNTINIAKNDFSDIELAAIPFNTLADHYGERLAREQLALEHESYEMXEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 2 |
| E350X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVXDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 3 |
| D351X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEXIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV | 4 |

TABLE 2-continued

RNA Polymerase Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFA | |
| K387X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRXDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 5 |
| R394X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSXRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 6 |
| R425X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>XVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 7 |
| Y427X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVXAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 8 |

TABLE 2-continued

RNA Polymerase Variants

| RNA Polymerase Variants | Amino Acid Sequence | SEQ ID NO |
|---|---|---|
| N437X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGXDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 9 |
| K441X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTXGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 10 |
| R632X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKXSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 11 |
| H811X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIXDSFGTIPADAANLFKAVRETMVDTYESCDVLADFYDQ FADQLHESQLDKMPALPAKGNLNLRDILESDFAFA | 12 |

TABLE 2-continued

RNA Polymerase Variants

| RNA Polymerase Variants | Amino Acid Sequence | SEQ ID NO |
|---|---|---|
| F880X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDXAFA | 13 |
| 884X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAX | 14 |
| D506X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQXSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 45 |
| S628X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRXVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 46 |

TABLE 2-continued

RNA Polymerase Variants

| RNA Polymerase Variants | Amino Acid Sequence | SEQ ID NO |
|---|---|---|
| D653X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEXTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 47 |
| P657X | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQXAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 48 |

TABLE 3

Exemplary Single-Substitution Variants

| RNA Polymerase Variants | Amino Acid Sequence | SEQ ID NO |
|---|---|---|
| G47A | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 15 |
| E350K | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVKDIPAIEREELPMKPEDIDMNP EALTAWKRAAAAVYRKDKARKSRRISLEFMLEQANKFANHKAIWFPYNMDWRG | 16 |

TABLE 3-continued

Exemplary Single-Substitution Variants

| RNA Polymerase Variants | Amino Acid Sequence | SEQ ID NO |
|---|---|---|
| | RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | |
| E350N | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVNDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 17 |
| E350A | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 18 |
| E350W | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVWDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 19 |
| D351V | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEVIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC | 20 |

TABLE 3-continued

Exemplary Single-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | |
| K387S | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 21 |
| K387H | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 22 |
| K387N | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 23 |
| D506W | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQWSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT | 49 |

TABLE 3-continued

Exemplary Single-Substitution Variants

| RNA Polymerase Variants | Amino Acid Sequence | SEQ ID NO |
|---|---|---|
| | LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | |
| S628W | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 50 |
| D653W | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 51 |
| P657W | MNTINIAKNDFSDIELAAIPFNTLADHYGERLAREQLALEHESYEMGEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 52 |

TABLE 4

Exemplary Multi-Substitution Variants

| RNA Polymerase Variants | Amino Acid Sequence | SEQ ID NO |
|---|---|---|
| G47A E350K | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA | 24 |

TABLE 4-continued

Exemplary Multi-Substitution Variants

| RNA Polymerase Variants | Amino Acid Sequence | SEQ ID NO |
|---|---|---|
| | KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVKDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | |
| G47A<br>E350N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVNDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 25 |
| G47A<br>E350A | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 26 |
| G47A<br>E350W | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVWDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 27 |
| G47A<br>D351V | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS | 28 |

TABLE 4-continued

Exemplary Multi-Substitution Variants

| RNA Polymerase Variants | Amino Acid Sequence | SEQ ID NO |
|---|---|---|
| | PMFQPCVVPPKPWTGITGGGYWANGRRPLALVRTHSKKALMRYEDVYMPEVYK AINIAQNTAWKINKKVLAVANVITKWKHCPVEVIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | |
| G47A K387S | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 29 |
| G47A K387H | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 30 |
| G47A K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 31 |
| G47A D506W | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP | 53 |

TABLE 4-continued

Exemplary Multi-Substitution Variants

| RNA Polymerase Variants | Amino Acid Sequence | SEQ ID NO |
|---|---|---|
| | EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQWSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | |
| G47A S628W | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 54 |
| G47A D653W | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 55 |
| G47A P657W | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFA | 56 |

TABLE 5

Exemplary Multi-Substitution + C-Terminal G Variants

| RNA Polymerase Variants | Amino Acid Sequence | SEQ ID NO |
|---|---|---|
| G47A E350K C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVKDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 32 |
| G47A E350N C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 33 |
| G47A E350A C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVADIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 34 |
| G47A E350W C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 35 |

TABLE 5-continued

Exemplary Multi-Substitution + C-Terminal G Variants

| RNA Polymerase Variants | Amino Acid Sequence | SEQ ID NO |
|---|---|---|
| G47A D351V C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEVIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 36 |
| G47A K387S C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 37 |
| G47A K387H C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 38 |
| G47A K387N C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 39 |

TABLE 5-continued

| Exemplary Multi-Substitution + C-Terminal G Variants | | |
|---|---|---|
| RNA Polymerase Variants | Amino Acid Sequence | SEQ ID NO |
| G47A<br>D506W<br>C-Terminal G | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQWSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 57 |
| G47A<br>S628W<br>C-Terminal G | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRWVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 58 |
| G47A<br>D653W<br>C-Terminal G | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 59 |
| G47A<br>P657W<br>C-Terminal G | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 60 |

TABLE 6

Additional Multi-Substitution Variants

| RNA Polymerase Variants | Amino Acid Sequence | SEQ ID NO |
|---|---|---|
| G47A E350X$_1$, wherein X$_1$ is A, K, N, or W D351V K387X$_2$, wherein X$_2$ is S, H, or N C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVX$_1$VIPAIEREELPMKPEDIDMN PEALTAWKRAAAAVYRX$_2$DKARKSRRISLEFMLEQANKFANHKAIWFPYNMDW RGRVYAVSMFNPQGNDMTKGLLTLAKGKPIGKEGYYWLKIHGANCAGVDKVPF PERIKFIEENHENIMACAKSPLENTWWAEQDSPFCFLAFCFEYAGVQHHGLSY NCSLPLAFDGSCSGIQHFSAMLRDEVGGRAVNLLPSETVQDIYGIVAKKVNEI LQADAINGTDNEVVTVTDENTGEISEKVKLGTKALAGQWLAYGVTRSVTKRSV MTLAYGSKEFGFRQQVLEDTIQPAIDSGKGLMFTQPNQAAGYMAKLIWESVSV TVVAAVEAMNWLKSAAKLLAAEVKDKKTGEILRKRCAVHWVTPDGFPVWQEYK KPIQTRLNLMFLGQFRLQPTINTNKDSEIDAHKQESGIAPNFVHSQDGSHLRK TVVWAHEKYGIESFALIHDSFGTIPADAANLFKAVRETMVDTYESCDVLADFY DQFADQLHESQLDKMPALPAKGNLNLRDILESDFAFAG | 40 |
| G47A N437X$_1$, wherein X$_1$ is T, Y, 1, or F K441R C-Terminal G | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGXDMTRGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 41 |
| G47A F880Y C-Terminal X, wherein X is A, S, T, or P | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDYAFAX | 42 |
| G47A R632X$_1$, wherein X$_1$ is K or T D653X$_2$, wherein X$_2$ is T or K P657X$_3$, wherein X$_3$ is W, R, or A C-Terminal G | MNTINIAKNDFSDIELAAIPFNTLADHYGERLAREQLALEHESYEMEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKX$_1$SVM TLAYGSKEFGFRQQVLEX$_2$TIQX$_3$AIDSGKGLMFTQPNQAAGYMAKLIWESVS VTVVAAVEAMNWLKSAAKLLAAEVKDKKTGEILRKRCAVHWVTPDGFPVWQEY KKPIQTRLNLMFLGQFRLQPTINTNKDSEIDAHKQESGIAPNFVHSQDGSHLR KTVVWAHEKYGIESFALIHDSFGTIPADAANLFKAVRETMVDTYESCDVLADF YDQFADQLHESQLDKMPALPAKGNLNLRDILESDFAFAG | 43 |

TABLE 6-continued

Additional Multi-Substitution Variants

| RNA Polymerase Variants | Amino Acid Sequence | SEQ ID NO |
|---|---|---|
| G47A, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 61 |
| G47A, G884T | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 62 |
| G47A, G884T, K387N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 63 |
| G47A, G884S | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAS | 64 |

TABLE 6-continued

Additional Multi-Substitution Variants

| RNA Polymerase Variants | Amino Acid Sequence | SEQ ID NO |
|---|---|---|
| G47A, G884S, K387N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAS | 65 |
| G47A, G884P | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAP | 66 |
| G47A, G884P, K387N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAP | 67 |
| G47A, D653W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 68 |

TABLE 6-continued

Additional Multi-Substitution Variants

| RNA Polymerase Variants | Amino Acid Sequence | SEQ ID NO |
|---|---|---|
| G47A, D653W, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 69 |
| G47A, D653W, G884T | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 70 |
| G47A, D653W, G884T, K387N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 71 |
| G47A, D653W, G884S | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAS | 72 |

TABLE 6-continued

Additional Multi-Substitution Variants

| RNA Polymerase Variants | Amino Acid Sequence | SEQ ID NO |
|---|---|---|
| G47A, D653W, G884S, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAS | 73 |
| G47A, D653W, G884P | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 74 |
| G47A, D653W, G884P, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 75 |
| G47A, D653T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLETTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 76 |

TABLE 6-continued

Additional Multi-Substitution Variants

| RNA Polymerase Variants | Amino Acid Sequence | SEQ ID NO |
|---|---|---|
| G47A, D653T, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 77 |
| G47A, D653T, G884T | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 78 |
| G47A, D653T, G884T, K387N | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 79 |
| G47A, D653T, G884S | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAS | 80 |

TABLE 6-continued

Additional Multi-Substitution Variants

| RNA Polymerase Variants | Amino Acid Sequence | SEQ ID NO |
|---|---|---|
| G47A, D653T, G884S, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLETTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAS | 81 |
| G47A, D653T, G884P | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLETTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 82 |
| G47A, D653T, G884P, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLETTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 83 |
| G47A, D653K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT | 84 |

TABLE 6-continued

Additional Multi-Substitution Variants

| RNA Polymerase Variants | Amino Acid Sequence | SEQ ID NO |
|---|---|---|
| | LAYGSKEFGFRQQVLEKTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653K, K387N, G884 | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEKTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 85 |
| G47A, D653K, G884T | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEKTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 86 |
| G47A, D653K, G884T, K387N | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEKTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAT | 87 |
| G47A, D653K, G884S | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEKTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP | 88 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAS | |
| G47A, D653K, G884S, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAS | 89 |
| G47A, D653K, G884P | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 90 |
| G47A, D653K, G884P, K387N | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAP | 91 |
| G47A, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC | 92 |

TABLE 6-continued

Additional Multi-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, K387H, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRHDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 93 |
| G47A, E350A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 94 |
| G47A, E350A, K387S, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRSDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 95 |
| G47A, E350A, K387H, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRHDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT | 96 |

TABLE 6-continued

Additional Multi-Substitution Variants

| RNA Polymerase Variants | Amino Acid Sequence | SEQ ID NO |
|---|---|---|
| | LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, E350A, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVADIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 97 |
| G47A, E350K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVKDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 98 |
| G47A, E350K, K387S, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVKDIPAIEREELPMKPEDIDMNP<br>EALTAWKRAAAAVYRSDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 99 |
| G47A, E350K, K387H, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVKDIPAIEREELPMKPEDIDMNP<br>EALTAWKRAAAAVYRHDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP | 100 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, E350K, K387N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVKDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 101 |
| G47A, E350N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 102 |
| G47A, E350N, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 103 |
| G47A, E350N, K387H, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNDIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ | 104 |

TABLE 6-continued

Additional Multi-Substitution Variants

| RNA Polymerase Variants | Amino Acid Sequence | SEQ ID NO |
|---|---|---|
| | FADQLHESQLDKMPALPAKGNLNLRDILESDFAFAG | |
| G47A, E350N, K387N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 105 |
| G47A, E350W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 106 |
| G47A, E350W, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWDIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 107 |
| G47A, E350W, K387H, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWDIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT | 108 |

TABLE 6-continued

Additional Multi-Substitution Variants

| RNA Polymerase Variants | Amino Acid Sequence | SEQ ID NO |
|---|---|---|
| | LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, E350W, K387N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWDIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 109 |
| G47A, D351V, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEVIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 110 |
| G47A, D351V, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEVIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 111 |
| G47A, D351V, K387H, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEVIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP | 112 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D351V, K387N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEVIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 113 |
| G47A, D351V, E350A, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVAVIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 114 |
| G47A, D351V, E350A, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVAVIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 115 |
| G47A, D351V, E350A, K387H, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVAVIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV | 116 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D351V, E350A, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVAVIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 117 |
| G47A, D351V, E350K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVKVIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 118 |
| G47A, D351V, E350K, K387S, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVKVIPAIEREELPMKPEDIDMNP<br>EALTAWKRAAAAVYRSDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 119 |
| G47A, D351V, E350K, K387H, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVKVIPAIEREELPMKPEDIDMNP<br>EALTAWKRAAAAVYRHDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV | 120 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D351V,<br>E350K, K387N,<br>G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVKVIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 121 |
| G47A, D351V,<br>E350N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVNVIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 122 |
| G47A, D351V,<br>E350N, K387S,<br>G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVNVIPAIEREELPMKPEDIDMNP<br>EALTAWKRAAAAVYRSDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 123 |
| G47A, D351V,<br>E350N, K387H,<br>G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVNVIPAIEREELPMKPEDIDMNP<br>EALTAWKRAAAAVYRHDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 124 |

TABLE 6-continued

Additional Multi-Substitution Variants

| RNA Polymerase Variants | Amino Acid Sequence | SEQ ID NO |
|---|---|---|
| G47A, D351V, E350N, K387N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVNVIPAIEREELPMKPEDIDMNP EALTAWKRAAAAVYRNDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 125 |
| G47A, D351V, E350W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWVIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 126 |
| G47A, D351V, E350W, K387S, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWVIPAIEREELPMKPEDIDMNP EALTAWKRAAAAVYRSDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 127 |
| G47A, D351V, E350W, K387H, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVWVIPAIEREELPMKPEDIDMNP EALTAWKRAAAAVYRHDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV | 128 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D351V, E350W, K387N, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVWVIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 129 |
| G47A, D653A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEATIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 130 |
| G47A, D653F, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEFTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 131 |
| G47A, D653G, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEGTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV | 132 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653H, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEHTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 133 |
| G47A, D653I, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEITIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 134 |
| G47A, D653L, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLELTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 135 |
| G47A, D653M, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEMTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 136 |

TABLE 6-continued

Additional Multi-Substitution Variants

| RNA Polymerase Variants | Amino Acid Sequence | SEQ ID NO |
|---|---|---|
| G47A, D653N, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLENTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 137 |
| G47A, D653P, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEPTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 138 |
| G47A, D653Q, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEQTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 139 |
| G47A, D653R, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLERTIQPAIDSGKGLMFTQPNQAAGYMAKLIWESVSVTV | 140 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653S, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLESTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 141 |
| G47A, D653V, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEVTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 142 |
| G47A, D653Y, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEYTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 143 |
| G47A, P657W, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV | 144 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFAG | |
| G47A, P657R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 145 |
| G47A, P657A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 146 |
| G47A, D653W, P657W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 147 |
| G47A, D653W, P657R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 148 |

TABLE 6-continued

Additional Multi-Substitution Variants

| RNA Polymerase Variants | Amino Acid Sequence | SEQ ID NO |
|---|---|---|
| G47A, D653W, P657A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEWTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 149 |
| G47A, D653T, P657W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 150 |
| G47A, D653T, P657R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 151 |
| G47A, D653T, P657A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT | 152 |

TABLE 6-continued

Additional Multi-Substitution Variants

| RNA Polymerase Variants | Amino Acid Sequence | SEQ ID NO |
|---|---|---|
| | LAYGSKEFGFRQQVLETTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653K, P657W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 153 |
| G47A, D653K, P657R, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 154 |
| G47A, D653K, P657A, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEKTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 155 |
| G47A, N437T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGTDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP | 156 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, N437Y, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGYDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 157 |
| G47A, N437I, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGIDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 158 |
| G47A, N437F, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGFDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 159 |
| G47A, K441R, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTRGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT | 160 |

TABLE 6-continued

Additional Multi-Substitution Variants

| RNA Polymerase Variants | Amino Acid Sequence | SEQ ID NO |
|---|---|---|
| | LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, K441R, N437T, G884 | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGTDMTRGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 161 |
| G47A, K441R, N437Y, G884 | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGYDMTRGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 162 |
| G47A, K441R, N437I, G884 | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGIDMTRGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 163 |
| G47A, K441R, N437F, G884 | MNTINIAKNDFSDIELAAIPFNTLADHYGERLAREQLALEHESYEMAAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGFDMTRGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP | 164 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, S628W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 165 |
| G47A, D506W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQWSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 166 |
| G47A, D506W, S628W, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQWSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 167 |
| G47A, D506F, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQFSPFCFLAFCFEYAGVQHHGLSYNC | 168 |

TABLE 6-continued

Additional Multi-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D506F, S628W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQFSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRWVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 169 |
| G47A, D506Y, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQYSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 170 |
| G47A, D506Y, S628W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQYSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRWVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMLFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 171 |
| G47A, D506R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQRSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT | 172 |

TABLE 6-continued

Additional Multi-Substitution Variants

| RNA Polymerase Variants | Amino Acid Sequence | SEQ ID NO |
|---|---|---|
| | LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D506R, S628W, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQRSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 173 |
| G47A, D506L, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQLSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 174 |
| G47A, D506L, S628W, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQLSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRWVTKRSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 175 |
| G47A, D653C, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLECTIQPAIDSGKGLMFTQPNQAAGYMAKLIWESVSVTV VAAVEAMNWLKSAAKLLAAEVKDKKTGEILRKRCAVHWVTPDGFPVWQEYKKP | 176 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653E, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEETIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 177 |
| G47A, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 178 |
| G47A, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEDTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 179 |
| G47A, P657W, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC | 180 |

TABLE 6-continued

Additional Multi-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEDTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, P657W, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEDTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 181 |
| G47A, P657R, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEDTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 182 |
| G47A, P657R, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEDTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 183 |
| G47A, P657A, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT | 184 |

TABLE 6-continued

Additional Multi-Substitution Variants

| RNA Polymerase Variants | Amino Acid Sequence | SEQ ID NO |
|---|---|---|
| | LAYGSKEFGFRQQVLEDTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, P657A, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEDTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 185 |
| G47A, D653W, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 186 |
| G47A, D653W, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEWTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 187 |
| G47A, D653W, P657W, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEWTIQWAIDSGKGLMFTQPNQAAGYMAKLIWESVSVTV VAAVEAMNWLKSAAKLLAAEVKDKKTGEILRKRCAVHWVTPDGFPVWQEYKKP | 188 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653W, P657W, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEWTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 189 |
| G47A, D653W, P657R, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEWTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 190 |
| G47A, D653W, P657R, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEWTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 191 |
| G47A, D653W, P657A, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ | 192 |

TABLE 6-continued

Additional Multi-Substitution Variants

| RNA Polymerase Variants | Amino Acid Sequence | SEQ ID NO |
|---|---|---|
| | ADAINGTDNEVVTVTDENTGEISEKVKLGTKALAGQWLAYGVTRSVTKKSVMT<br>LAYGSKEFGFRQQVLEWTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653W, P657A, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEWTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 193 |
| G47A, D653F, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEFTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 194 |
| G47A, D653F, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEFTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 195 |
| G47A, D653F, P657W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEFTIQWAIDSGKGLMFTQPNQAAGYMAKLIWESVSVTV | 196 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653F, P657W, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEFTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 197 |
| G47A, D653F, P657W, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEFTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 198 |
| G47A, D653F, P657R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEFTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 199 |
| G47A, D653F, P657R, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEFTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV | 200 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ FADQLHESQLDKMPALPAKGNLNLRDILESDFAFAG | |
| G47A, D653F, P657R, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEFTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 201 |
| G47A, D653F, P657A, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKRSVMT LAYGSKEFGFRQQVLEFTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 202 |
| G47A, D653F, P657A, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEFTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 203 |
| G47A, D653F, P657A, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE | 204 |

TABLE 6-continued

Additional Multi-Substitution Variants

| RNA Polymerase Variants | Amino Acid Sequence | SEQ ID NO |
|---|---|---|
| | RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEFTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653Y, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEYTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 205 |
| G47A, D653Y, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEYTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 206 |
| G47A, D653Y, P657W, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEYTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 207 |
| G47A, D653Y, P657W, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ | 208 |

TABLE 6-continued

Additional Multi-Substitution Variants

| RNA Polymerase Variants | Amino Acid Sequence | SEQ ID NO |
|---|---|---|
| | ADAINGTDNEVVTVTDENTGEISEKVKLGTKALAGQWLAYGVTRSVTKKSVMT<br>LAYGSKEFGFRQQVLEYTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653Y, P657W, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEYTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 209 |
| G47A, D653Y, P657R, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEYTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 210 |
| G47A, D653Y, P657R, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEYTIQRAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 211 |
| G47A, D653Y, P657R, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEYTIQRAIDSGKGLMFTQPNQAAGYMAKLIWESVSVTV | 212 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653Y, P657A, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEYTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 213 |
| G47A, D653Y, P657A, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLEYTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 214 |
| G47A, D653Y, P657A, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLEYTIQAAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 215 |
| G47A, D653T, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV | 216 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFAG | |
| G47A, D653T, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGIGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 217 |
| G47A, D653T, P657W, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGIGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKKSVMT<br>LAYGSKEFGFRQQVLETTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 218 |
| G47A, D653T, P657W, R632T, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGIGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKTSVMT<br>LAYGSKEFGFRQQVLETTIQWAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFAG | 219 |
| G47A, D653T, P657R, R632K, G884 | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGIGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC | 220 |

TABLE 6-continued

Additional Multi-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTTKKSVMT LAYGSKEFGFRQQVLETTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653T, P657R, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLETTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 221 |
| G47A, D653T, P657A, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTTKKSVMT LAYGSKEFGFRQQVLETTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 222 |
| G47A, D653T, P657A, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLETTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 223 |
| G47A, D653K, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTTKKSVMT | 224 |

TABLE 6-continued

Additional Multi-Substitution Variants

| RNA Polymerase Variants | Amino Acid Sequence | SEQ ID NO |
|---|---|---|
| | LAYGSKEFGFRQQVLEKTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653K, R632T, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEKTIQPAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 225 |
| G47A, D653K, P657W, R632K, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEKTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 226 |
| G47A, D653K, P657W, R632T, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEKTIQWAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 227 |
| G47A, D653K, P657R, R632K, G884 | MNTINIAKNDFSDIELAAIPFNTLADHYGERLAREQLALEHESYEMAAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVYMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEKTIQRAIDSGKGLMFTQPNQAAGYMAKLIWESVSVTV VAAVEAMNWLKSAAKLLAAEVKDKKTGEILRKRCAVHWVTPDGFPVWQEYKKP | 228 |

TABLE 6-continued

Additional Multi-Substitution Variants

| RNA Polymerase Variants | Amino Acid Sequence | SEQ ID NO |
|---|---|---|
| | IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | |
| G47A, D653K, P657R, R632T, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEKTIQRAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 229 |
| G47A, D653K, P657A, R632K, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKKSVMT LAYGSKEFGFRQQVLEKTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 230 |
| G47A, R632T, D653K, P657A, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ ADAINGTDNEVVTVTDENTGEISEKVKLGTKALAGQWLAYGVTRSVTKTSVMT LAYGSKEFGFRQQVLEKTIQAAIDSGKGLMFTQPNQAAGYMAKLIWESVSVTV VAAVEAMNWLKSAAKLLAAEVKDKKTGEILRKRCAVHWVTPDGFPVWQEYKKP IQTRLNLMFLGQFRLQPTINTNKDSEIDAHKQESGIAPNFVHSQDGSHLRKTV VWAHEKYGIESFALIHDSFGTIPADAANLFKAVRETMVDTYESCDVLADFYDQ FADQLHESQLDKMPALPAKGNLNLRDILESDFAFAG | 231 |
| G47A, F880Y, G884 | MNTINIAKNDFSDIELAAIPFNTLADHYGERLAREQLALEHESYEMAEARFRK MFERQLKAGEVADNAAAKPLITTLLPKMIARINDWFEEVKAKRGKRPTAFQFL QEIKPEAVAYITIKTTLACLTSADNTTVQAVASAIGRAIEDEARFGRIRDLEA KHFKKNVEEQLNKRVGHVYKKAFMQVVEADMLSKGLLGGEAWSSWHKEDSIHV GVRCIEMLIESTGMVSLHRQNAGVVGQDSETIELAPEYAEAIATRAGALAGIS PMFQPCVVPPKPWTGITGGGYWANGRRPLALVRTHSKKALMRYEDVVMPEVYK AINIAQNTAWKINKKVLAVANVITKWKHCPVEDIPAIEREELPMKPEDIDMNP EALTAWKRAAAAVYRKDKARKSRRISLEFMLEQANKFANHKAIWFPYNMDWRG RVYAVSMFNPQGNDMTKGLLTLAKGKPIGKEGYYWLKIHGANCAGVDKVPFPE RIKFIEENHENIMACAKSPLENTWWAEQDSPFCFLAFCFEYAGVQHHGLSYNC SLPLAFDGSCSGIQHFSAMLRDEVGGRAVNLLPSETVQDIYGIVAKKVNEILQ | 232 |

TABLE 6-continued

Additional Multi-Substitution Variants

| RNA Polymerase Variants | Amino Acid Sequence | SEQ ID NO |
|---|---|---|
|  | ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDYAFAG |  |
| G47A, F880Y, G884S | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDYAFAS | 233 |
| G47A, F880Y, G884T | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDYAFAT | 234 |
| G47A, F880Y, G884P | MNTINIAKNDFSDIELAAIPFNTLADHYGERLAREQLALEHESYEMAEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDYAFAP | 235 |
| E350W, D351V | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVWVIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV | 236 |

TABLE 6-continued

Additional Multi-Substitution Variants

| RNA Polymerase Variants | Amino Acid Sequence | SEQ ID NO |
|---|---|---|
| | VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | |
| E350W, K387N | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVWDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 237 |
| E350W, D653T | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVWDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 238 |
| D351V, K387N | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEVIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 239 |
| D351V, D653T | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVMPEVYK<br>AINIAQNTAWKINKKVLAVANVITKWKHCPVEVIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV | 240 |

TABLE 6-continued

Additional Multi-Substitution Variants

| RNA Polymerase Variants | Amino Acid Sequence | SEQ ID NO |
|---|---|---|
| | VWAHEKYGIESFALIHDSFGTIPADAANLFKAVRETMVDTYESCDVLADFYDQ<br>FADQLHESQLDKMPALPAKGNLNLRDILESDFAFA | |
| K387N, D653T | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVYMPEVYK<br>AINIAQNTAWKINKKVLAVANVITKWKHCPVEDIPAIEREELPMKPEDIDMNP<br>EALTAWKRAAAAVYRNDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLETTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 241 |
| E350X, D351X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVYMPEVYK<br>AINIAQNTAWKINKKVLAVANVITKWKHCPVXXIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 242 |
| E350X, K387X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVYMPEVYK<br>AINIAQNTAWKINKKVLAVANVITKWKHCPVXDIPAIEREELPMKPEDIDMNP<br>EALTAWKRAAAAVYRXDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 243 |
| E350X, D653X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVVYMPEVYK<br>AINIAQNTAWKINKKVLAVANVITKWKHCPVXDIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTAKGKPIGKEGYYWLKIHGANCAGVDKVPFPE<br>RIKFIEENHENIMACAKSPLENTWWAEQDSPFCFLAFCFEYAGVQHHGLSYNC | 244 |

TABLE 6-continued

Additional Multi-Substitution Variants

| RNA Polymerase Variants | Amino Acid Sequence | SEQ ID NO |
|---|---|---|
| | SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEXTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | |
| D351X, K387X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEXIPAIEREELPMKPEDIDMNP<br>EALTAWKRAAAAVYRXDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEDTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 245 |
| D351X, D653X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEXIPAIEREELPMKPEDIDMNP<br>EALTAWKRAAAAVYRKDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEXTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 246 |
| K387X, D653X | MNTINIAKNDFSDIELAAIPFNTLADHYGERLAREQLALEHESYEMGEARFRK<br>MFERQLKAGEVADNAAAKPLITTLLPKMIARINDWFEEVKAKRGKRPTAFQFL<br>QEIKPEAVAYITIKTTLACLTSADNTTVQAVASAIGRAIEDEARFGRIRDLEA<br>KHFKKNVEEQLNKRVGHVYKKAFMQVVEADMLSKGLLGGEAWSSWHKEDSIHV<br>GVRCIEMLIESTGMVSLHRQNAGVVGQDSETIELAPEYAEAIATRAGALAGIS<br>PMFQPCVVPPKPWTGITGGGYWANGRRPLALVRTHSKKALMRYEDVYMPEVYK<br>AINIAQNTAWKINKKVLAVANVITKWKHCPVEDIPAIEREELPMKPEDIDMNP<br>EALTAWKRAAAAVYRXDKARKSRRISLEFMLEQANKFANHKAIWFPYNMDWRG<br>RVYAVSMFNPQGNDMTKGLLTLAKGKPIGKEGYYWLKIHGANCAGVDKVPFPE<br>RIKFIEENHENIMACAKSPLENTWWAEQDSPFCFLAFCFEYAGVQHHGLSYNC<br>SLPLAFDGSCSGIQHFSAMLRDEVGGRAVNLLPSETVQDIYGIVAKKVNEILQ<br>ADAINGTDNEVVTVTDENTGEISEKVKLGTKALAGQWLAYGVTRSVTKRSVMT<br>LAYGSKEFGFRQQVLEXTIQPAIDSGKGLMFTQPNQAAGYMAKLIWESVSVTV<br>VAAVEAMNWLKSAAKLLAAEVKDKKTGEILRKRCAVHWVTPDGFPVWQEYKKP<br>IQTRLNLMFLGQFRLQPTINTNKDSEIDAHKQESGIAPNFVHSQDGSHLRKTV<br>VWAHEKYGIESFALIHDSFGTIPADAANLFKAVRETMVDTYESCDVLADFYDQ<br>FADQLHESQLDKMPALPAKGNLNLRDILESDFAFA | 247 |

Example 2. IVT Reactions Using Multi-Substitution+C-Terminal G RNA Polymerase Variants In vitro transcription (IVT) reactions were performed using DNA template, GAG cap analog, and multi-substitution+C-Terminal G RNA polymerase variants, as provided in Table 5. All polymerase variants used in this example included a G47A mutation, a C-Terminal G addition, and one further genetic substitution at position E350, D351, K487, R394, R425, Y427, N437, K441, R632, H811, F880, or G884.

The following RNA polymerase variants generated yields of total RNA in IVT reactions that were 60% to >100% of the total yields in control IVT reactions performed using a control RNA polymerase variant (G47A+C-terminal G): E350R, E350K, E350D, E350Q, E350N, E350T, E350S, E350C, E350G, E350A, E350V, E350L, E350I, E350P, E350Y, E350W, and E350F; D351R, D351K, D351Q, D351T, D351S, D351C, D351V, D351L, D351I, D351M, D351P, D351Y, and D351W; K387R, K387H, K387T, K387S, K387V, K387L, K387I, and K387M; R394K; N437Q, N437T, N437S, N437G, and N437F; F880Y; and 884S and 884A (C-terminal additions) (data not shown).

The following RNA polymerase variants generated RNA with levels of 3' homogeneity in IVT reactions that were equivalent to, or higher than levels of 3' homogeneity in RNA produced in control IVT reactions performed using a control RNA polymerase variant (G47A+C-terminal G): E350N, E350C, E350G, E350Y, E350W, and E350F; D351R, D351S, D351L, D351M, and D351Y; K387R, K387T, K387L, and K387M; R394K; N437R, N437K, N437H, N437T, N437V, N437I, and N437W; R632K and R632T; and 884Q, 884T, and 884P (C-terminal additions) (data not shown).

The following RNA polymerase variants generated RNA with equivalent or higher (up to 20% increase) % capped RNA (percentage of total RNA comprising a GAG cap) relative to RNA produced in control IVT reactions performed using a control RNA polymerase variant (G47A+C-terminal G): E350R, E350K, E350D, E350Q, E350N, E350T, E350S, E350C, E350G, E350A, E350V, E350L, E350I, E350Y, E350W, and E350F; D351R, D351K, D351Q, D35IT, D351C, D351V, D351L, D351M, and D351W; K387H, K387E, K387N, K387T, K387S, K387G, K387A, K387Y, K387W, and K387F; N437T, N437I, N437Y, N437W, and N437F; K441R; R632K and R632T; F880Y; and 884Q, 884T, 884S, 884A, and 884P (C-terminal additions) (data not shown).

Example 3. Multi-Substitution+C-Terminal G RNA Polymerase Variants Produce RNA Products with More Desired Characteristics Relative to a Control Polymerase Variant In vitro transcription reactions were performed using DNA template, GAG cap analog (0.75 mM, 2.25 mM, 3.75 mM, and 7.5 mM), and (1) a G47A+C-terminal G RNA polymerase variant (control polymerase variant; G47A+C-terminal G), (2) a G47A/K387S+C-terminal G RNA polymerase variant (K387S), (3) a G47A/K387H+C-terminal G RNA polymerase variant (K387H), (4) a G47A/K387N+C-terminal G RNA polymerase variant (K387N), (5) a G47A/E350K+C-terminal G RNA polymerase variant (E350K), (6) a G47A/E350N+C-terminal G RNA polymerase variant (E350N), (7) a G47A/E350A+C-terminal G RNA polymerase variant (E350A), (8) a G47A/E350W+C-terminal G RNA polymerase variant (E350W), and (9) a G47A/D351V+C-terminal G RNA polymerase variant (D351V). Following IVT reactions, transcribed RNA products from each reaction was characterized to address the quality of said RNA products, including % capping, dsRNA contamination, purity, and 3' homogeneity.

The overall yields of total RNA produced using the multi-substitution variants (K387S, K387H, K387N, E350K, E350N, E350A, E350W, and D351V) were comparable to the yield using control RNA polymerase variant, following an oligo dT purification (FIG. 1A). RNA yield was measured by UV absorption.

Figure 1B:
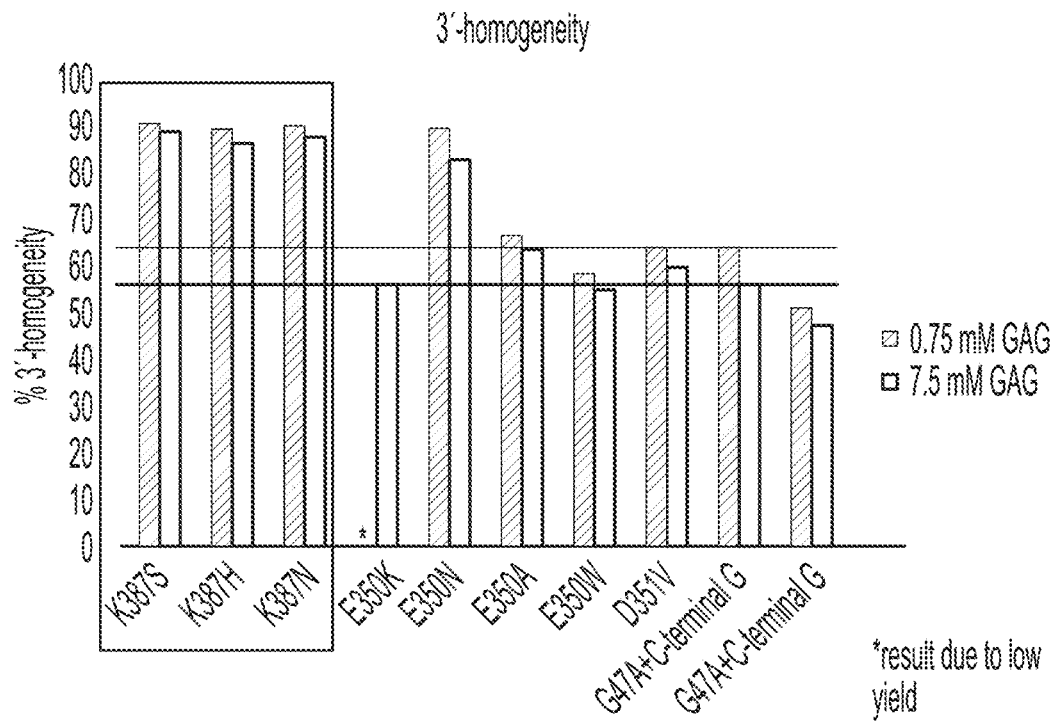

The 3' homogeneity of RNA transcripts were measured using a RNAse T1 digest. RNAse T1 cleaves mRNA specifically after a G nucleotide. Endonucleolytic cleavage results in a 5' hydroxide (OH) and 3' monophosphate (mP) 'scar', while exonucleolytic cleavage results in a clean 5' OH/3' OH cut. Thus, a RNAse T1 digest can be used to differentiate between transcripts that do and do not have non-templated additions at the 3' end. In this Example, RNA produced using the multi-substitution variants had equivalent or higher percent 3' end homogeneity relative to control polymerase variant (FIG. 1B). In particular, as shown in FIG. 1B, K387S, K387H, K387N, and E350N variants produced RNA comprising 3' homogenous ends that was >20 percentage points higher than control variant.

Figure 1C:
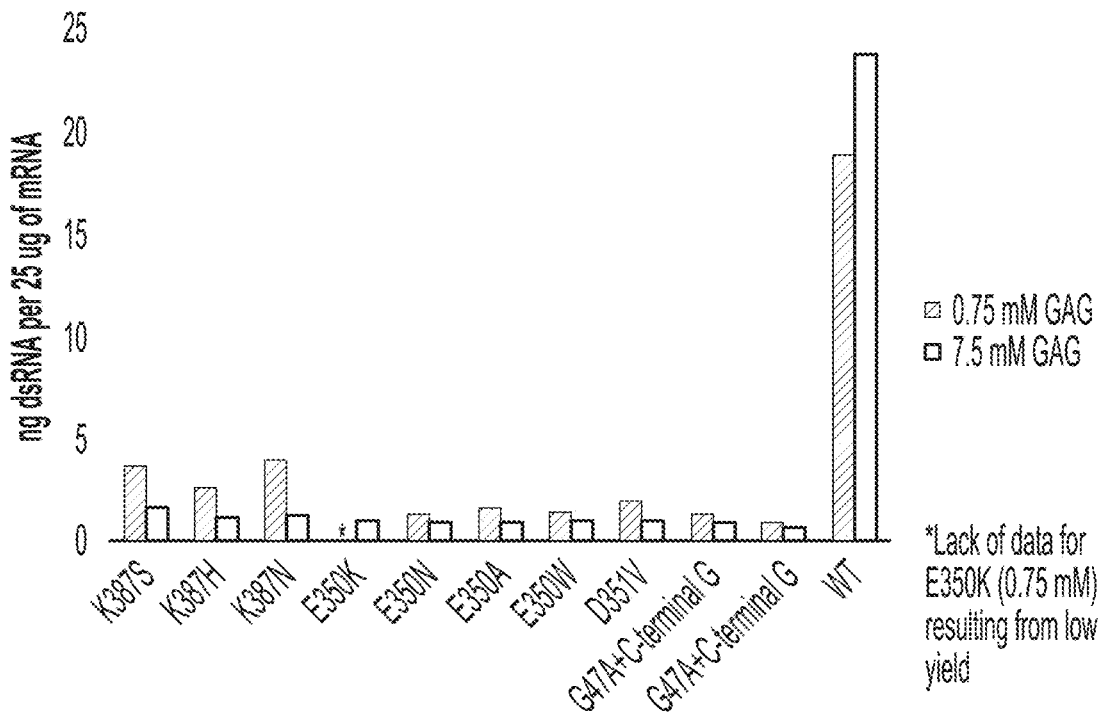
Figure 1C:
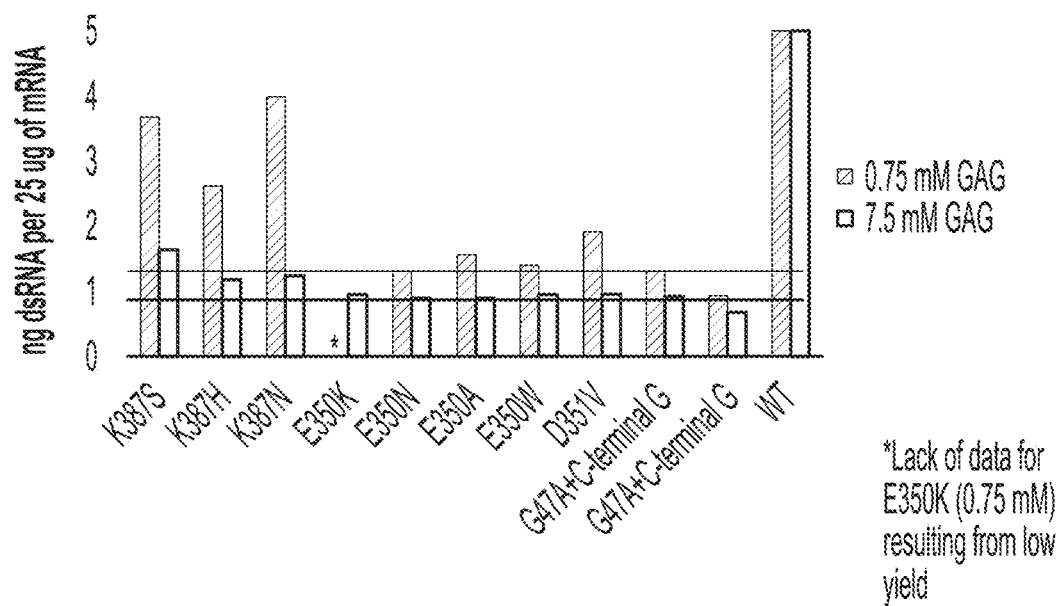

A standard ELISA was used to assess dsRNA contaminants (e.g., dsRNA longer than 40 nucleotide base pairs) following IVT reactions in this Example. All IVT reaction mixtures resulting from multi-substitution variants and the control variant contained less than ~4 ng dsRNA per 25 μg of mRNA (FIG. 1C). Conversely, IVT reaction mixtures resulting from WT T7 polymerase contain ~20 ng dsRNA per 25 μg of mRNA.

Figure 1D:
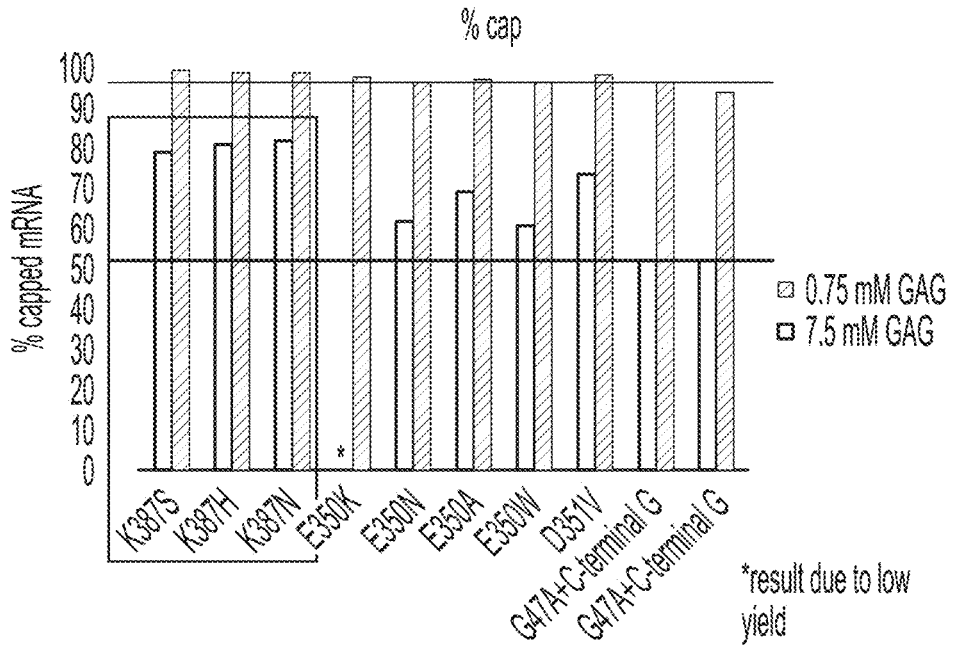
Figure 1E:
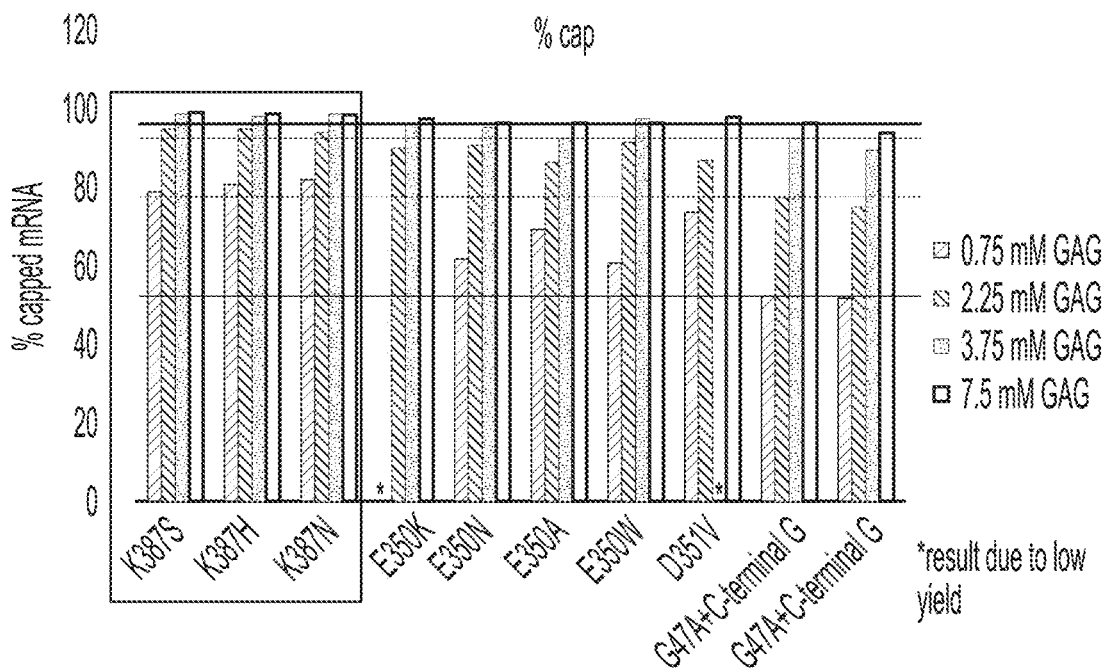

The total RNA products were analyzed by LC-MS to determine % capped RNA (i.e., percent of transcribed RNA comprising a GAG cap). All multi-substitution variants produced RNA with higher levels of % capped RNA relative to control variant (FIGS. 1D-1E) at low and high amounts of GAG cap analog in the starting IVT reaction. In particular, as shown in FIG. 1D-1E, K387S, K387H, K387N, E350A, and D351V variants produced RNA with % capped RNA levels that were 10-25 percentage points higher than control variant, when using 0.75 mM GAG cap analog, the lowest CAP concentration used in this IVT reaction series.

Figure 1F:
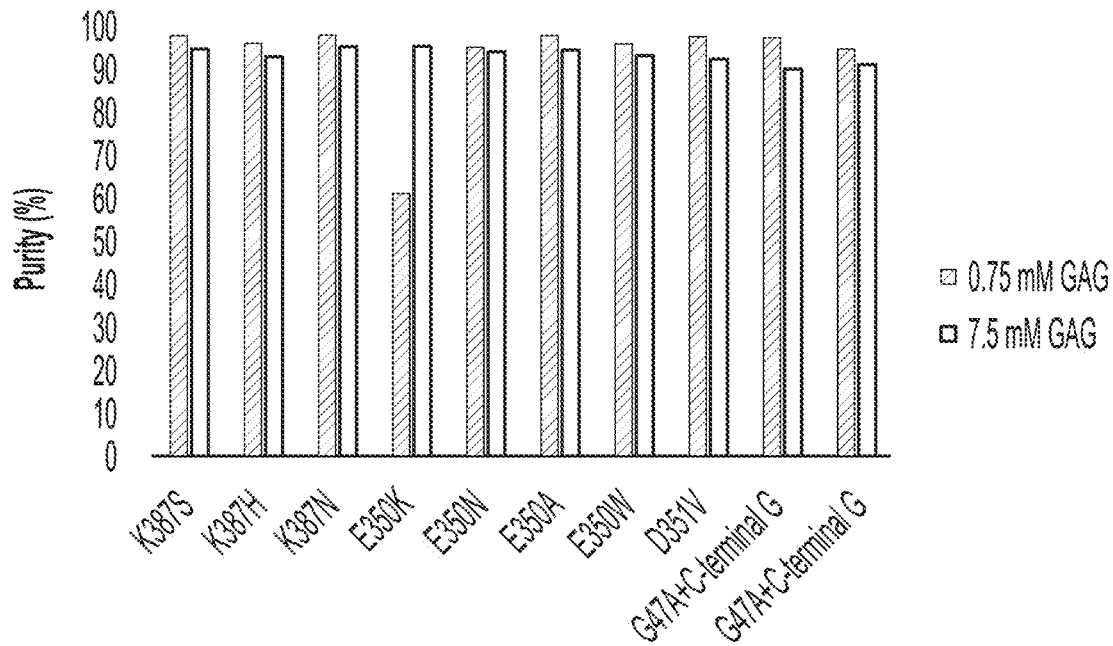

A DBAA (dibutylammonium acetate) HPLC method was used to assess purity of transcribed RNA. Multi-substitution variants produced RNA with comparable purity relative to control variant (>90% purity in most experimental examples) (FIG. 1F)

Figure 1G:
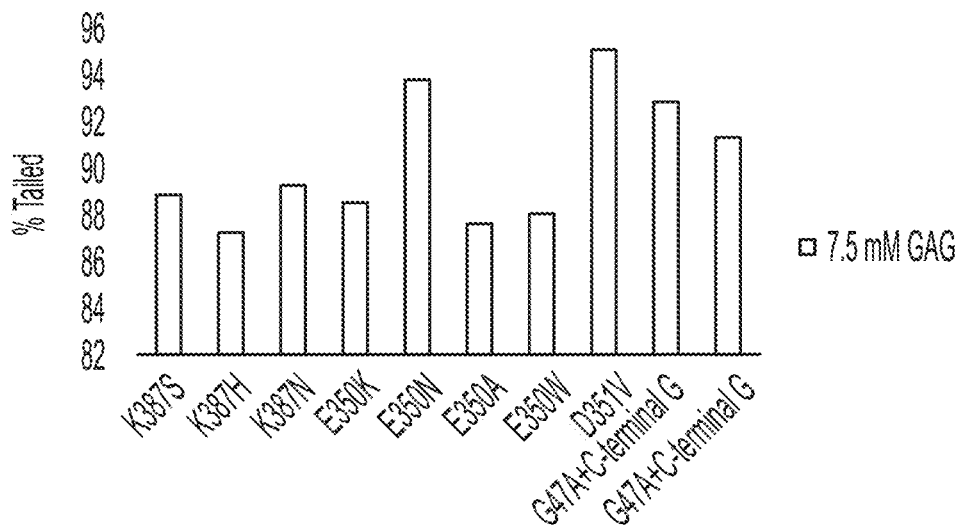

A Tris RP (reverse-phase) method was used to assess percent tailed RNA (i.e., percent of transcribed RNA comprising a polyA tail). Multi-substitution variants produced RNA with comparable % tailing relative to control variant (>85% tailed) (FIG. 1G).

The indel frequencies (insertions/deletion/single point mutations) in transcribed RNA produced by all multi-substitution variants were comparable to indel frequencies produced by control variant polymerase (FIG. 1H). On homopolymeric stretches of >7 A (A7 in FIG. 1H), all variants caused indel frequencies of ~25%, compared to an incidence of ~15% caused by WT polymerase. However, all variants caused marginal indel frequencies in homopolymeric stretches of 5 or 6 A (A5 and A6 in FIG. 1H, respectively), equal to levels caused by WT polymerase.

As demonstrated herein, multi-substitution variants used in this Example produced RNA products in IVT reactions with more desired or improved characteristics relative to a control polymerase variant. Most notably, K387S, K387H, K387N, E350K, E350N, E350A, E350W, and D351V variants showed improved capping efficiency at all tested concentrations of GAG cap analog, relative to control variant.

Figure 2B:
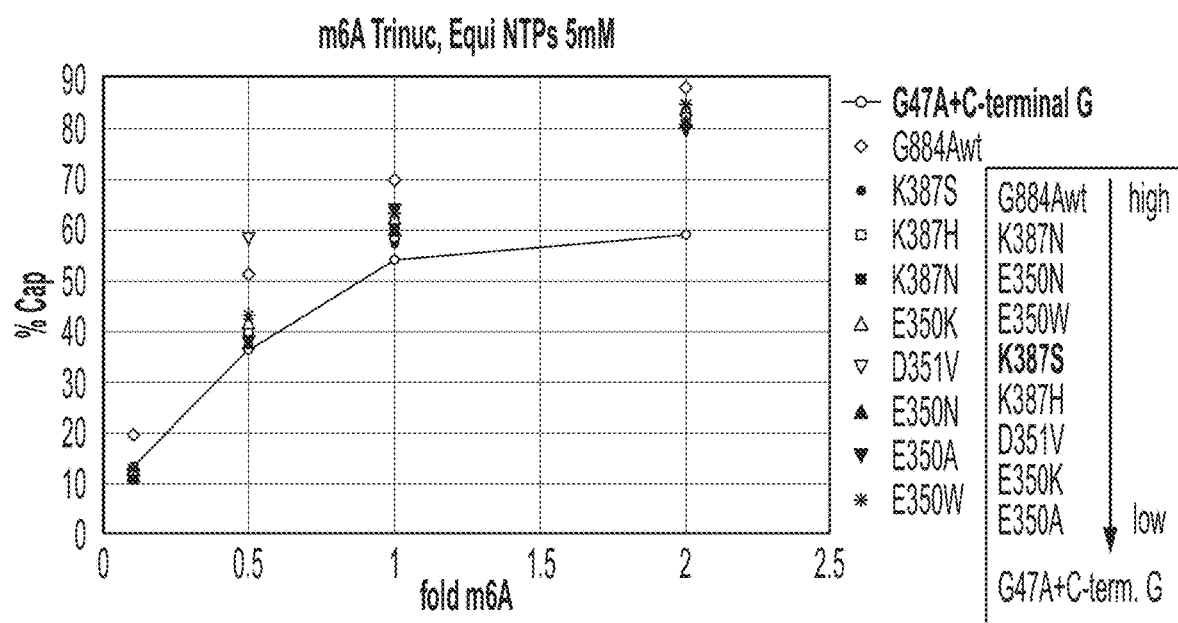
Figure 2B:
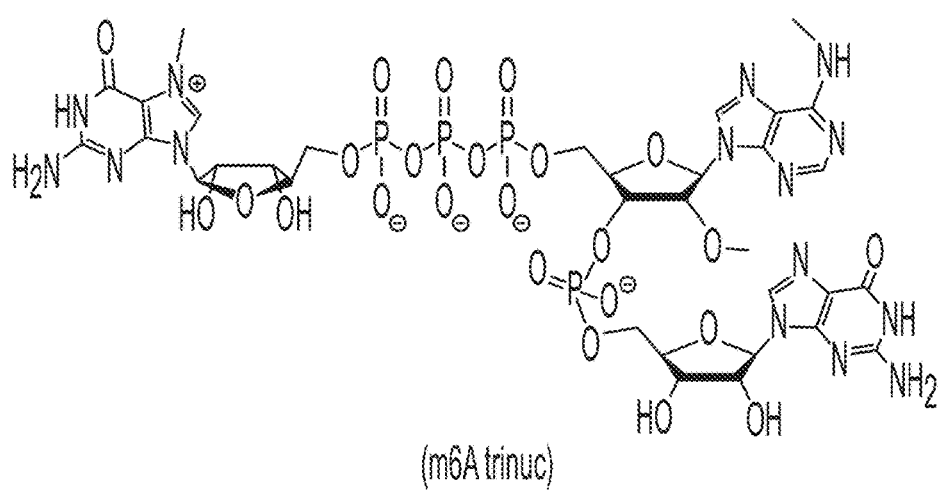
Figure 2C:
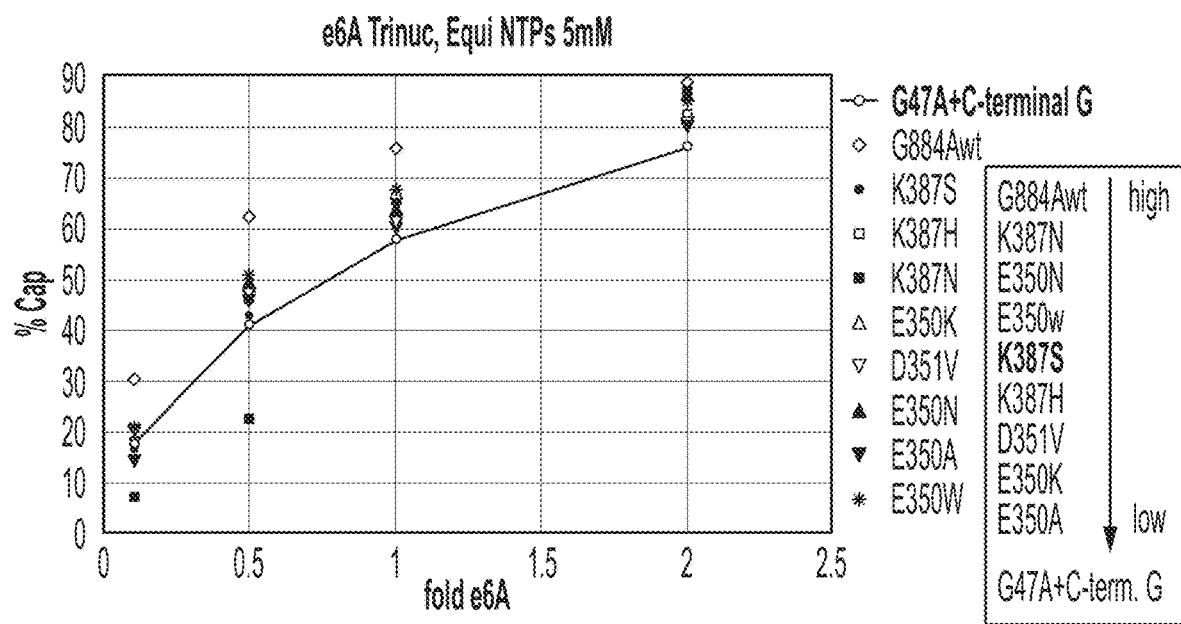
Figure 2C:
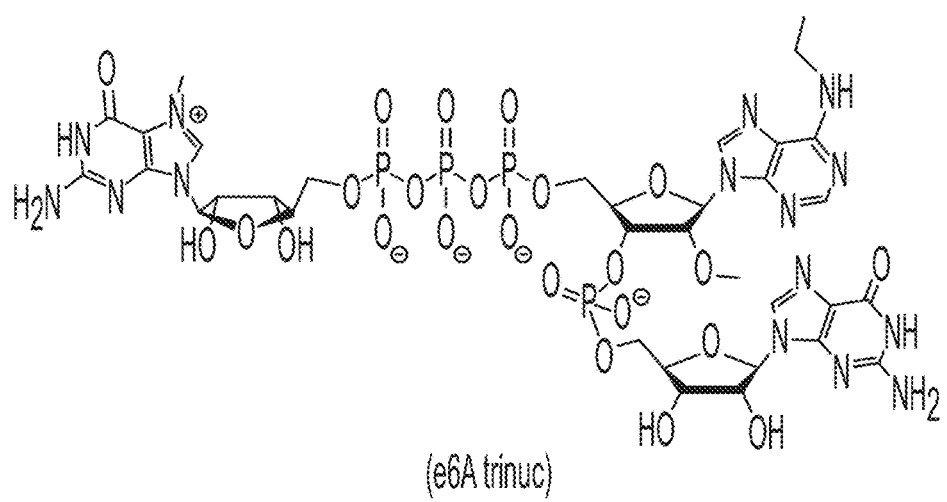

Example 4. Multi-Substitution+C-Terminal G RNA Polymerase Variants Produce RNA Products with Increased Capping Efficiency Relative to a Control Polymerase Variant In vitro transcription reactions were performed using DNA template, one of three cap analogs (GGG cap, Gm6AG cap (referred to as m6A), and Ge6AG (referred to as e6A) cap) at varying concentrations, and (1) a G47A+C-terminal G RNA polymerase variant (control polymerase variant; G47A+C-terminal G), (2) a G47A/K387S+C-terminal G RNA polymerase variant (K387S), (3) a G47A/K387H+C- terminal G RNA polymerase variant (K387H), (4) a G47A/K387N+C-terminal G RNA polymerase variant (K387N), (5) a G47A/E350K+C-terminal G RNA polymerase variant (E350K), (6) a G47A/E350N+C-terminal G RNA polymerase variant (E350N), (7) a G47A/E350A+C-terminal G RNA polymerase variant (E350A), (8) a G47A/E350W+C-terminal G RNA polymerase variant (E350W), (9) a G47A/D351V+C-terminal G RNA polymerase variant (D351V), and (10) G884 RNA polymerase variant (G884 wt). IVT reactions using the GGG cap were initiated using a 5' GTP; IVT reactions using the m6A and e6A caps were initiated using a 5' ATP (FIG. 2A-2C). Following the IVT reactions, each experiment was subjected to LC-MS to determine the % capped RNA (i.e., percent of transcribed RNA comprising a cap).

All tested multi-substitution variants (K387S, K387H, K387N, E350K, E350N, and E350W) produced significantly higher levels of capped RNA when incorporating GGG cap analog during an IVT reaction, relative to control variant (FIG. 2A), at all tested concentrations of GGG cap analog. Multi-substitution variants produced 50-65% capped RNA in experiments using 2-fold concentrations of GGG cap. The control variant produced only 30% capped RNA in experiments using 2-fold concentrations of GGG cap.

All tested multi-substitution variants (K387S, K387H, K387N, E350K, E350N, E350A, E350W, and D351V) produced significantly higher levels of capped RNA when incorporating m6A cap analog during an IVT reaction, relative to control variant (FIG. 2B), at low (0.5-fold conc. m6A) and high (2-fold conc. m6A) concentrations of m6A cap analog. Multi-substitution variants produced 80-85% capped RNA in experiments using 2-fold concentrations of m6A cap. The control variant produced only 60% capped RNA in experiments using 2-fold concentrations of m6A cap. G884 variant also produced higher levels of % capped RNA than control, with >85% capped RNA in experiments using 2-fold concentration of m6A cap.

Tested multi-substitution variants (K387S, K387H, K387N, E350K, E350N, E350A, E350W, and D351V) produced higher levels of capped RNA when incorporating e6A cap analog during an IVT reaction, relative to control variant (FIG. 2C), at low (0.5-fold conc. e6A) and high (2-fold conc. e6A) concentrations of e6A cap analog. Multi-substitution variants produced 80-88% capped RNA in experiments using 2-fold concentrations of e6A cap. The control variant produced ~75% capped RNA in experiments using 2-fold concentrations of e6A cap. G884 variant also produced higher levels of % capped RNA than control, with ~90% capped RNA in experiments using 2-fold concentration of e6A cap.

As demonstrated herein, multi-substitution+C-Terminal G RNA polymerase variants, such as K387S, K387H, K387N, E350K, E350N, E350A, E350W, and D351V produce transcribed RNA products with increased capping efficiency relative to a control polymerase variant when incorporating a variety of different cap analogs.

Example 5. Multi-Substitution+C-Terminal G RNA Polymerase Variants Produce RNA Products with More Desired Characteristics Relative to a Control Polymerase Variant In vitro transcription reactions were performed using DNA template, GAG cap analog (0.75 mM and 7.5 mM), and (1) a wild-type (WT) RNA polymerase (2) a G47A+C-terminal G RNA polymerase variant (control polymerase variant; G47A+C-terminal G), (3) a G47A/D506W+C-terminal G RNA polymerase variant (D506W), (4) a G47A/S628W+C-terminal G RNA polymerase variant (S628W), (5) a G47A/D653W+C-terminal G RNA polymerase variant (D653W), and (6) a G47A/P657W+C-terminal G RNA polymerase variant (P657W). Following IVT reactions, transcribed RNA products from each reaction was characterized to address the quality of said RNA products, including % capping, dsRNA contamination, purity, and 3' homogeneity.

Figure 3A:
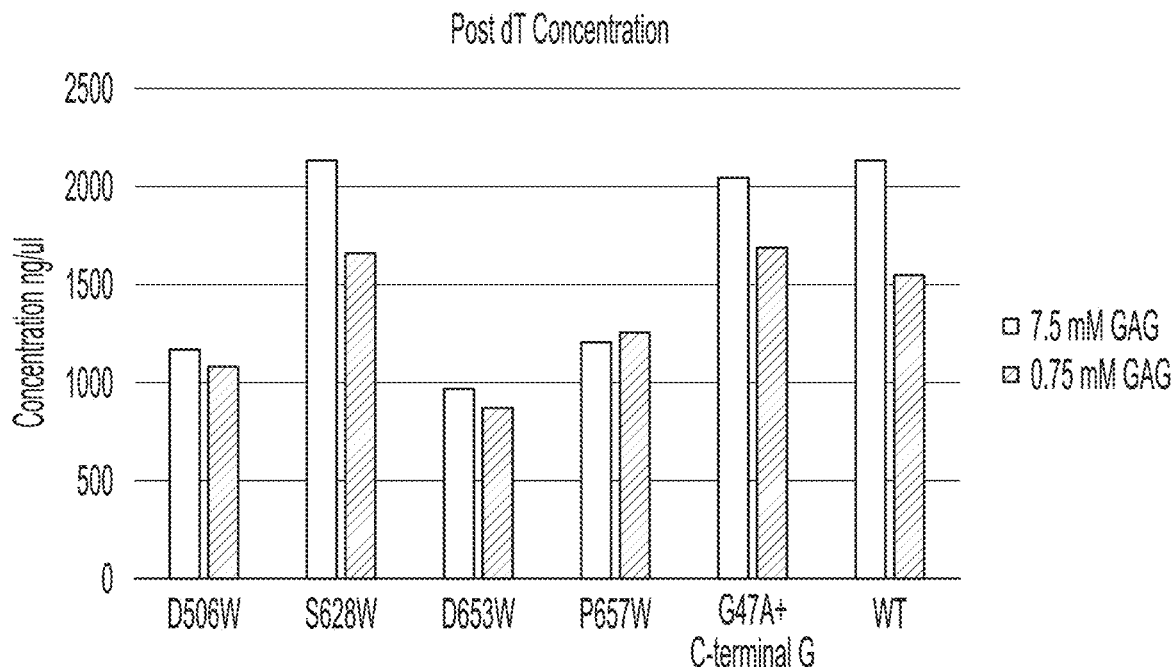

The overall yields, based on concentration in ng/µL, of total RNA produced using the S628W multi-substitution variant was comparable to the yield using control RNA polymerase variant, following an oligo dT purification (FIG. 3A). Yield of total RNA produced using the D506W, D653W, and P657W multi-substitution variants were lower than the yield using control RNA polymerase variant, although remained at viable yields for downstream experimentation and continued use of said multi-substitution variants. RNA yield was measured by UV absorption.

Figure 3B:
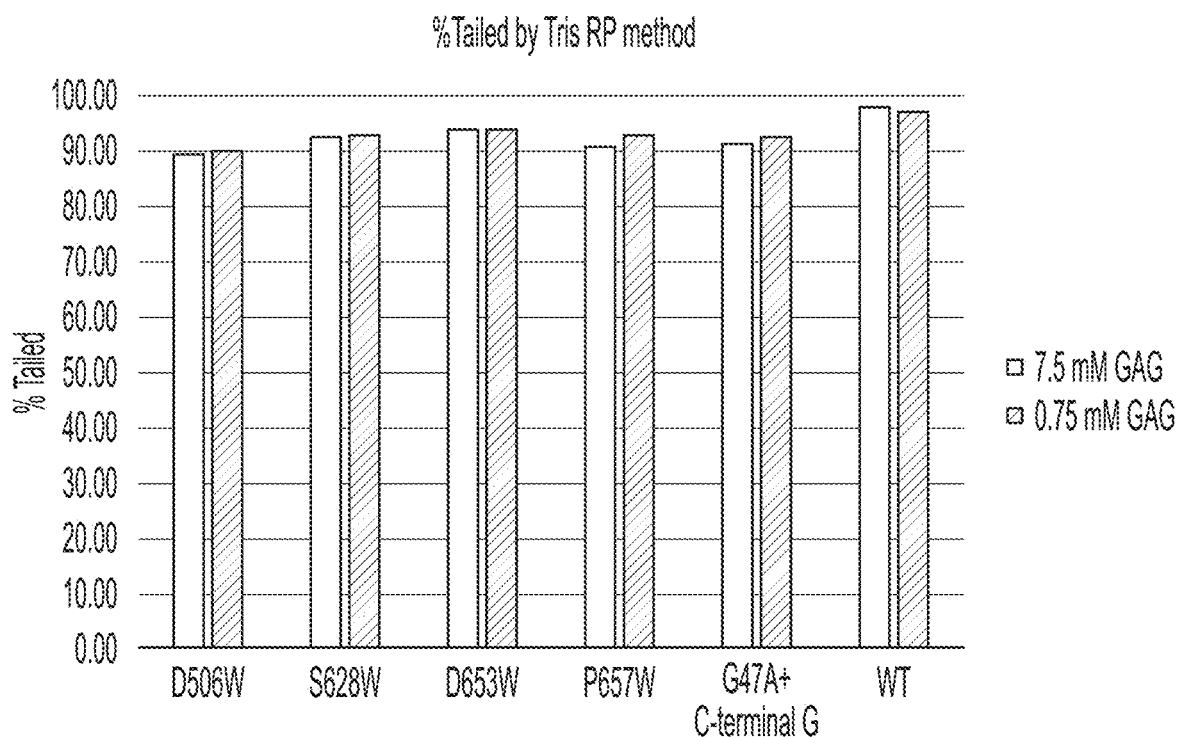

A Tris RP (reverse-phase) method was used to assess percent tailed RNA (i.e., percent of transcribed RNA comprising a polyA tail). Multi-substitution variants produced RNA with comparable % tailing relative to control variant and WT polymerase (≥90% tailed) (FIG. 3B).

A DBAA (dibutylammonium acetate) HPLC method was used to assess purity of transcribed RNA. Multi-substitution variants produced RNA with comparable purity relative to control variant and WT polymerase (≥85% purity) (FIG. 3C).

The 3' homogeneity of RNA transcripts were measured using a RNAse T1 digest. RNAse T1 cleaves mRNA specifically after a G nucleotide. Endonucleolytic cleavage results in a 5' hydroxide (OH) and 3' monophosphate (mP) 'scar', while transcription terminates in 3' hydroxide (OH). Since the last templated nucleotide is a G, a RNAse T1 digest can be used to differentiate between transcripts that do and do not have non-templated additions at the 3' end. In this Example, RNA produced using the multi-substitution variants had equivalent or higher percent 3' end homogeneity relative to control polymerase variant (FIG. 3D). In particular, D506W, D653W, and P657W variants produced RNA comprising 3' homogenous ends that was significantly higher than control variant.

Figure 3E:
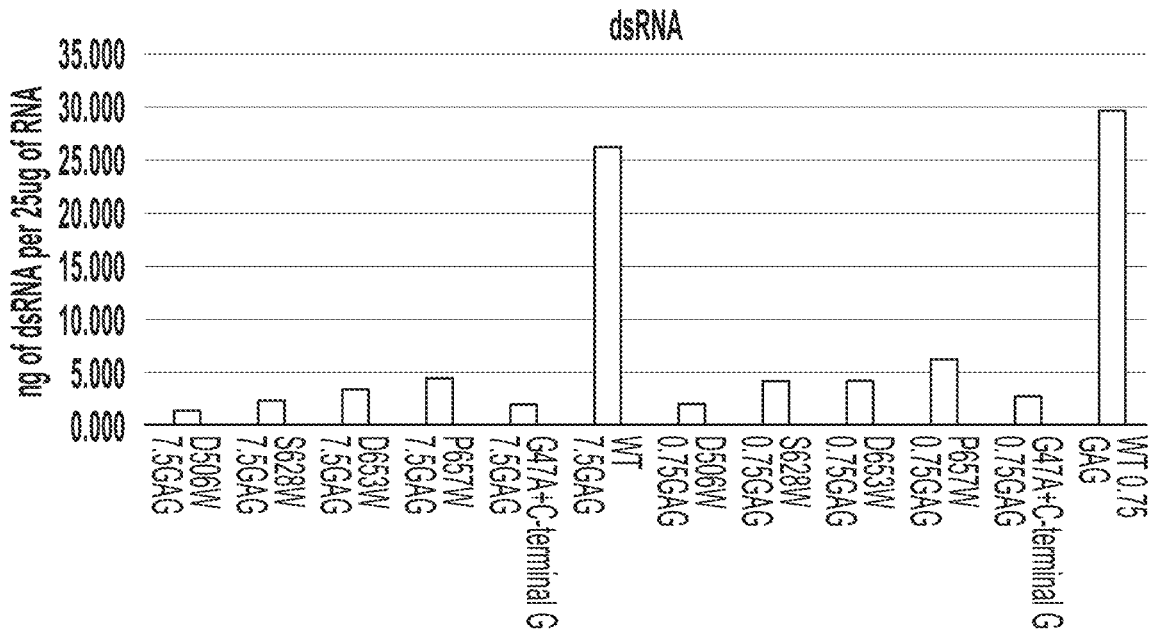

A standard dsRNA ELISA was used to assess dsRNA contaminants (e.g., longer than 40 nucleotide base pairs) following IVT reactions in this Example. All IVT reaction mixtures resulting from multi-substitution variants and the control variant contained less than ~5 ng dsRNA per 25 µg of mRNA (FIG. 3E). Conversely, IVT reaction mixtures resulting from WT T7 polymerase contain more than ~20 ng dsRNA per 25 µg of mRNA.

As demonstrated herein, multi-substitution variants, such as D506W, D653W, and P657W, used in this Example produced RNA products in IVT reactions with comparable or improved characteristics relative to a control polymerase variant.

Example 6. Multi-Substitution+C-Terminal G RNA Polymerase Variants Produce RNA Products with Increased Capping Efficiency Relative to a Control Polymerase Variant In vitro transcription reactions were performed using DNA template, one of three cap analogs (GAG cap, m6A cap, and e6A cap) at varying concentrations, and (1) a G47A+C-terminal G RNA polymerase variant (control polymerase variant; G47A+C-terminal G), (2) a G47A/D506W+C-terminal G RNA polymerase variant (D506W), (3) a G47A/S628W+C-terminal G RNA polymerase variant (S628W), (4) a G47A/D653W+C-terminal G RNA polymerase variant (D653W), and (5) a G47A/P657W+C-terminal G RNA polymerase variant (P657W). IVT reactions using the m6A and e6A cap analogs were incorporated using a DNA template that encodes for a 5'A followed by G. Following the IVT reactions, each experiment was subjected to LC-MS to determine the % capped RNA (i.e., percent of transcribed RNA comprising a cap).

Figure 4A:
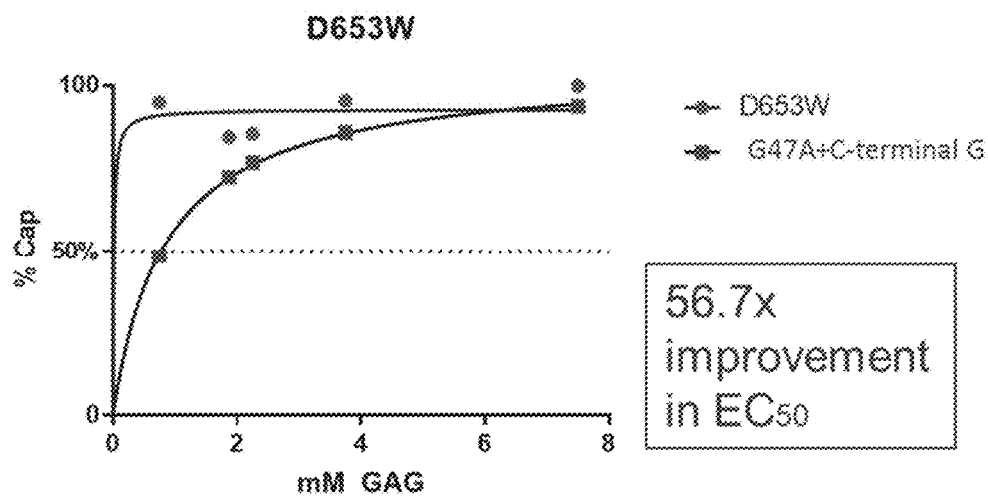
FIGS. 4A-4E show graphs depicting the percent capped RNA resulting from in vitro transcription (IVT) reactions involving mutant variants of a control T7 RNA polymerase variant (G47A+C-terminal G) in the presence of varying levels of GAG cap.
Figure 4B:
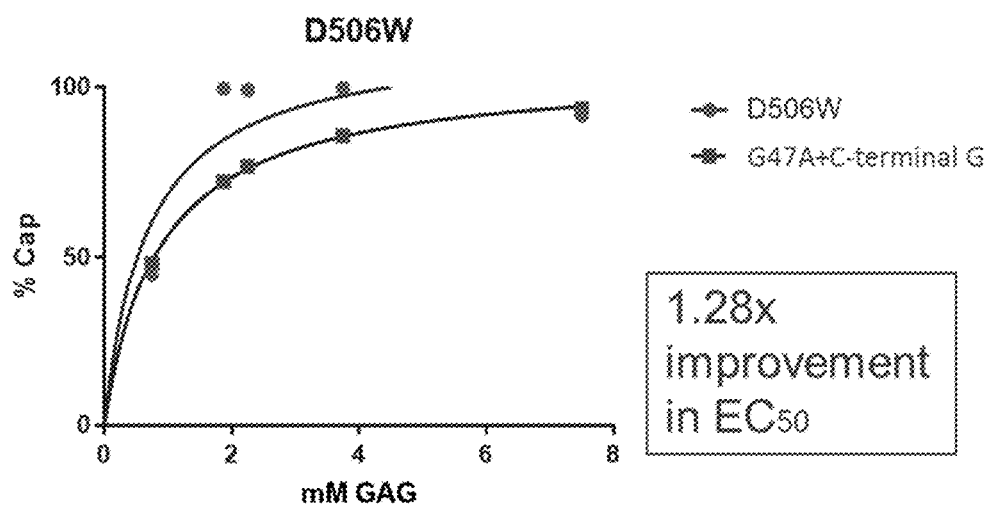
Figure 4C:
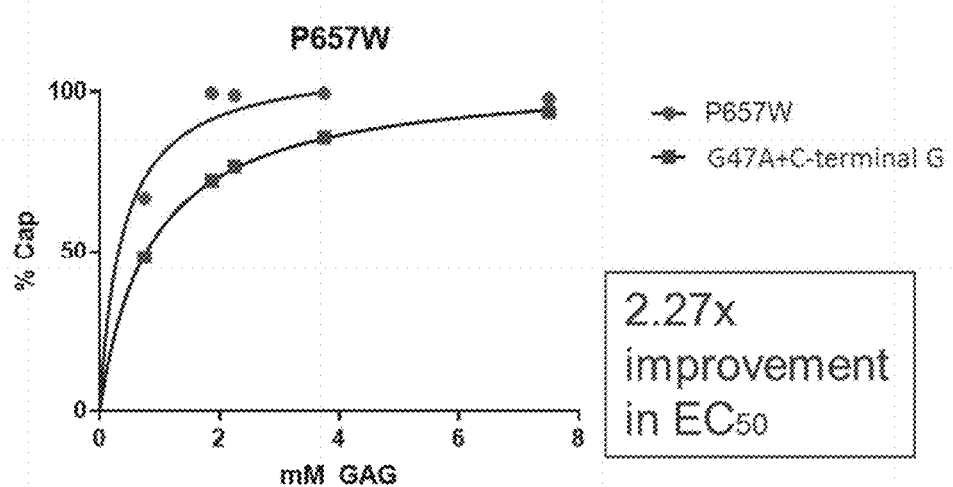
Figure 4D:
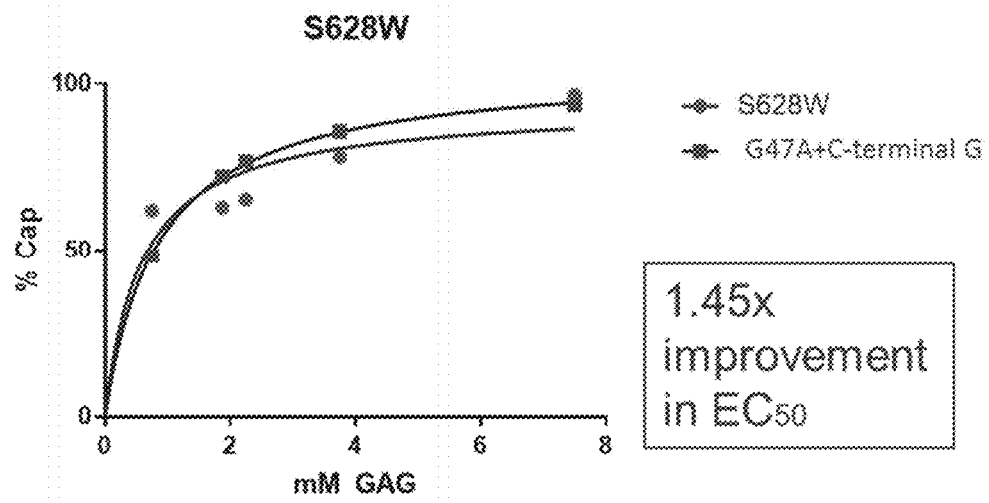
Figure 4E:
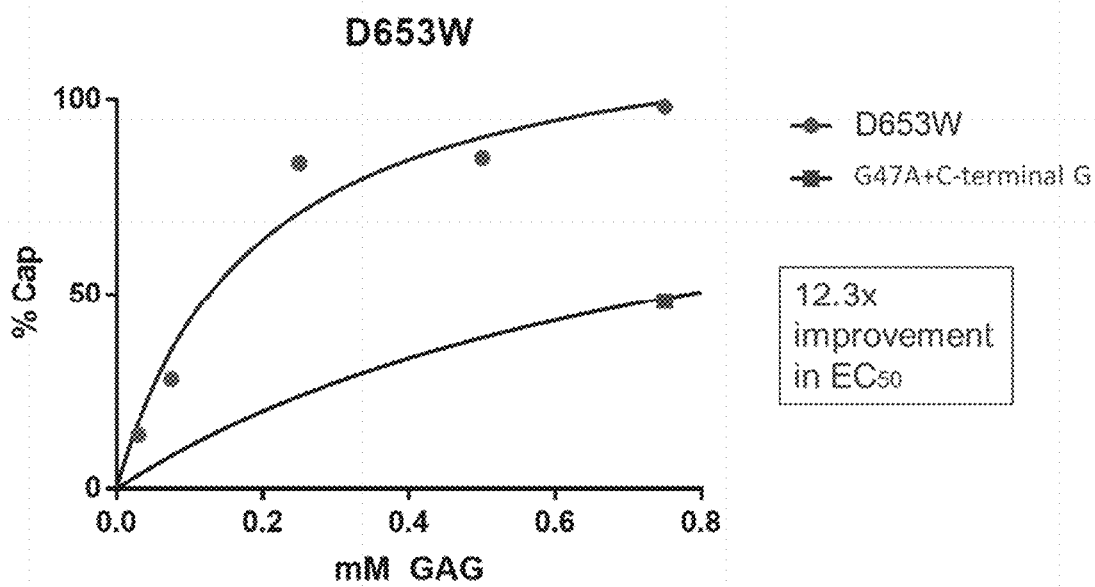
Figure 5A:
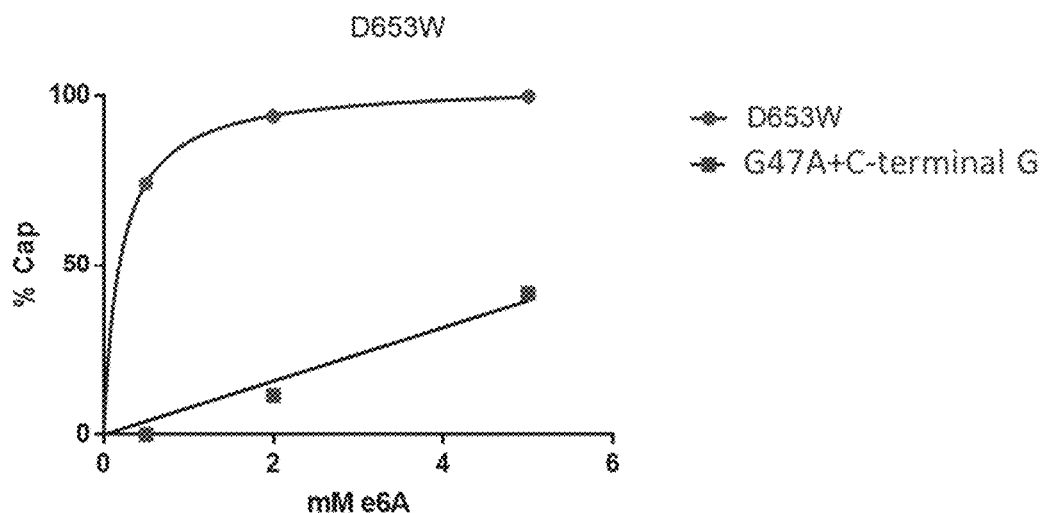
FIGS. 5A-5D show graphs depicting the percent capped RNA resulting from IVT reactions involving mutant variants of a control T7 RNA polymerase variant (G47A+C-terminal G) in the presence of varying levels of e6A trinucleotide (trinuc).
Figure 5B:
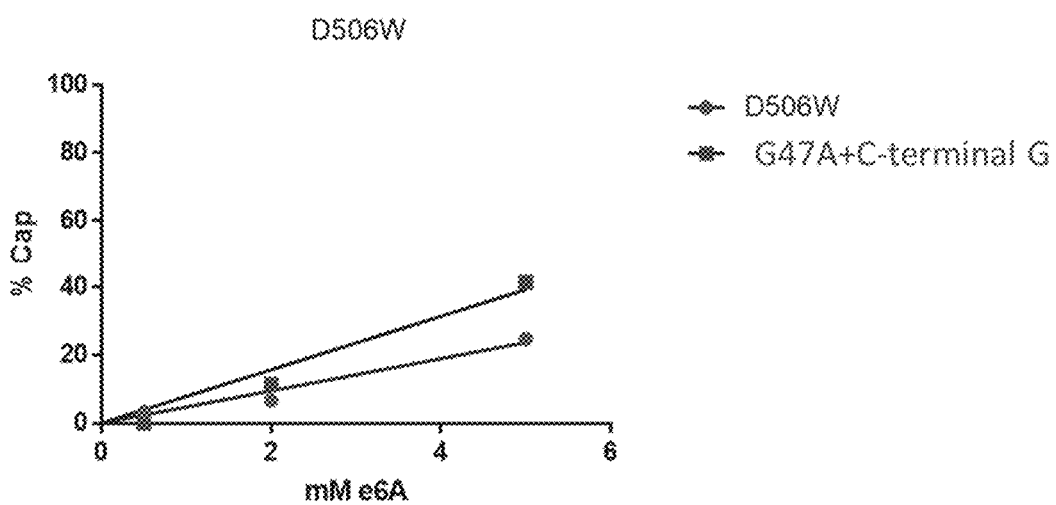
Figure 5C:
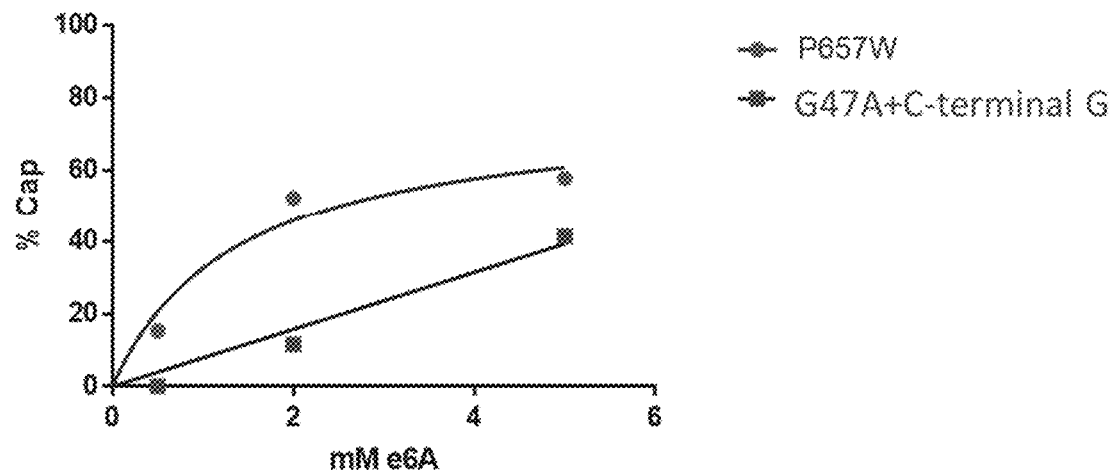
Figure 5D:
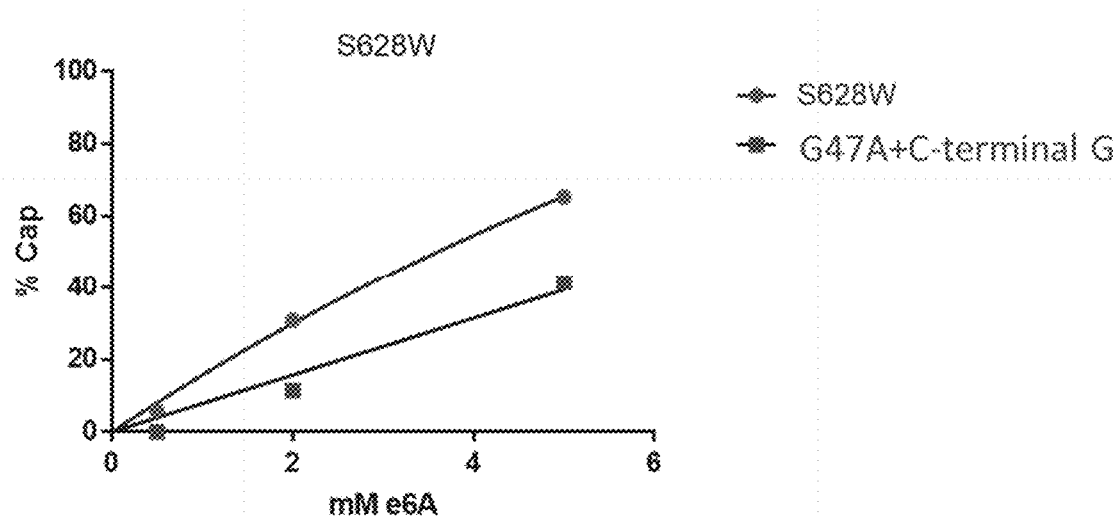
Figure 6A:
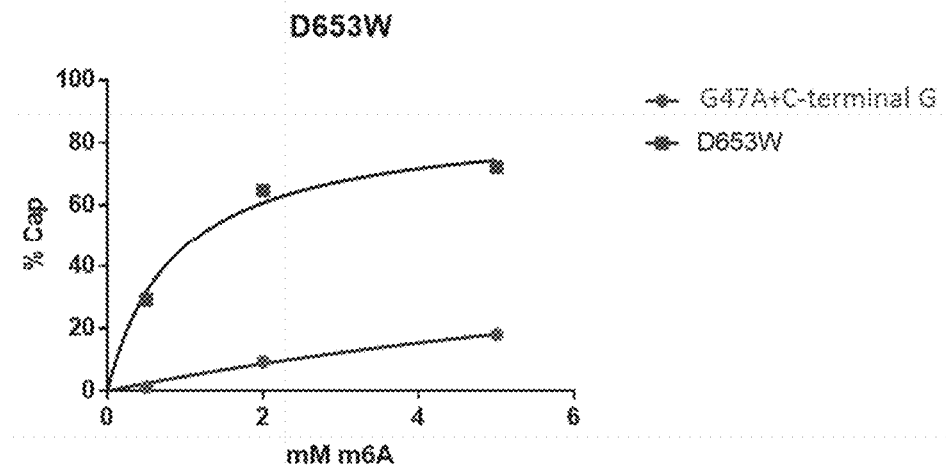
FIGS. 6A-6D show graphs depicting the percent capped RNA resulting from IVT reactions involving mutant variants of a control T7 RNA polymerase variant (G47A+C-terminal G) in the presence of varying levels of m6A trinuc.
Figure 6B:
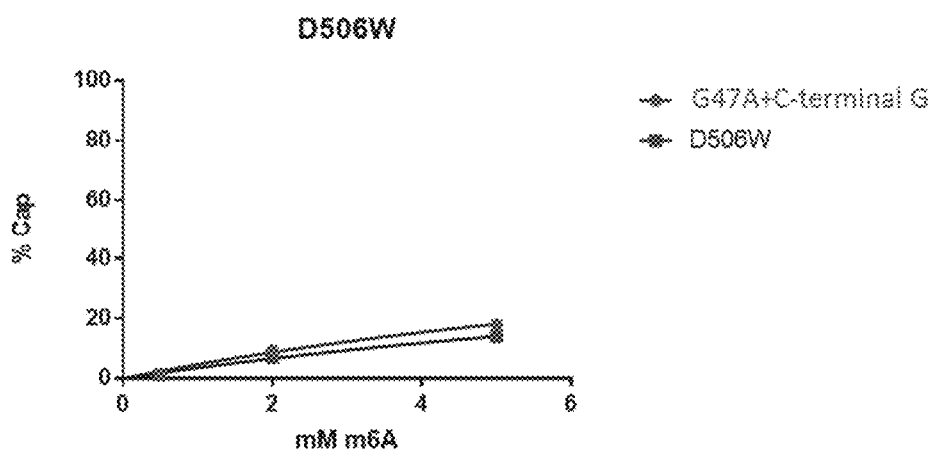
Figure 6C:
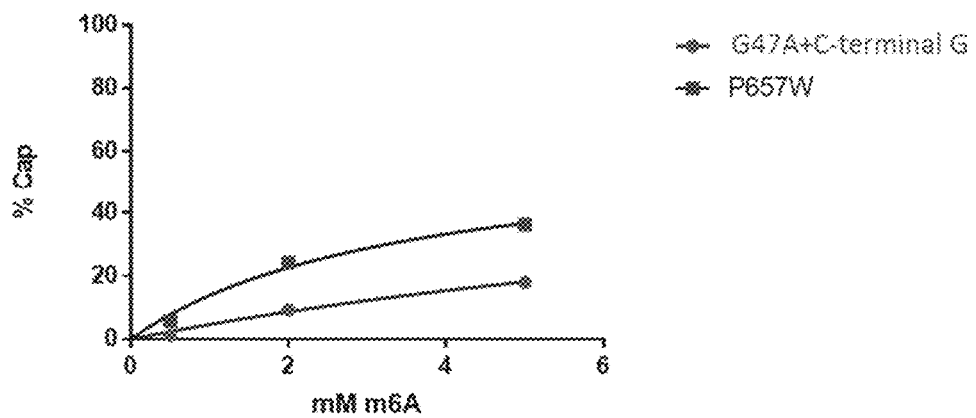
Figure 6D:
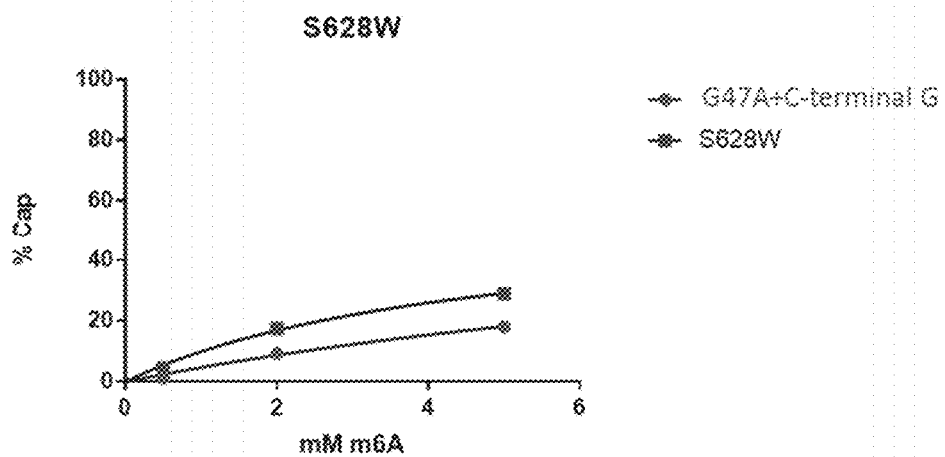

All tested multi-substitution variants (D653W, D506W, P657W, S628W) required lesser effective concentrations of GAG cap analog in order to produce RNA with 50% cap incorporation ($EC_{50}$), relative to control variant, in IVT reactions involving 5 mM of each NTP (FIGS. 4A-4D). Most notably, D653W provided a significant improvement in $EC_{50}$ for GAG cap incorporation, relative to the control variant, with nearly 100% of total RNA incorporating GAG cap at concentrations of GAG as low as 0.75 mM. D506W, P657W, and S628W provided 1.28-, 2.27-, and 1.45-fold improvements (reductions) in $EC_{50}$ for GAG cap incorporation, relative to the control variant. D653W also significantly outperformed the control variant in IVT reactions involving 7.5 mM of each NTP, with a 12.3-fold improvement (reduction) in $EC_{50}$ for GAG cap incorporation, relative to the control variant (FIG. 4E).

All tested multi-substitution variants (D653W, D506W, P657W, S628W) required lesser effective concentrations of e6A cap analog in order to produce RNA with cap incorporation, relative to control variant, in IVT reactions involving 5 mM of each NTP (FIGS. 5A-5D). Most notably, D653W provided nearly 100% of total RNA with incorporated e6A cap at 2 mM e6A. Conversely, even at 5 mM e6A, the control variant provided ~40% of total RNA with incorporated e6A.

All tested multi-substitution variants (D653W, D506W, P657W, S628W) required lesser effective concentrations of m6A cap analog in order to produce RNA with cap incorporation, relative to control variant, in IVT reactions involving 5 mM of each NTP (FIGS. 6A-6D). Most notably, D653W provided nearly 100% of total RNA with incorporated m6A cap at 5 mM m6A. Conversely, even at 5 mM m6A, the control variant provided less than 30% of total RNA with incorporated m6A.

Figure 7:
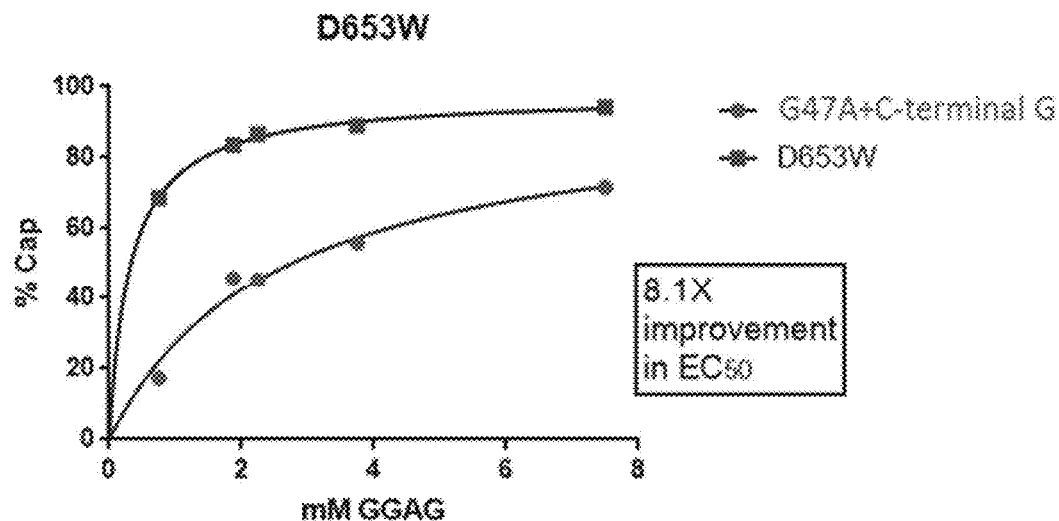
FIG. 7 shows a graph depicting the percent capped RNA resulting from IVT reactions involving mutant variants of a control T7 RNA polymerase variant (G47A+C-terminal G) in the presence of varying levels of a GGAG tetranucleotide (tetranuc). The structure of the GGAG tetranucleotide is provided in the lower half of FIG. 7.
Figure 7:
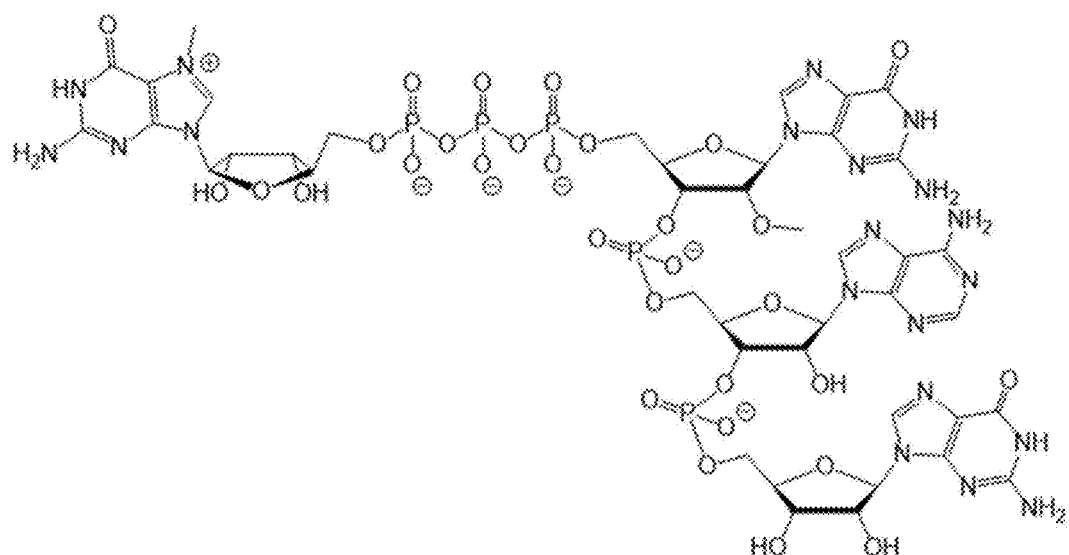
Figure 8A:
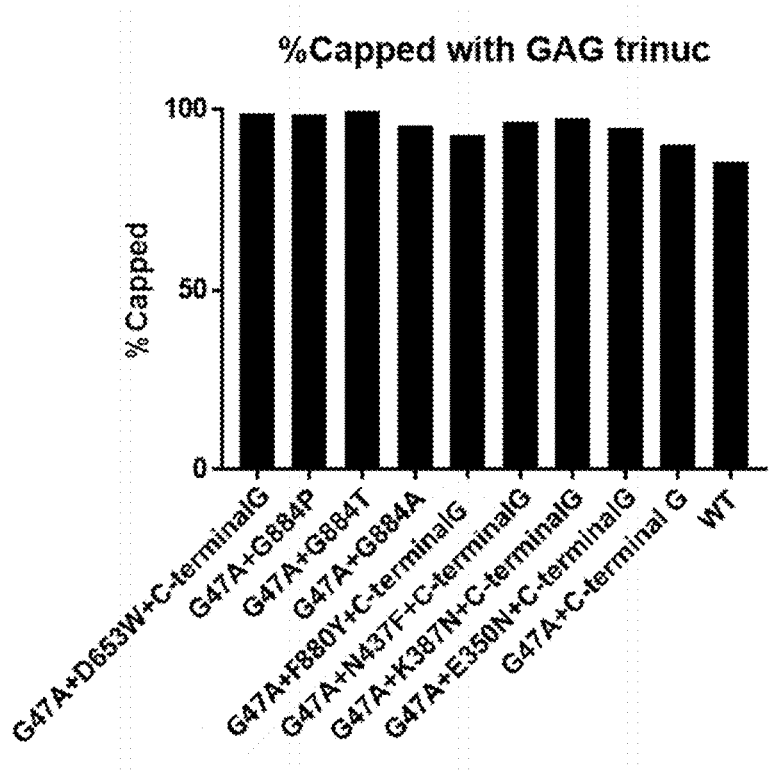
FIGS. 8A-8I show graphs depicting the percent capped RNA (FIGS. 8A-8D) and relative RNA yield (FIG. 8E-8I) resulting from IVT reactions involving mutant variants of a control T7 RNA polymerase variant (G47A+C-terminal G) in the presence of a GAG trinuc, m6A trinuc, e6A trinuc, or tetranuc.
Figure 8B:
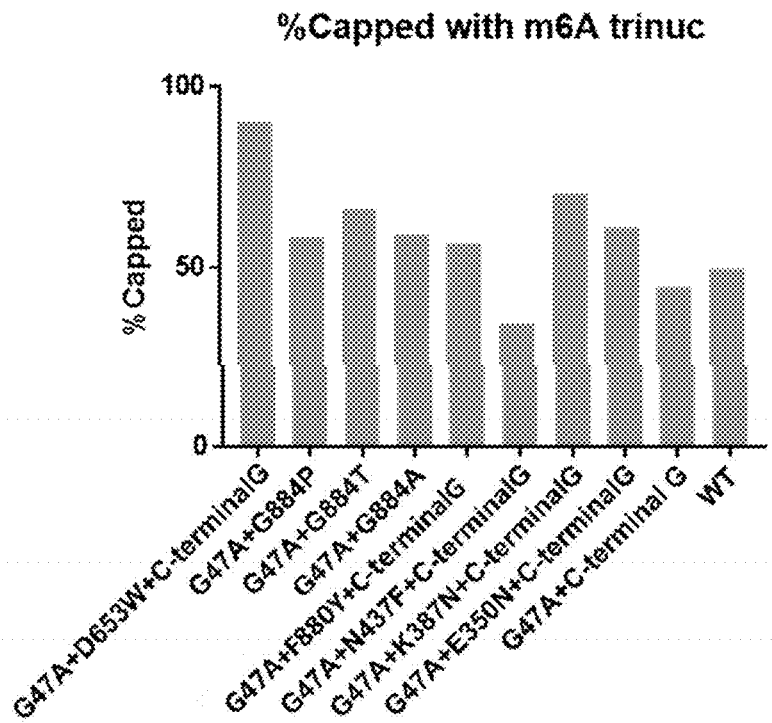
Figure 8C:
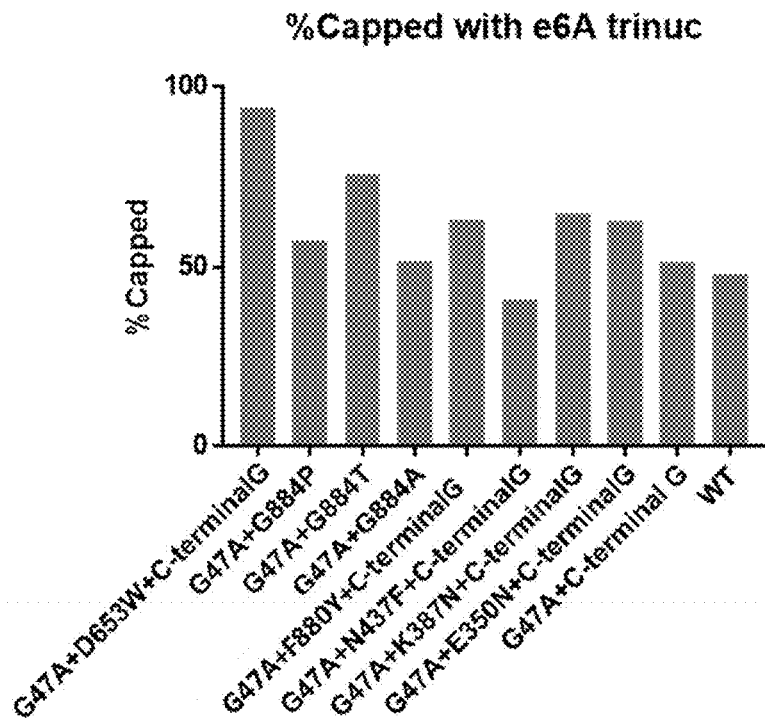
Figure 8D:
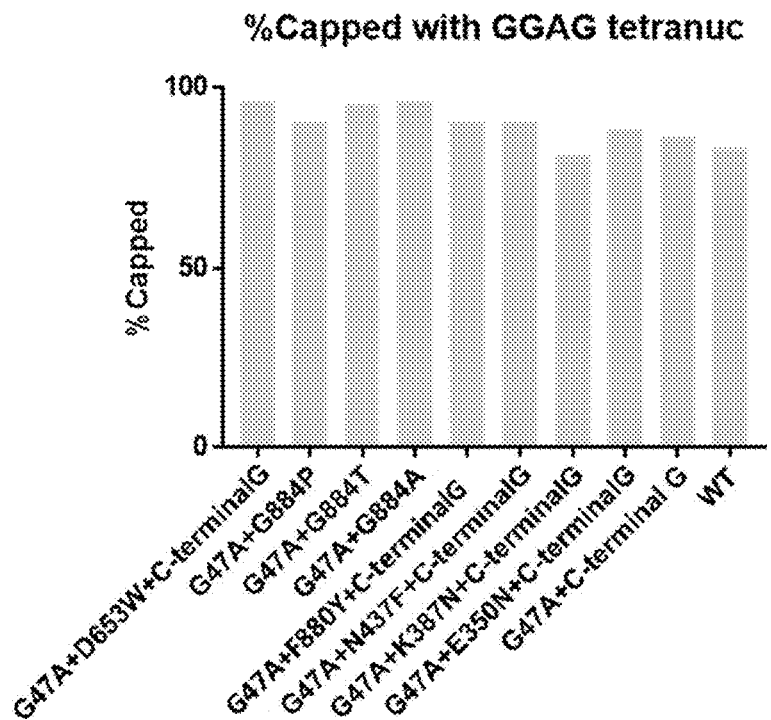
Figure 8E:
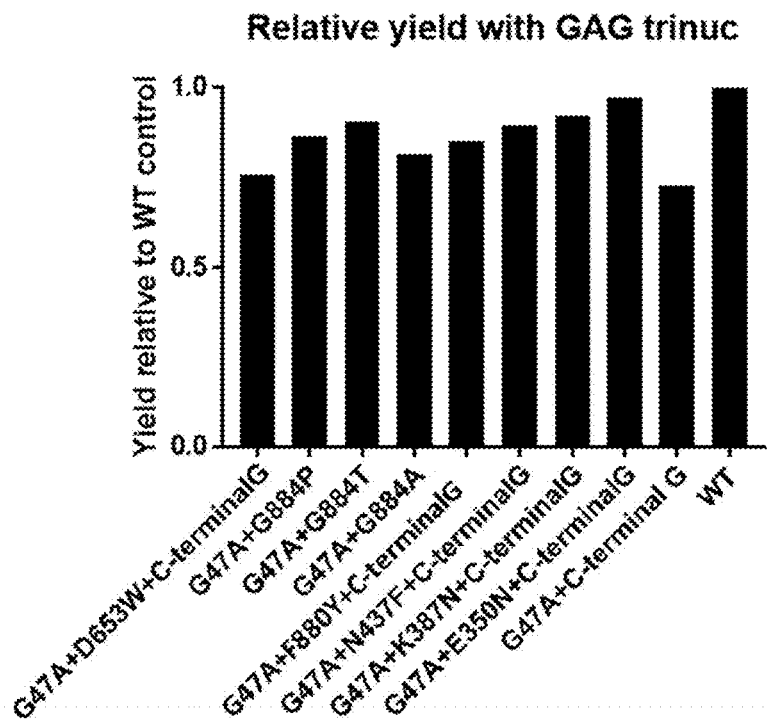
Figure 8F:
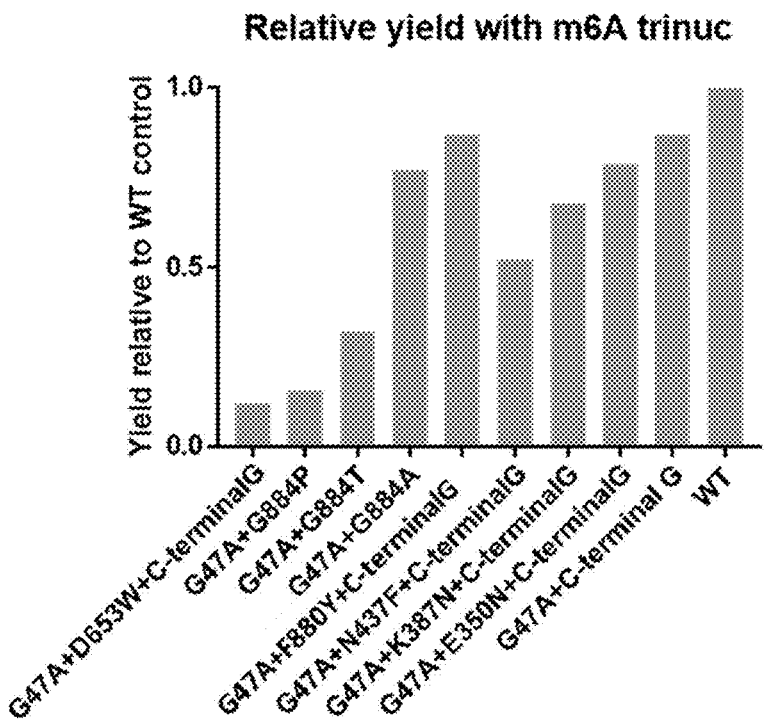
Figure 8G:
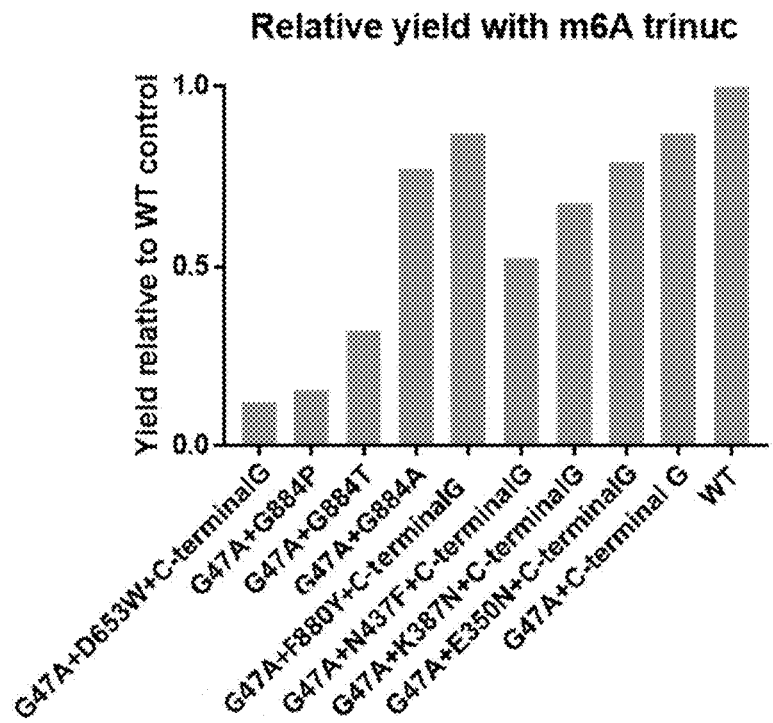
Figure 8H:
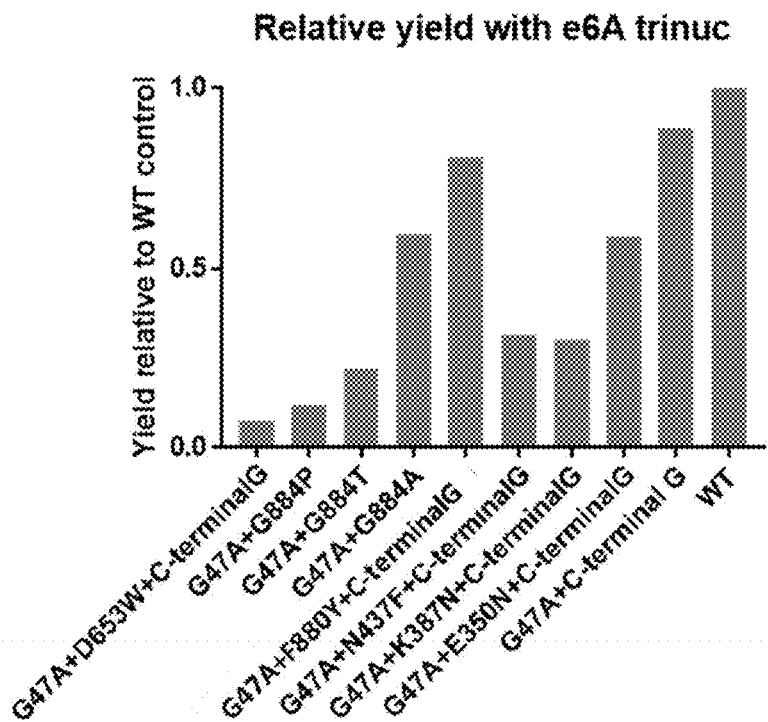
Figure 8I:
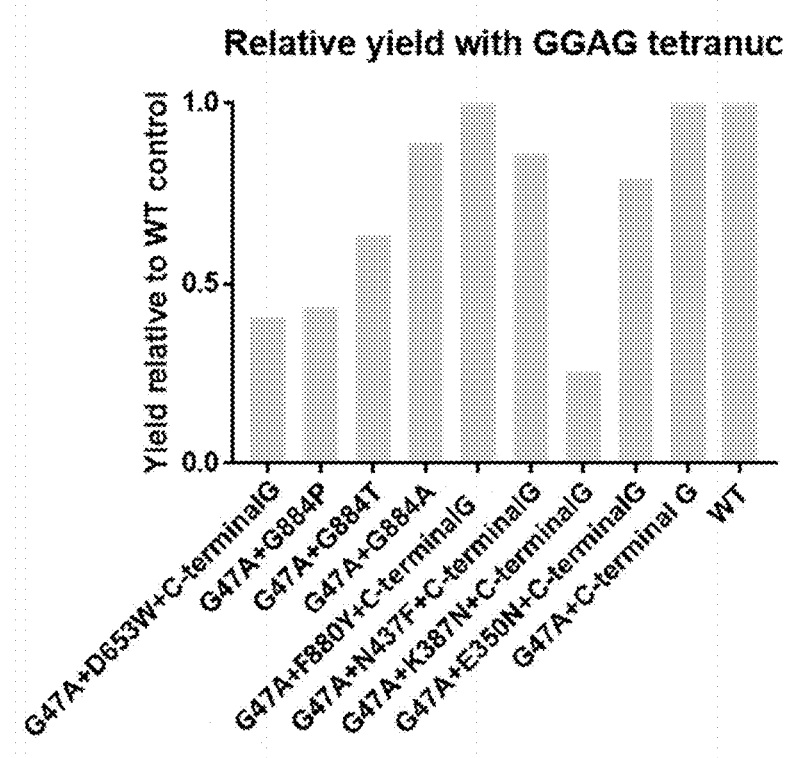
Figure 9A:
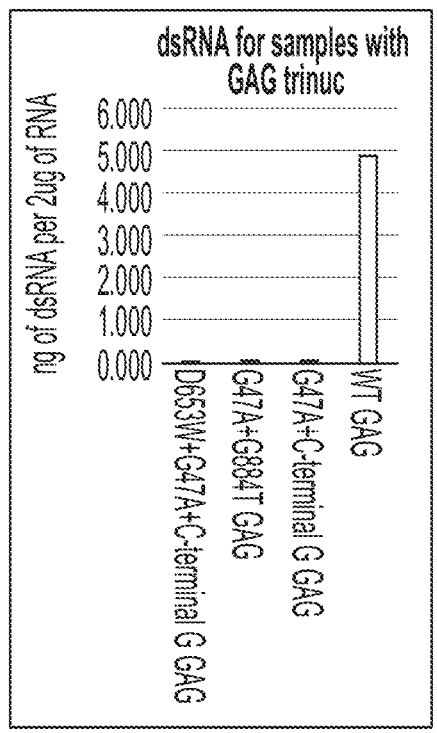
FIGS. 9A-9D show graphs depicting dsRNA content resulting from IVT reactions involving mutant variants of a control T7 RNA polymerase in the presence of GAG trinuc (FIG. 9A), m6A trinuc (FIG. 9B), e6A trinuc (FIG. 9C), and GGAG tetranuc (FIG. 9D).
Figure 9B:
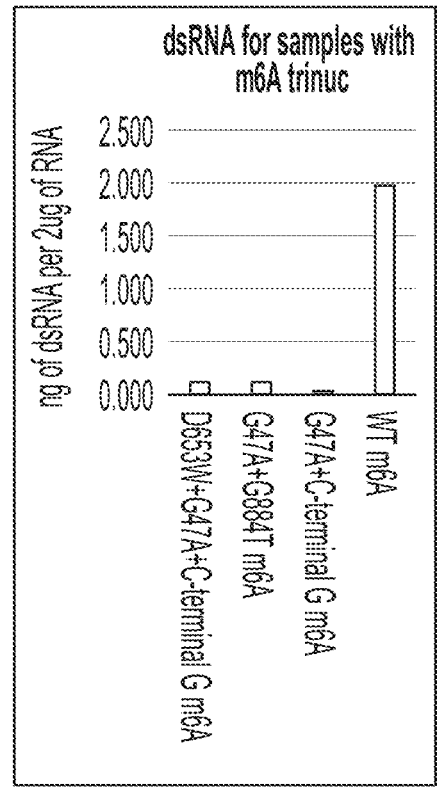
Figure 9C:
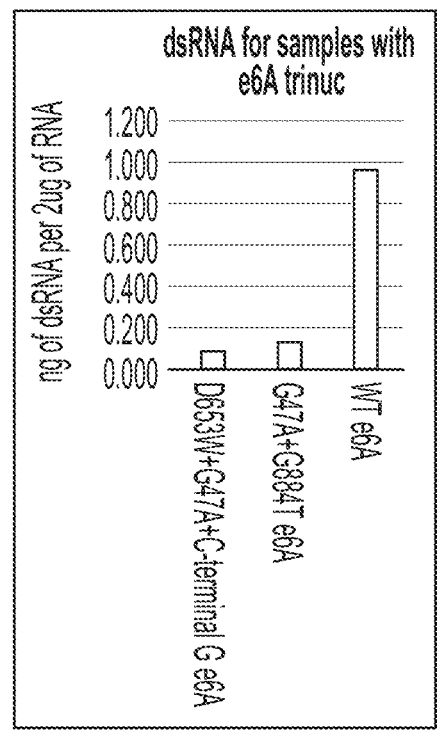
Figure 9D:
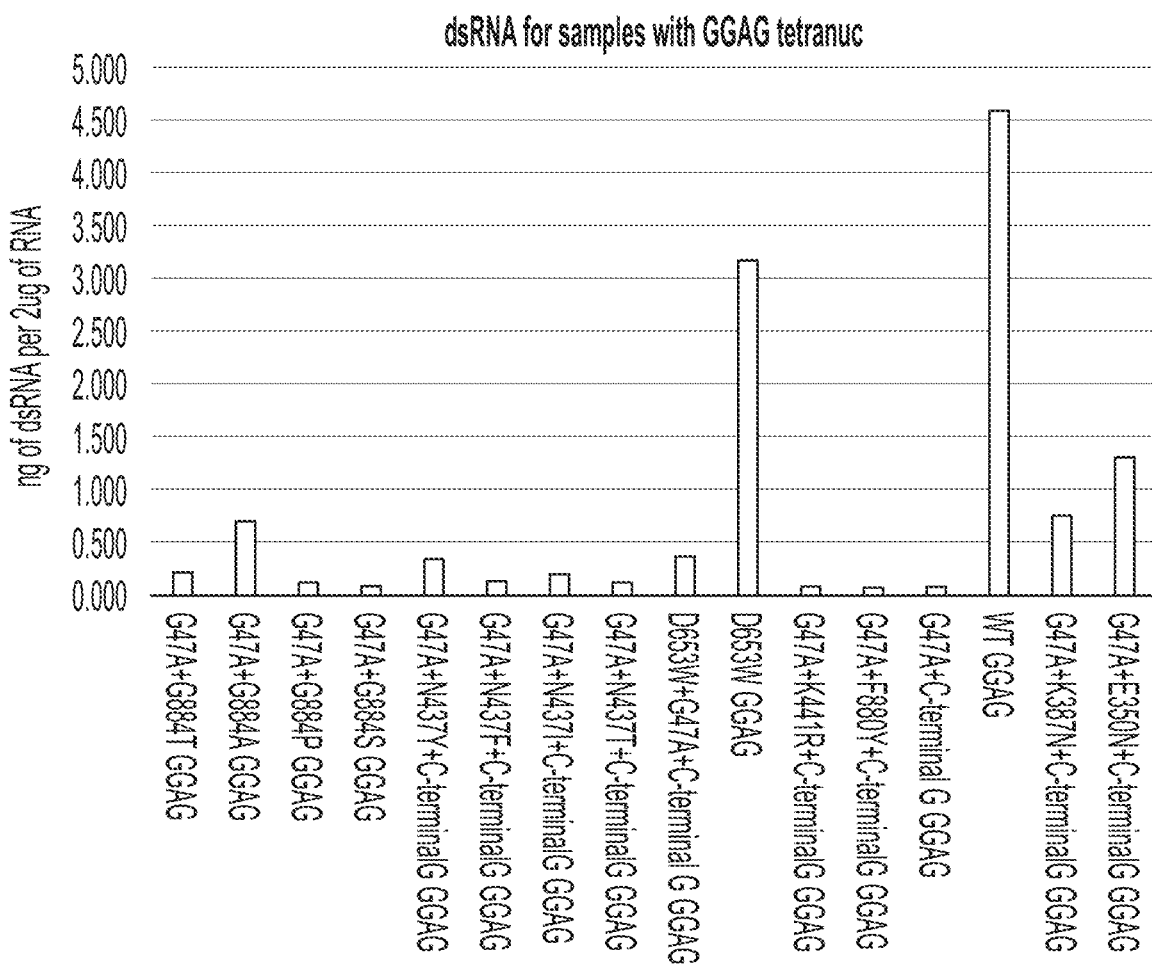

The D653W multi-substitution variant required lesser effective concentrations of GGAG tetranuc cap analog in order to produce RNA with cap incorporation, relative to control variant, in IVT reactions involving 7.5 mM of each NTP (FIG. 7). Most notably D653W provided nearly 100% of total RNA with incorporated GGAG cap at 7.5 mM GGAG tetranuc. Conversely, even at 7.5 mM GGAG tetranuc, the control variant provided less than 70% of total RNA with incorporated GGAG.

As demonstrated herein, multi-substitution+C-Terminal G RNA polymerase variants, such as D653W, D506W, P657W, and S628W produce transcribed RNA products with increased capping efficiency relative to a control polymerase variant when incorporating a variety of different cap analogs (e.g., GAG, e6A, m6A, GGAG tetranuc).

Example 7. Multi-Substitution+C-Terminal G RNA Polymerase Variants Produce RNA Products with Increased Capping Efficiency and RNA Yield Relative to a Control Polymerase In vitro transcription reactions were performed using DNA template, 5 mM equimolar NTPs, 5 mM cap analog (GAG trinuc, e6A trinuc, $m^6A$ trinuc, or GGAG tetranuc), and 500 nM T7 RNA polymerase-(1) a G47A+C-terminal G RNA polymerase variant (control polymerase variant; G47A+C-terminal G); (2) a G47A/D653W+C-terminal G RNA polymerase variant (D653W); (3) a G47A/G884P+C-terminal G RNA polymerase variant (G884P); (4) a G47A/G884T+C-terminal G RNA polymerase variant (G884T); (5) a G47A/G884A+C-terminal G RNA polymerase variant (G884A); (6) a G47A/F880Y+C-terminal G RNA polymerase variant (F880Y); (7) a G47A/N437F+C-terminal G RNA polymerase variant (N437F); (8) a G47A/K387N+C-terminal G RNA polymerase variant (K387N); or (9) a G47A/E350N+C-terminal G RNA polymerase variant (E350N).

Following the IVT reaction, mRNA products were oligo-dT purified before being analyzed by LC-MS to determine the % capped RNA (i.e., percent of transcribed RNA comprising a cap) and by HPLC to determine the RNA yield of the reaction.

All tested multi-substitution variants (D653W, G884P, G884T, G884A, F880Y, N437F, K387N, E350N) produced RNA with percent capped RNA at comparable or higher levels than the control polymerase variant in the presence of any one of GAG trinuc, e6A trinuc, m6A trinuc, or GGAG tetranuc (FIGS. 8A-8I). Notably, D653W provided a significant increase in percent capped RNA relative to the control polymerase variant or WT polymerase, particularly in the presence of m6A trinuc (~85% capped) and e6A trinuc (~90% capped). See FIGS. 8B and 8C.

All tested multi-substitution variants (D653W, G884P, G884T, G884A, F880Y, N437F, K387N, E350N) produced higher or comparable yields of total RNA than the control polymerase variant in the presence of GAG trinuc (FIGS. 8E-8I). G884A, F880Y, K387N, and E350N variants produced higher or comparable yields of total RNA than the control polymerase variant in the presence of m6A trinuc.

All tested multi-substitution variants (D653W, G884P, G884T, G884A, F880Y, N437F, K387N, E350N) produced higher yields of percent capped RNA than the control polymerase variant in the presence of GAG trinuc (FIGS. 8A-8D). G884A, F880Y, K387N, and E350N variants produced higher yields of percent capped RNA than the control polymerase variant in the presence of m6A trinuc. F880Y produced higher yields of percent capped RNA than the control polymerase variant in the presence of e6A trinuc.

IVT reactions of the Example were then further analyzed for double-stranded RNA (dsRNA) content, an undesired by-product of IVT reactions, and compared to additional IVT reactions (FIGS. 9A-9D). Notably, none of the tested multi-substitution variants (D653W, G884P, G884T, G884A, F880Y, N437F, K387N, E350N) generated more than ~0.75 ng of dsRNA per 2 µg of total RNA in IVT reactions. This is in contrast to WT T7 polymerase which generates 2-5 ng dsRNA of dsRNA per 2 µg of total RNA in IVT reactions in presence of all tested trinuc and tetranuc cap analogs.

Example 8. G47A/D653W+C-Terminal G RNA Polymerase Produces RNA Products with Increased 3' Homogeneity and Capping Efficiency Relative to Related Singly and Doubly Mutated RNA Polymerases In vitro transcription reactions were performed using DNA template, 5 mM equimolar NTPs, 0.5 mM GAG trinuc, and a T7 RNA polymerase—(1) WT RNA polymerase, (2) G47A RNA polymerase variant, (3) G884A RNA polymerase variant, (4) D653W RNA polymerase variant, (5) G47A/D653W RNA polymerase variant; (6) D653W+C-terminal G RNA polymerase variant; (7) G47A/D653W+C-terminal G RNA polymerase variant; or (8) G47A+C-terminal G RNA polymerase variant.

Figure 10A:
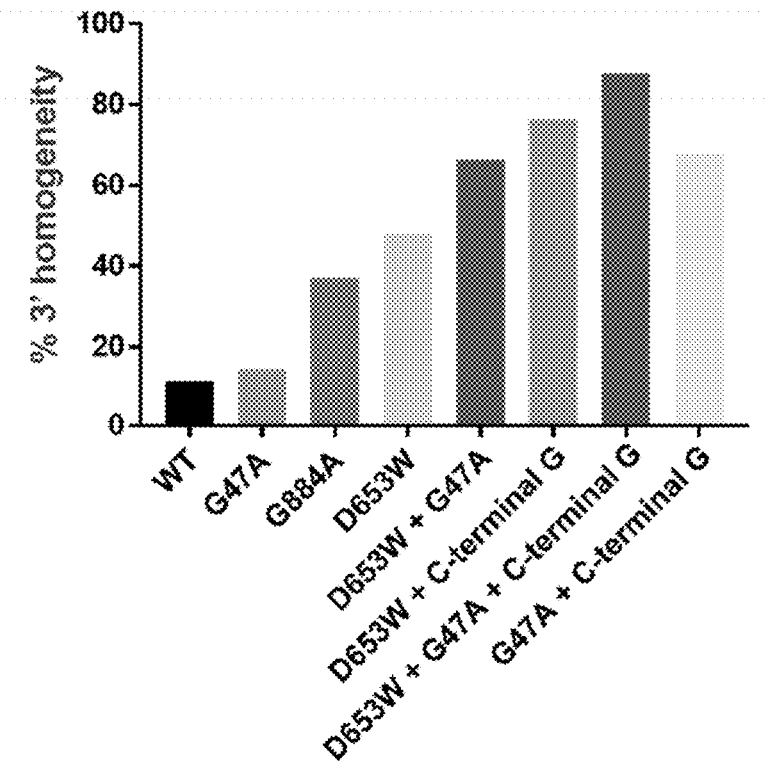
FIGS. 10A-10D show graphs depicting the 3' homogeneity (FIG. 10A), percent capped RNA (FIG. 10B), percent full-length RNA product (FIG. 10C), and crude yield over time (FIG. 10D) resulting from IVT reactions involving mutant variants of a control T7 RNA polymerase in the presence of a GAG trinuc.
Figure 10B:
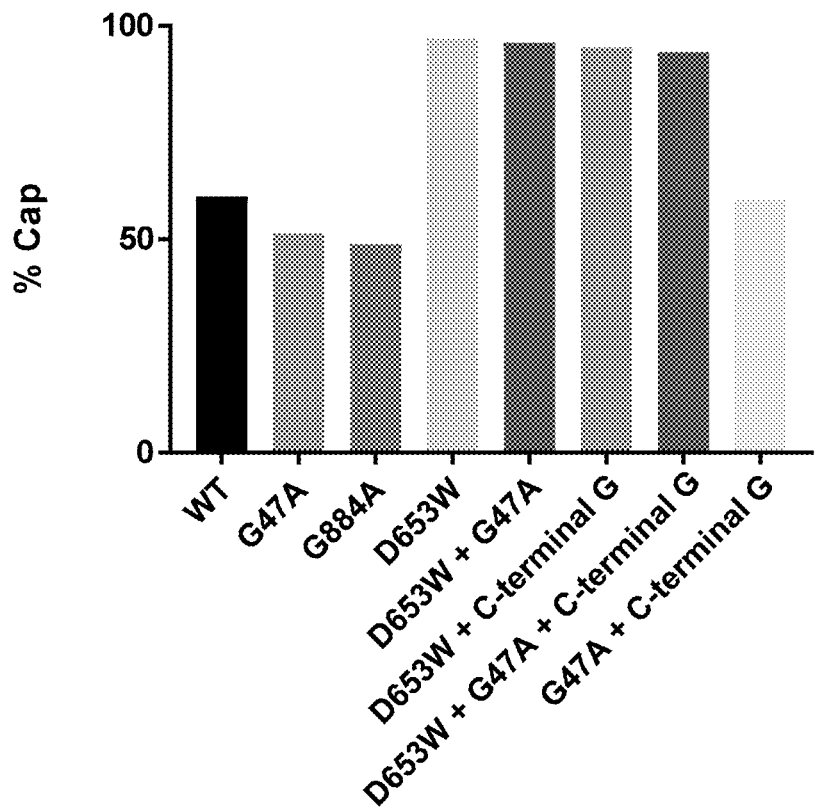
Figure 10C:
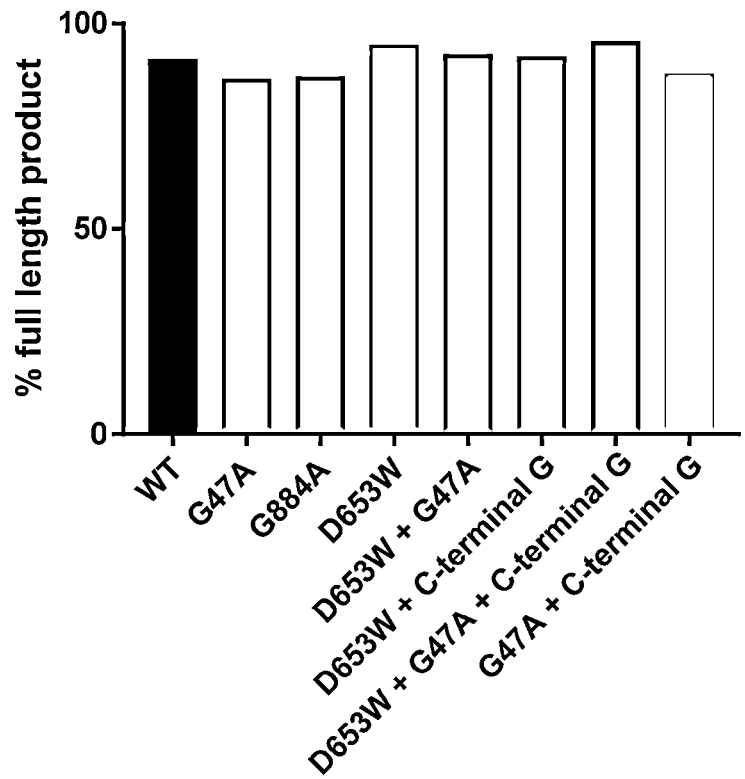
Figure 10D:
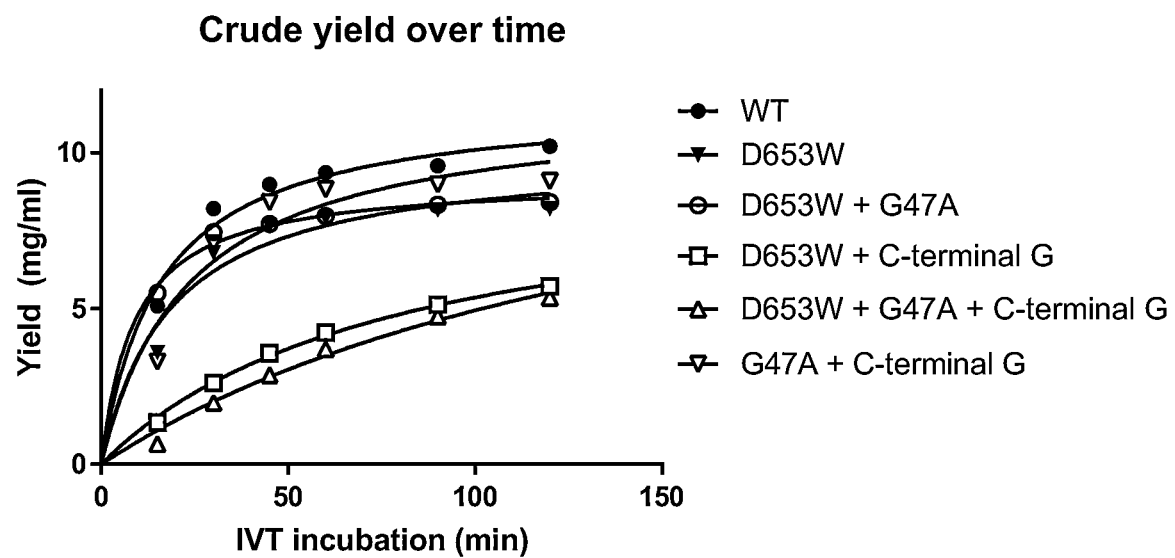

Samples of IVT reactions were collected throughout the length of each reaction (120 min) and analyzed for crude RNA yield over time (FIG. 10D). Following the IVT reaction, mRNA products were oligo-dT purified before being analyzed for 3' homogeneity (FIG. 10A), % capped RNA (i.e., percent of transcribed RNA comprising a cap) (FIG. 10B) and percent full length product (i.e., percent of total RNA comprising full length transcript) (FIG. 10C).

The G47A/D653W+C-terminal G RNA polymerase performed best among tested polymerases, with the D653W+C-terminal G RNA polymerase and G47A+C-terminal G RNA polymerase also providing RNA of excellent quality and yield. The G47A/D653W+C-terminal G RNA polymerase produced RNA wherein ~90% of total RNA comprised 3' homogeneity; the D653W+C-terminal G RNA polymerase produced RNA wherein ~75% of total RNA comprised 3' homogeneity; and the G47A+C-terminal G RNA produced RNA wherein ~70% of total RNA comprised 3' homogeneity. For comparison, WT polymerase produced RNA wherein only ~10% of total RNA comprised 3' homogeneity. All tested polymerases comprising the D653W mutation produced 90-95% capped RNA. Comparatively, WT polymerase only produced ~60% capped RNA in these experiments. All mutant variants of RNA polymerase produced good (>85%) levels of percent full length product. Further, as demonstrated in FIG. 10D, mutant variants of RNA polymerase were able to maintain acceptable RNA yields (5-9 mg/mL at 120 min of reaction time) in these experiments, even while producing RNA of higher quality (higher 3' homogeneity and higher percent capped RNA) than WT polymerase.

Example 9. A D653W+G47A RNA Polymerase Variant Produces RNA Products with Increased Capping Efficiency Relative to a Control Polymerase Variant In vitro transcription reactions were performed using DNA template, one of four cap analogs (GGAG cap, Gm6AAG, Gm6AG cap, or Ge6AG cap) at varying concentrations (1-7 mM cap analog), and either a G47A+C-terminal G RNA polymerase variant (control polymerase variant) or a G47A+D653W RNA polymerase variant. Following the IVT reactions, each experiment was subjected to LC-MS to determine the % capped RNA (i.e., percent of transcribed RNA comprising a cap).

Figure 11:
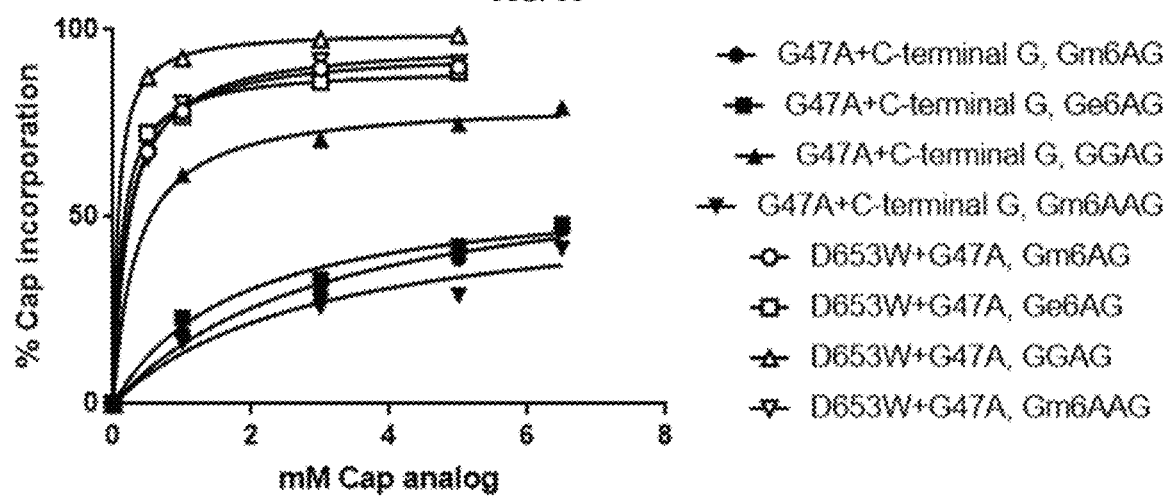
FIG. 11 shows a graph depicting the percent capped RNA resulting from IVT reactions involving the D653W+G47A RNA polymerase variant in the presence of varying concentrations of cap analogs.

The G47A+D653W RNA polymerase variant produced RNA with higher percent incorporated cap analog for all four test cap analogs, across all concentrations of cap analog, relative to the control polymerase variant (FIG. 11).

Example 10. A Panel of Multi-Substitution RNA Polymerase Variants Produce RNA Products with Increased Capping Efficiency Relative to a Control Polymerase Variant Individual in vitro transcription reactions were performed using DNA template, 5 mM equimolar NTPs, 0.5 mM GAG trinuc, and one of the T7 RNA polymerase variants as shown in Table 7.

Following the IVT reaction, mRNA products were oligo-dT purified before being analyzed by LC-MS to determine the % capped RNA (i.e., percent of transcribed RNA comprising a cap) and by HPLC to determine the RNA yield of the reaction.

TABLE 7

RNA polymerase variant used in Example 9

| RNA Polymerase variant | RNA Yield normalized to G47A + C-terminal G |
|---|---|
| D653T + G884S + G47A | 1.31 |
| WT | 1.28 |
| G884S + K387N + G47A | 1.20 |
| D351V + E350N + G47A + C-terminal G | 1.16 |
| G884T + G47A | 1.12 |
| E350A + G47A + C-terminal G | 1.11 |
| D351V + E350W + G47A + C-terminal G | 1.09 |
| K387H + G47A + C-terminal G | 1.06 |
| G47A + C-terminal G | 1.00 |
| E350N + G47A + C-terminal G | 0.98 |
| D653K + G47A + C-terminal G | 0.96 |
| E350K+ G47A + C-terminal G | 0.96 |
| D351V + E350K + K387S + G47A + C-terminal G | 0.93 |
| D653H + G47A + C-terminal G | 0.93 |
| E350K + K387H + G47A + C-terminal G | 0.89 |
| D653Y + G47A + C-terminal G | 0.89 |
| D653T + G47A + C-terminal G | 0.82 |
| D351V + E350A + K387S + G47A + C-terminal G | 0.76 |
| E350K + K387N + G47A + C-terminal G | 0.75 |
| E350N + K387N + G47A + C-terminal G | 0.75 |
| D653Q + G47A + C-terminal G | 0.68 |
| D351V + E350K + K387H + G47A + C-terminal G | 0.68 |
| D653S + G47A + C-terminal G | 0.67 |
| G884P + G47A | 0.67 |
| K387S + G47A + C-terminal G | 0.66 |
| D653A + G47A + C-terminal G | 0.65 |
| E350N + K387S + G47A + C-terminal G | 0.65 |
| D351V + E350A + K387H + G47A + C-terminal G | 0.64 |
| D351V + E350N + K387S + G47A + C-terminal G | 0.64 |
| P657A + G47A + C-terminal G | 0.63 |
| G884T + K387N + G47A | 0.60 |
| D351V + E350A + K387N + G47A + C-terminal G | 0.60 |
| D351V + E350W + K387H + G47A + C-terminal G | 0.58 |
| D351V + E350K + K387N + G47A + C-terminal G | 0.58 |
| D653N + G47A + C-terminal G | 0.56 |
| D653L + G47A + C-terminal G | 0.50 |
| E350A + K387N + G47A + C-terminal G | 0.49 |
| E350W + K387N + G47A + C-terminal G | 0.46 |
| D653G + G47A + C-terminal G | 0.42 |
| E350W + K387H | 0.41 |
| G884P + K387N + G47A | 0.24 |

Figure 12:
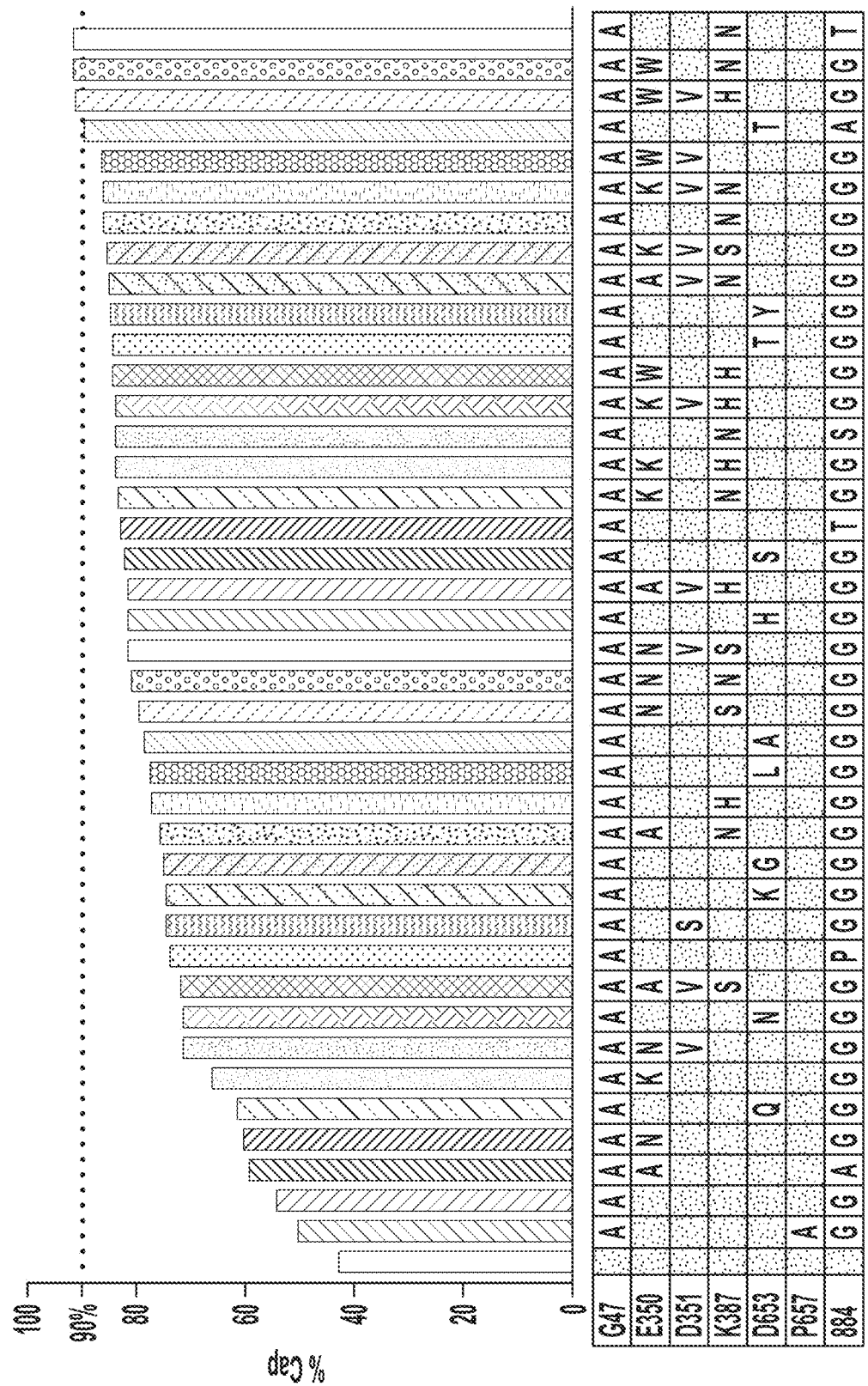
FIG. 12 shows a graph depicting the capping efficiency of multi-substitution RNA polymerase variants in the presence of a GAG trinucleotide cap analog.

41 of the 42 tested multi-substitution variants as shown in Table 7 produced higher relative amounts of percent capped RNA than the control polymerase variant (G47A+C-terminal G) or a wild-type RNA polymerase in the presence of GAG trinuc (FIG. 12). Several variants produced more than 85% capped RNA, including G47A+K387N+C-terminal T; E350W+K387N+G47A+C-terminal G; D351V+E350W+K387H+G47A+C-terminal G; G47A+D653T+C-terminal A; D351V+E350W+G47A+C-terminal G; D351V+E350K+

K387N+G47A+C-terminal G; K387N+G47A+C-terminal G; D351V+E350K+K387S+G47A+C-terminal G; and D351V+E350A+K387N+G47A+C-terminal G.

Example 11. Multi-Substitution RNA Polymerase Variants Produce RNA Products with High Levels of Capping Efficiency at Low Concentrations of GGAG Cap Analog In vitro transcription reactions were performed using DNA template, 6 mM equimolar NTPs, a variable amount of GGAG tetranucleotide cap analog (0.6 mM/0.1:1 GGAG: NTP; 0.8 mM; 1.0 mM; 1.2 mM/0.2:1 GGAG:NTP; 1.4 mM; or 1.6 mM) and 0.025 mg/mL T7 RNA polymerase-(1) G47A+C-terminal G (control polymerase variant; G47A+C-terminal G); (2) D563T+G47A+C-terminal G; (3) D653W+G47A; (4) E350W+D351V+G47A+C-terminal G; (5) D653T+G47A+C-terminal S (G884S); (6) E350W+K387N+G47A+C-terminal G; or (7) D653T+K387N+G47A+C-terminal G.

Following the IVT reaction, mRNA products were oligo-dT purified before being analyzed by LC-MS to determine the % capped RNA (i.e., percent of transcribed RNA comprising a cap) and by HPLC to determine the RNA yield of the reaction.

Figure 13A:
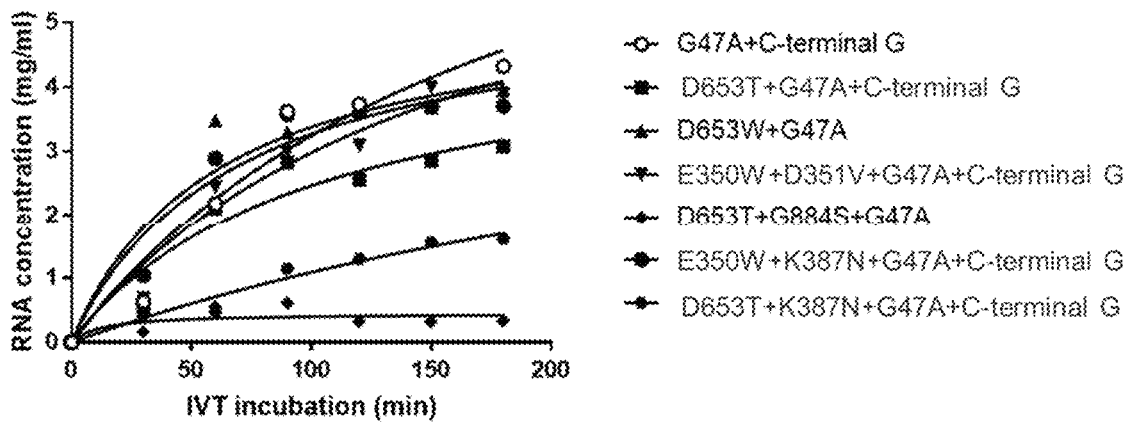
FIGS. 13A-13B show graphs depicting the relative RNA yield (FIG. 13A) and percent capped RNA (FIG. 13B) resulting from IVT reactions involving multi-substitution RNA polymerase variants in the presence of GGAG tetranucleotide cap analog.
Figure 13B:
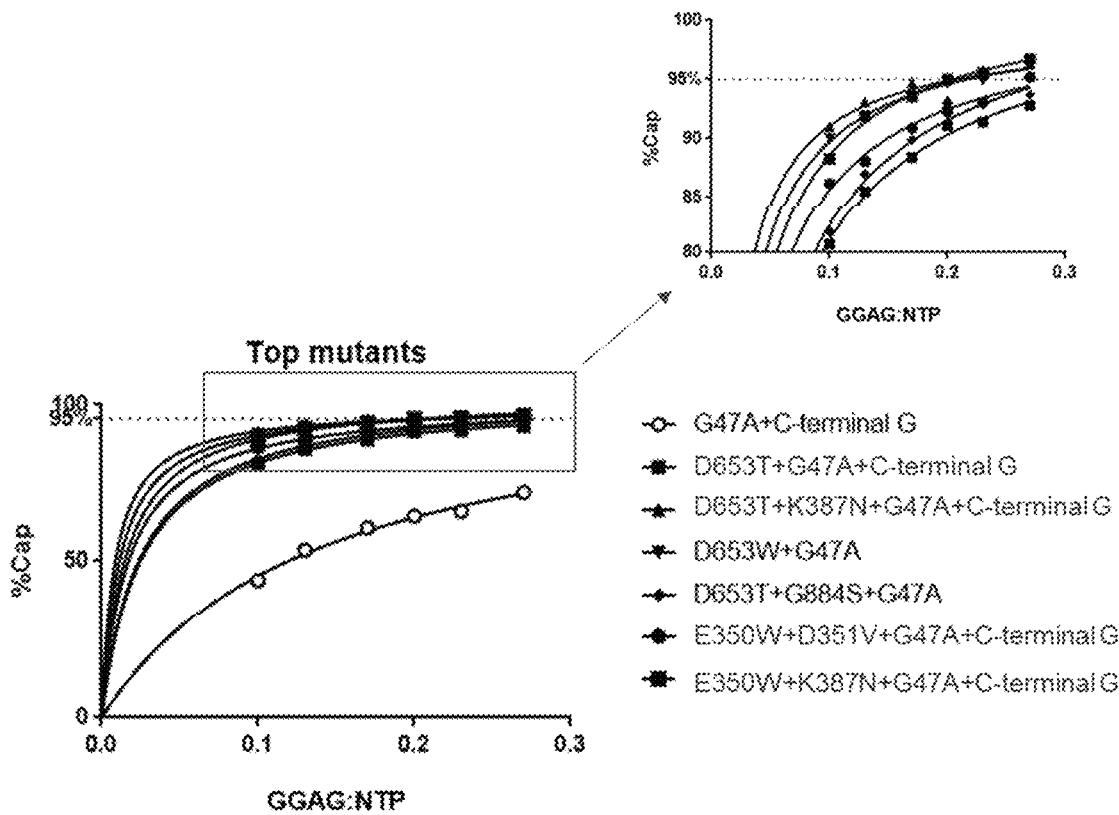

All tested multi-substitution variants produced RNA with percent capped RNA at higher levels than the control polymerase variant in the presence of GGAG cap analog, regardless of the concentration of the GGAG analog (FIG. 13B). Even at the lowest tested concentrations of GGAG cap analog (0.6 mM), all multi-substitution variants produced at least 80% capped RNA, considerably higher than the 45% capped RNA produced by the control polymerase variant. At 1.6 mM GGAG cap analog, all tested variants produced about 93-97% capped RNA.

Example 12. Multi-Substitution RNA Polymerase Variants Produce High-Quality RNA Products Regardless of DNA Template In vitro transcription reactions were performed using three different DNA templates (Construct 1, 2, and 3), 6 mM equimolar NTPs, 1.2 mM GGAG cap analog, and T7 RNA polymerase-(1) a G47A+C-terminal G RNA polymerase variant (control polymerase variant; G47A+C-terminal G); (2) a D653W+G47A RNA polymerase variant; (3) a D653T+K387N+G47A+C-terminal G RNA polymerase variant; (4) a E350W+D351V+G47A+C-terminal G RNA polymerase variant; (5) a E350W+K387N+G47A+C-terminal G RNA polymerase variant; or (6) a D653T+G47A+C-terminal G RNA polymerase variant.

Following the IVT reaction, mRNA products were oligo-dT purified before being analyzed by LC-MS to determine the % capped RNA (i.e., percent of transcribed RNA comprising a cap) and by HPLC to determine the RNA yield of the reaction.

Figure 14A:
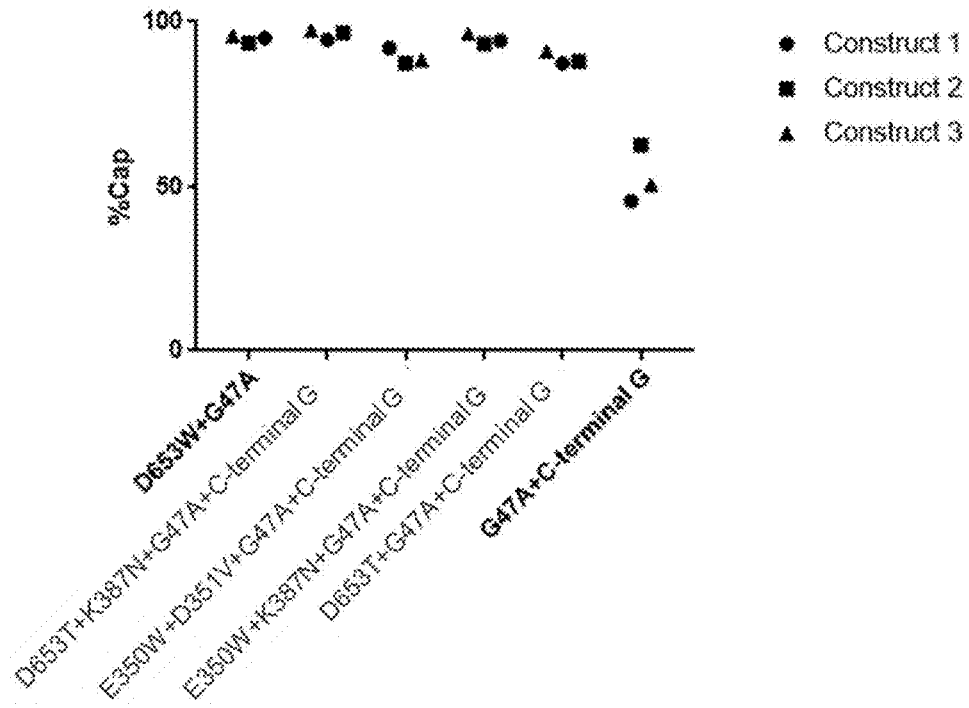
FIGS. 14A-14E show graphs depicting the functional characteristics of transcribed RNA products resulting from IVT reactions involving multi-substitution RNA polymerase variants and three different DNA templates in the presence of GGAG tetranucleotide cap analog. Following an oligo dT purification, transcribed RNA products were analyzed for percent capped RNA (FIG. 14A), percent tailed RNA (i.e., percent of RNA comprising a polyA tail) according to a Tris RP (reverse-phase) method (FIG. 14B), purity according to a RP HPLC method (FIG. 14C), 3' homogeneity (FIG. 14D), and amount of dsRNA (FIG. 14E).

All tested multi-substitution variants produced RNA with 90-95% capped RNA in the presence of GGAG tetranuc (FIG. 14A) for all three DNA templates. Each variant produced percent capped RNA at higher levels than the control polymerase variant.

Figure 14B:
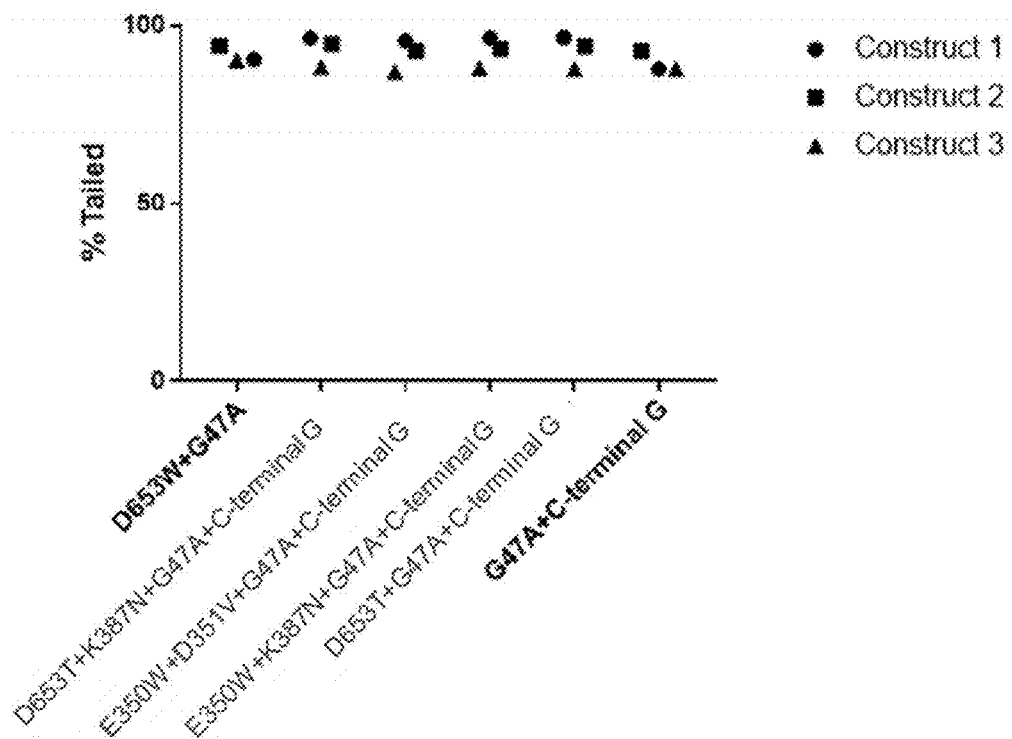

A Tris RP (reverse-phase) method was used to assess percent tailed RNA (i.e., percent of transcribed RNA comprising a polyA tail). Multi-substitution variants produced RNA with comparable % tailing relative to control variant (>90% tailed) for all three DNA templates (FIG. 14B).

Figure 14C:
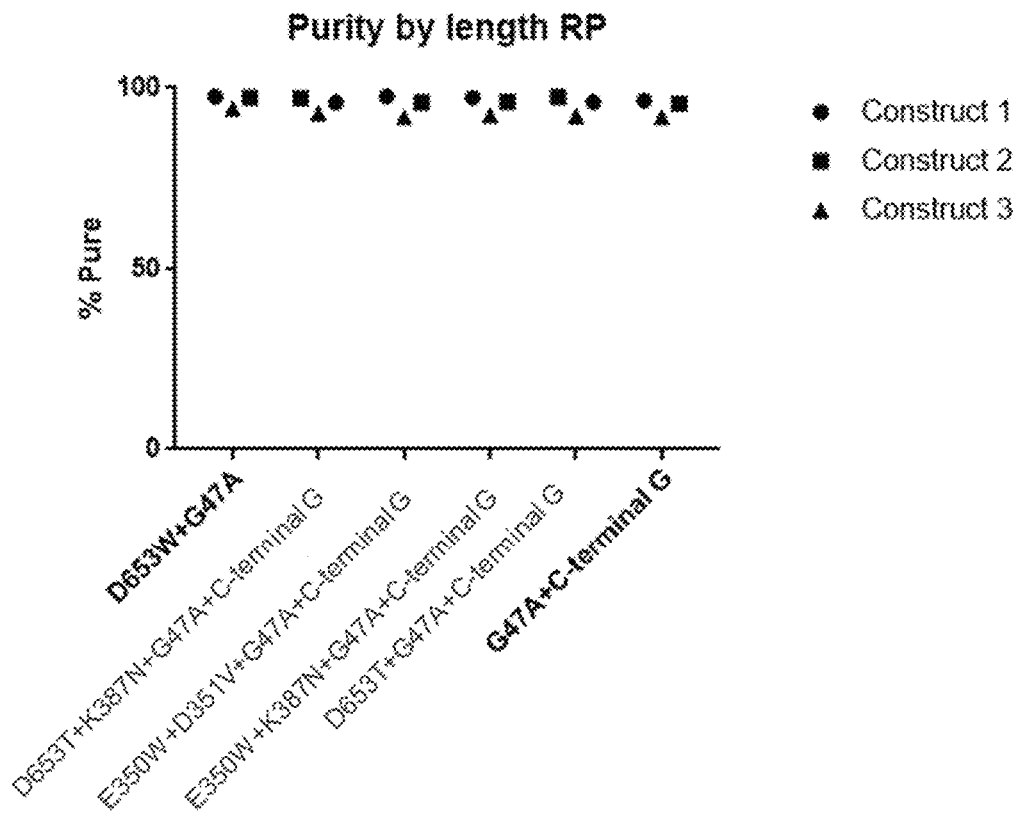

A reverse-phase HPLC method was used to assess purity of transcribed RNA. Multi-substitution variants produced RNA with comparable purity relative to control variant and WT polymerase (about 95% purity) for all three DNA templates (FIG. 14C).

Figure 14D:
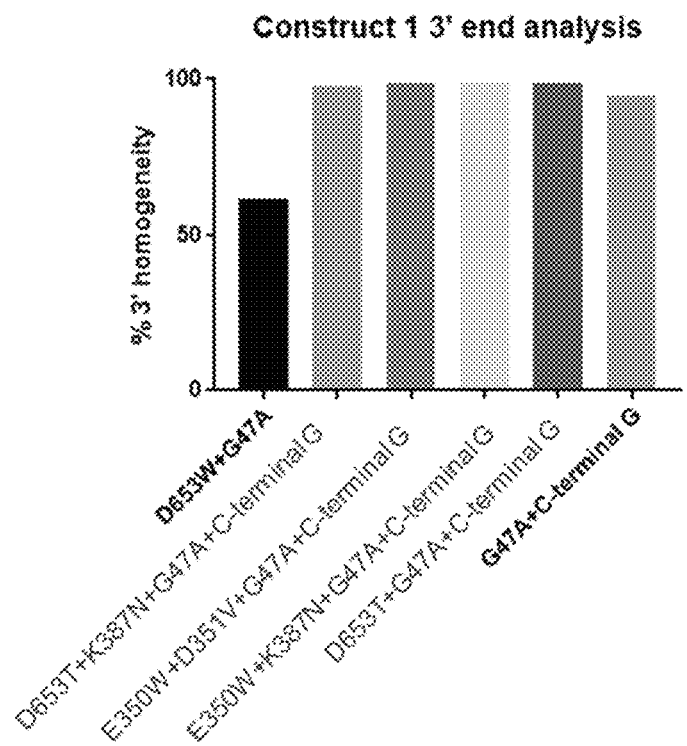

The 3' homogeneity of RNA transcripts produced from Construct 1 were measured using a RNAse T1 digest. RNA produced using the multi-substitution variants had higher percent 3' end homogeneity relative to control polymerase variant (FIG. 14D), with about 95% of total RNA having 3' homogeneity.

Figure 14E:
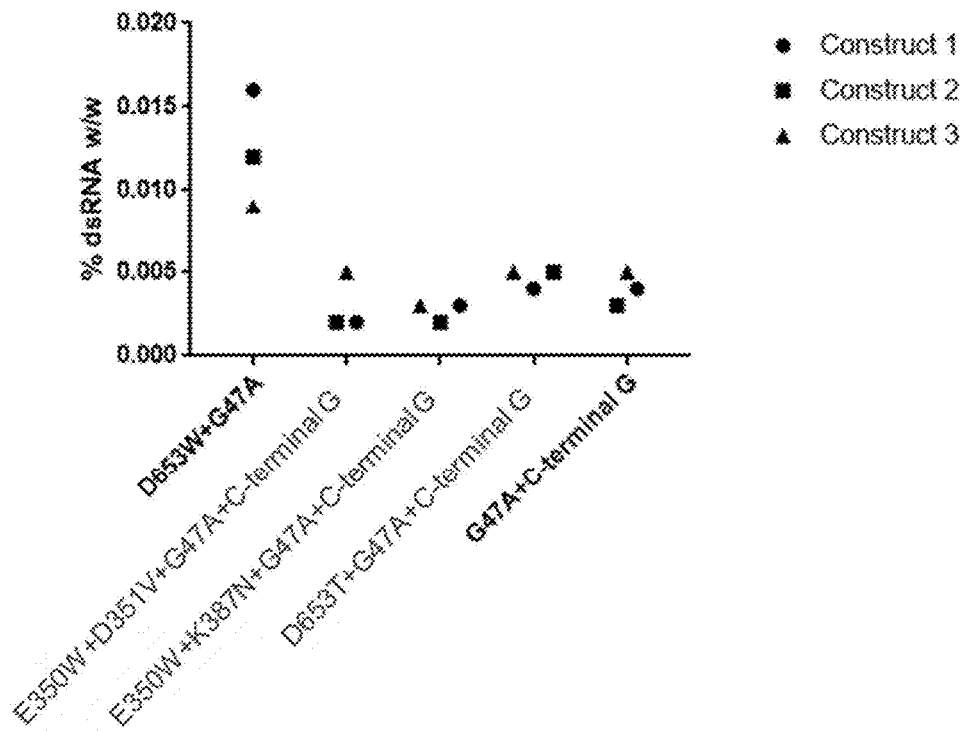

A standard dsRNA ELISA was used to assess dsRNA contaminants (e.g., longer than 40 nucleotide base pairs) following IVT reactions in this Example. All IVT reaction mixtures resulting from multi-substitution variants and the control variant contained less than ~0.015% w/w dsRNA (FIG. 14E) for all three DNA templates. In particular, IVT reaction mixtures resulting from the D653T+K387N+G47A+C-terminal G RNA polymerase variant; the E350W+D351V+G47A+C-terminal G RNA polymerase variant; the E350W+K387N+G47A+C-terminal G RNA polymerase variant; and the D653T+G47A+C-terminal G RNA polymerase variant comprised less than 0.005% w/w dsRNA for all three DNA templates.

Example 13. Multi-Substitution RNA Polymerase Variants Produce High-Quality RNA Products In vitro transcription reactions were performed using a DNA template, 6 mM equimolar NTPs, 1.5 mM GGAG cap analog, and a T7 RNA polymerase-(1) wild-type RNA polymerase; (2) G47A+C-terminal G RNA polymerase variant; (3) E350W+K387N RNA polymerase variant; (4) E350W+D351V RNA polymerase variant; or (5) K387N+D653T RNA polymerase variant; (6) E350W+K387N+G47A+C-terminal G RNA polymerase variant; (7) E350W+D351V+G47A+C-terminal G RNA polymerase variant; or (8) K387N+D653T+G47A+C-terminal G RNA polymerase variant.

Following the IVT reaction, mRNA products were oligo-dT purified before being analyzed by LC-MS to determine the % capped RNA (i.e., percent of transcribed RNA comprising a cap) and by HPLC to determine the RNA yield of the reaction.

Figure 15A:
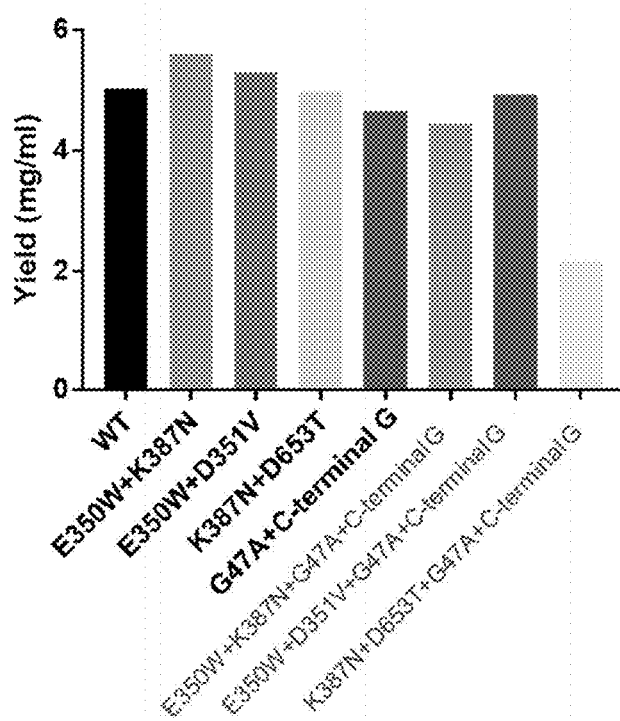
FIGS. 15A-15E show graphs depicting the functional characteristics of transcribed RNA products resulting from IVT reactions involving multi-substitution RNA polymerase variants in the presence of GGAG tetranucleotide cap analog. Following an oligo dT purification, transcribed RNA products were analyzed for yield of RNA (FIG. 15A), percent capped RNA (FIG. 15B), amount of dsRNA (FIG. 15C), purity according to a RP HPLC method (FIG. 15D), and percent tailed RNA (i.e., percent of RNA comprising a polyA tail) (FIG. 15E).

Most of the tested multi-substitution variants in this Example produced comparable yields of total RNA relative to the wild-type polymerase in the presence of GGAG tetranuc (FIG. 15A), with approximately 5 mg/mL total RNA.

Figure 15B:
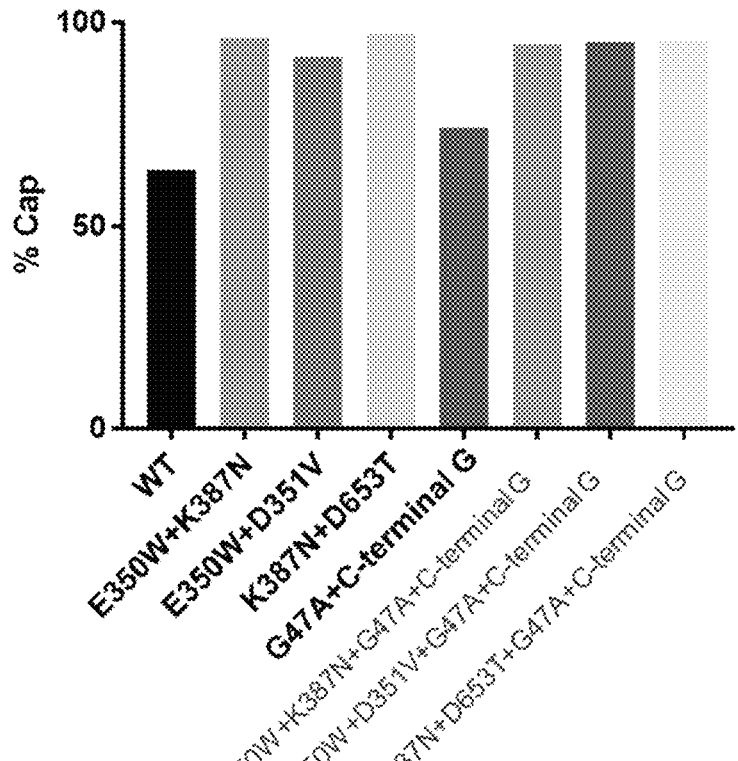

All tested multi-substitution variants in this Example produced RNA with higher amounts of capped RNA in the presence of GGAG tetranuc (FIG. 15B) relative to the wild-type polymerase variant and the G47A+C-terminal G polymerase variant. 90-95% of the total RNA produced by each of E350W+K387N RNA polymerase variant; E350W+D351V RNA polymerase variant; K387N+D653T RNA polymerase variant; E350W+K387N+G47A+C-terminal G RNA polymerase variant; E350W+D351V+G47A+C-terminal G RNA polymerase variant; and K387N+D653T+G47A+C-terminal G RNA polymerase variant comprised the GGAG tetranuc cap.

Figure 15C:
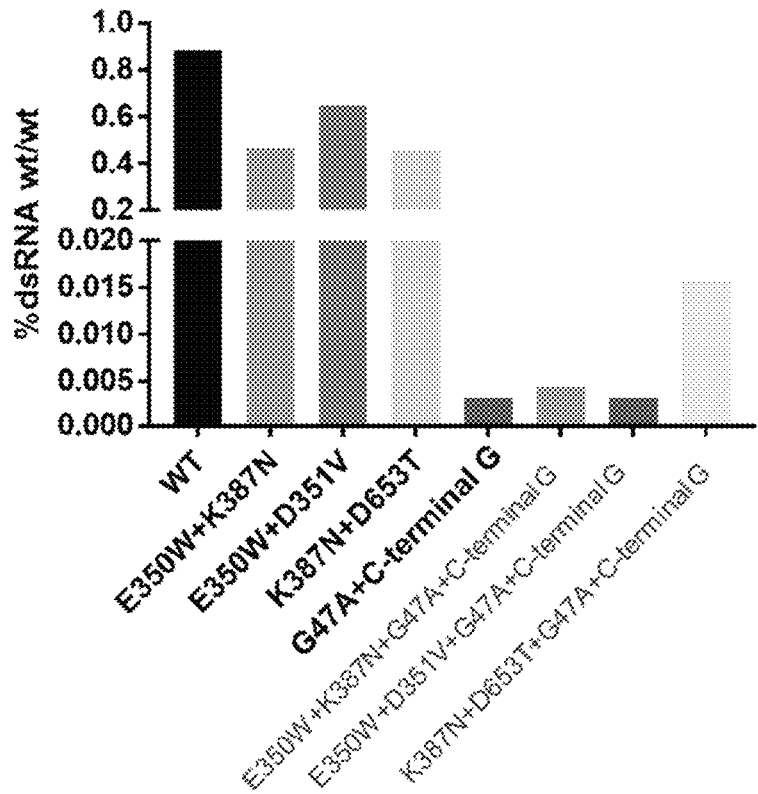

A standard dsRNA ELISA was used to assess dsRNA (e.g., longer than 40 nucleotide base pairs) produced by IVT reactions in this Example. Double mutant polymerase variants (E350W+K387N; E350W+D351V; and K387N+D653T) produced approximately 0.4% to 0.6% wt/wt dsRNA/total RNA (FIG. 15C). The other mutant variants (E350W+K387N+G47A+C-terminal G; E350W+D351V+G47A+C-terminal G; and K387N+D653T+G47A+C-terminal G) produced less than 0.015% wt/wt dsRNA/total RNA.

Figure 15D:
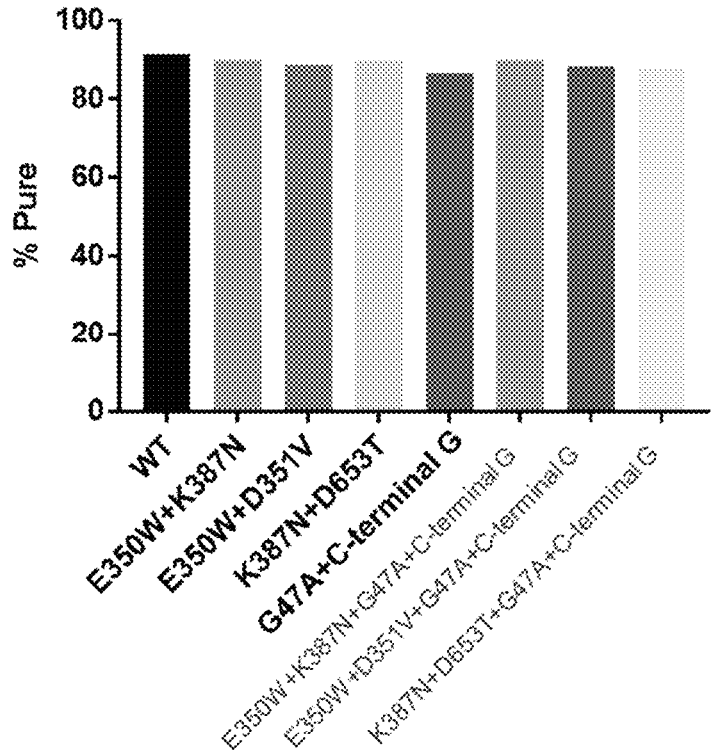

A reverse-phase HPLC method was used to assess purity of transcribed RNA. All tested multi-substitution variants in this Example produced RNA with comparable purity relative to G47A+C-terminal G variant and wild-type polymerase (about 90% purity) (FIG. 15D).

Figure 15E:
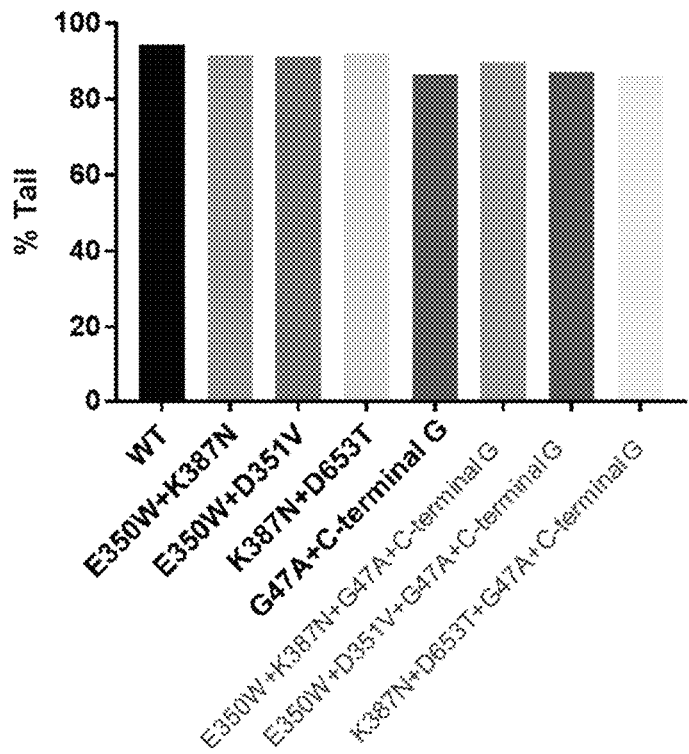

A Tris RP (reverse-phase) method was used to assess percent tailed RNA (i.e., percent of transcribed RNA comprising a polyA tail). All tested multi-substitution variants in this Example produced RNA with comparable % tailing relative to G47A+C-terminal G variant and wild-type polymerase (≥85% tailed) (FIG. 15E).

Example 14. Multi-Substitution RNA Polymerase Variants do not Cause an Increase in Indels or Point Mutations in Produced RNA In vitro transcription reactions were performed using a DNA template, 6 mM equimolar NTPs, 1.5 mM GGAG cap analog, and a T7 RNA polymerase-(1) G47A+C-terminal G variant; (2) D653T+G47A+C-terminal G variant; (3) D653W+G47A variant; (4) E350W+K387N+G47A+C-terminal G variant; (5) E350W+D351V+G47A+C-terminal G variant; or (6) D653+K387N+G47A+C-terminal G variant.

The produced mRNAs were evaluated using Next Generation Sequencing to test for insertion and deletions (indels) as well as point mutations in the produced RNA sequence. Importantly, none of the tested polymerase variants produced mRNA with significant numbers of indels or point mutations. All of the tested variants produced mRNA with 0.0-0.4% indels, below the threshold for indel percentage associated with wild-type RNA polymerase. Accordingly, this Example demonstrated that none of the tested polymerase variants or their individual mutations negatively impact the fidelity of the enzyme.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
incubating a deoxyribonucleic acid (DNA) in an in vitro transcription reaction that comprises nucleoside triphosphates, buffer, and a ribonucleic acid (RNA) polymerase variant, wherein the RNA polymerase variant (i) comprises an amino acid substitution at position D351 relative to an RNA polymerase comprising the amino acid sequence of SEQ ID NO: 1 and (ii) has at least 95% identity to the amino acid sequence of SEQ ID NO: 1, thereby producing a messenger RNA (mRNA).

2. The method of claim 1, wherein the amino acid substitution at position D351 is selected from D351C, D351I, D351K, D351L, D351M, D351P, D351Q, D351R, D351S, D351T, D351V, and D351W.

3. The method of claim 2, wherein the amino acid substitution at position D351 is D351V.

4. The method of claim 1, wherein the RNA polymerase variant further comprises an amino acid substitution at position E350, relative to a wild-type RNA polymerase comprising the amino acid sequence of SEQ ID NO: 1.

5. The method of claim 4, wherein the RNA polymerase variant further comprises an amino acid substitution at position E350, and the amino acid substitution at position E350 is selected from E350W, E350A, E350K, and E350N.

6. The method of claim 5, wherein the amino acid substitution at position E350 is E350W.

7. The method of claim 1, wherein the RNA polymerase variant further comprises a C-terminal G and an amino acid substitution at positions G47 and E350, relative to a wild-type RNA polymerase comprising the amino acid sequence of SEQ ID NO: 1.

8. The method of claim 7, wherein the amino acid substitution at position G47 is G47A, the amino acid substitution at position E350 is E350W, and the amino acid substitution at position D351 is D351V.

9. The method of claim 1, wherein the RNA polymerase variant has at least 98% identity to the amino acid sequence of SEQ ID NO: 1.

10. The method of claim 9, wherein the RNA polymerase variant comprises the amino acid sequence of SEQ ID NO: 126.

11. The method of claim 1, wherein the in vitro transcription reaction further comprises a cap analog.

12. The method of claim 11, wherein the cap analog is a dinucleotide cap, a trinucleotide cap, or a tetranucleotide cap.

13. The method of claim 11, wherein the DNA includes a 2'-deoxythymidine residue or 2'-deoxycytidine residue at template position +1.

14. The method of claim 11, wherein the cap analog and nucleoside triphosphates are present in the reaction at equimolar concentrations.

15. The method of claim 11, wherein the molar ratio of cap analog to nucleosides in the reaction is greater than 1:1.

16. The method of claim 11, wherein the in vitro transcription reaction comprises a concentration of the cap analog that is at least 5-fold lower than a concentration of the cap analog required to produce an equivalent amount of mRNA using a control T7 RNA polymerase.

17. The method of claim 1, wherein the buffer comprises dithiothreitol (DTT), magnesium ions, and tris.

18. The method of claim 1, wherein the nucleoside triphosphates are naturally-occurring, synthetic, or modified.

19. The method of claim 1, wherein greater than 50% of the mRNA produced is homogeneous at the 3' end.

20. The method of claim 1, wherein less than 5 ng of double-stranded RNA is produced per 25 μg of mRNA produced.

* * * * *

```
                         SEQUENCE LISTING

Sequence total quantity: 247
SEQ ID NO: 1            moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 1
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                   883

SEQ ID NO: 2            moltype = AA  length = 883
FEATURE                 Location/Qualifiers
REGION                  1..883
                        note = Synthetic Polypeptide
SITE                    47
                        note = misc_feature - Xaa can be Arg, Lys, His, Glu, Asp,
                         Gln, Asn, Thr, Ser, Cys, Gly,Ala, Val, Leu, Ile, Met, Pro,
                         Tyr, Trp, or Phe
source                  1..883
                        mol_type = protein
                        organism = synthetic construct
SEQUENCE: 2
MNTINIAKND FSDIELAAIP FNTLADHYGE RLAREQLALE HESYEMXEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
```

```
APFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYAS KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 3              moltype = AA  length = 883
FEATURE                   Location/Qualifiers
REGION                    1..883
                          note = Synthetic Polypeptide
SITE                      350
                          note = misc_feature - Xaa can be Arg, Lys, His, Glu, Asp,
                          Gln, Asn, Thr, Ser, Cys, Gly,Ala, Val, Leu, Ile, Met, Pro,
                          Tyr, Trp, or Phe
source                    1..883
                          mol_type = protein
                          organism = synthetic construct
SEQUENCE: 3
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVX DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 4              moltype = AA  length = 883
FEATURE                   Location/Qualifiers
REGION                    1..883
                          note = Synthetic Polypeptide
SITE                      351
                          note = misc_feature - Xaa can be Arg, Lys, His, Glu, Asp,
                          Gln, Asn, Thr, Ser, Cys, Gly,Ala, Val, Leu, Ile, Met, Pro,
                          Tyr, Trp, or Phe
source                    1..883
                          mol_type = protein
                          organism = synthetic construct
SEQUENCE: 4
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE XIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 5              moltype = AA  length = 883
FEATURE                   Location/Qualifiers
REGION                    1..883
                          note = Synthetic Polypeptide
SITE                      387
                          note
                          = misc_feature - Xaa can be Arg, Lys, His, Glu, Asp,
                          Gln, Asn, Thr, Ser, Cys, Gly,Ala, Val, Leu, Ile, Met, Pro,
                          Tyr, Trp, or Phe
source                    1..883
                          mol_type = protein
```

```
                         organism = synthetic construct
SEQUENCE: 5
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRXDKA RKSSRRISLEF MLEQANKFAN HKAIWFPYNM  420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 6             moltype = AA  length = 883
FEATURE                  Location/Qualifiers
REGION                   1..883
                         note = Synthetic Polypeptide
SITE                     394
                         note = misc_feature - Xaa can be Arg, Lys, His, Glu, Asp,
                          Gln, Asn, Thr, Ser, Cys, Gly,Ala, Val, Leu, Ile, Met, Pro,
                          Tyr, Trp, or Phe
source                   1..883
                         mol_type = protein
                         organism = synthetic construct
SEQUENCE: 6
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSXRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 7             moltype = AA  length = 883
FEATURE                  Location/Qualifiers
REGION                   1..883
                         note = Synthetic Polypeptide
SITE                     425
                         note = misc_feature - Xaa can be Arg, Lys, His, Glu, Asp,
                          Gln, Asn, Thr, Ser, Cys, Gly,Ala, Val, Leu, Ile, Met, Pro,
                          Tyr, Trp, or Phe
source                   1..883
                         mol_type = protein
                         organism = synthetic construct
SEQUENCE: 7
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSSRRISLEF MLEQANKFAN HKAIWFPYNM  420
DWRGXVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 8             moltype = AA  length = 883
FEATURE                  Location/Qualifiers
REGION                   1..883
                         note = Synthetic Polypeptide
SITE                     427
```

-continued

```
                          note = misc_feature - Xaa can be Arg, Lys, His, Glu, Asp,
                              Gln, Asn, Thr, Ser, Cys, Gly,Ala, Val, Leu, Ile, Met, Pro,
                              Tyr, Trp, or Phe
source                    1..883
                          mol_type = protein
                          organism = synthetic construct
SEQUENCE: 8
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVXAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 9              moltype = AA   length = 883
FEATURE                   Location/Qualifiers
REGION                    1..883
                          note = Synthetic Polypeptide
SITE                      437
                          note = misc_feature - Xaa can be Arg, Lys, His, Glu, Asp,
                              Gln, Asn, Thr, Ser, Cys, Gly,Ala, Val, Leu, Ile, Met, Pro,
                              Tyr, Trp, or Phe
source                    1..883
                          mol_type = protein
                          organism = synthetic construct
SEQUENCE: 9
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGXDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 10             moltype = AA   length = 883
FEATURE                   Location/Qualifiers
REGION                    1..883
                          note = Synthetic Polypeptide
SITE                      441
                          note = misc_feature - Xaa can be Arg, Lys, His, Glu, Asp,
                              Gln, Asn, Thr, Ser, Cys, Gly,Ala, Val, Leu, Ile, Met, Pro,
                              Tyr, Trp, or Phe
source                    1..883
                          mol_type = protein
                          organism = synthetic construct
SEQUENCE: 10
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT XGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883
```

```
SEQ ID NO: 11               moltype = AA  length = 883
FEATURE                     Location/Qualifiers
REGION                      1..883
                            note = Synthetic Polypeptide
SITE                        632
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 11
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KXSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 12               moltype = AA  length = 883
FEATURE                     Location/Qualifiers
REGION                      1..883
                            note = Synthetic Polypeptide
SITE                        811
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 12
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI XDSFGTIPAD AANLFKAVRE TMVDTYESCD   840
VLADFYDQFA DQLHESQLDK MPALPAKGNL NLRDILESDF AFA                    883

SEQ ID NO: 13               moltype = AA  length = 883
FEATURE                     Location/Qualifiers
REGION                      1..883
                            note = Synthetic Polypeptide
SITE                        880
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 13
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
```

```
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDX AFA                     883

SEQ ID NO: 14           moltype = AA  length = 884
FEATURE                 Location/Qualifiers
REGION                  1..884
                        note = Synthetic Polypeptide
SITE                    884
                        note = misc_feature - Xaa can be Arg, Lys, His, Glu, Asp,
                         Gln, Asn, Thr, Ser, Cys, Gly,Ala, Val, Leu, Ile, Met, Pro,
                         Tyr, Trp, or Phe
source                  1..884
                        mol_type = protein
                        organism = synthetic construct
SEQUENCE: 14
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAX                    884

SEQ ID NO: 15           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 15
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 16           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 16
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVK DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
```

```
VLADFYDQFA DQLHESQLDK MPALPAKGNL NLRDILESDF AFA              883

SEQ ID NO: 17           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 17
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVN DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA              883

SEQ ID NO: 18           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 18
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVA DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA              883

SEQ ID NO: 19           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 19
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA              883

SEQ ID NO: 20           moltype = AA  length = 883
FEATURE                 Location/Qualifiers
REGION                  1..883
                        note = Synthetic Polypeptide
source                  1..883
```

```
                        mol_type = protein
                        organism = synthetic construct
SEQUENCE: 20
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 21          moltype = AA   length = 883
FEATURE                Location/Qualifiers
REGION                 1..883
                        note = Synthetic Polypeptide
source                 1..883
                        mol_type = protein
                        organism = synthetic construct
SEQUENCE: 21
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRSDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 22          moltype = AA   length = 883
FEATURE                Location/Qualifiers
REGION                 1..883
                        note = Synthetic Polypeptide
source                 1..883
                        mol_type = protein
                        organism = synthetic construct
SEQUENCE: 22
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRHDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 23          moltype = AA   length = 883
FEATURE                Location/Qualifiers
REGION                 1..883
                        note = Synthetic Polypeptide
source                 1..883
                        mol_type = protein
                        organism = synthetic construct
SEQUENCE: 23
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
```

```
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 24           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 24
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVK DIPAIEREEL   360
PMKPEDIDMN PEALTAWKRA AAAVYRDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 25           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 25
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN DIPAIEREEL   360
PMKPEDIDMN PEALTAWKRA AAAVYRDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 26           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 26
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVA DIPAIEREEL   360
PMKPEDIDMN PEALTAWKRA AAAVYRDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
```

```
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 27           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 27
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 28           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 28
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 29           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 29
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRSDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 30           moltype = AA  length = 883
FEATURE                 Location/Qualifiers
```

```
REGION                    1..883
                          note = Synthetic Polypeptide
source                    1..883
                          mol_type = protein
                          organism = synthetic construct
SEQUENCE: 30
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRHDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 31             moltype = AA   length = 883
FEATURE                   Location/Qualifiers
REGION                    1..883
                          note = Synthetic Polypeptide
source                    1..883
                          mol_type = protein
                          organism = synthetic construct
SEQUENCE: 31
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 32             moltype = AA   length = 884
FEATURE                   Location/Qualifiers
REGION                    1..884
                          note = Synthetic Polypeptide
source                    1..884
                          mol_type = protein
                          organism = synthetic construct
SEQUENCE: 32
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVK DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 33             moltype = AA   length = 884
FEATURE                   Location/Qualifiers
REGION                    1..884
                          note = Synthetic Polypeptide
source                    1..884
                          mol_type = protein
                          organism = synthetic construct
SEQUENCE: 33
MNTINIAKND FSDIELAAIP FNTLADHYGE RLAREQLALE HESYEMAEAR FRKMFERQLK    60
```

```
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVN DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 34           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 34
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 35           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 35
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVW DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 36           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 36
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE VIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
```

```
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 37           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 37
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRSDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 38           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 38
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRHDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 39           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 39
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884
```

```
SEQ ID NO: 40           moltype = AA  length = 884
FEATURE                 Location/Qualifiers
REGION                  1..884
                        note = Synthetic Polypeptide
SITE                    350
                        note = misc_feature - Xaa can be Ala, Lys, Asn, or Trp
SITE                    387
                        note = misc_feature - Xaa can be Ser, His, or Asn
source                  1..884
                        mol_type = protein
                        organism = synthetic construct
SEQUENCE: 40
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVX VIPAIEREEL   360
PMKPEDIDMN PEALTAWKRA AAVYRXDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 41           moltype = AA  length = 884
FEATURE                 Location/Qualifiers
REGION                  1..884
                        note = Synthetic Polypeptide
SITE                    437
                        note = misc_feature - Xaa can be Thr, Tyr, Ile, or Phe
source                  1..884
                        mol_type = protein
                        organism = synthetic construct
SEQUENCE: 41
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRKDKA RKSRRISLEF MLEQANKFAN HKAIWFPYNM   420
DWRGRVYAVS MFNPQGXDMT RGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 42           moltype = AA  length = 884
FEATURE                 Location/Qualifiers
REGION                  1..884
                        note = Synthetic Polypeptide
SITE                    884
                        note = misc_feature - Xaa can be Ala, Ser, Thr, or Pro
source                  1..884
                        mol_type = protein
                        organism = synthetic construct
SEQUENCE: 42
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
```

```
VLADFYDQFA DQLHESQLDK MPALPAKGNL NLRDILESDY AFAX         884

SEQ ID NO: 43            moltype = AA  length = 884
FEATURE                  Location/Qualifiers
REGION                   1..884
                         note = Synthetic Polypeptide
SITE                     632
                         note = misc_feature - Xaa can be Lys or Thr
SITE                     653
                         note = misc_feature - Xaa can be Thr or Lys
SITE                     657
                         note = misc_feature - Xaa can be Trp, Arg, or Ala
source                   1..884
                         mol_type = protein
                         organism = synthetic construct
SEQUENCE: 43
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK 480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KXSVMTLAYG SKEFGFRQQV LEXTIQXAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 44            moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 44
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK 480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 45            moltype = AA  length = 883
FEATURE                  Location/Qualifiers
REGION                   1..883
                         note = Synthetic Polypeptide
SITE                     506
                         note = misc_feature - Xaa can be Arg, Lys, His, Glu, Asp,
                         Gln, Asn, Thr, Ser, Cys, Gly,Ala, Val, Leu, Ile, Met, Pro,
                         Tyr, Trp, or Phe
source                   1..883
                         mol_type = protein
                         organism = synthetic construct
SEQUENCE: 45
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK 480
FIEENHENIM ACAKSPLENT WWAEQXSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
```

```
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 46            moltype = AA  length = 883
FEATURE                  Location/Qualifiers
REGION                   1..883
                         note = Synthetic Polypeptide
SITE                     628
                         note = misc_feature - Xaa can be Arg, Lys, His, Glu, Asp,
                           Gln, Asn, Thr, Ser, Cys, Gly,Ala, Val, Leu, Ile, Met, Pro,
                           Tyr, Trp, or Phe
source                   1..883
                         mol_type = protein
                         organism = synthetic construct
SEQUENCE: 46
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRXVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 47            moltype = AA  length = 883
FEATURE                  Location/Qualifiers
REGION                   1..883
                         note = Synthetic Polypeptide
SITE                     653
                         note = misc_feature - Xaa can be Arg, Lys, His, Glu, Asp,
                           Gln, Asn, Thr, Ser, Cys, Gly,Ala, Val, Leu, Ile, Met, Pro,
                           Tyr, Trp, or Phe
source                   1..883
                         mol_type = protein
                         organism = synthetic construct
SEQUENCE: 47
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEXTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 48            moltype = AA  length = 883
FEATURE                  Location/Qualifiers
REGION                   1..883
                         note = Synthetic Polypeptide
SITE                     657
                         note = misc_feature - Xaa can be Arg, Lys, His, Glu, Asp,
                           Gln, Asn, Thr, Ser, Cys, Gly,Ala, Val, Leu, Ile, Met, Pro,
                           Tyr, Trp, or Phe
source                   1..883
                         mol_type = protein
                         organism = synthetic construct
SEQUENCE: 48
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
```

```
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQXAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 49           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 49
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQWSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 50           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 50
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 51           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 51
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
```

```
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 52           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 52
MNTINIAKND FSDIELAAIP FNTLADHYGE RLAREQLALE HESYEMGEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQWAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 53           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 53
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQWSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 54           moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 54
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRWVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 55           moltype = AA  length = 883
FEATURE                 Location/Qualifiers
REGION                  1..883
                        note = Synthetic Polypeptide
```

```
source                     1..883
                           mol_type = protein
                           organism = synthetic construct
SEQUENCE: 55
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 56              moltype = AA  length = 883
FEATURE                    Location/Qualifiers
REGION                     1..883
                           note = Synthetic Polypeptide
source                     1..883
                           mol_type = protein
                           organism = synthetic construct
SEQUENCE: 56
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 57              moltype = AA  length = 884
FEATURE                    Location/Qualifiers
REGION                     1..884
                           note = Synthetic Polypeptide
source                     1..884
                           mol_type = protein
                           organism = synthetic construct
SEQUENCE: 57
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQWSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 58              moltype = AA  length = 884
FEATURE                    Location/Qualifiers
REGION                     1..884
                           note = Synthetic Polypeptide
source                     1..884
                           mol_type = protein
                           organism = synthetic construct
SEQUENCE: 58
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
```

```
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 59           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 59
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 60           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 60
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 61           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 61
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
```

```
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 62           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 62
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAT                    884

SEQ ID NO: 63           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 63
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAT                    884

SEQ ID NO: 64           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 64
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 65           moltype = AA  length = 884
```

```
FEATURE                 Location/Qualifiers
REGION                  1..884
                        note = Synthetic Polypeptide
source                  1..884
                        mol_type = protein
                        organism = synthetic construct
SEQUENCE: 65
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVV KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 66           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 66
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAP                    884

SEQ ID NO: 67           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 67
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAP                    884

SEQ ID NO: 68           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 68
```

```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 69          moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 69
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 70          moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 70
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAT                   884

SEQ ID NO: 71          moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 71
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
```

```
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEWTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAT                  884

SEQ ID NO: 72           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 72
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEWTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAS                  884

SEQ ID NO: 73           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 73
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEWTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAS                  884

SEQ ID NO: 74           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 74
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEWTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
```

```
VLADFYDQFA DQLHESQLDK MPALPAKGNL NLRDILESDF AFAP              884

SEQ ID NO: 75           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 75
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRNDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEWTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAP              884

SEQ ID NO: 76           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 76
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LETTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG              884

SEQ ID NO: 77           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 77
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRNDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LETTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG              884

SEQ ID NO: 78           moltype = AA  length = 884
FEATURE                 Location/Qualifiers
REGION                  1..884
                        note = Synthetic Polypeptide
source                  1..884
```

```
                        mol_type = protein
                        organism = synthetic construct
SEQUENCE: 78
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAT                    884

SEQ ID NO: 79           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 79
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAT                    884

SEQ ID NO: 80           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 80
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 81           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 81
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
```

```
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSSRRISLEF MLEQANKFAN HKAIWFPYNM  420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGAP    780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 82            moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 82
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEAR PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAP                    884

SEQ ID NO: 83            moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 83
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAP                    884

SEQ ID NO: 84            moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 84
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQPAID   660
```

```
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 85           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 85
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEKTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 86           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 86
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEKTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAT                    884

SEQ ID NO: 87           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 87
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEKTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAT                    884

SEQ ID NO: 88           moltype = AA  length = 884
FEATURE                 Location/Qualifiers
```

```
REGION                    1..884
                          note = Synthetic Polypeptide
source                    1..884
                          mol_type = protein
                          organism = synthetic construct
SEQUENCE: 88
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 89             moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 89
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAS                    884

SEQ ID NO: 90             moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 90
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAP                    884

SEQ ID NO: 91             moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 91
MNTINIAKND FSDIELAAIP FNTLADHYGE RLAREQLALE HESYEMAEAR FRKMFERQLK    60
```

```
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEKTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAP                    884

SEQ ID NO: 92            moltype = AA   length = 884
FEATURE                  Location/Qualifiers
REGION                   1..884
                         note = Synthetic Polypeptide
source                   1..884
                         mol_type = protein
                         organism = synthetic construct
SEQUENCE: 92
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRSDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 93            moltype = AA   length = 884
FEATURE                  Location/Qualifiers
REGION                   1..884
                         note = Synthetic Polypeptide
source                   1..884
                         mol_type = protein
                         organism = synthetic construct
SEQUENCE: 93
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRHDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 94            moltype = AA   length = 884
FEATURE                  Location/Qualifiers
REGION                   1..884
                         note = Synthetic Polypeptide
source                   1..884
                         mol_type = protein
                         organism = synthetic construct
SEQUENCE: 94
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
```

```
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 95           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 95
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA DIPAIEREEL    360
PMKPEDIDMN PEALTAWKRA AAAVYRSDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 96           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 96
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA DIPAIEREEL    360
PMKPEDIDMN PEALTAWKRA AAAVYRHDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 97           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 97
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884
```

```
SEQ ID NO: 98           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 98
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 99           moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 99
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK DIPAIEREEL  360
PMKPEDIDMN PEALTAWKRA AAAVYRSDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 100          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 100
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK DIPAIEREEL  360
PMKPEDIDMN PEALTAWKRA AAAVYRHDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 101          moltype = AA  length = 884
FEATURE                 Location/Qualifiers
REGION                  1..884
                        note = Synthetic Polypeptide
source                  1..884
                        mol_type = protein
```

```
                        organism = synthetic construct
SEQUENCE: 101
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVK DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 102          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 102
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 103          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 103
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN DIPAIEREEL   360
PMKPEDIDMN PEALTAWKRA AAAVYRSDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 104          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 104
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
```

```
SKKALMRYED VYMPEVYKAI NIAQNTAWKI NKKVLAVANV ITKWKHCPVN DIPAIEREEL  360
PMKPEDIDMN PEALTAWKRA AAAVYRHDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 105          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 105
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVN DIPAIEREEL  360
PMKPEDIDMN PEALTAWKRA AAAVYRNDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 106          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 106
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 107          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 107
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW DIPAIEREEL  360
PMKPEDIDMN PEALTAWKRA AAAVYRSDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
```

```
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 108           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 108
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVW DIPAIEREEL    360
PMKPEDIDMN PEALTAWKRA AAAVYRHDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 109           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 109
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVW DIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 110           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 110
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE VIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 111           moltype = AA  length = 884
FEATURE                  Location/Qualifiers
REGION                   1..884
```

```
                         note        = Synthetic Polypeptide
source                   1..884
                         mol_type    = protein
                         organism    = synthetic construct
SEQUENCE: 111
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRSDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 112           moltype = AA   length = 884
FEATURE                  Location/Qualifiers
REGION                   1..884
                         note        = Synthetic Polypeptide
source                   1..884
                         mol_type    = protein
                         organism    = synthetic construct
SEQUENCE: 112
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRHDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 113           moltype = AA   length = 884
FEATURE                  Location/Qualifiers
REGION                   1..884
                         note        = Synthetic Polypeptide
source                   1..884
                         mol_type    = protein
                         organism    = synthetic construct
SEQUENCE: 113
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 114           moltype = AA   length = 884
FEATURE                  Location/Qualifiers
REGION                   1..884
                         note        = Synthetic Polypeptide
source                   1..884
                         mol_type    = protein
                         organism    = synthetic construct
SEQUENCE: 114
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
```

```
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA VIPAIEREEL    360
PMKPEDIDMN PEALTAWKRA AAAVYRKDKA RKSRRISLEF MLEQANKHAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 115           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 115
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA VIPAIEREEL    360
PMKPEDIDMN PEALTAWKRA AAAVYRSDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 116           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 116
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA VIPAIEREEL    360
PMKPEDIDMN PEALTAWKRA AAAVYRHDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 117           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 117
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVA VIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
```

```
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 118          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 118
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK VIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 119          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 119
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK VIPAIEREEL  360
PMKPEDIDMN PEALTAWKRA AAAVYRSDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 120          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 120
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVK VIPAIEREEL  360
PMKPEDIDMN PEALTAWKRA AAAVYRHDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884
```

| SEQ ID NO: 121 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 121
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVK VIPAIEREEL   360
PMKPEDIDMN PEALTAWKRA AAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 122 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 122
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN VIPAIEREEL   360
PMKPEDIDMN PEALTAWKRA AAVYRDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 123 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 123
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN VIPAIEREEL   360
PMKPEDIDMN PEALTAWKRA AAVYRSDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 124 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

```
SEQUENCE: 124
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN VIPAIEREEL   360
PMKPEDIDMN PEALTAWKRA AAAVYRHDKA RKSRRISLEF MLEQANKFAN HKAIWFPYNM   420
DWRGRVYAVS MFNPQGNDMT KGLLTLAKGK PIGKEGYYAV KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 125           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 125
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVN VIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 126           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 126
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW VIPAIEREEL   360
PMKPEDIDMN PEALTAWKRA AAAVYRDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 127           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 127
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW VIPAIEREEL   360
```

```
PMKPEDIDMN PEALTAWKRA AAAVYRSDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 128         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 128
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW VIPAIEREEL  360
PMKPEDIDMN PEALTAWKRA AAVYRHDKA  RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 129         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 129
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW VIPAIEREEL  360
PMKPEDIDMN PEALTAWKRA AAVYRNDKA  RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 130         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 130
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAVYRKDKA  RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEATIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
```

```
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 131          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 131
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEFTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 132          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 132
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEGTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 133          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 133
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEHTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 134          moltype = AA  length = 884
FEATURE                 Location/Qualifiers
REGION                  1..884
                        note = Synthetic Polypeptide
```

```
source                  1..884
                        mol_type = protein
                        organism = synthetic construct
SEQUENCE: 134
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEITIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 135          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 135
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LELTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 136          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 136
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEMTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 137          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 137
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
```

```
APFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LENTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 138           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 138
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEPTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 139           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 139
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEQTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 140           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 140
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
```

```
NTGEISEKVK LGTKALAGQW LAYGVTRSVT KRSVMTLAYG SKEFGFRQQV LERTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 141          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 141
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LESTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 142          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 142
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEVTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 143          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 143
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEYTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 144          moltype = AA  length = 884
```

```
FEATURE                 Location/Qualifiers
REGION                  1..884
                        note = Synthetic Polypeptide
source                  1..884
                        mol_type = protein
                        organism = synthetic construct
SEQUENCE: 144
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVV KRSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 145          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 145
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 146          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 146
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 147          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 147
```

```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 148         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 148
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 149         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 149
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEWTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 150         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 150
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
```

```
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LETTIQWAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 151          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 151
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LETTIQRAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 152          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 152
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LETTIQAAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 153          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 153
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK   180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEKTIQWAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
```

```
VLADFYDQFA DQLHESQLDK MPALPAKGNL NLRDILESDF AFAG                884

SEQ ID NO: 154          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 154
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 155          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 155
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEKTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 156          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 156
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGTDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 157          moltype = AA  length = 884
FEATURE                 Location/Qualifiers
REGION                  1..884
                        note = Synthetic Polypeptide
source                  1..884
```

```
                        mol_type = protein
                        organism = synthetic construct
SEQUENCE: 157
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGYDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 158           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 158
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGIDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 159           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 159
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGYDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 160           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 160
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
```

```
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT RGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 161          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 161
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEAR PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGTDMT RGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 162          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 162
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGYDMT RGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                  884

SEQ ID NO: 163          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 163
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGIDMT RGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
```

```
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 164         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 164
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKPAN HKAIWFPYNM   420
DWRGRVYAVS MFNPQGFDMT RGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 165         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 165
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKPAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 166         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 166
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKPAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQWSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 167         moltype = AA  length = 884
FEATURE                Location/Qualifiers
```

```
REGION                    1..884
                          note = Synthetic Polypeptide
source                    1..884
                          mol_type = protein
                          organism = synthetic construct
SEQUENCE: 167
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQWSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 168            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 168
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQFSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 169            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 169
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HPFKKNVEEQL NKRVGHVYKK  180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQFSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 170            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 170
MNTINIAKND FSDIELAAIP FNTLADHYGE RLAREQLALE HESYEMAEAR FRKMFERQLK    60
```

```
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQTNAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQYSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 171           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 171
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQTNAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQYSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRWVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 172           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 172
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQTNAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQRSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 173           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 173
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQTNAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
```

```
FIEENHENIM ACAKSPLENT WWAEQRSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 174           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 174
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQLSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 175           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 175
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQLSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRWVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 176           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 176
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LECTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884
```

```
SEQ ID NO: 177          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 177
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEETIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 178          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 178
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 179          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 179
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 180          moltype = AA  length = 884
FEATURE                 Location/Qualifiers
REGION                  1..884
                        note = Synthetic Polypeptide
source                  1..884
                        mol_type = protein
```

```
                        organism = synthetic construct
SEQUENCE: 180
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 181           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 181
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEDTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 182           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 182
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEDTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 183           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 183
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
```

```
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KTSVMTLAYG SKEFGFRQQV LEDTIQRAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 184          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 184
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KKSVMTLAYG SKEFGFRQQV LEDTIQAAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 185          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 185
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KTSVMTLAYG SKEFGFRQQV LEDTIQAAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                     884

SEQ ID NO: 186          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 186
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KKSVMTLAYG SKEFGFRQQV LEWTIQPAID    660
SGKGLMFTQP NQAAGYMAKL IWESVSVTVV AAVEAMNWLK SAAKLLAAEV KDKKTGEILR    720
```

-continued

```
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 187            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 187
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEWTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 188            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 188
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEWTIQAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 189            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 189
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEWTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 190            moltype = AA  length = 884
FEATURE                   Location/Qualifiers
REGION                    1..884
```

```
                        note = Synthetic Polypeptide
source                  1..884
                        mol_type = protein
                        organism = synthetic construct
SEQUENCE: 190
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KKSVMTLAYG SKEFGFRQQV LEWTIQRAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 191          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 191
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KTSVMTLAYG SKEFGFRQQV LEWTIQRAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 192          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 192
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KKSVMTLAYG SKEFGFRQQV LEWTIQAAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 193          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 193
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
```

```
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEWTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 194          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 194
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEFTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 195          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 195
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEFTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 196          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 196
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
```

```
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEFTIQWAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 197          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 197
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KKSVMTLAYG SKEFGFRQQV LEFTIQWAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 198          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 198
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KTSVMTLAYG SKEFGFRQQV LEFTIQWAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 199          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 199
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEFTIQRAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884
```

| SEQ ID NO: 200 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 200
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEFTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 201 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 201
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEFTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 202 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

SEQUENCE: 202
```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEFTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884
```

| SEQ ID NO: 203 | moltype = AA length = 884 |
| --- | --- |
| FEATURE | Location/Qualifiers |
| REGION | 1..884 |
| | note = Synthetic Polypeptide |
| source | 1..884 |
| | mol_type = protein |
| | organism = synthetic construct |

```
SEQUENCE: 203
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KKSVMTLAYG SKEFGFRQQV LEFTIQAAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG                  884

SEQ ID NO: 204          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 204
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KTSVMTLAYG SKEFGFRQQV LEFTIQAAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG                  884

SEQ ID NO: 205          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 205
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KKSVMTLAYG SKEFGFRQQV LEYTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG                  884

SEQ ID NO: 206          moltype = AA   length = 884
FEATURE                 Location/Qualifiers
REGION                  1..884
                        note = Synthetic Polypeptide
source                  1..884
                        mol_type = protein
                        organism = synthetic construct
SEQUENCE: 206
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
```

```
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KTSVMTLAYG SKEFGFRQQV LEYTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG        884

SEQ ID NO: 207          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 207
MNTINIAKND FSDIELAAIP FNTLADHYGE RLAREQLALE HESYEMAEAR FRKMFERQLK 60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEYTIQWAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG        884

SEQ ID NO: 208          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 208
MNTINIAKND FSDIELAAIP FNTLADHYGE RLAREQLALE HESYEMAEAR FRKMFERQLK 60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KKSVMTLAYG SKEFGFRQQV LEYTIQWAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG        884

SEQ ID NO: 209          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 209
MNTINIAKND FSDIELAAIP FNTLADHYGE RLAREQLALE HESYEMAEAR FRKMFERQLK 60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KTSVMTLAYG SKEFGFRQQV LEYTIQWAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
```

```
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 210          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 210
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEYTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 211          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 211
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEYTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 212          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 212
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEYTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 213          moltype = AA  length = 884
FEATURE                 Location/Qualifiers
REGION                  1..884
                        note = Synthetic Polypeptide
```

```
                                 -continued source                  1..884
                        mol_type = protein
                        organism = synthetic construct
SEQUENCE: 213
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEYTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 214          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 214
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEYTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 215          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 215
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEYTIQAAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                    884

SEQ ID NO: 216          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 216
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
```

```
APFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 217          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 217
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 218          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 218
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LETTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 219          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 219
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
APFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
```

```
NTGEISEKVK LGTKALAGQW LAYGVTRSVT KTSVMTLAYG SKEFGFRQQV LETTIQWAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 220           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 220
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KKSVMTLAYG SKEFGFRQQV LETTIQRAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 221           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 221
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KTSVMTLAYG SKEFGFRQQV LETTIQRAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 222           moltype = AA  length = 884
FEATURE                  Location/Qualifiers
REGION                   1..884
                         note = Synthetic Polypeptide
source                   1..884
                         mol_type = protein
                         organism = synthetic construct
SEQUENCE: 222
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KKSVMTLAYG SKEFGFRQQV LETTIQAAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884

SEQ ID NO: 223           moltype = AA  length = 884
```

| | | |
|---|---|---|
| FEATURE | Location/Qualifiers | |
| REGION | 1..884 | |
| | note = Synthetic Polypeptide | |
| source | 1..884 | |
| | mol_type = protein | |
| | organism = synthetic construct | |

SEQUENCE: 223

```
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KTSVMTLAYG SKEFGFRQQV LETTIQAAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884
```

| | | |
|---|---|---|
| SEQ ID NO: 224 | moltype = AA  length = 884 | |
| FEATURE | Location/Qualifiers | |
| REGION | 1..884 | |
| | note = Synthetic Polypeptide | |
| source | 1..884 | |
| | mol_type = protein | |
| | organism = synthetic construct | |

SEQUENCE: 224

```
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KKSVMTLAYG SKEFGFRQQV LEKTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884
```

| | | |
|---|---|---|
| SEQ ID NO: 225 | moltype = AA  length = 884 | |
| FEATURE | Location/Qualifiers | |
| REGION | 1..884 | |
| | note = Synthetic Polypeptide | |
| source | 1..884 | |
| | mol_type = protein | |
| | organism = synthetic construct | |

SEQUENCE: 225

```
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KTSVMTLAYG SKEFGFRQQV LEKTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFAG                   884
```

| | | |
|---|---|---|
| SEQ ID NO: 226 | moltype = AA  length = 884 | |
| FEATURE | Location/Qualifiers | |
| REGION | 1..884 | |
| | note = Synthetic Polypeptide | |
| source | 1..884 | |
| | mol_type = protein | |
| | organism = synthetic construct | |

SEQUENCE: 226

```
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEKTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 227         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 227
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KTSVMTLAYG SKEFGFRQQV LEKTIQWAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 228         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 228
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KKSVMTLAYG SKEFGFRQQV LEKTIQRAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAG                   884

SEQ ID NO: 229         moltype = AA  length = 884
FEATURE                Location/Qualifiers
REGION                 1..884
                       note = Synthetic Polypeptide
source                 1..884
                       mol_type = protein
                       organism = synthetic construct
SEQUENCE: 229
MNTINIAKND FSDIELAAIP FNTLADHYGE RLAREQLALE HESYEMAEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
```

```
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KTSVMTLAYG SKEFGFRQQV LEKTIQRAID    660
SGKGLMFTQP NQAAGYMAKL IWESVSVTVV AAVEAMNWKL SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 230            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 230
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KKSVMTLAYG SKEFGFRQQV LEKTIQAAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 231            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 231
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KTSVMTLAYG SKEFGFRQQV LEKTIQAAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAG                    884

SEQ ID NO: 232            moltype = AA  length = 884
FEATURE                   Location/Qualifiers
REGION                    1..884
                          note = Synthetic Polypeptide
source                    1..884
                          mol_type = protein
                          organism = synthetic construct
SEQUENCE: 232
MNTINIAKND FSDIELAAIP FNTLADHYGE RLAREQLALE HESYEMAEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HPFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
```

```
VLADFYDQFA DQLHESQLDK MPALPAKGNL NLRDILESDY AFAG            884

SEQ ID NO: 233          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 233
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDY AFAS            884

SEQ ID NO: 234          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 234
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDY AFAT            884

SEQ ID NO: 235          moltype = AA  length = 884
FEATURE                 Location/Qualifiers
REGION                  1..884
                        note = Synthetic Polypeptide
source                  1..884
                        mol_type = protein
                        organism = synthetic construct
SEQUENCE: 235
MNTINIAKND FSDIELAAIP FNTLADHYGE RLAREQLALE HESYEMAEAR FRKMFERQLK   60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVE DIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDY AFAP            884

SEQ ID NO: 236          moltype = AA  length = 883
FEATURE                 Location/Qualifiers
REGION                  1..883
                        note = Synthetic Polypeptide
source                  1..883
```

```
                        mol_type = protein
                        organism = synthetic construct
SEQUENCE: 236
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW VIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE TAFLQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 237          moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 237
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 238          moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 238
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVW DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 239          moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 239
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
```

```
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE VIPAIEREEL    360
PMKPEDIDMN PEALTAWKRA AAAVYRNDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 240          moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 240
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQGER PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE VIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 241          moltype = AA  length = 883
FEATURE                 Location/Qualifiers
REGION                  1..883
                        note = Synthetic Polypeptide
source                  1..883
                        mol_type = protein
                        organism = synthetic construct
SEQUENCE: 241
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRNDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LETTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                     883

SEQ ID NO: 242          moltype = AA  length = 883
FEATURE                 Location/Qualifiers
REGION                  1..883
                        note = Synthetic Polypeptide
REGION                  350..351
                        note = misc_feature - Xaa can be Arg, Lys, His, Glu, Asp,
                         Gln, Asn, Thr, Ser, Cys, Gly, Ala, Val, Leu, Ile, Met, Pro,
                         Tyr, Trp, or Phe
source                  1..883
                        mol_type = protein
                        organism = synthetic construct
SEQUENCE: 242
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVX XIPAIEREEL   360
PMKPEDIDMN PEALTAWKRA AAAVYRNDKA RKSRRISLEF MLEQANKFAN HKAIWFPYNM   420
```

```
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                      883

SEQ ID NO: 243             moltype = AA  length = 883
FEATURE                    Location/Qualifiers
REGION                     1..883
                           note = Synthetic Polypeptide
SITE                       350
                           note = misc_feature - Xaa can be Arg, Lys, His, Glu, Asp,
                             Gln, Asn, Thr, Ser, Cys, Gly,Ala, Val, Leu, Ile, Met, Pro,
                             Tyr, Trp, or Phe
SITE                       387
                           note = misc_feature - Xaa can be Arg, Lys, His, Glu, Asp,
                             Gln, Asn, Thr, Ser, Cys, Gly,Ala, Val, Leu, Ile, Met, Pro,
                             Tyr, Trp, or Phe
source                     1..883
                           mol_type = protein
                           organism = synthetic construct
SEQUENCE: 243
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVX DIPAIEREEL    360
PMKPEDIDMN PEALTAWKRA AAVYRXDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                      883

SEQ ID NO: 244             moltype = AA  length = 883
FEATURE                    Location/Qualifiers
REGION                     1..883
                           note = Synthetic Polypeptide
SITE                       350
                           note = misc_feature - Xaa can be Arg, Lys, His, Glu, Asp,
                             Gln, Asn, Thr, Ser, Cys, Gly,Ala, Val, Leu, Ile, Met, Pro,
                             Tyr, Trp, or Phe
SITE                       653
                           note = misc_feature - Xaa can be Arg, Lys, His, Glu, Asp,
                             Gln, Asn, Thr, Ser, Cys, Gly,Ala, Val, Leu, Ile, Met, Pro,
                             Tyr, Trp, or Phe
source                     1..883
                           mol_type = protein
                           organism = synthetic construct
SEQUENCE: 244
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVX DIPAIEREEL    360
PMKPEDIDMN PEALTAWKRA AAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEXTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                      883

SEQ ID NO: 245             moltype = AA  length = 883
FEATURE                    Location/Qualifiers
REGION                     1..883
                           note = Synthetic Polypeptide
SITE                       351
                           note = misc_feature - Xaa can be Arg, Lys, His, Glu, Asp,
```

```
                            Gln, Asn, Thr, Ser, Cys, Gly,Ala, Val, Leu, Ile, Met, Pro,
                            Tyr, Trp, or Phe
SITE                        387
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 245
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE XIPAIEREEL   360
PMKPEDIDMN PEALTAWKRA AAAVYRXDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 246              moltype = AA  length = 883
FEATURE                     Location/Qualifiers
REGION                      1..883
                            note = Synthetic Polypeptide
SITE                        351
                            note = misc_feature - Xaa can be Arg, Lys, His, Glu, Asp,
                             Gln, Asn, Thr, Ser, Cys, Gly,Ala, Val, Leu, Ile, Met, Pro,
                            Tyr, Trp, or Phe
SITE                        653
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 246
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE XIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYYWL KIHGANCAGV DKVPFPERIK   480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEXTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFA                    883

SEQ ID NO: 247              moltype = AA  length = 883
FEATURE                     Location/Qualifiers
REGION                      1..883
                            note = Synthetic Polypeptide
SITE                        387
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
SITE                        653
                            note = misc_feature - Xaa can be Arg, Lys, His, Glu, Asp,
                            Gln, Asn, Thr, Ser, Cys, Gly,Ala, Val, Leu, Ile, Met, Pro,
                            Tyr, Trp, or Phe
source                      1..883
                            mol_type = protein
                            organism = synthetic construct
SEQUENCE: 247
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
```

-continued

```
SKKALMRYED VYMPEVYKAI NIAQNTAWKI NKKVLAVANV ITKWKHCPVE DIPAIEREEL  360
PMKPEDIDMN PEALTAWKRA AAAVYRXDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEXTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                   883
```